(12) United States Patent
Showalter et al.

(10) Patent No.: US 10,214,536 B2
(45) Date of Patent: Feb. 26, 2019

(54) AMLEXANOX ANALOGS

(71) Applicant: The Regents of the University of Michigan, Ann Arbor, MI (US)

(72) Inventors: Hollis D. Showalter, Ann Arbor, MI (US); Alan R. Saltiel, Ann Arbor, MI (US); John J. Tesmer, Ann Arbor, MI (US); Xinmin Gan, Ann Arbor, MI (US)

(73) Assignee: THE REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 0 days.

(21) Appl. No.: 15/418,244

(22) Filed: Jan. 27, 2017

(65) Prior Publication Data

US 2017/0217980 A1 Aug. 3, 2017

Related U.S. Application Data

(60) Provisional application No. 62/288,917, filed on Jan. 29, 2016, provisional application No. 62/315,335, filed on Mar. 30, 2016.

(51) Int. Cl.
*C07D 491/052* (2006.01)
*C07D 491/147* (2006.01)

(52) U.S. Cl.
CPC ..... *C07D 491/052* (2013.01); *C07D 491/147* (2013.01)

(58) Field of Classification Search
None
See application file for complete search history.

(56) References Cited

U.S. PATENT DOCUMENTS

| | | |
|---|---|---|
| 4,108,663 A | 8/1978 | Okazaki et al. |
| 4,143,042 A | 3/1979 | Nohara |
| 4,192,749 A | 3/1980 | Jackson |
| 4,299,963 A * | 11/1981 | Nohara ................ C07D 311/58 546/62 |
| 4,657,760 A | 4/1987 | Kung |
| 4,683,195 A | 7/1987 | Mullis |
| 4,683,202 A | 7/1987 | Mullis |
| 4,728,509 A | 3/1988 | Shimizu et al. |
| 4,800,159 A | 1/1989 | Mullis |
| 4,965,188 A | 10/1990 | Mullis |
| 5,130,238 A | 7/1992 | Malek |
| 5,206,344 A | 4/1993 | Katre |
| 5,223,409 A | 6/1993 | Ladner |
| 5,225,212 A | 7/1993 | Martin |
| 5,225,326 A | 7/1993 | Bresser |
| 5,270,184 A | 12/1993 | Walker |
| 5,283,174 A | 2/1994 | Arnold, Jr. |
| 5,362,737 A | 11/1994 | Vora et al. |
| 5,399,491 A | 3/1995 | Kacian |
| 5,455,166 A | 10/1995 | Walker |
| 5,480,784 A | 1/1996 | Kacian |
| 5,545,524 A | 8/1996 | Trent |
| 5,641,673 A | 6/1997 | Haseloff |
| 5,710,029 A | 1/1998 | Ryder |
| 5,814,447 A | 9/1998 | Ishiguro |
| 5,824,518 A | 10/1998 | Kacian |
| 5,925,517 A | 7/1999 | Tyagi |
| 5,928,862 A | 7/1999 | Morrison |
| 5,981,180 A | 11/1999 | Chandler |
| 6,074,822 A | 6/2000 | Henry |
| 6,121,489 A | 9/2000 | Dorner |
| 6,150,097 A | 11/2000 | Tyagi |
| 6,200,763 B1 | 3/2001 | Craig et al. |
| 6,221,335 B1 | 4/2001 | Foster |
| 6,291,491 B1 | 9/2001 | Weber et al. |
| 6,303,305 B1 | 10/2001 | Wittwer |
| 6,309,863 B1 | 10/2001 | Anderson |
| 6,358,945 B1 | 3/2002 | Breitfelder et al. |
| 6,534,274 B2 | 3/2003 | Becker |
| 6,541,205 B1 | 4/2003 | Yokoyama |
| 6,566,354 B1 | 5/2003 | Rose et al. |
| 6,573,043 B1 | 6/2003 | Cohen |
| 6,603,008 B1 | 8/2003 | Ando et al. |
| 6,630,312 B2 | 10/2003 | Shoelson |
| 6,673,908 B1 | 1/2004 | Stanton |
| 6,758,848 B2 | 7/2004 | Burbank |
| 6,924,361 B1 | 8/2005 | Laudano |
| 7,049,151 B2 | 5/2006 | Nguyen |
| 7,085,439 B2 | 8/2006 | Andrieu |
| 7,374,885 B2 | 5/2008 | Becker |
| 8,299,084 B2 | 10/2012 | Rao et al. |
| 8,445,679 B2 | 5/2013 | Wang et al. |
| 8,946,424 B2 | 2/2015 | Saltiel et al. |

(Continued)

FOREIGN PATENT DOCUMENTS

EP 0684315 11/1995
JP 2963496 10/1999

(Continued)

OTHER PUBLICATIONS

Nohara ., J. Med. Chem. 1985, 28(5), pp. 559-568.*
CAPLUS 1991 5832264.*
Kang et al., Randomized controlled trial to investigate the effects of a newly developed formulation of phentermine diffuse-controlled release for obesity. Diabetes Obes Metab. Oct. 2010;12(10):876-82.
European Search Report of related EP 14881460.1, dated Aug. 18, 2017, 10 pages.
Abad-Zapatero et al., Ligand efficiency indices as guideposts for drug discovery. Drug Discov Today 2005, 10(7):464-9.
Adli et al. IKK-i/IKKepsilon controls constitutive, cancer cell-associated NF-kappaB activity via regulation of Ser-536 p65/RelA phosphorylation. J Biol Chem. Sep. 15, 2006;281(37):26976-84.
Akira et al., Toll-like receptor signalling. Nat Rev Immunol. Jul. 2004;4(7):499-511.
Anderson & Young, Chapter 4. Quantitative Filter Hybridization. In Nucleic Acid Hybridization, eds Hames & Higgins, 1985. 41 pages.

(Continued)

*Primary Examiner* — Heidi Reese
(74) *Attorney, Agent, or Firm* — Casimir Jones, S.C.; David W. Staple

(57) ABSTRACT

Provided herein are amlexanox analogs and methods for the treatment and/or prevention of diabetes, impaired insulin signaling, obesity, or other related diseases and conditions therewith.

4 Claims, 7 Drawing Sheets

(56) References Cited

U.S. PATENT DOCUMENTS

| | | |
|---|---|---|
| 9,394,303 B2 | 7/2016 | Nikolovska-Coleska et al. |
| 9,486,422 B2 | 11/2016 | Nikolovska-Coleska et al. |
| 2002/0103219 A1 | 8/2002 | Jacob |
| 2003/0064408 A1 | 4/2003 | Cimbora |
| 2003/0105086 A1 | 6/2003 | Michaelis et al. |
| 2003/0124178 A1 | 7/2003 | Haley |
| 2005/0042638 A1 | 2/2005 | Arnold, Jr. |
| 2005/0197333 A1 | 9/2005 | Van Duzer et al. |
| 2005/0261262 A1 | 11/2005 | Ma et al. |
| 2005/0282818 A1 | 12/2005 | Ramesh |
| 2006/0004003 A1 | 1/2006 | Abe et al. |
| 2006/0094682 A1 | 5/2006 | Westwick et al. |
| 2007/0060595 A1 | 3/2007 | Yoshizawa et al. |
| 2007/0135473 A1 | 6/2007 | Alexandre et al. |
| 2007/0149519 A1 | 6/2007 | Bamborough |
| 2007/0203236 A1 | 8/2007 | Smith |
| 2009/0054402 A1 | 2/2009 | Wang et al. |
| 2009/0143373 A1 | 6/2009 | Ding et al. |
| 2009/0196912 A1 | 8/2009 | Eickhoff |
| 2009/0304714 A1 | 12/2009 | Saltiel et al. |
| 2010/0009934 A1 | 1/2010 | Rickles et al. |
| 2010/0167989 A1 | 7/2010 | Grant |
| 2010/0256141 A1 | 10/2010 | Nemecek et al. |
| 2012/0125325 A1 | 5/2012 | Bannister et al. |
| 2012/0208836 A1 | 8/2012 | Saltiel et al. |
| 2013/0030007 A1 | 1/2013 | Penninger et al. |
| 2015/0224089 A1 | 8/2015 | Saltiel et al. |
| 2016/0060271 A1 | 3/2016 | Saltiel et al. |
| 2016/0251366 A1 | 9/2016 | Saltiel et al. |

FOREIGN PATENT DOCUMENTS

| | | | |
|---|---|---|---|
| WO | WO1997/049420 | 12/1997 | |
| WO | WO2004/022580 | 3/2004 | |
| WO | WO2004/097009 | 11/2004 | |
| WO | WO2005/075465 | 8/2005 | |
| WO | WO2009/120801 | 10/2009 | |
| WO | WO2009/149192 | 12/2009 | |
| WO | WO2009/150614 | 12/2009 | |
| WO | WO2010/005534 | 1/2010 | |
| WO | WO2010/080478 | 7/2010 | |
| WO | WO2010/102286 | 9/2010 | |
| WO | WO2010/139985 | 12/2010 | |
| WO | WO2010/151799 | 12/2010 | |
| WO | WO2012/016930 | 2/2012 | |
| WO | WO2012/112558 | 8/2012 | |
| WO | WO2012/178036 | 12/2012 | |
| WO | WO2013/039988 | 3/2013 | |
| WO | WO2013/052943 | 4/2013 | |
| WO | WO2013/086415 | 6/2013 | |
| WO | WO 2014111957 A1 * | 7/2014 | ........... A61K 31/216 |
| WO | WO2015/119624 | 8/2015 | |
| WO | WO2015/153959 | 10/2015 | |

OTHER PUBLICATIONS

Arkan et al., IKK-beta links inflammation to obesity-induced insulin resistance. Nature Medicine, 2005, 11:191-198.

Armoni et al., FOXO1 represses peroxisome proliferator-activated receptor-gamma1 and -gamma2 gene promoters in primary adipocytes. A novel paradigm to increase insulin sensitivity. J Biol Chem. Jul. 21, 2006;281(29):19881-91.

Bailey, The Use of Stable Isotopes in Pharmacological Research. Pharmacological Reviews 1981;33(2):81-132.

Bamborough et al., 5-(1H-Benzimidazol-1-yl)-3-alkoxy-2-thiophenecarbonitriles as potent, selective, inhibitors of IKK-epsilon kinase, Bioorganic and Medicinal Chemistry Letters, 2006, 16:6236-6240.

Bass, 2001, RNA interference. The short answer. Nature. May 24, 2001;411(6836):428-9.

Baumann et al., CAP defines a second signalling pathway required for insulin-stimulated glucose transport. Nature. Sep. 14, 2000;407(6801):202-7.

Bayard et al., Nonalcoholic Fatty Liver Disease. Am Fam Physician. Jun. 1, 2006;73(11):1961-8.

Berge et al., Pharmaceutical salts. J Pharm Sci. Jan. 1977;66(1):1-19.

Berger et al., Phosphodiesterase 3B is localized in caveolae and smooth ER in mouse hepatocytes and is important in the regulation of glucose and lipid metabolism. PLoS One, 2009, 4:e4671.

Bertola et al., "Hepatic expression patterns of inflammatory and immune response genes associated with obesity and NASH in morbidly obese patients." PLoS One. Oct. 22, 2010;5(10):e13577.

Bogan et al., Insulin-responsive compartments containing GLUT4 in 3T3-L1 and CHO cells: regulation by amino acid concentrations. Mol Cell Biol. Jul. 2001;21(14):4785-806.

Bodner Research Web, The Chemistry of the Halogens. © Apr. 2009. http://web.argive.org/web/20090414155348/http://chemed.chem.purdue.edu/genchem/topicreview/bg/ch10/group7.php. Retrieved Jun. 2, 2014, 11 pages.

Bradbury, Lipid metabolism and liver inflammation. I. Hepatic fatty acid uptake: possible role in steatosis. Am J Physiol Gastrointest Liver Physiol. Feb. 2006;290(2):G194-8.

Browne et al., Stable isotope techniques in early drug development: an economic evaluation. J Clin Pharmacol. Mar. 1998;38(3):213-20.

Buss et al., Constitutive and interleukin-1-inducible phosphorylation of p65 NF-{kappa}B at serine 536 is mediated by multiple protein kinases including I{kappa}B kinase (IKK)-{alpha}, IKK{beta}, IKK{epsilon}, TRAF family member-associated (TANK)-binding kinase 1 (TBK1), and an unknown kinase and couples p65 to TATA-binding protein-associated factor II31-mediated interleukin-8 transcription. J Biol Chem. Dec. 31, 2004;279(53):55633-43.

Cai et al., Local and systemic insulin resistance resulting from hepatic activation of IKK-beta and NF-kappaB. Nat Med. Feb. 2005;11(2):183-90.

Calay et al., Turning off the inflammatory, but not the metabolic, flames. Nature Medicine, 2013, 19:265-267.

Carey & Kingwell, Novel Pharmacological approaches to combat obesity and insulin resistance: targeting skeletal muscle with 'exercise mimetics'. Diabetologia. Oct. 2009;52(10):2015-26.

Carrell et al., A Novel Procedure for the Synthesis of Libraries Containing Small Organic Molecules. Angew Chem Int Ed Engl, 1994;33:2059-2061.

Cech, Ribozyme engineering. Curr Opin Struct Biol 1992;2:605-609.

Chen et al. Alterations in Hepatic Metabolism in fld Mice Reveal a Role for Lipin 1 in Regulating VLDL-Triacylglyceride Secretion. Arterioscler Thromb Vasc Biol 2008;28:1738-44.

Chen et al., Mcl-1 down-regulation potentiates ABT-737 lethality by cooperatively inducing Bak activation and Bax translocation. Cancer Res. Jan. 15, 2007;67(2):782-91.

Chiang et al., The protein kinase IKKepsilon regulates energy balance in obese mice. Cell. Sep. 4, 2009; 138(5):961-75.

Cho et al., An Unnatural Biopolymer. Science 1993;261:1303-5.

Choi et al., Alterations in regulation of energy homeostasis in cyclic nucleotide phosphodiesterase 3B-null mice. The Journal of Clinical Investigation, 2006, 116:3240-3251.

Clark et al., Novel cross-talk within the IKK family controls innate immunity. Biochemical Journal, 2011, 434:93-104.

Clark et al., Use of the pharmacological inhibitor BX795 to study the regulation and physiological roles of TBK1 and IkappaB kinase epsilon: a distinct upstream kinase mediates Ser-172 phosphorylation and activation. The Journal of Biological Chemistry. 2009, 284:14136-14146.

Cole et al., The EEV-Hybridoma Technique and Its Application to Human Lung Cancer. Monoclonal Antibodies and Cancer Therapy 1985, pp. 77-96.

Coppack et al., In vivo regulation of lipolysis in humans. Journal of Lipid Research, 1994, 35:177-193.

Cull et al., Screening for receptor ligands using large libraries of peptides linked to the C terminus of the lac repressor. PNAS 1992;89:1865-1869.

Cwirla et al., Peptides on phage: A vast library of peptides for identifying ligands. PNAS 1990;87:6378-6382.

(56) References Cited

OTHER PUBLICATIONS

Czabotar et al., Structural insights into the degradation of Mcl-1 induced by BH3 domains. Proc Natl Acad Sci U S A 2007, 104:6217-22.
Dai et al., Synthesis of the parent and substituted tetracyclic ABCD ring cores of camptothecins via 1-(3-aryl-2-propynyl)-1,6-dihydro-6-oxo-2-pyridinecarbonitriles. Org Lett 2006, 8:4665-7.
Dandona et al., Inflammation: the link between insulin resistance, obesity and diabetes. Trends Immunol. Jan. 2004; 25(1):4-7.
Dash et al., Apogossypol derivative BI-97C1 (Sabutoclax) targeting Mcl-1 sensitizes prostate cancer cells to mda-7/IL-24-mediated toxicity. Proc Natl Acad Sci U S A. 2011, 108(21):8785-90.
Day et al., Solution structure of prosurvival Mcl-1 and characterization of its binding by proapoptotic BH3-only ligands. J Biol Chem. Feb. 11, 2005;280(6):4738-44.
Day et al., Structure of the BH3 domains from the p53-inducible BH3-only proteins Noxa and Puma in complex with Mcl-1. J Mol Biol. Jul. 25, 2008;380(5):958-71.
Degerman et al., From PDE3B to the regulation of energy homeostasis. Current Opinion in Pharmacology, 2011, 11:676-682.
Devlin Random Peptide Libraries: A Source of Specific Protein Binding Molecules. Science 1990;249:404-406.
Dewitt et al., "Diversomers": an approach to nonpeptide, nonoligomeric chemical diversity. Proc Natl Acad Sci U S A. Aug. 1, 1993;90(15):6909-13.
Dorwald, Side Reactions in Organic Synthesis, 2005, Wiley: VCH, Weinhelm. 37 pages.
Du et al., A dual-readout F2 assay that combines fluorescence resonance energy transfer and fluorescence polarization for monitoring bimolecular interactions. Assay Drug Dev Technol 2011, 9:382-93.
Dyck et al., Effects of deuterium substitution on the catabolism of beta-phenylethylamine: an in vivo study. J Neurochem. Feb. 1986;46(2):399-404.
Elbashir et al., Duplexes of 21-nucleotide RNAs mediate RNA interference in cultured mammalian cells. Nature 2001;411:494-8.
Ettmayer et al., Lessons learned from marketed and investigational prodrugs. J Med Chem. May 6, 2004;47(10):2393-404.
Ezquerra et al., Obesity, Metabolic Syndrome, and Diabetes: Cardiovascular Implications and Therapy. Rev Esp Cardiol. Jul. 2008;61(7):752-64.
Festuccia et al., Control of brown adipose tissue glucose and lipid metabolism by PPARgamma. Frontiers in Endocrinology. 2011, 2:84. 6 pages.
Fitzgerald et al., IKKepsilon and TBK1 are essential components of the IRF3 signaling pathway. Nature Immunology,2003, 4:491-496.
Fulop et al., The metabolic syndrome. Pathol Biol (Paris). Sep. 2006;54(7):375-86.
Ganesan et al., Synthesis of unsymmetrical pyrazines by reaction of an oxadiazinone with enamines. Journal of Organic Chemistry 1993, 58:6155-6157.
Ghorbani et al., Appearance of brown adipocytes in white adipose tissue during CL 316,243-induced reversal of obesity and diabetes in Zucker fa/fa rats. Int J Obes Relat Metab Disord. Jun. 1997;21(6):465-75.
Green et al., Stimulation of lipolysis by tumor necrosis factor-alpha in 3T3-L1 adipocytes is glucose dependent: implications for long-term regulation of lipolysis. Diabetes, 2004, 53:74-81.
Gregor et al., Inflammatory mechanisms in obesity. Annual Review of Immunology, 2011, 29:415-445.
Greig et al., Development and characterization of biphenylsulfonamides as novel inhibitors of bone resorption. J Med Chem 2006, 49:7487-92.
Griffiths et al., Cell damage-induced conformational changes of the pro-apoptotic protein Bak in vivo precede the onset of apoptosis. J Cell Biol. Mar. 8, 1999;144(5):903-1.
Guoan et al., Adenovirus-mediated siRNA targeting Mcl-1 gene increases radiosensitivity of pancreatic carcinoma cells in vitro and in vivo. Surgery. Apr. 2010;147(4):553-61.

Hacker et al., Regulation and function of IKK and IKK-related kinases. Science's STKE, 2006, 2006(357):re13.
Hajduk, Fragment-based drug design: how big is too big? J. Med Chem 2006, 49:6972-6.
Han et al., Targeted prodrug design to optimize drug delivery. AAPS PharmSci. 2000;2(1):E6.
Hanahan et al., The hallmarks of cancer. Cell. Jan. 7, 2000;100(1):57-70.
Handbook of Pharmaceutical Salts, Properties, and Use, Stahl and Wermuth ed. 2002.
Hemmi et al., The roles of two IkappaB kinase-related kinases in lipopolysaccharide and double stranded RNA signaling and viral Infection. The Journal of Experimental Medicine, 2004, 199:1641-1650.
Hotamisligil, Inflammation and metabolic disorders. Nature, 2006, 444:860-867.
Huang et al., BH3 mimetic ABT-737 potentiates TRAIL-mediated apoptotic signaling by unsequestering Bim and Bak in human pancreatic cancer cells. Cancer Res. Apr. 15, 2008;68(8):2944-51.
Ikeda et al., Involvement of the ubiquitin-like domain of TBK1/IKK-i kinases in regulation of IFN-inducible genes. The EMBO Journal, 2007, 26:3451-3462.
Khandwala et al., 5% amlexanox oral paste, a new treatment for recurrent minor aphthous ulcers II: Pharmacokinetics and demonstration of clinical safety. Oral Surg Oral Med Oral Pathol Oral Radiol Endod. Feb. 1997;83(2):231-8.
Kishore et al., IKK-i and TBK-1 are enzymatically distinct from the homologous enzyme IKK-2: comparative analysis of recombinant human IKK-i, TBK-1, and IKK-2. J Biol Chem. Apr. 19, 2002;277(16):13840-7.
Kitamura et al., Insulin-induced phosphorylation and activation of cyclic nucleotide phosphodiesterase 3B by the serine-threonine kinase Akt. Molecular and Cellular Biology, 1999, 19:6286-6296.
Krawczyk et al., Nonalcoholic fatty liver disease. Best Pract Res Clin Gastroenterol. Oct. 2010;24(5):695-708.
Kuriki et al., Antiallergic action of amoxanox (AA-673), its main metabolite M-I and tranilast. Yakuri to Chiryo (1973-2000), 13(11): 6435-46, Journal, 1985, Abstract Only.
Kurita et al., Efficient and convenient heterogeneous palladium-catalyzed regioselective deuteration at the benzylic position. Chem. Eur. J. 2008; 14(2):664-73.
Langin, Adipose tissue lipolysis as a metabolic pathway to define pharmacological strategies against obesity and the metabolic syndrome. Pharmacological Research, 2006, 53:482-491.
Li et al., Selective TBK1/IKKi dual inhibitors with anticancer potency, Int J Cancer, 2014, 134:1972-1980.
Li et al., Structure-based design, synthesis, and antimicrobial activity of indazole-derived SAH/MTA nucleosidase inhibitors. J Med Chem 2003, 46:5663-73.
Lindh et al., Multisite phosphorylation of adipocyte and hepatocyte phosphodiesterase 3B. Biochimica et Biophysica Acta, 2007, 1773:584-592.
Lipinski et al., Experimental and computational approaches to estimate solubility and permeability in drug discovery and development settings. Adv Drug Deliv Rev 2001, 46:3-26.
Lumeng et al., Macrophages block insulin action in adipocytes by altering expression of signaling and glucose transport proteins. American Journal of Physiology Endocrinology and Metabolism, 2007, 292:E166-E174.
Macarron et al., Impact of high-throughput screening in biomedical research. Nat Rev Drug Discov 2011, 10: 188-95.
Martins et al., Synthesis of substituted benzoxacycles via a domino ortho-alkylation/Heck coupling sequence. J Org Chem 2006, 71:4937-42.
MeSH Descriptor Data for Isoproterenol, accessed Jul. 5, 2016, 5 pages.
Misra et al., 1H-Pyrazolo[3,4-b]pyridine inhibitors of cyclin-dependent kinases. Bioorg Med Chem Lett 2003, 13:1133-6.
Miyamoto et al., Immunohistochemical analysis of Bcl-2, Bax, Bcl-X, and Mcl-1 expression in pancreatic cancers. Oncology. 1999;56(1):73-82.

(56) References Cited

OTHER PUBLICATIONS

Mowers et al., Inflammation produces catecholamine resistance in obesity via activation of PDE3B by the protein kinases IKKε and TBK1, eLife, 2013, 2:e01119.
Muilenburg et al., Targeting Bcl-2-mediated cell death as a novel therapy in pancreatic cancer. J Surg Res., 2010, 163(2):276-81.
Neres et al., Non-nucleoside inhibitors of BasE, an adenylating enzyme in the siderophore biosynthetic pathway of the opportunistic pathogen Acinetobacter baumannii. J Med Chem 2013, 56, 2385-405.
Nikolovska-Coleska et al., Development and optimization of a binding assay for the XIAP BIR3 domain using fluorescence polarization. Anal Biochem 2004, 332:261-73.
Pal et al. CCN6/WISP3 exerts its tumor suppressor function through regulation of BMP signaling by direct binding to BMP4 in the extracellular environment, 102nd AACR Annual Meeting, 2011, abstract No. 2200 for poster presentation, Abstract Only.
Nohara et al., Studies on antianaphylactic agents. 5. Synthesis of 3-(1H-tetrazol-5-yl)chromones, a new series of antiallergic substances. J Med Chem. Jan. 1977; 20(1):141-5.
Nohara et al., Studies on antianaphylactic agents. 7. Synthesis of antiallergic 5-oxo-5H-[1]benzopyrano[2,3-b]pyridines. J Med Chem. May 1985; 28(5):559-68.
Nohara et al., Studies on antianaphylactic agents—I : A facile synthesis of 4-oxo-4H-1-benzopyran-3-carboxaldehydes by Vilsmeier reagents. Tetrahedron 1974, vol. 30(19):3553-3561.
Norris et al., Muscle-specific PPARgamma-deficient mice develop increased adiposity and insulin resistance but respond to thiazolidinediones. J Clin Invest. Aug. 2003; 112(4):608-18.
Obach, Mechanism of cytochrome P4503A4- and 2D6-catalyzed dehydrogenation of ezlopitant as probed with isotope effects using five deuterated analogs. Drug Metab Dispos. Dec. 2001;29(12):1599-607.
Oltersdorf et al., An inhibitor of Bcl-2 family proteins induces regression of solid tumours. Nature. Jun. 2, 2005;435(7042):677-81.
Ouchi et al., Adipokines in inflammation and metabolic disease. Nature Reviews Immunology, 2011, 11:85-97.
Palmer et al., Protein kinase A phosphorylation of human phosphodiesterase 3B promotes 14-3-3 protein binding and inhibits phosphatase-catalyzed inactivation, J Biol Chem, 2007, 282:9411-9419.
Park et al., Characterization of molecular recognition of STAT3 SH2 domain inhibitors through molecular simulation. J Mol Recognit. Mar.-Apr. 2011;24(2):254-65.
Parvatiyar et al., TAX1BP1 and A20 inhibit antiviral signaling by targeting TBK1-IKKi kinases, J Biol Chem, 2010, 285:14999-15009.
Petros et al., Discovery of a potent and selective Bcl-2 inhibitor using SAR by NMR. Bioorg Med Chem Lett. 2010, 20(22):6587-91.
Plomgaard et al., Tumor necrosis factor-alpha modulates human in vivo lipolysis, The Journal of Clinical Endocrinology and Metabolism, 2008, 93:543-549.
Pubchem Compound Summary for 6-(furan-2-yl)-3-methyl-1-pheylpyrazolo[3,4-b]pyridine-4-carboxylic acid. Https://pubchem.ncbi.nlm.hih.gov/compound/2998778#section=Top. Retrieved May 30, 2015, 13 pages.
Reilly et al., An inhibitor of the protein kinases TBK1 and IKK-epsilon improves obesity-related metabolic dysfunctions in mice. Nature Medicine, 2013, 19:313-321.
Reilly et al., A subcutaneous adipose tissue-liver signalling axis controls hepatic gluconeogenesis. Nat Commun. Jan. 12, 2015;6:6047.
Remington's Pharmaceutical Sciences. A.R. Gennaro et al., eds. 1985; Mack Publishing Co. TOC only.
Ren et al., Endocrine glands-derived vascular endothelial growth factor protects pancreatic cancer cells from apoptosis via upregulation of the myeloid cell leukemia-1 protein. Biochem Biophys Res Commun. Aug. 14, 2009;386(1):35-9.
Reynisdottir et al., Catecholamine resistance in fat cells of women with upper-body obesity due to decreased expression of beta 2-adrenoceptors. Diabetologia, 1994, 37:428-435.
Saltiel, Insulin resistance in the defense against obesity. Cell Metabolism, 2012, 15:798-804.
Sawhney et al., Bioerodible hydrogels based on photopolymerized poly(ethylene glycol)-co-poly(alpha-hydroxy acid) diacrylate macromers. Macromolecules 1993, 26(4): 581-587.
Schniewind et al., Resistance of pancreatic cancer to gemcitabine treatment is dependent on mitochondria-mediated apoptosis. Int J Cancer. Mar. 20, 2004;109(2):182-8.
Schrödinger Suite 2011 Induced Fit Docking protocol; Glide version 5.7, Schrödinger, LLC, New York, NY, 2009; Prime version 3.0, Schrödinger, LLC, New York, NY. 2011, 2 pages.
Schudt et al., Zardaverine as a selective inhibitor of phosphodiesterase isozymes, Biochemical Pharmacology, 1991, 42:153-162.
Sercel et al., Simple Synthesis of 4 Substituted 1(2H) Isoquinolinones via Electrophilic Trapping of Lithiated Mono and Dianion Precursors, Synthetic Communications: An International Journal for Rapid Communication of Synthetic Organic Chemistry 2007, 37: 23, 4199-4208.
Shoelson et al., Obesity, inflammation, and insulin resistance. Gastroenterology, 2007, 132:2169-2180.
Soares et al., Profiling the NIH Small Molecule Repository for compounds that generate H2O2 by redox cycling in reducing environments. Assay Drug Dev Technol. Apr. 2010;8(2):152-74.
Souza et al., TNF-alpha induction of lipolysis is mediated through activation of the extracellular signal related kinase pathway in 3T3-L1 adipocytes, Journal of Cellular Biochemistry, 2003, 89:1077-1086.
Stich et al., Hypocaloric diet reduces exercise-induced alpha 2-adrenergic antilipolytic effect and alpha 2-adrenergic receptor mRNA levels in adipose tissue of obese women, The Journal of Clinical Endocrinology and Metabolism, 2002, 87:1274-1281.
Testa, Prodrug research: futile or fertile? Biochem Pharmacol. Dec. 1, 2004;68(11):2097-106.
Tonn et al., Simultaneous analysis of diphenhydramine and a stable isotope analog (2H10)diphenhydramine using capillary gas chromatography with mass selective detection in biological fluids from chronically instrumented pregnant ewes. Biol Mass Spectrom. Nov. 1993;22(11):633-42.
Tsaioun et al., ADDME—Avoiding Drug Development Mistakes Early: central nervous system drug discovery perspective. BMC Neurol. Jun. 12, 2009;9 Suppl 1:S1.
Tse et al., ABT-263: a potent and orally bioavailable Bcl-2 family inhibitor. Cancer Res. May 1, 2008;68(9):3421-8.
Ukawa et al., Synthesis of the metabolites and degradation products of 2-amino-7-isopropyl-5-oxo-5H-[1]benzopyrano[2,3-b]pyridine-3-carboxylic acid (Amoxanox). Chem Pharm Bull (Tokyo). Oct. 1985; 33(10):4432-7.
Van Delft et al., The BH3 mimetic ABT-737 targets selective Bcl-2 proteins and efficiently induces apoptosis via Bak/Bax if Mcl-1 is neutralized. Cancer Cell. 2006;10:389-99.
Venkatesh et al., Role of the development scientist in compound lead selection and optimization. J Pharm Sci. Feb. 2000;89(2):145-54.
Volochnyuk et al., Approach to the library of fused pyridine-4-carboxylic acids by Combes-type reaction of acyl pyruvates and electron-rich amino heterocycles. J Comb Chem 2010, 12, 510-7.
Waibel et al., Bibenzyl- and stilbene-core compounds with non-polar linker atom substituents as selective ligands for estrogen receptor beta. Eur J Med Chem. Sep. 2009; 44(9):3412-24.
Wolen et al., The application of stable isotopes to studies of drug bioavailability and bioequivalence. J Clin Pharmacol. Jul.-Aug. 1986;26(6):419-24.
Wei et al., Inducing apoptosis and enhancing chemosensitivity to gemcitabine via RNA interference targeting Mcl-1 gene in pancreatic carcinoma cell. Cancer Chemother Pharmacol. Nov. 2008;62(6):1055-64.
Wellen et al., Inflammation, stress, and diabetes, The Journal of Clinical Investigation, 2005, 115:1111-1119.

(56) References Cited

OTHER PUBLICATIONS

Werner et al., Disruptive Yeast Tri-Hybrid Identifies Inducible IKK (IKKi) as a New Insulin Resistance Kinase. Abstract No. 158-OR, 64th Scientific Sessions, 2004, American Diabetes Association, 1 page.

Wertz et al., Sensitivity to antitubulin chemotherapeutics is regulated by MCL1 and FBW7. Nature. 2011, 471(7336):110-4.

Wunderlich et al., Hepatic NF-kappa B essential modulator deficiency prevents obesity-induced insulin resistance but synergizes with high-fat feeding in tumorigenesis, PNAS, 2008, 105:1297-1302.

Xu et al., Chemical probes that competitively and selectively inhibit Stat3 activation. PLoS One. 2009;4(3):e4783.

Ye et al., Regulation of energy metabolism by inflammation: a feedback response in obesity and calorie restriction. Aging, 2010, 2:361-368.

Yuan et al., Reversal of obesity- and diet-induced insulin resistance with salicylates or targeted disruption of Ikkbeta. Science, 2001, 293:1673-1677.

Zhang et al., Tumor necrosis factor-alpha stimulates lipolysis in differentiated human adipocytes through activation of extracellular signal-related kinase and elevation of intracellular cAMP. Diabetes, 2002, 51:2929-2935.

Zhou et al., Mcl-1, a Bcl-2 family member, delays the death of hematopoietic cells under a variety of apoptosis-inducing conditions. Blood. Jan. 15, 1997;89(2):630-43.

Zmuda-Trzebiatowska et al., Role of PDE3B in insulin-induced glucose uptake, GLUT-4 translocation and lipogenesis in primary rat adipocytes, 2006, Cell Signal 18:382-390.

European Search Report of related EP 14791582.1, dated Sep. 8, 2016, 7 pages.

International Search Report and Written Opinion for PCT/US2012/059216, dated Mar. 25, 2013,12 pages.

International Search Report and Written Opinion for PCT/US2012/068570, dated Feb. 28, 2013, 9 pages.

International Search Report and Written Opinion for PCT/US2014/015387, dated May 14, 2014, 9 pages.

International Search Report and Written Opinion, International Application No. PCT/US2015/024231, dated Oct. 1, 2015, 10 pages.

International Search Report and Written Opinion for PCT/US2017/015391, dated Apr. 7, 2017, 6 pages.

\* cited by examiner

AMLEXANOX ANALOGS

CROSS-REFERENCE TO RELATED APPLICATIONS

The present invention claims priority to U.S. Provisional Patent Application 62/288,917, filed Jan. 29, 2016, and U.S. Provisional Patent Application 62/315,335 filed Mar. 30, 2016, each of which are incorporated by reference in their entirety.

STATEMENT REGARDING FEDERAL FUNDING

This invention was made with government support under grant DK100319 awarded by the U.S. National Institutes of Health. The government has certain rights in the invention.

FIELD

Provided herein are amlexanox analogs and methods for the treatment and/or prevention of diabetes, impaired insulin signaling, obesity, nonalcoholic steatotic hepatitis (NASH), or other related diseases and conditions therewith.

BACKGROUND

There currently is a worldwide epidemic of diabetes. Insulin resistance is recognized as a characteristic trait of the disease and is usually closely associated with obesity. Obesity also leads to a state of chronic, low-grade inflammation in liver and fat tissue, which in turn increases the levels of a pair of kinases: IKK-ε and TBK1. The asthma drug amlexanox is currently in clinical trials for the treatment of obesity and related metabolic disorders. Mechanistic studies in mice reveal that the compound improves the metabolism of sugar by generating a new signal between fat cells and the liver. Specifically, it exerts its effects by increasing the level of the second messenger molecule cAMP, which in turn increases the rate by which cells "burn" fat so that the animal loses weight. Amlexanox also triggers the release of the hormone interleukin-6 (IL-6) from fat cells, which then circulates to the liver. In the livers of diabetic mice, IL-6 reduces production of glucose, so that overall blood sugar is lowered. Amlexanox also improves nonalcoholic fatty liver disease (NAFLD) and NASH in mice and patients. However, clinically, amlexanox shows modest potency and non-optimal pharmacokinetics.

SUMMARY

Provided herein are amlexanox analogs and methods for the treatment and/or prevention of diabetes, impaired insulin signaling, NAFLD, NASH, and/or obesity therewith. In some embodiments, provided herein are amlexanox analogs modified at the 2, 3, and 7 positions. In some embodiments, provided herein are amlexanox analogs with C to S, N, and/or O modification on the ring system. In particular embodiments, the 7 position is modified with a cyclic group that provides increased secretion of IL-6 in adipocytes and upregulation of cAMP levels relative to amlexanox. In certain embodiments, the 3 position is modified to present a carboxylic acid bioisostere, alcohol, tetrazole, etc. Further, in some embodiments, the analogs herein exhibit increased inhibition of IKK-ε and TBK1.

Provided in some embodiments herein are treatment methods related to obesity, insulin resistance, diabetes, weight loss, and related disorders. In particular, the present invention provides methods of treating such conditions with amlexanox analogs and methods of screening candidate amlexanox analogs.

In some embodiments, methods of treatment comprise: administering an amlexanox analog to a subject with a condition associated with impaired insulin receptor signaling, wherein the administering causes a reduction in one or more symptoms of the condition.

In some embodiments, provided herein are compounds of one of:

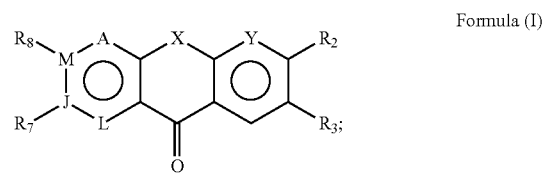

Formula (I)

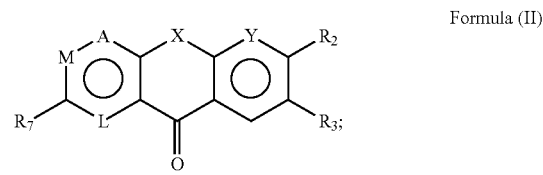

Formula (II)

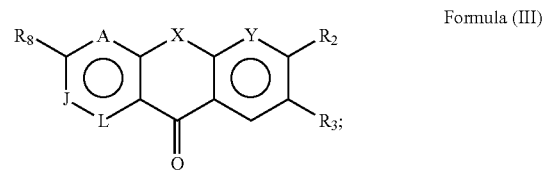

Formula (III)

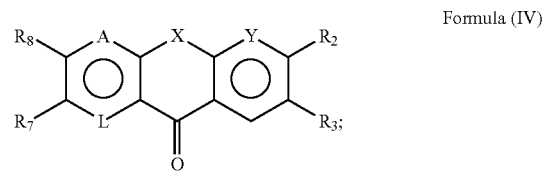

Formula (IV)

wherein, in some embodiments, $R_7$ is —Z—$R_{10}$ and/or $R_8$ is -G-$R_{11}$; and having substituents (e.g., $R_2$, $R_3$, $R_7$, $R_8$, $R_{10}$, $R_{11}$, A, G, J, L, M, X, Y, Z, etc.) as depicted in, for example, Tables 1-3, Examples 1-6, and/or described in the Detailed Description. For example, in particular embodiments: $R_2$ is an amine (e.g., $NH_2$), an amine bioisostere, an amidino, or an amidino bioisostere; $R_3$ is a carboxylic acid (e.g., COOH), carboximide, alcohol, tetrazole, ester, amide, heterocycle, etc., or a bioisostere thereof; X is N, O, or S; Y A, J, M, and L are independently C or N; and $R_7$ (or —Z—$R_{10}$) and/or $R_8$ (or -G-$R_{11}$), when present, are a cyclic group (e.g., aromatic, non-aromatic, heterocyclic, heteroaromatic, bicyclic, etc.), substituted cyclic group (e.g., aromatic, non-aromatic, heterocyclic, heteroaromatic, bicyclic, etc.), alkyl-cyclic group (e.g., aromatic, non-aromatic, heterocyclic, heteroaromatic, bicyclic, etc.), alkyl-substituted cyclic group (e.g., aromatic, non-aromatic, heterocyclic, heteroaromatic, bicyclic, etc.), alkyl group, substituted alkyl group (e.g., alkene, alkyne, alcohol, amine, haloalkyl, etc.), halogen, amine, alcohol, or combinations thereof.

In some embodiments, provided herein are compounds of one of Formula (1) through Formula (73). Formulas (1) through (25) are exemplified below:

Formula (1)
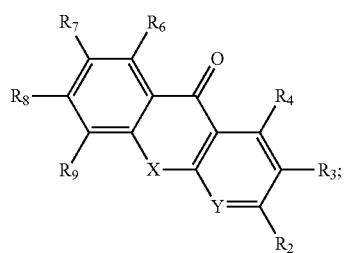
Formula (2)
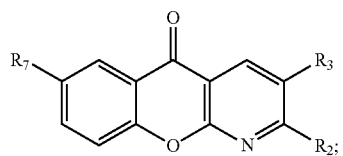
Formula (3)
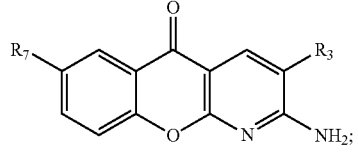
Formula (4)
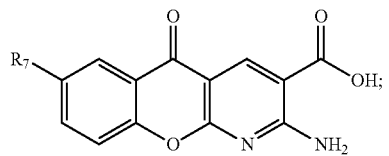
Formula (5)
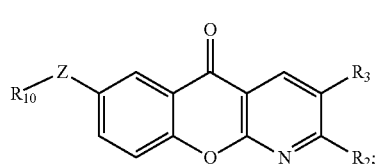
Formula (6)
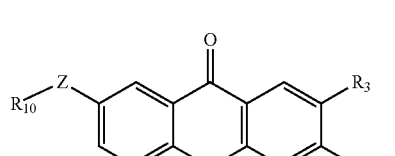
Formula (7)
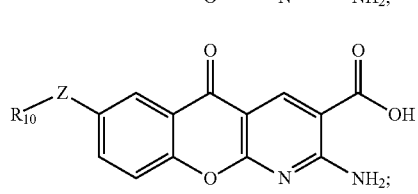
Formula (8)
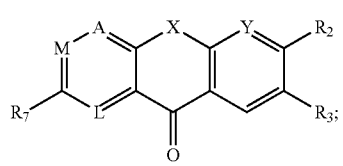
Formula (9)
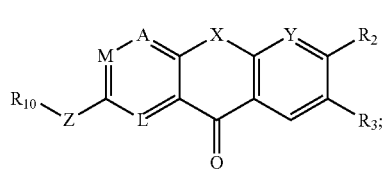
Formula (10)
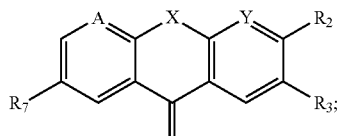
Formula (11)
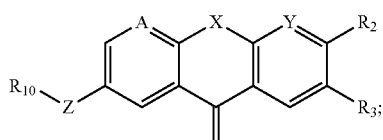
Formula (12)
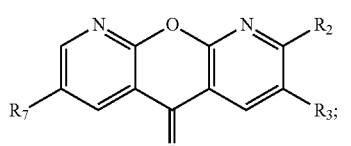
Formula (13)
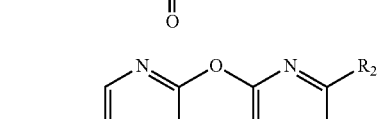
Formula (14)
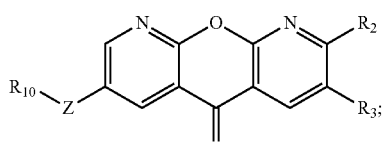
Formula (15)
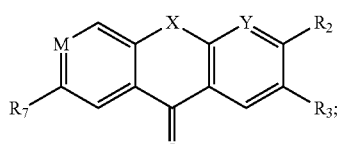
Formula (16)
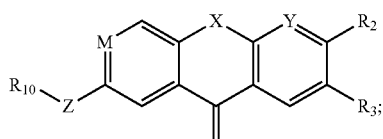
Formula (17)
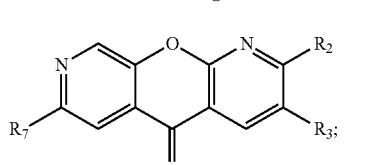
Formula (18)
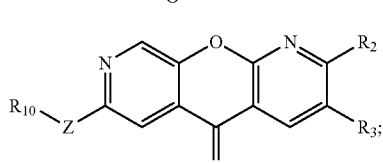
Formula (19)
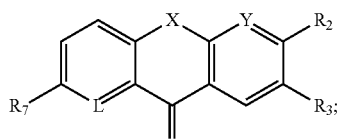

-continued

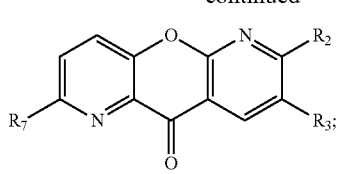

Formula (20)

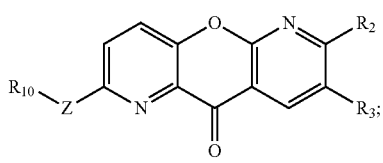

Formula (21)

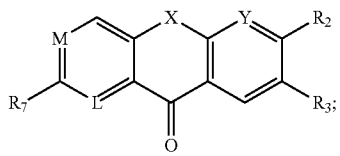

Formula (22)

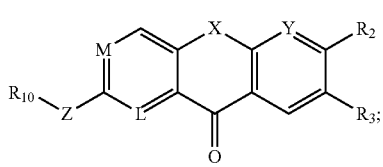

Formula (23)

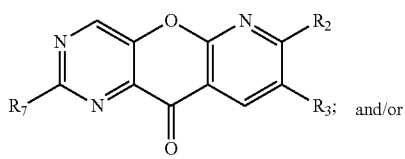

Formula (24) and/or

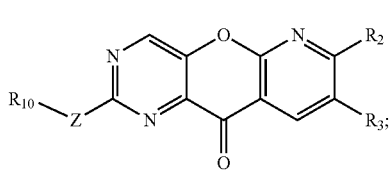

Formula (25)

having substituents (e.g., $R_2$, $R_3$, $R_4$, $R_6$, $R_7$, $R_8$, $R_9$, $R_{10}$, A, M, L, X, Y, Z) as depicted in Table 1, Table 2, Example 5, and/or described in greater detail in the Detailed Description. For example, in particular embodiments $R_4$, $R_6$, $R_8$, and $R_9$ are H; $R_2$ is an amine (e.g., $NH_2$), an amine bioisostere, an amidino, or an amidino bioisostere; $R_3$ is a carboxylic acid (e.g., COOH), carboximide, alcohol, tetrazole, ester, amide, heterocycle, etc., or a bioisostere thereof; X and Y and are independently N, O, or S; A, M, and L are independently C or N, and $R_7$ (or Z—$R_{10}$) is a cyclic group (e.g., aromatic, non-aromatic, heterocyclic, heteroaromatic, bicyclic, etc.), substituted cyclic group (e.g., aromatic, non-aromatic, heterocyclic, heteroaromatic, bicyclic, etc.), alkyl group, substituted alkyl group (e.g., alkene, alkyne, alcohol, amine, haloalkyl, etc.), halogen, amine, alcohol, or combinations thereof. Formulas (26) through (49) correspond to Formulas (2) through (25); however, $R_7$ or —Z—$R_{10}$ is H, M is C, J is C or N (See Formula (III)), and $R_8$ (or G-$R_{11}$) (See Formula (III)) is a cyclic group (e.g., aromatic, non-aromatic, heterocyclic, heteroaromatic, bicyclic, etc.), substituted cyclic group (e.g., aromatic, non-aromatic, heterocyclic, heteroaromatic, bicyclic, etc.), alkyl group, substituted alkyl group (e.g., alkene, alkyne, alcohol, amine, haloalkyl, etc.), halogen, amine, alcohol, or combinations thereof; any $R_7$ or —Z—$R_{10}$ substituents described for Formulas (2) through (25) apply to $R_8$ or -G-$R_{11}$ substituents of Formulas (26) through (49). Formulas (50) through (73) correspond to Formulas (2) through (25); however, M is C, and $R_8$ (or G-$R_{11}$) (See Formula (IV)) is a cyclic group (e.g., aromatic, non-aromatic, heterocyclic, heteroaromatic, bicyclic, etc.), substituted cyclic group (e.g., aromatic, non-aromatic, heterocyclic, heteroaromatic, bicyclic, etc.), alkyl group, substituted alkyl group (e.g., alkene, alkyne, alcohol, amine, haloalkyl, etc.), halogen, amine, alcohol, or combinations thereof; any $R_7$ or —Z—$R_{10}$ substituents described for Formulas (2) through (25) also apply to $R_8$ or -G-$R_{11}$ substituents of Formulas (26) through (73).

In some embodiments, provided herein are amlexanox analog compounds for the treatment of obesity, insulin resistance, diabetes, and steatosis. In addition, the amlexanox analog compounds are anti-inflammatory antiallergic immunomodulators, e.g., for the treatment of diseases associated with inflammation.

In some embodiments, provided herein is technology related to a composition comprising an amlexanox analog or a pharmaceutically acceptable salt thereof.

In some embodiments, provided herein are compositions comprising a compound synthesized by the synthesis schemes of Examples 2 and 4.

In some embodiments, provided herein are methods for the treatment of obesity, insulin resistance, diabetes, and steatosis comprising administering an amlexanox analog or a pharmaceutically acceptable salt thereof.

In some embodiments, provided herein are methods for the treatment of diseases or conditions associated with inflammation (e.g., diseases or conditions resulting from inflammation and/or causing inflammation) comprising administering an amlexanox analog or a pharmaceutically acceptable salt thereof.

In some embodiments, provided herein are methods of treating conditions associated with impaired insulin, comprising: providing a subject experiencing or at risk for impaired insulin signaling and administering to the subject a therapeutically effective dose of an amlexanox analog, wherein the administration results in improved insulin signaling in the subject. In some embodiments, the impaired insulin signaling occurs in such as adipocyte cells, adipose tissue macrophage cells, adipose tissue, liver cells, and liver tissue. In some embodiments, the subject is experiencing or is at risk of experiencing a condition such as obesity, diabetes, and insulin resistance. In some embodiments, the administering of an amlexanox analog results in an outcome of increased glucose metabolism, reduction in body fat, lack of increase in body fat, increased insulin receptor signaling, decreased level of insulin receptor phosphorylation, reduction in or prevention of chronic inflammation in liver, reduction in or prevention of chronic inflammation in adipose tissue, reduction in or prevention of hepatic steatosis and NASH, promotion of metabolic energy expenditure, reduction in circulating free fatty acids, and/or reduction in cholesterol.

In some embodiments, the present invention provides a method of reducing body fat or preventing an increase in body fat in a subject, comprising: providing a subject experiencing or at risk of overweight or obese body composition, and administering to the subject a therapeutically effective dose of an amlexanox analog, wherein the administration results in reduction of or prevention of increase in body fat in the subject. In some embodiments, the subject is experiencing or is at risk of experiencing a condition such as diabetes and insulin resistance. In some embodiments, the administering of an amlexanox analog results in an outcome such as increased glucose metabolism, increased insulin receptor signaling, decreased level of insulin receptor phosphorylation, reduction in or prevention of chronic inflammation in liver, reduction in or prevention of chronic inflammation in adipose tissue, reduction in or prevention of hepatic steatosis, promotion of metabolic energy expenditure, reduction in circulating free fatty acids, and/or reduction in cholesterol.

Conditions and disease states which may be treated by methods and compositions herein include but are not limited to diabetes mellitus, type I diabetes, type II diabetes, gestational diabetes, metabolic syndrome, metabolic syndrome X, syndrome X, insulin resistance syndrome, Reaven's syndrome, CHAOS, and malnutrition-related diabetes mellitus.

Lipid metabolic conditions and disease states which may be treated using methods and compositions of the present invention include but are not limited to lipodystrophy, congenital generalized lipodystrophy (Beradinelli-Seip syndrome), familial partial lipodystrophy, acquired partial lipodystrophy (Barraquer-Simons syndrome), acquired generalized lipodystrophy, centrifugal abdominal lipodystrophy (Lipodystrophia centrifugal is abdominalis infantilis), lipoatrophia annularis (Ferreira-Marques lipoatrophia), localized lipodystrophy, HIV-associated lipodystrophy, hypercholesterolemia, hyperlipidemia, obesity, hypertriglyceridemia. Lipid metabolic conditions may occur in concert with or in absence of conditions such as vascular disease, hypertension, atherosclerosis, arteriosclerosis, peripheral vascular disease (PVD), peripheral arterial disease (also known as peripheral artery disease or PAD), claudication, intermittent claudication, vascular diseases, peripheral arterial occlusive disease (PAOD), coronary artery disease (CAD), cardiovascular disease, obesity, metabolic syndrome, and critical limb ischemia.

Methods and treatments herein find use in the treatment of high total cholesterol (hypercholesterolemia). Primary causes of hypercholesterolemia include but are not limited to high-fat diet, smoking or tobacco use, hypothyroidism, renal disease, liver disease, use of progestins, use of anabolic steroids, and use of glucocorticoids. Hypercholesterolemia may be polygenic or familial. Known familial hypercholesterolemia diseases include but are not limited to familial ligand defective apoB-100 (FLDB) and autosomal recessive hypercholesterolemia.

Methods and compositions herein find use in the treatment of hepatic steatosis disease, also referred to as fatty liver disease. Fatty liver disease can range from fatty liver alone (steatosis) to fatty liver associated with inflammation (steatohepatitis). This condition can occur with the use of alcohol (alcohol-related fatty liver) or in the absence of alcohol (nonalcoholic fatty liver disease [NAFLD]). Other factors that may lead to fatty liver disease include but are not limited to drugs (e.g., amiodarone, tamoxifen, methotrexate), alcohol, metabolic abnormalities (eg, galactosemia, glycogen storage diseases, homocystinuria, tyrosemia), nutritional status (e.g., overnutrition, severe malnutrition, total parenteral nutrition [TPN], starvation diet), or other health problems (e.g., celiac sprue, Wilson disease, etc.). Individuals genetically predisposed to fatty liver disease may exhibit normal or underweight body composition.

Embodiments herein find use in the treatment or prevention of overweight and obesity. The most widely accepted clinical definition of obesity is the World Health Organization (WHO) criteria based on BMI. Under this convention for adults, grade 1 overweight (commonly and simply called overweight) is a BMI of 25-29.9 kg/m$^2$. Grade 2 overweight (commonly called obesity) is a BMI of 30-39.9 kg/m$^2$. Grade 3 overweight (commonly called severe or morbid obesity) is a BMI greater than or equal to 40 kg/m$^2$. The surgical literature often uses a different classification to recognize particularly severe obesity. In this setting, a BMI greater than 40 kg/m$^2$ is described as severe obesity, a BMI of 40-50 kg/m$^2$ is termed morbid obesity, and a BMI greater than 50 kg/m$^2$ is termed super obese. The definition of obesity in children involves BMIs greater than the 85th (commonly used to define overweight) or the 95th (commonly used to define obesity) percentile, respectively, for age-matched and sex-matched control subjects. Secondary causes of obesity include but are not limited to hypothyroidism, Cushing syndrome, insulinoma, hypothalamic obesity, polycystic ovarian syndrome, genetic syndromes (e.g., Prader-Willi syndrome, Alstrom syndrome, Bardet-Biedl syndrome, Cohen syndrome, Borjeson-Forssman-Lehmann syndrome, Frohlich syndrome), growth hormone deficiency, oral contraceptive use, medication-induced obesity (e.g., phenothiazines, sodium valproate, carbamazepine, tricyclic antidepressants, lithium, glucocorticoids, megestrol acetate, thiazolidine diones, sulphonylureas, insulin, adrenergic antagonists, serotonin antagonists [especially cyproheptadine]), eating disorders (especially binge-eating disorder, bulimia nervosa, night-eating disorder), hypogonadism, pseudohypoparathyroidism, and obesity related to tube feeding.

In some embodiments, provided herein is the use of an amlexanox analog in the manufacture of a medicament for the treatment of a condition such as impaired insulin signaling, obesity, diabetes, insulin resistance, high cholesterol, metabolic syndrome, hepatic stenosis, chronic inflammation in liver, and chronic inflammation in adipose tissue.

In some embodiments, provided herein is the use of an amlexanox analog for the treatment of a condition such as impaired insulin signaling, obesity, diabetes, insulin resistance, high cholesterol, metabolic syndrome, hepatic stenosis, chronic inflammation in liver, and chronic inflammation in adipose tissue.

DEFINITIONS

Figure 1:
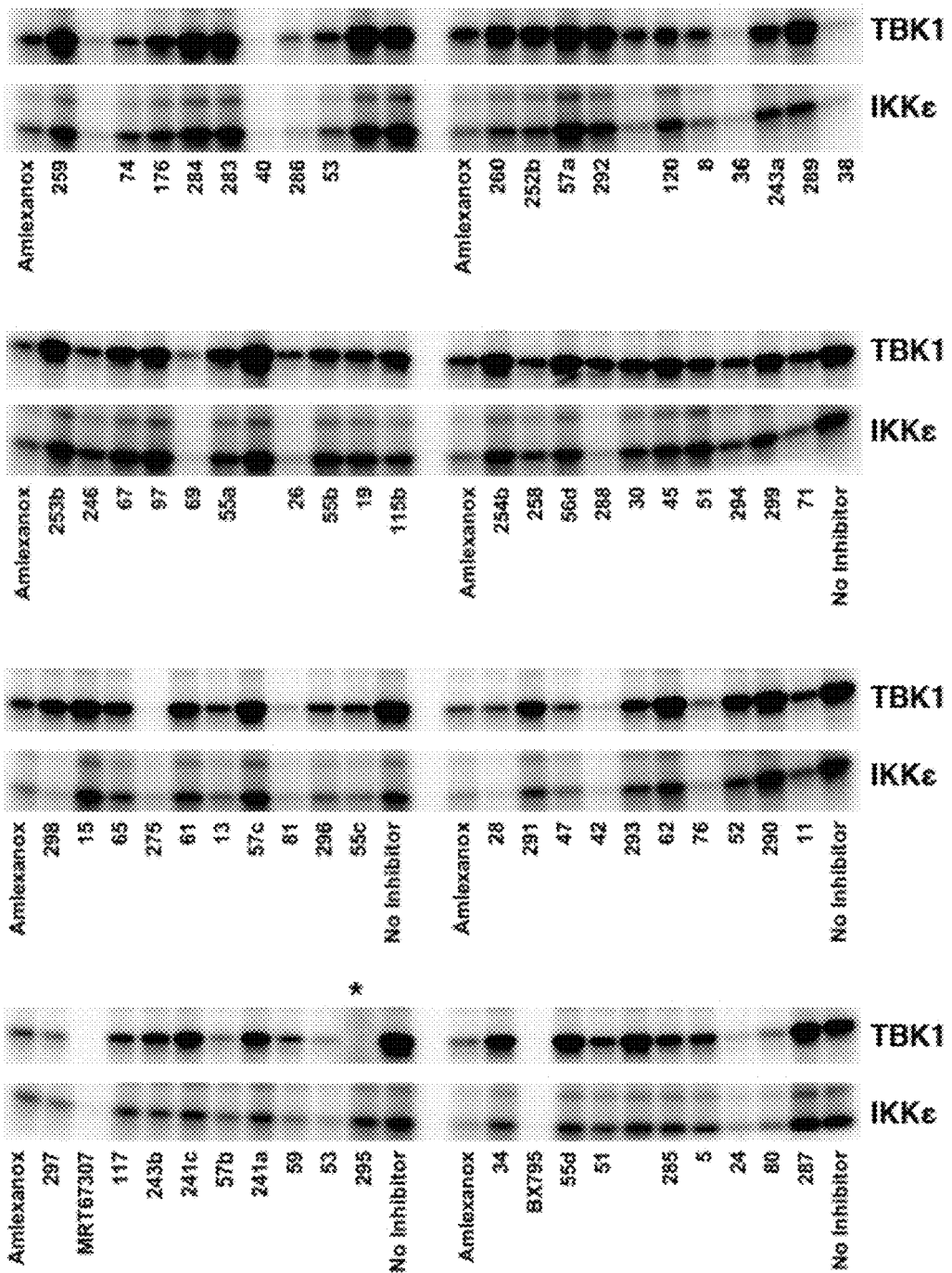
FIG. 1. TBK1 and IKKε single-point kinase assays with inhibitors at 2 μM, approximately the published IC50 of amlexanox. The intensity of the bands represents the amount of phosphorylated substrate. Darker bands indicate greater phosphorylation as a result of decreased kinase inhibition. The potent commercial inhibitors BX795 and MRT67307 were included as positive controls.

Although any methods and materials similar or equivalent to those described herein can be used in the practice or testing of embodiments described herein, some preferred methods, compositions, devices, and materials are described herein. However, before the present materials and methods are described, it is to be understood that this invention is not limited to the particular molecules, compositions, methodologies or protocols herein described, as these may vary in accordance with routine experimentation and optimization. It is also to be understood that the terminology used in the description is for the purpose of describing the particular versions or embodiments only, and is not intended to limit the scope of the embodiments described herein.

Unless otherwise defined, all technical and scientific terms used herein have the same meaning as commonly understood by one of ordinary skill in the art to which this invention belongs. However, in case of conflict, the present specification, including definitions, will control. Accordingly, in the context of the embodiments described herein, the following definitions apply.

As used herein and in the appended claims, the singular forms "a", "an" and "the" include plural reference unless the context clearly dictates otherwise. Thus, for example, reference to "a compound" is a reference to one or more compounds and equivalents thereof known to those skilled in the art, and so forth.

As used herein, the term "comprise" and linguistic variations thereof denote the presence of recited feature(s), element(s), method step(s), etc. without the exclusion of the presence of additional feature(s), element(s), method step(s), etc. Conversely, the term "consisting of" and linguistic variations thereof, denotes the presence of recited feature(s), element(s), method step(s), etc. and excludes any unrecited feature(s), element(s), method step(s), etc., except for ordinarily-associated impurities. The phrase "consisting essentially of" denotes the recited feature(s), element(s), method step(s), etc. and any additional feature(s), element(s), method step(s), etc. that do not materially affect the basic nature of the composition, system, or method. Many embodiments herein are described using open "comprising" language. Such embodiments encompass multiple closed "consisting of" and/or "consisting essentially of" embodiments, which may alternatively be claimed or described using such language.

All chemical names of substituents should be interpreted in light of IUPAC and/or a modified format in which functional groups within a substituent are read in the order in which they branch from the scaffold or main structure. For example, in the modified nomenclature, methyl-sulfonyl-propanol refers to $CH_2SO_2CH_2CH_2CH_2OH$ or:

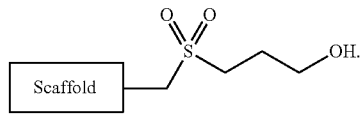

A methyl amino substituent refers to:

while an amino-methyl substituent is:

All chemical names of substituents should be interpreted in light of IUPAC and/or the modified nomenclature and with reference to the chemical structures depicted and/or described herein.

The term "system" refers a group of objects, compounds, methods, and/or devices that form a network for performing a desired objective.

As used herein a "sample" refers to anything capable of being subjected to the compositions and methods provided herein. The sample may be in vitro or in vivo. In some embodiments, samples are "mixture" samples, in which samples are from more than one subject or individual. In some embodiments, the methods provided herein comprise purifying or isolating the sample. In some embodiments, the sample is purified or unpurified protein. In some embodiments, a sample may be from a clinical or research setting. In some embodiments, a sample may comprise cells, fluids (e.g. blood, urine, cytoplasm, etc.), tissues, organs, lysed cells, whole organisms, etc. In some embodiments, a sample may be derived from a subject. In some embodiments, a sample may comprise one or more partial or whole subjects.

As used herein, the term "subject" refers to any animal including, but not limited to, humans, non-human primates, bovines, equines, felines, canines, pigs, rodents (e.g., mice), and the like. The terms "subject" and "patient" may be used interchangeably, wherein the term "patient" generally refers to a human subject seeking or receiving treatment or preventative measures from a clinician or health care provider.

The terms "test agent" and "candidate agent" refer to any chemical entity, pharmaceutical, drug, peptide, antibody, etc. that is a candidate for use to treat or prevent a disease, illness, sickness, or disorder of bodily function (e.g., diabetes, obesity, etc.). Test agents (e.g., test compounds) comprise both known and potential therapeutic compounds. A test agent (e.g., test compound) can be determined to be therapeutic by screening using the screening methods of the present invention.

As used herein, the term "effective amount" refers to the amount of a compound (e.g., a compound having a structure presented above or elsewhere described herein) sufficient to effect beneficial or desired results. An effective amount can be administered in one or more administrations, applications or dosages and is not limited to or intended to be limited to a particular formulation or administration route.

As used herein, the term "co-administration" refers to the administration of at least two agent(s) (e.g., a compound having a structure presented above or elsewhere described herein) or therapies to a subject. In some embodiments, the co-administration of two or more agents/therapies is concurrent. In other embodiments, a first agent/therapy is administered prior to a second agent/therapy. Those of skill in the art understand that the formulations and/or routes of administration of the various agents/therapies used may vary. The appropriate dosage for co-administration can be readily determined by one skilled in the art. In some embodiments, when agents/therapies are co-administered, the respective agents/therapies are administered at lower dosages than appropriate for their administration alone. Thus, co-administration is especially desirable in embodiments where the co-administration of the agents/therapies lowers the requisite dosage of a known potentially harmful (e.g., toxic) agent(s).

As used herein, the term "pharmaceutical composition" refers to the combination of an active agent with a carrier, inert or active, making the composition especially suitable for diagnostic or therapeutic use in vivo, in vivo or ex vivo.

As used herein, the term "pharmaceutically acceptable carrier" refers to any of the standard pharmaceutical carriers, such as a phosphate buffered saline solution, water, emulsions (e.g., such as an oil/water or water/oil emulsions), and various types of wetting agents. The compositions also can include stabilizers and preservatives. For examples of carriers, stabilizers and adjuvants. (See e.g., Martin, Remington's Pharmaceutical Sciences, 15th Ed., Mack Publ. Co., Easton, Pa. [1975]).

As used herein, the term "pharmaceutically acceptable salt" refers to any pharmaceutically acceptable salt (e.g., acid or base) of a compound of the present invention which, upon administration to a subject, is capable of providing a compound of this invention or an active metabolite or residue thereof. As is known to those of skill in the art, "salts" of the compounds of the present invention may be derived from inorganic or organic acids and bases. Examples of acids include, but are not limited to, hydrochloric, hydrobromic, sulfuric, nitric, perchloric, fumaric, maleic, phosphoric, glycolic, lactic, salicylic, succinic, toluene-p-sulfonic, tartaric, acetic, citric, methanesulfonic, ethanesulfonic, formic, benzoic, malonic, naphthalene-2-sulfonic, benzenesulfonic acid, and the like. Other acids, such as oxalic, while not in themselves pharmaceutically acceptable, may be employed in the preparation of salts useful as intermediates in obtaining the compounds of the invention and their pharmaceutically acceptable acid addition salts.

Examples of bases include, but are not limited to, alkali metals (e.g., sodium) hydroxides, alkaline earth metals (e.g., magnesium), hydroxides, ammonia, and compounds of formula $NW_4^+$, wherein W is $C_{1-4}$ alkyl, and the like.

Examples of salts include, but are not limited to: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, flucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, palmoate, pectinate, persulfate, phenylpropionate, picrate, pivalate, propionate, succinate, tartrate, thiocyanate, tosylate, undecanoate, and the like.

Other examples of salts include anions of the compounds of the present invention compounded with a suitable cation such as $Na^+$, $NH_4^+$, and $NW_4^+$ (wherein W is a $C_{1-4}$ alkyl group), and the like.

For therapeutic use, salts of the compounds of the present invention are contemplated as being pharmaceutically acceptable. However, salts of acids and bases that are non-pharmaceutically acceptable may also find use, for example, in the preparation or purification of a pharmaceutically acceptable compound.

As used herein, the term "instructions for administering said compound to a subject," and grammatical equivalents thereof, includes instructions for using the compositions contained in a kit for the treatment of conditions (e.g., providing dosing, route of administration, decision trees for treating physicians for correlating patient-specific characteristics with therapeutic courses of action).

As used herein, the term "alkyl" refers to a moiety consisting of carbon and hydrogen containing no double or triple bonds. An alkyl may be linear, branched, cyclic, or a combination thereof, and may contain from one to fifty carbon atoms, such as straight chain or branched $C^1$-$C^{20}$ alkane. Examples of alkyl groups include but are not limited to methyl, ethyl, propyl, isopropyl, cyclopropyl, butyl isomers (e.g. n-butyl, iso-butyl, tert-butyl, etc.) cyclobutyl isomers (e.g. cyclobutyl, methylcyclopropyl, etc.), pentyl isomers, cyclopentane isomers, hexyl isomers, cyclohexane isomers, and the like. Unless specified otherwise (e.g., substituted alkyl group, heteroalkyl, alkoxy group, haloalkyl, alkylamine, thioalkyl, etc.), an alkyl group contains carbon and hydrogen atoms only.

As used herein, "alkylene" or "alkylene chain" refers to a straight or branched divalent hydrocarbon chain linking the rest of the molecule to a radical group, consisting solely of carbon and hydrogen, containing no unsaturation, and preferably having from one to twelve carbon atoms, for example, methylene, ethylene, propylene, n-butylene, and the like. The alkylene chain is attached to the rest of the molecule through a single bond and to the radical group through a single bond. The points of attachment of the alkylene chain to the rest of the molecule and to the radical group may be through any two carbons within the chain. In certain embodiments, an alkylene comprises one to ten carbon atoms (i.e., $C_1$-$C_{10}$ alkylene). In certain embodiments, an alkylene comprises one to eight carbon atoms (i.e., $C_1$-$C_8$ alkylene). In other embodiments, an alkylene comprises one to five carbon atoms (i.e., $C_1$-$C_5$ alkylene). In other embodiments, an alkylene comprises one to four carbon atoms (i.e., $C_1$-$C_4$ alkylene). In other embodiments, an alkylene comprises one to three carbon atoms (i.e., $C_1$-$C_3$ alkylene). In other embodiments, an alkylene comprises one to two carbon atoms (i.e., $C_1$-$C_2$ alkylene). In other embodiments, an alkylene comprises one carbon atom (i.e., $C_1$ alkylene). Unless stated otherwise specifically in the specification, an alkylene chain is optionally substituted by one or more substituents such as those substituents described herein.

As used herein, the term "alkenyl" refers to a straight or branched hydrocarbon chain radical group consisting solely of carbon and hydrogen atoms, containing at least one carbon-carbon double bond, and preferably having from two to twelve carbon atoms (i.e., $C_2$-$C_{12}$ alkenyl). In certain embodiments, an alkenyl comprises two to eight carbon atoms (i.e., $C_2$-$C_8$ alkenyl). In certain embodiments, an alkenyl comprises two to six carbon atoms (i.e., $C_2$-$C_6$ alkenyl). In other embodiments, an alkenyl comprises two to four carbon atoms (i.e., $C_2$-$C_4$ alkenyl). The alkenyl is attached to the rest of the molecule by a single bond, for example, ethenyl (i.e., vinyl), prop-1-enyl (i.e., allyl), but-1-enyl, pent-1-enyl, penta-1,4-dienyl, and the like. Unless stated otherwise specifically in the specification, an alkenyl group is optionally substituted by one or more substituents such as those substituents described herein.

As used herein, "alkenylene" or "alkenylene chain" refers to a straight or branched divalent hydrocarbon chain linking the rest of the molecule to a radical group, consisting solely of carbon and hydrogen, containing at least one carbon-carbon double bond, and preferably having from two to twelve carbon atoms. The alkenylene chain is attached to the rest of the molecule through a single bond and to the radical group through a single bond. The points of attachment of the alkenylene chain to the rest of the molecule and to the radical group may be through any two carbons within the chain. In certain embodiments, an alkenylene comprises two to ten carbon atoms (i.e., $C_2$-$C_{10}$ alkenylene). In certain embodiments, an alkenylene comprises two to eight carbon atoms (i.e., $C_2$-$C_8$ alkenylene). In other embodiments, an alkenylene comprises two to five carbon atoms (i.e., $C_2$-$C_5$ alkenylene). In other embodiments, an alkenylene comprises two to four carbon atoms (i.e., $C_2$-$C_4$ alkenylene). In other embodiments, an alkenylene comprises two to three carbon atoms (i.e., $C_2$-$C_3$ alkenylene). In other embodiments, an alkenylene comprises two carbon atom (i.e., $C_2$ alkenylene). Unless stated otherwise specifically in the specification, an alkenylene chain is optionally substituted by one or more substituents such as those substituents described herein.

As used herein, the term "alkynyl" refers to a straight or branched hydrocarbon chain radical group consisting solely of carbon and hydrogen atoms, containing at least one carbon-carbon triple bond, and preferably having from two to twelve carbon atoms (i.e., $C_2$-$C_{12}$ alkynyl). In certain embodiments, an alkynyl comprises two to eight carbon atoms (i.e., $C_2$-$C_8$ alkynyl). In other embodiments, an alkynyl comprises two to six carbon atoms (i.e., $C_2$-$C_6$ alkynyl). In other embodiments, an alkynyl comprises two to four carbon atoms (i.e., $C_2$-$C_4$ alkynyl). The alkynyl is attached to the rest of the molecule by a single bond, for example, ethynyl, propynyl, butynyl, pentynyl, hexynyl, and the like. Unless stated otherwise specifically in the specification, an alkynyl group is optionally substituted by one or more substituents such as those substituents described herein.

As used herein "alkynylene" or "alkynylene chain" refers to a straight or branched divalent hydrocarbon chain linking the rest of the molecule to a radical group, consisting solely of carbon and hydrogen, containing at least one carbon-carbon triple bond, and preferably having from two to twelve carbon atoms. The alkynylene chain is attached to the rest of the molecule through a single bond and to the radical group through a single bond. The points of attachment of the alkynylene chain to the rest of the molecule and to the radical group may be through any two carbons within the chain. In certain embodiments, an alkynylene comprises two to ten carbon atoms (i.e., $C_2$-$C_{10}$ alkynylene). In certain embodiments, an alkynylene comprises two to eight carbon atoms (i.e., $C_2$-$C_8$ alkynylene). In other embodiments, an alkynylene comprises two to five carbon atoms (i.e., $C_2$-$C_5$ alkynylene). In other embodiments, an alkynylene comprises two to four carbon atoms (i.e., $C_2$-$C_4$ alkynylene). In other embodiments, an alkynylene comprises two to three carbon atoms (i.e., $C_2$-$C_3$ alkynylene). In other embodiments, an alkynylene comprises two carbon atom (i.e., $C_2$ alkynylene). Unless stated otherwise specifically in the specification, an alkynylene chain is optionally substituted by one or more substituents such as those substituents described herein.

As used herein, the term "amine" or "amino" includes primary, secondary, and tertiary amines wherein each non-hydrogen group on nitrogen may be selected from alkyl, aryl, and the like. Amines include but are not limited to —$NH_2$, —NH-phenyl, —NH—$CH_3$, —NH—$CH_2CH_3$, and —N($CH_3$)benzyl.

The term "amide" or "amido" includes C- and N-amide groups, i.e., —C(O)$NR_2$, and —NRC(O)R groups, respectively, where R can be H, alkyl, aryl, etc. Amide groups therefore include but are not limited to —C(O)$NH_2$, —NHC(O)H, —C(O)NH$CH_2CH_3$, —NHC(O)$CH_3$, —C(O)N($CH_2CH_3$)phenyl.

As used herein, the term "linear alkyl" refers to a chain of carbon and hydrogen atoms (e.g., ethane, propane, butane, pentane, hexane, etc.). A linear alkyl group may be referred to by the designation —$(CH_2)_qCH_3$, where q is 0-49. The designation "$C_{1-12}$ alkyl" or a similar designation, refers to alkyl having from 1 to 12 carbon atoms such as methyl, ethyl, propyl isomers (e.g. n-propyl, isopropyl, etc.), butyl isomers, cyclobutyl isomers (e.g. cyclobutyl, methylcyclopropyl, etc.), pentyl isomers, cyclopentyl isomers, hexyl isomers, cyclohexyl isomer, heptyl isomers, cycloheptyl isomers, octyl isomers, cyclooctyl isomers, nonyl isomers, cyclononyl isomers, decyl isomer, cyclodecyl isomers, etc. Similar designations refer to alkyl with a number of carbon atoms in a different range.

The term "$C_{x-y}$," when used in conjunction with a chemical moiety, such as alkyl, alkenyl, alkynyl, or carbocycle is meant to include groups that contain from x to y carbons in the chain or ring. For example, the term "$C_{x-y}$alkyl" refers to substituted or unsubstituted saturated hydrocarbon groups, including straight-chain alkyl and branched-chain alkyl groups that contain from x to y carbons in the chain, including haloalkyl groups such as trifluoromethyl and 2,2,2-trifluoroethyl, etc. The terms "$C_{x-y}$alkenyl" and "$C_{x-y}$alkynyl" refer to substituted or unsubstituted unsaturated aliphatic groups analogous in length and possible substitution to the alkyls described above, but that contain at least one double or triple bond respectively. The term "$C_{x-y}$ carbocycle" refers to a substituted or unsubstituted carbocycle, that contain from x to y ring carbons.

As used herein, the term "branched alkyl" refers to a chain of carbon and hydrogen atoms, without double or triple bonds, that contains a fork, branch, and/or split in the chain (e.g., 3,5-dimethyl-2-ethylhexane, 2-methyl-pentane, 1-methyl-cyclobutane, ortho-diethyl-cyclohexane, etc.). "Branching" refers to the divergence of a carbon chain, whereas "substitution" refers to the presence of non-carbon/non-hydrogen atoms in a moiety. Unless specified otherwise (e.g., substituted branched alkyl group, branched heteroalkyl, branched alkoxy group, branched haloalkyl, branched alkylamine, branched thioalkyl, etc.), a branched alkyl group contains carbon and hydrogen atoms only.

As used herein, the term "carbocycle" refers to a saturated, unsaturated, or aromatic ring in which each atom of the ring is carbon. Carbocycle includes monocyclic, bicyclic and polycyclic rings, wherein bicyclic or polycyclic rings may include fused, or spiro rings. Carbocycle may include 3- to 10-membered monocyclic rings, 6- to 12-membered bicyclic rings, and 6- to 12-membered bridged rings. Each ring of a bicyclic or polycyclic carbocycle may be selected from saturated, unsaturated, and aromatic rings. In an exemplary embodiment, an aromatic carbocycle, e.g., phenyl, is fused to a saturated or unsaturated ring, e.g., cyclohexane, cyclopentane, or cyclohexene. In some embodiments, the carbocycle is an aromatic carbocycle. In some embodiments, the carbocycle is a cycloalkyl. In some embodiments, the carbocycle is a cycloalkenyl. Exemplary carbocycles include cyclopentyl, cyclohexyl, cyclohexenyl, adamantyl, phenyl, indanyl, and naphthyl. Unless stated otherwise specifically in the specification, a carbocycle is optionally substituted by one or more substituents, such as those substituents described herein.

As used herein, the term "cycloalkyl" refers to a completely saturated mono- or multi-cyclic hydrocarbon ring system. When composed of two or more rings, the rings may be joined together in a fused, bridged or spiro-connected fashion. Cycloalkyl groups of the present application may range from three to ten carbons ($C_3$ to $C_{10}$). A cycloalkyl group may be unsubstituted, substituted, branched, and/or unbranched. Typical cycloalkyl groups include, but are not limited to, cyclopropyl, cyclobutyl, cyclopentyl, cyclohexyl, and the like. If substituted, the substituent(s) may be an alkyl or selected from those indicated above with regard to substitution of an alkyl group unless otherwise indicated. Unless specified otherwise (e.g., substituted cycloalkyl group, heterocyclyl, cycloalkoxy group, halocycloalkyl, cycloalkylamine, thiocycloalkyl, etc.), an alkyl group contains carbon and hydrogen atoms only.

As used herein, the term "cycloalkenyl" refers to a stable unsaturated non-aromatic monocyclic, bicyclic or polycyclic hydrocarbon radical consisting solely of carbon and hydrogen atoms, which includes fused or bridged ring systems, preferably having from three to twelve carbon atoms and comprising at least one double bond. In certain embodiments, a cycloalkenyl comprises three to ten carbon atoms. In other embodiments, a cycloalkenyl comprises five to seven carbon atoms. The cycloalkenyl may be attached to the rest of the molecule by a single bond. Examples of monocyclic cycloalkenyls include, e.g., cyclopentenyl, cyclohexenyl, cycloheptenyl, and cyclooctenyl. Unless otherwise stated specifically in the specification, the term "cycloalkenyl" is meant to include cycloalkenyl radicals that are optionally substituted by one or more substituents such as those substituents described herein.

As used herein, the term "heteroalkyl" refers to an alkyl group, as defined herein, wherein one or more carbon atoms are independently replaced by one or more heteroatoms (e.g., oxygen, sulfur, nitrogen, phosphorus, silicon, or combinations thereof). The alkyl group containing the non-carbon substitution(s) may be a linear alkyl, branched alkyl, cycloalkyl (e.g., cycloheteroalkyl), or combinations thereof. Non-carbons may be at terminal locations (e.g., 2-hexanol) or integral to an alkyl group (e.g., diethyl ether). Unless stated otherwise specifically in the specification, the heteroalkyl group may be optionally substituted as described herein.

Representative heteroalkyl groups include, but are not limited to —$OCH_2OMe$, —$OCH_2CH_2OMe$, or —$OCH_2CH_2OCH_2CH_2NH_2$.

As used herein, the term "heteroalkylene" refers to an alkyl radical as described above where one or more carbon atoms of the alkyl is replaced with a heteroatom, e.g., O, N or S. "Heteroalkylene" or "heteroalkylene chain" refers to a straight or branched divalent heteroalkyl chain linking the rest of the molecule to a radical group. Unless stated otherwise specifically in the specification, the heteroalkylene group may be optionally substituted as described herein. Representative heteroalkylene groups include, but are not limited to —$OCH_2CH_2O$—, —$OCH_2CH_2OCH_2CH_2O$—, or —$OCH_2CH_2OCH_2CH_2OCH_2CH_2O$—.

The term "substituted" refers to moieties having substituents replacing a hydrogen on one or more carbons or substitutable heteroatoms, e.g., NH, of the structure. It will be understood that "substitution" or "substituted with" includes the implicit proviso that such substitution is in accordance with permitted valence of the substituted atom and the substituent, and that the substitution results in a stable compound, i.e., a compound which does not spontaneously undergo transformation such as by rearrangement, cyclization, elimination, etc. In some embodiments, substituted refers the replacing hydrogens on adjacent carbons (or heteroatoms) with a double (or triple) bond between the adjacent carbons (or heteroatoms). For example, a "substituted alkyl" encompasses alkynes and alkenes, in addition to alkanes displaying substituent moieties. In certain embodiments, substituted refers to moieties having substituents replacing two hydrogen atoms on the same carbon atom, such as substituting the two hydrogen atoms on a single carbon with an oxo, imino or thioxo group. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of this disclosure, the heteroatoms such as nitrogen may have hydrogen substituents and/or any permissible substituents of organic compounds described herein which satisfy the valences of the heteroatoms.

The term "optionally substituted", as used herein, means that the referenced group (e.g., alkyl, cycloalkyl, etc.) may or may not be substituted with one or more additional group(s). Non-limiting examples of substituents include, for example: halogen, hydroxy, oxo (=O), thioxo (=S), cyano (—CN), nitro (—$NO_2$), imino (=N—H), oximo (=N—OH), hydrazino (=N—$NH_2$), —$R^b$—$OR^a$, —$R^b$—OC(O)-$R^a$, —$R^b$—OC(O)—$OR^a$, —$R^b$—OC(O)—N($R^a$)$_2$, —$R^b$—N($R^a$)$_2$, —$R^b$—C(O)$R^a$, —$R^b$—C(O)$OR^a$, —$R^b$—C(O)N($R^a$)$_2$, —$R^b$—O—$R^c$—C(O)N($R^a$)$_2$, —$R^b$—N($R^a$)C(O)$OR^a$, —$R^b$—N($R^a$)C(O)$R^a$, —$R^b$—N($R^a$)S(O)$_t$$R^a$ (where t is 1 or 2), —$R^b$—S(O)$_t$$R^a$ (where t is 1 or 2), —$R^b$—S(O)$_t$$OR^a$ (where t is 1 or 2), and —$R^b$—S(O)$_t$N($R^a$)$_2$ (where t is 1 or 2); and alkyl, alkenyl, alkynyl, each of which may be optionally substituted by halogen, oxo (=O), thioxo (=S), cyano (—CN), nitro (—$NO_2$), imino (=N—H), oximo (=N—OH), hydrazine (=N—$NH_2$), —$R^b$—$OR^a$, —$R^b$—OC(O)—$R^a$, —$R^b$—OC(O)—$OR^a$, —$R^b$—OC(O)—N($R^a$)$_2$, —$R^b$—N($R^a$)$_2$, —$R^b$—C(O)$R^a$, —$R^b$—C(O)$OR^a$, —$R^b$—C(O)N($R^a$)$_2$, —$R^b$—O—$R^c$—C(O)N($R^a$)$_2$, —$R^b$—N($R^a$)C(O)$OR^a$, —$R^b$—N($R^a$)C(O)$R^a$, —$R^b$—N($R^a$)S(O)$_t$$R^a$ (where t is 1 or 2), —$R^b$—S(O)$_t$$R^a$ (where t is 1 or 2), —$R^b$—S(O)$_t$$OR^a$ (where t is 1 or 2), —$R^b$—S(O)$_t$N($R^a$)$_2$ (where t is 1 or 2), carbocycle and heterocycle; wherein each $R^a$ is independently selected from hydrogen, alkyl, alkenyl, alkynyl, carbocycle and heterocycle, wherein each $R^a$, valence permitting, may be optionally substituted with halogen, oxo (=O), thioxo (=S), cyano (—CN), nitro (—$NO_2$), imino (=N—H), oximo (=N—OH), hydrazine (=N—$NH_2$), —$R^b$—$OR^a$, —$R^b$—OC(O)—$R^a$, —$R^b$—OC(O)—$OR^a$, —$R^b$—OC(O)—N($R^a$)$_2$, —$R^b$—N($R^a$)$_2$, —$R^b$—C(O)$R^a$, —$R^b$—C(O)$OR^a$, —$R^b$—C(O)N($R^a$)$_2$, —$R^b$—O—$R^c$—C(O)N($R^a$)$_2$, —$R^b$—N($R^a$)C(O)$OR^a$, —$R^b$—N($R^a$)C(O)$R^a$, —$R^b$—N($R^a$)S(O)$_t$$R^a$ (where t is 1 or 2), —$R^b$—S(O)$_t$$R^a$ (where t is 1 or 2), —$R^b$—S(O)$_t$$OR^a$ (where t is 1 or 2) and —$R^b$—S(O)$_t$N($R^a$)$_2$ (where t is 1 or 2); and wherein each $R^b$ is independently selected from a direct bond or a straight or branched alkylene, alkenylene, or alkynylene chain, and each $R^c$ is a straight or branched alkylene, alkenylene or alkynylene chain. Substituent groups may be selected from, but are not limited to: alkyl, alkenyl, alkynyl, cycloalkyl, aryl, heteroaryl, heterocycloalkyl, hydroxyl, alkoxy, mercaptyl, cyano, halo, carbonyl, thiocarbonyl, isocyanato, thiocyanato, isothiocyanato, nitro, perhaloalkyl, perfluoroalkyl, and amino, including mono- and di-substituted amino groups, and the protected derivatives thereof.

As used herein, the term "haloalkyl" or "haloalkane" refers to an alkyl radical, as defined above, that is substituted by one or more halogen radicals, for example, trifluoromethyl, dichloromethyl, bromomethyl, 2,2,2-trifluoroethyl, 1-fluoromethyl-2-fluoroethyl, and the like. In some embodiments, the alkyl part of the fluoroalkyl radical is optionally further substituted. Examples of halogen substituted alkanes ("haloalkanes") include halomethane (e.g., chloromethane, bromomethane, fluoromethane, iodomethane), di- and trihalomethane (e.g., trichloromethane, tribromomethane, trifluoromethane, triiodomethane), 1-haloethane, 2-haloethane, 1,2-dihaloethane, 1-halopropane, 2-halopropane, 3-halopropane, 1,2-dihalopropane, 1,3-dihalopropane, 2,3-dihalopropane, 1,2,3-trihalopropane, and any other suitable combinations of alkanes (or substituted alkanes) and halogens (e.g., Cl, Br, F, I, etc.). When an alkyl group is substituted with more than one halogen radicals, each halogen may be independently selected e.g., 1-chloro,2-fluoroethane.

As used herein, the terms "aromatic ring" or "aryl" refer to aromatic carbocycles and aromatic heterocycles. Exemplary atomatic rings include furan, benzofuran, isobenzofuran, pyrrole, indole, isoindole, thiophene, benzothiophene, benzo[c]thiophene, imidazole, benzimidazole, purine, pyrazole, indazole, oxazole, benzooxazole, isoxazole, benzisoxazole, thiazole, benzothiazole, benzene, napthalene, pyridine, quinolone, isoquinoline, pyrazine, quinoxaline, pyrimidine, quinazoline, pyridazine, cinnoline, phthalazine, triazine (e.g., 1,2,3-triazine; 1,2,4-triazine; 1,3,5 triazine), and thiadiazole.

As used herein, the terms "heteroaryl" or "heteroaromatic" refer to monocyclic, bicyclic, or polycyclic ring systems, wherein at least one ring in the system is aromatic and contains at least one heteroatom, for example, nitrogen, oxygen and sulfur. Each ring of the heteroaromatic ring systems may contain 3 to 7 ring atoms. Exemplary heteroaromatic monocyclic ring systems include 5- to 7-membered rings whose ring structures include one to four heteroatoms, for example, one or two heteroatoms. Heteroaryl groups include, for example, pyrrole, furan, thiophene, imidazole, oxazole, thiazole, pyrazole, pyridine, pyrazine, pyridazine, and pyrimidine, and the like.

Unless otherwise defined herein, suitable substituents on a heteroaryl group are generally selected from halogen; —R, —OR, —SR, —NO$_2$, —CN, —N(R)$_2$, —NRC(O)R, —NRC(S)R, —NRC(O)N(R)$_2$, —NRC(S)N(R)$_2$, —NRCO$_2$R, —NRNRC(O)R, —NRNRC(O)N(R)$_2$, —NRNRCO$_2$R, —C(O)C(O)R, —C(O)CH$_2$C(O)R, —CO$_2$R, —C(S)R, —C(O)N(R)$_2$, —C(S)N(R)$_2$, —OC(O)N(R)$_2$, —OC(O)R, —C(O)N(OR)R, —C(NOR)R, —S(O)$_2$R, —S(O)$_3$R, —SO$_2$N(R)$_2$, —S(O)R, —NRSO$_2$N(R)$_2$, —NRSO$_2$R, —N(OR)R, —C(=NH)—N(R)$_2$, —P(O)$_2$R, —PO(R)$_2$, —OPO(R)$_2$, —(CH$_2$)O$_2$NHC(O)R, phenyl (Ph) optionally substituted with R, —O(Ph) optionally substituted with R, —(CH$_2$)1-2(Ph), optionally substituted with R, or —CH=CH(Ph), optionally substituted with R, wherein each independent occurrence of R is selected from hydrogen, optionally substituted C$_1$-C$_6$ alkyl, optionally substituted C$_1$-C$_6$ alkoxy, an unsubstituted 5-6 membered heteroaryl, phenyl, —O(Ph), or —CH$_2$(Ph), or two independent occurrences of R, on the same substituent or different substituents, taken together with the atom(s) to which each R is bound, to form an optionally substituted 3-12 membered saturated, partially unsaturated, or fully unsaturated monocyclic or bicyclic ring having 0-4 heteroatoms independently selected from nitrogen, oxygen, or sulfur. Non-limiting examples of heteroaryl groups, as used herein, include benzofuranyl, benzofurazanyl, benzoxazolyl, benzopyranyl, benzthiazolyl, benzothienyl, benzazepinyl, benzimidazolyl, benzothiopyranyl, benzo[1,3]dioxole, benzo[b]furyl, benzo[b]thienyl, cinnolinyl, furazanyl, furyl, furopyridinyl, imidazolyl, indolyl, indolizinyl, indolin-2-one, indazolyl, isoindolyl, isoquinolinyl, isoxazolyl, isothiazolyl, 1,8-naphthyridinyl, oxazolyl, oxaindolyl, oxadiazolyl, pyrazolyl, pyrrolyl, phthalazinyl, pteridinyl, purinyl, pyridyl, pyridazinyl, pyrazinyl, pyrimidinyl, quinoxalinyl, quinolinyl, quinazolinyl, 4H-quinolizinyl, thiazolyl, thiadiazolyl, thienyl, triazinyl, triazolyl and tetrazolyl. Any substituents depicted in structures or examples herein, should be viewed as suitable substituents for use in embodiments of the present invention.

As used herein, the term "heterocycle" refers to a saturated, unsaturated or aromatic ring comprising one or more heteroatoms. Exemplary heteroatoms include N, O, Si, P, B, and S atoms. Heterocycles include monocyclic, bicylic or polycyclic rings, wherein bicyclic or polycyclic rings may include fused, or spiro rings. For bicyclic and polycyclic rings, at least one ring of the bicyclic or polycyclic ring comprises one or more heteroatoms. Heterocycles may include 3- to 10-membered monocyclic rings, 6- to 12-membered bicyclic rings, and 6- to 12-membered bridged rings. Each ring of a bicyclic or polycyclic heterocycle may be selected from saturated, unsaturated, and aromatic rings, as valence permits. In an exemplary embodiment, a heterocycle, e.g., pyridyl, may be fused to a saturated or unsaturated ring, e.g., cyclohexane, cyclopentane, or cyclohexene. In some embodiments, heterocyclic is selected from heteroaryl, heterocycloalkyl and heterocycloalkenyl.

As used herein, the term "non-aromatic heterocycle" refers to a cycloalkyl or cycloalkenyl, as defined herein, wherein one or more of the ring carbons are replaced by a moiety selected from —O—, —N=, —NR—, —C(O)—, —S—, —S(O)— or —S(O)$_2$—, wherein R is hydrogen, C$_1$-C$_8$ alkyl or a nitrogen protecting group, with the proviso that the ring of said group does not contain two adjacent O or S atoms. Non-limiting examples of non-aromatic heterocycles, as used herein, include morpholino, pyrrolidinyl, pyrrolidinyl-2-one, piperazinyl, piperidinyl, piperidinylone, 1,4-dioxa-8-aza-spiro[4.5]dec-8-yl, 2H-pyrrolyl, 2-pyrrolinyl, 3-pyrrolinyl, 1,3-dioxolanyl, 2-imidazolinyl, imidazolidinyl, 2-pyrazolinyl, pyrazolidinyl, 1,4-dioxanyl, 1,4-dithianyl, thiomorpholinyl, azepanyl, hexahydro-1,4-diazepinyl, tetrahydrofuranyl, dihydrofuranyl, tetrahydrothienyl, tetrahydropyranyl, dihydropyranyl, tetrahydrothiopyranyl, thioxanyl, azetidinyl, oxetanyl, thietanyl, oxepanyl, thiepanyl, 1,2,3,6-tetrahydropyridinyl, 2H-pyranyl, 4H-pyranyl, dioxanyl, 1,3-dioxolanyl, dithianyl, dithiolanyl, dihydropyranyl, dihydrothienyl, dihydrofuranyl, imidazolinyl, imidazolidinyl, 3-azabicyclo[3.1.0]hexanyl, and 3-azabicyclo[4.1.0]heptanyl, 3,8-diazabicyclo[3.2.1]octanyl, and 2,5-diazabicyclo[2.2.1]heptanyl. In certain embodiments, a non-aromatic heterocyclic ring is aziridine, thiirane, oxirane, oxaziridine, dioxirane, azetidine, oxetan, thietane, diazetidine, dioxetane, dithietane, pyrrolidine, tetrahydrofuran, thiolane, imidazolidine, pyrazolidine, oxazolidine, isoxazolidine, thiazolidine, isothiazolidine, dioxolane, dithiolane, piperdine, oxane, thiane, piperazine, morpholine, thiomorpholine, dioxane, dithiane, trioxane, thithiane, azepane, oxepane, thiepane, homopiperazine, or azocane.

DETAILED DESCRIPTION

Provided herein are amlexanox analogs and methods for the treatment and/or prevention of diabetes, impaired insulin signaling, obesity, or other related diseases and conditions therewith.

I. General

In some embodiments, the amlexanox analogs described herein are compounds bearing structural similarity to amlexanox:

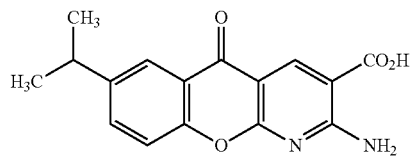 [SMILES: CC(C)c1ccc2oc3nc(N)c(C(=O)O)cc3c(=O)c2c1]

but having one or more substituted functional groups or additional substituents. In some embodiments, an amlexanox analog exhibits one or more similar activities to amlexanox (e.g., IKKi inhibition, TBK1 inhibition, etc.), although not necessarily to the same degree (e.g., decreased or increased (e.g., 1.1-fold, 1.2-fold, 1.5-fold, 2-fold, 3-fold, 4-fold, 5-fold, 10-fold, 20-fold, 50-fold, 100-fold, 200-fold, 500-fold, $10^2$-fold, $10^4$-fold, $10^5$-fold, $10^6$-fold)). As used herein, the term "amlexanox analog" refers to a compound defined by the structures and substituents provided herein. In some embodiments, compounds herein are amlexanox analogs, but are not amlexanox.

In some embodiments, provided herein are compounds that inhibit: (i) TANK-binding kinase 1 (TBK1) and/or (ii) inhibitor of nuclear factor kappa-B kinase subunit epsilon (IKKi, IKK-ε, IKBKE), resulting in, for example: weight loss, improved insulin sensitivity, reduced inflammation, attenuated hepatic steatosis, etc. However, the compounds are not limited to such indications. For example, the compounds of the disclosure may be used in methods for the treatment of a wide variety of cancers, inflammatory conditions (e.g., causing inflammation or resulting from inflammation), and other diseases (e.g., associated with TBK1 and/or IKKi).

II. Amlexanox Analogs

In certain embodiments, provided herein are compounds represented by a structure of Formula (I): <<<

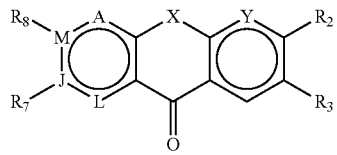

wherein J, M, A, X, Y, R2, R3, R7, and R8 are any of the various atoms or groups depicted in the Compounds described herein (e.g., Compounds 1-299), in any suitable combinations (e.g., $R_3$ from Compound 290 and $R_7$ from compound 297). In some embodiments, J, M, A, X, Y, R2, R3, R7, and R8 are any of the various atoms or groups described herein.

In some embodiments, $R_2$ of Formula (I) is selected from: $CH_3$, $NH_2$, $NHCH_3$, OH, $NH(CH_2)_2OH$, $NH(CH_2)_3OH$, amidino, F, Br, and Cl, and other suitable bioisosters of $NH_2$.

In some embodiments, $R_2$ of Formula (I) is selected from: cycloalkyl, heterocycle, aryl, heteroaryl, NH—$(CH_2)_m$-cycloalkyl, NH—$(CH_2)_m$-heterocycle (e.g., $R_2$ of compound 147), NH—$(CH_2)_m$-aryl, and NH—$(CH_2)_m$-heteroaryl; wherein m is 0-6 (e.g., 0, 1, 2, 3, 4, 5, 6, or any ranges therebetween). In some embodiments, cycloalkyl, heterocycle, aryl, and/or heteroaryl ring groups may be further substituted (e.g., $R_2$ of compound 148), for example, with an alkyl group (e.g., methyl, ethyl, propyl, etc.), an alcohol (e.g., OH, $CH_2OH$, $(CH_2)_2OH$, etc.), amine (e.g., $NH_2$, $CH_2NH_2$, $(CH_2)_2NH_2$, etc.), CN, halogen, etc.

In some embodiments, $R_3$ of a Formula (I) is selected from: a carboxylic acid (e.g., C(O)OH), carboximide (C(O)NHCH_3), an alcohol (e.g., OH, $CH_2OH$, $(CH_2)_2OH$, etc.), an ether an amine (e.g., $NH_2$, $CH_2NH_2$, $(CH_2)_2NH_2$, $(CH_2)_2N(CH_2)_2(CH_2)_2$, (e.g., compound 283), etc.), an ester (e.g., $CO_2CH_3$, $CO_2Et$, etc.), a hydroxamic acid (e.g., C(O)N(OH)H), a phosphoric acid (e.g., $P(O)(OH)_2$), a phosphinic acid (e.g., P(O)(OH)H), a sulphonic acid (e.g., S(O)(O)OH), a sulfonamide (e.g., $S(O)(O)NH_2$), an acylsulfonamide (e.g., C(O)NHS(O)(O)H), C(O)NHS(O)(O)CH_3), C(O)NHS(O)(O)NH_2), a sulfonylurea (e.g., NHC(O)NHS(O)(O)CH_3), a tetrazole, a thiazolidinedione, an oxazolidinedione, 5-oxo-1,2,4-oxadiazole, 5-oxo-1,2,4-thiadiazole, 5-thioxo-1,2,4-thiadiazole, an isothiazole, an isoxazole, a difluorophenol, tetramic acid, tetronic acid, cyclopentane-1,3-dione, a squaric acid, an amide (e.g., C(O)NH-(alkyl) (e.g., C(O)NHCH_3, C(O)NHCH_2CH_3, etc.), C(O)NH-(cycloalkyl), C(O)NH-(alkyl-cycloalkyl) (e.g., C(O)NHCH_2(C_6H_{11}), C(O)NHCH_2(C_5H_9), C(O)NHCH_2CH_2(C_6H_{11}), C(O)NHCH_2CH_2(C_5H_9), etc.), C(O)NH-(heteroalkyl) (e.g., C(O)NHCH_2N(CH_2)_2, C(O)NHCH_2N(CH_2)_2, C(O)NHCH_2NHCH_2CH_3, C(O)NHCH_2NHCH_3, C(O)NHCH_2OCH_2CH_3, C(O)NHCH_2CH_2OCH_3, C(O)NHCH_2SCH_2CH_3, C(O)NHCH_2CH_2SCH_3, etc.), C(O)NH-(heterocycle), C(O)NH-(alkyl-heterocycle) (e.g., C(O)NHCH_2(C_5H_9O), C(O)NHCH_2CH_2(C_5H_9O), C(O)NHCH_2(C_5H_9S), C(O)NHCH_2CH_2(C_5H_9S), C(O)NHCH_2(C_5H_{10}N), C(O)NHCH_2CH_2(C_5H_{10}N), etc.), and other suitable bioisosteres of a carboxylic acid substituent.

In some embodiments, other suitable bioisosteres of a carboxylic acid substituent include, but are not limited to:

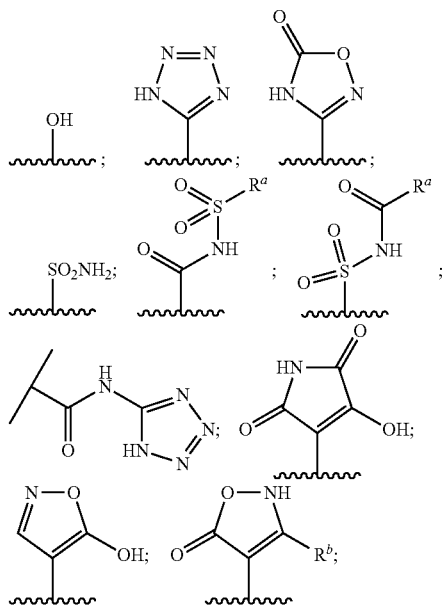

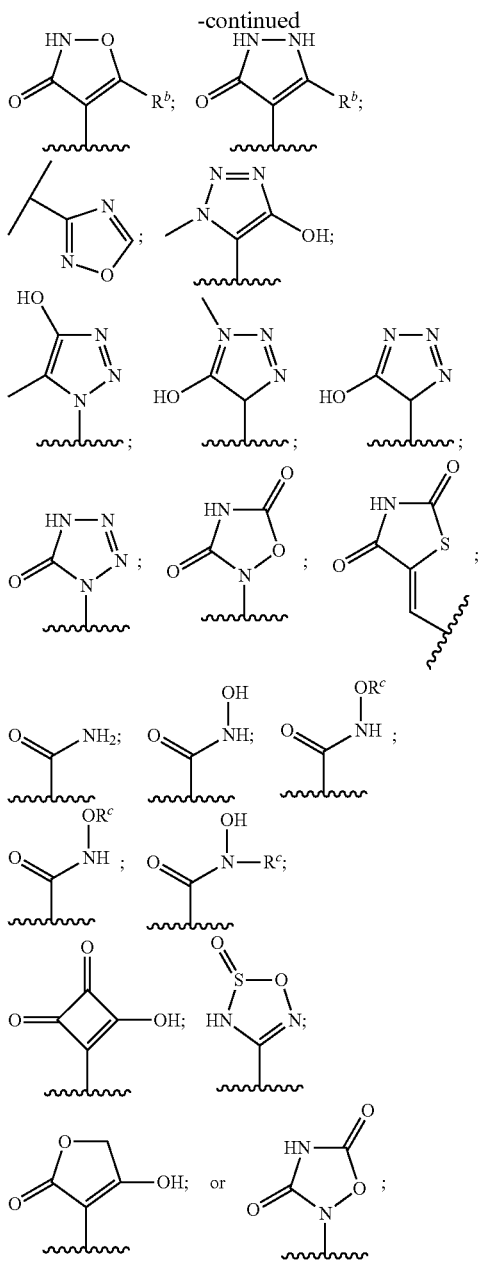

or other suitable 5-member heterocyclic rings, optionally substituted, for example, with =O and/or —OH substituents (e.g., Compound 289); wherein $R^a$, $R^b$ and $R^c$ are independently selected from —$CF_3$, —$CH_3$, phenyl, or benzyl, with the phenyl or benzyl groups being optionally substituted by from 1 to 3 groups selected from $C_6$ alkyl, alkoxy, $C_6$ thioalkyl, $CF_3$, halogen, —OH, or —COOH.

In some embodiments, $R_3$ of a Formula (I) is selected from: cycloalkyl, heterocycle (e.g., tetrazole), aryl, heteroaryl, NH—$(CH_2)_m$-cycloalkyl, NH—$(CH_2)_m$-heterocycle, NH—$(CH_2)_m$-aryl, and NH—$(CH_2)_m$-heteroaryl; wherein m is 0-6 (e.g., 0, 1, 2, 3, 4, 5, 6, or any ranges therebetween). In some embodiments, cycloalkyl, heterocycle (e.g., morpholine), aryl, and/or heteroaryl ring groups may be further substituted, for example, with an alkyl group (e.g., methyl, ethyl, propyl, etc.), an alcohol (e.g., OH, $CH_2OH$, $(CH_2)_2OH$, etc.), amine (e.g., $NH_2$, $CH_2NH_2$, $(CH_2)_2NH_2$, etc.), CN, halogen, etc.

In some embodiments, $R_7$ of Formula (I) is selected from: H, Br, Cl, F, I, D (deuterium), alkane (e.g., methyl, ethyl, propyl, isopropyl, butyl, etc.), haloalkane (e.g., monohaloalkane (e.g., $CH_2F$, $CH_2CH_2Cl$, $CHBrCH_3$, etc.), dihaloalkane (e.g., $CF_2H$, $CH_2CCl_2H$, etc.), trihaloalkane (e.g., $CBr_3$, $CF_3$, $CCl_3$, $CH_2CBr_3$, $CH_2CF_3$, $CH_2CCl_3$, etc.)), trihalomethyl-cycloalkyl (e.g., 1-(trifluoromethyl)cyclopropyl (e.g., $R_7$ of compound 84) 1-(trichloromethyl)cyclohexane, etc.), alkene (e.g. CH=$CH_2$, $R_7$ of Compound 299, etc.), alkyne (e.g. C≡CH, etc), amine (e.g., $NH_2$, NH-alkyl (e.g., NH-methyl, NH-ethyl, NH—$CH_2$-Ph, etc.), alkyl-amine (e.g., $(CH_2)_{1-6}$—$NH_2$), alkyl-amine-alkyl (e.g., $(CH_2)_{1-6}$—$NH_2$—$(CH_2)_{1-5}CH_3$, etc.), $(CH_2)_{1-6}$—$N(CH_3)_2$, alkene-$N(CH_3)_2$, alkyne-$N(CH_3)_2$, $N(CH_3)_2$, O-alkyl (e.g., $OCH_3$, $OCH_2CH_3$, etc.), NH-alcohol (e.g., NH—$CH_2$—$CH_2$—OH), etc.), hydroxy (e.g. —OH), an alcohol (e.g., $(CH_2)_{1-6}OH$, $CH_2CHOHCH_2OH$, etc.), cycloalkyl (e.g., cyclopropyl, cyclobutyl, cyclopentyl, cyclohexyl, cycloheptyl, etc.), alkyl-cycloalkyl (e.g., $(CH_2)_{1-6}$-cyclopropyl, $(CH_2)_{1-6}$-cyclobutyl, $(CH_2)_{1-6}$-cyclopentyl, $(CH_2)_{1-6}$-cyclohexyl, $(CH_2)_{1-6}$-cycloheptyl, etc.), alkene-cycloalkyl (e.g., $(CH)_2$-cyclopropyl, $(CH)_2$-cyclobutyl, $(CH)_2$-cyclopentyl, $(CH)_2$-cyclohexyl (e.g., compound 155), $(CH)_2$-cycloheptyl, etc.), cycloalkene (e.g., cyclopropenyl, cyclobutenyl, cyclopentenyl (e.g., $R_7$ of compound 153), cyclohexenyl (e.g., $R_7$ of compound 154), cycloheptenyl, etc.), alkyl-cycloalkenyl (e.g., $(CH_2)_{1-6}$-cyclopropenyl, $(CH_2)_{1-6}$-cyclobutenyl, $(CH_2)_{1-6}$-cyclopentenyl, $(CH_2)_{1-6}$-cyclohexenyl, $(CH_2)_{1-6}$-cycloheptenyl, etc.), alkene-cycloalkenyl (e.g., $(CH)_2$-cyclopropenyl, $(CH)_2$-cyclobutenyl, $(CH)_2$-cyclopentenyl, $(CH)_2$-cyclohexenyl, $(CH)_2$-cycloheptenyl, etc.), and $(CH_2)_{0-6}$-heterocycle (e.g., non-aromatic heterocycle (e.g., aziridine, thiirane, oxirane, oxaziridine, dioxirane, azetidine, oxetane, thietane, diazetidine, dioxetane, dithietane, pyrrolidine, tetrahydrofuran, thiolane, imidazolidine, pyrazolidine, oxazolidine, isoxazolidine, thiazolidine, isothiazolidine, dioxolane, dithiolane, piperdine, oxane, thiane, piperazine, morpholine, thiomorpholine, dioxane, dithiane, trioxane, thithiane, azepane, oxepane, thiepane, homopiperazine, azocane, etc.), heteroaryl (e.g., pyrrole, furan, thiophene, imidazole, oxazole, thiazole, pyrazole, pyridine, pyrazine, pyridazine, pyrimidine, etc.), unsaturated non-aromatic rings, etc.), or any combinations thereof (e.g., alkene and amine (e.g., Compound 292), alkane and amine (Compound 293), etc.).

In some embodiments, in which $R_7$ of a Formula (I) comprises a cyclic group (e.g., non-aromatic cycloalkane, non-aromatic heterocycle, aryl, heteroaryl, unsaturated non-aromatic, etc.) attached directly to $C_7$ or attached to $C_7$ by a linker (e.g., alkane, heteroalkyl, etc.), the cyclic group is further substituted at one or more positions. Suitable substituents off a $R_7$ cyclic group include, but are not limited to: $CH_3$, $CH_2CH_3$, $CHCH_2$, $NH_2$, OH, COH, COH, $COCH_3$, Br, Cl, F, $N(CH_3)_2$, CN, $CH(CH_3)_2$, $CH(CH_2CH_3)_2$, $CF_3$, $CCl_3$, $CBr_3$, $CHF_2$, $CHCl_2$, $CHBr_2$, $CFH_2$, $CClH_2$, $CBRH_2$, etc. In some embodiments, when possible, a single position (e.g., carbon) on a cyclic group at $R_7$ may comprise two non-hydrogen substituents (e.g., two of the aforementioned suitable substituents (e.g., F and F (difluoro), Br and $CH_3$, OH) and OH (diol), $CH_3$ and $CH_3$ (dimethyl), etc.)).

In some embodiments, $R_7$ of Formula (I) is —Z—$R_{10}$. In some embodiments, Z of Formula (I) is a cyclic group (e.g., saturated non-aromatic ring, aromatic ring, unsaturated non-aromatic ring, non-aromatic heterocycle, heteroaryl, etc.).

In some embodiments, Z of Formula (I) is selected from:

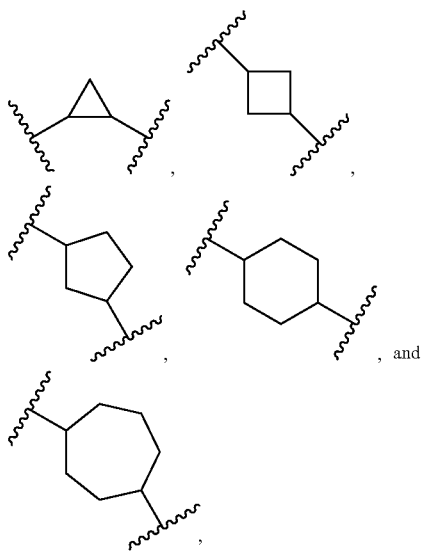

wherein Z connects the formula scaffold to $R_{10}$.

In certain embodiments, Z is a 4-, 5-, 6-, 7- or 8-membered saturated heterocycle. In some embodiments, Z is selected from azetidine, oxetane, piperidine, oxane, piperazine, pyrrolidine, tetrahydrofuran, thiolane, imidazolidine, morpholine, thiomorpholine, azepane, and homopiperazine. In some embodiments, Z is selected from:

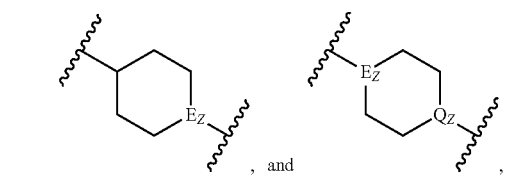

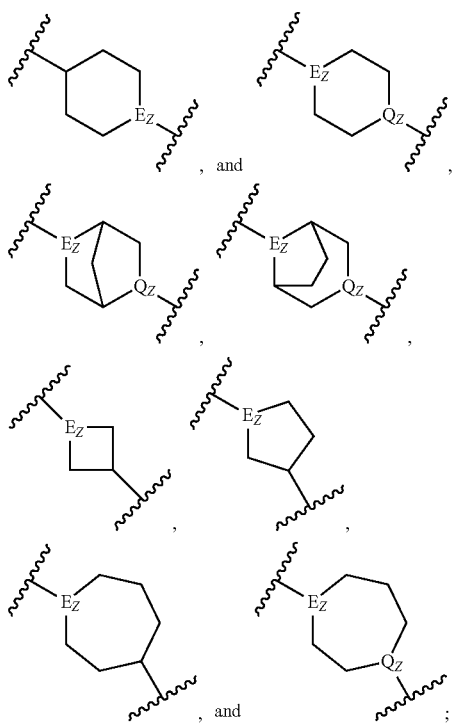

wherein Ez and Qz are independently selected from C, O, S, and N, and Z may adopt either orientation with respect to connection to $R_{10}$ and the formula scaffold. In some embodiments, Ez and Qz are independently selected from O, S, and N.

In certain embodiments, for a compound or salt of Formula (I) having a —Z—$R_{10}$ group, Z is selected from an unsaturated, aromatic, or heteroaromatic ring. In particular embodiments, Z is selected from phenyl, pyridine, pyrazine, pyrimidine, pyridazine, naphthalene, anthracene, quinoline, isoquinoline, quinoxaline, acridine, quinazoline, cinnoline, phthalazine, furan, dihydrofuran, thiophene, dihydrothiophene, imidazole, imidazoline, oxazole, oxazoline, pyrrole, dihydropyrrole, thiazole, dihydrothiazole, pyrazole, dihydropyrazole, isoxazole, dihydroisoxazole, isothiazole, dihydroisothiazole, benzofuran, isobenzofuran, indole, isoindole, benzothiophene, benzimidazole, purine, indazole, benzoxazole, benzisoxazole, and benzothiazole. In some embodiments, Z is selected from:

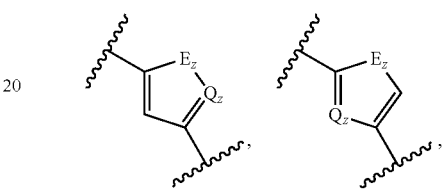

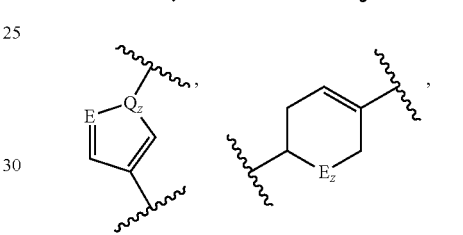

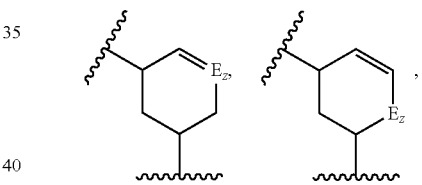

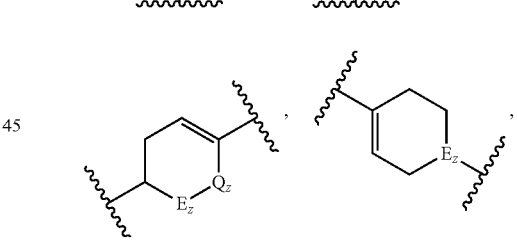

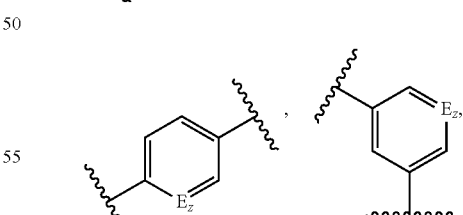

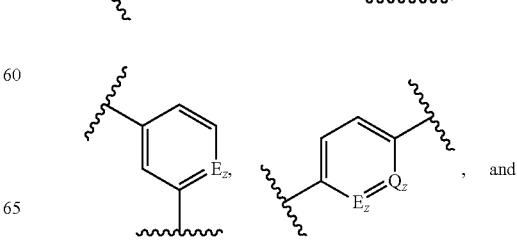

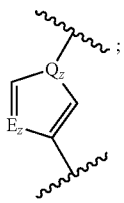

wherein Ez and Gz are independently selected from C, O, S, and N (or O, S, and N, but not C), and Z may adopt either orientation with respect to connection to $R_{10}$ and the scaffold of any Formula (I) having a —Z—$R_{10}$ group.

In some embodiments, $R_{10}$ of any Formula (I) having a —Z—$R_{10}$ group is selected from: H, Br, Cl, F, I, D (deuterium), CN, alkane (e.g., methyl, ethyl, propyl, isopropyl, butyl, etc.), haloalkane (e.g., monohaloalkane (e.g., $CH_2F$, $CH_2CH_2Cl$, $CHBrCH_3$, etc.), dihaloalkane (e.g., $CF_2H$, $CH_2CCl_2H$, etc.), trihaloalkane (e.g., $CBr_3$, $CF_3$, $CCl_3$, $CH_2CBr_3$, $CH_2CF_3$, $CH_2CCl_3$, etc.)), alkene (e.g. $CH=CH_2$, etc.), alkyne (e.g. C≡CH, etc), amine (e.g., $NH_2$, NH-alkyl (e.g., NH-methyl, NH-ethyl, NH—$CH_2$-Ph, etc.), alkyl-amine (e.g., $(CH_2)_{1-6}$—$NH_2$), alkyl-amine-alkyl (e.g., $(CH_2)_{1-6}$—$NH_2$—$(CH_2)_{1-5}CH_3$, etc.), $(CH_2)_{1-6}$—$N(CH_3)_2$, alkene-$N(CH_3)_2$, alkyne-$N(CH_3)_2$, $N(CH_3)_2$, O-alkyl (e.g., $OCH_3$, $OCH_2CH_3$, etc.), NH-alcohol (e.g., NH—$CH_2$—$CH_2$—OH), etc.), hydroxy (e.g. —OH), and an alcohol (e.g., methanol, ethanol, butanol, propanol, $CH_2CHOHCH_2OH$, etc.).

In some embodiments, Z of any Formula (I) having a —Z—$R_{10}$ group is further substituted at one or more additional ring positions (e.g., in addition to the $R_{10}$ substitution). Additional substituents on the Z ring may include: Br, Cl, F, I, CN, alkane (e.g., methyl, ethyl, propyl, isopropyl, butyl, etc.), haloalkane (e.g., monohaloalkane (e.g., $CH_2F$, $CH_2CH_2Cl$, $CHBrCH_3$, etc.), dihaloalkane (e.g., $CF_2H$, $CH_2CCl_2H$, etc.), trihaloalkane (e.g., $CBr_3$, $CF_3$, $CCl_3$, $CH_2CBr_3$, $CH_2CF_3$, $CH_2CCl_3$, etc.)), alkene (e.g. $CH=CH_2$, etc.), alkyne (e.g. C≡CH, etc), amine (e.g., $NH_2$, NH-alkyl (e.g., NH-methyl, NH-ethyl, NH—$CH_2$-Ph, etc.), alkyl-amine (e.g., $(CH_2)_{1-6}$—$NH_2$), alkyl-amine-alkyl (e.g., $(CH_2)_{1-6}$—$NH_2$—$(CH_2)_{1-5}CH_3$, etc.), $(CH_2)_{1-6}$—$N(CH_3)_2$, alkene-$N(CH_3)_2$, alkyne-$N(CH_3)_2$, $N(CH_3)_2$, O-alkyl (e.g., $OCH_3$, $OCH_2CH_3$, etc.), NH-alcohol (e.g., NH—$CH_2$—$CH_2$—OH), etc.), hydroxy (e.g. —OH), and an alcohol (e.g., methanol, ethanol, butanol, propanol, $CH_2CHOHCH_2OH$, etc.).

In some embodiments, $R_8$ of Formula (I) is selected from: H, Br, Cl, F, I, D (deuterium), alkane (e.g., methyl, ethyl, propyl, isopropyl, butyl, etc.), haloalkane (e.g., monohaloalkane (e.g., $CH_2F$, $CH_2CH_2Cl$, $CHBrCH_3$, etc.), dihaloalkane (e.g., $CF_2H$, $CH_2CCl_2H$, etc.), trihaloalkane (e.g., $CBr_3$, $CF_3$, $CCl_3$, $CH_2CBr_3$, $CH_2CF_3$, $CH_2CCl_3$, etc.)), trihalomethyl-cycloalkyl (e.g., 1-(trifluoromethyl)cyclopropyl (e.g., $R_7$ of compound 84) 1-(trichloromethyl)cyclohexane, etc.), alkene (e.g. $CH=CH_2$, etc.), alkyne (e.g. C≡CH, etc), amine (e.g., $NH_2$, NH-alkyl (e.g., NH-methyl, NH-ethyl, NH—$CH_2$-Ph, etc.), alkyl-amine (e.g., $(CH_2)_{1-6}$—$NH_2$), alkyl-amine-alkyl (e.g., $(CH_2)_{1-6}$—$NH_2$—$(CH_2)_{1-5}CH_3$, etc.), $(CH_2)_{1-6}$—$N(CH_3)_2$, alkene-$N(CH_3)_2$, alkyne-N$(CH_3)_2$, $N(CH_3)_2$, O-alkyl (e.g., $OCH_3$, $OCH_2CH_3$, etc.), NH-alcohol (e.g., NH—$CH_2$—$CH_2$—OH), etc.), hydroxy (e.g. —OH), an alcohol (e.g., $(CH_2)_{1-6}OH$, $CH_2CHOHCH_2OH$, etc.), cycloalkyl (e.g., cyclopropyl, cyclobutyl, cyclopentyl, cyclohexyl, cycloheptyl, etc.), alkyl-cycloalkyl (e.g., $(CH_2)_{1-6}$-cyclopropyl, $(CH_2)_{1-6}$-cyclobutyl, $(CH_2)_{1-6}$-cyclopentyl, $(CH_2)_{1-6}$-cyclohexyl, $(CH_2)_{1-6}$-cycloheptyl, etc.), alkene-cycloalkyl (e.g., $(CH_2)_2$-cyclopropyl, $(CH_2)_2$-cyclobutyl, $(CH_2)_2$-cyclopentyl, $(CH_2)_2$-cyclohexyl (e.g., compound 155), $(CH_2)_2$-cycloheptyl, etc.), cycloalkene (e.g., cyclopropenyl, cyclobutenyl, cyclopentenyl (e.g., $R_7$ of compound 153), cyclohexenyl (e.g., $R_7$ of compound 154), cycloheptenyl, etc.), alkyl-cycloalkenyl (e.g., $(CH_2)_{1-6}$-cyclopropenyl, $(CH_2)_{1-6}$-cyclobutenyl, $(CH_2)_{1-6}$-cyclopentenyl, $(CH_2)_{1-6}$-cyclohexenyl, $(CH_2)_{1-6}$-cycloheptenyl, etc.), alkene-cycloalkenyl (e.g., $(CH)_2$-cyclopropenyl, $(CH)_2$-cyclobutenyl, $(CH)_2$-cyclopentenyl, $(CH)_2$-cyclohexenyl, $(CH)_2$-cycloheptenyl, etc.), and $(CH_2)_{0-6}$-heterocycle (e.g., non-aromatic heterocycle (e.g., aziridine, thiirane, oxirane, oxaziridine, dioxirane, azetidine, oxetane, thietane, diazetidine, dioxetane, dithietane, pyrrolidine, tetrahydrofuran, thiolane, imidazolidine, pyrazolidine, oxazolidine, isoxazolidine, thiazolidine, isothiazolidine, dioxolane, dithiolane, piperdine, oxane, thiane, piperazine, morpholine, thiomorpholine, dioxane, dithiane, trioxane, thithiane, azepane, oxepane, thiepane, homopiperazine, azocane, etc.), heteroaryl (e.g., pyrrole, furan, thiophene, imidazole, oxazole, thiazole, pyrazole, pyridine, pyrazine, pyridazine, pyrimidine, etc.), unsaturated non-aromatic rings, etc.).

In some embodiments, in which $R_8$ of Formula (I) comprises a cyclic group (e.g., non-aromatic cycloalkane, non-aromatic heterocycle, aryl, heteroaryl, unsaturated non-aromatic, etc.) attached directly to $C_8$ or attached to $C_8$ by a linker (e.g., alkane, heteroalkyl, etc.), the cyclic group is further substituted at one or more positions. Suitable substituents off a $R_8$ cyclic group include, but are not limited to: $CH_3$, $CH_2CH_3$, $CHCH_2$, $NH_2$, OH, COH, $COCH_3$, Br, Cl, F, $N(CH_3)_2$, CN, $CH(CH_3)_2$, $CH(CH_2CH_3)_2$, $CF_3$, $CCl_3$, $CBr_3$, $CHF_2$, $CHCl_2$, $CHBr_2$, $CFH_2$, $CClH_2$, $CBrH_2$, etc. In some embodiments, when possible, a single position (e.g., carbon) on a cyclic group at $R_8$ may comprise two non-hydrogen substituents (e.g., two of the aforementioned suitable substituents (e.g., F and F (difluoro), Br and $CH_3$, OH and OH (diol), $CH_3$ and $CH_3$ (dimethyl), etc.)).

In some embodiments, R8 of Formula (I) is -G-$R_{11}$. In some embodiments, G of any Formula (I) having a G-$R_{11}$ is a cyclic group (e.g., saturated non-aromatic ring, aromatic ring, unsaturated non-aromatic ring, non-aromatic heterocycle, heteroaryl, etc.). In some embodiments, G is selected from:

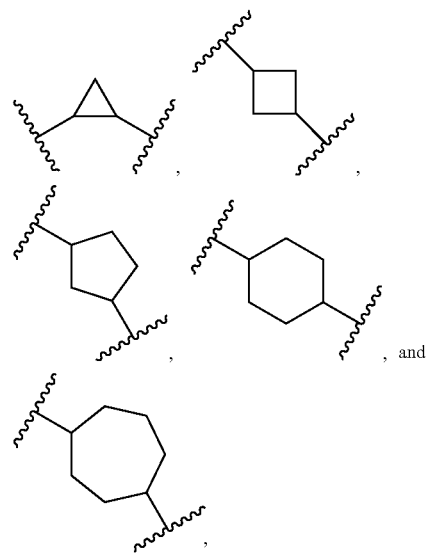

wherein G connects the formula scaffold to $R_{11}$.

In certain embodiments, G is a 4-, 5-, 6-, 7- or 8-membered saturated heterocycle. In some embodiments, G is selected from azetidine, oxetane, piperidine, oxane, piperazine, pyrrolidine, tetrahydrofuran, thiolane, imidazolidine, morpholine, thiomorpholine, azepane, and homopiperazine. In some embodiments, G is selected from:

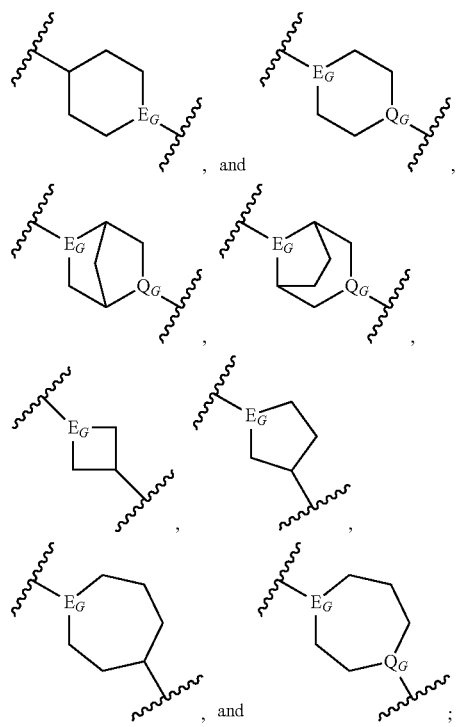

wherein $E_G$ and $Q_G$ are independently selected from C, O, S, and N, and Z may adopt either orientation with respect to connection to $R_{11}$ and the formula scaffold. In some embodiments, $E_G$ and $Q_G$ are independently selected from O, S, and N.

In certain embodiments, for a compound or salt of any Formula (I) having a -G-$R_{11}$ group, G is selected from an unsaturated, aromatic, or heteroaromatic ring. In particular embodiments, G is selected from phenyl, pyridine, pyrazine, pyrimidine, pyridazine, naphthalene, anthracene, quinoline, isoquinoline, quinoxaline, acridine, quinazoline, cinnoline, phthalazine, furan, dihydrofuran, thiophene, dihydrothiophene, imidazole, imidazoline, oxazole, oxazoline, pyrrole, dihydropyrrole, thiazole, dihydrothiazole, pyrazole, dihydropyrazole, isoxazole, dihydroisoxazole, isothiazole, dihydroisothiazole, benzofuran, isobenzofuran, indole, isoindole, benzothiophene, benzimidazole, purine, indazole, benzoxazole, benzisoxazole, and benzothiazole. In some embodiments, G is selected from:

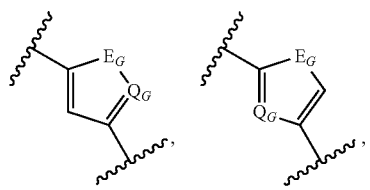

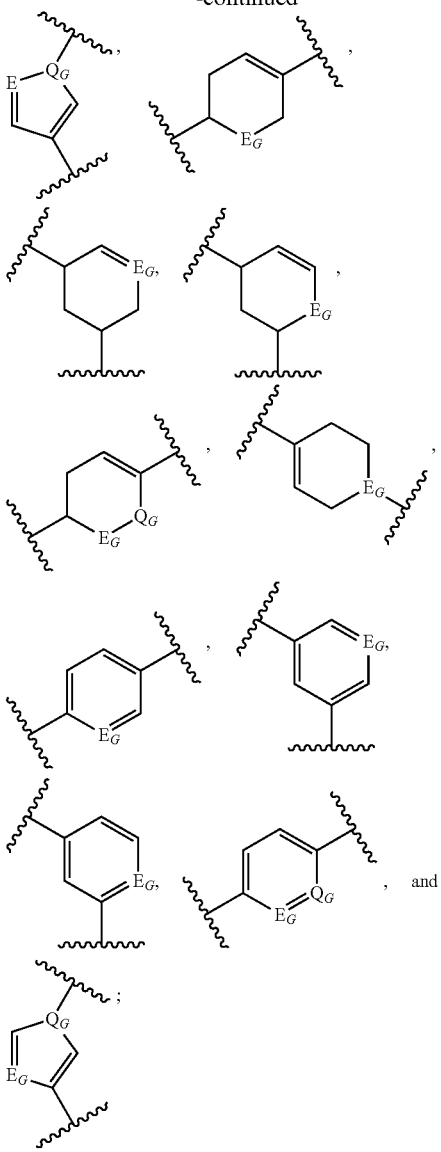

wherein $E_G$ and $G_G$ are independently selected from C, O, S, and N (or O, S, and N, but not C), and G may adopt either orientation with respect to connection to $R_{11}$ and the scaffold of any Formula (I) having a -G-$R_{11}$ group.

In some embodiments, $R_{11}$ of any Formula (I) having a -G-$R_{11}$ group is selected from: H, Br, Cl, F, I, D (deuterium), CN, alkane (e.g., methyl, ethyl, propyl, isopropyl, butyl, etc.), haloalkane (e.g., monohaloalkane (e.g., $CH_2F$, $CH_2CH_2Cl$, $CHBrCH_3$, etc.), dihaloalkane (e.g., $CF_2H$, $CH_2CCl_2H$, etc.), trihaloalkane (e.g., $CBr_3$, $CF_3$, $CCl_3$, $CH_2CBr_3$, $CH_2CF_3$, $CH_2CCl_3$, etc.)), alkene (e.g. $CH=CH_2$, etc.), alkyne (e.g. $C\equiv CH$, etc), amine (e.g., $NH_2$, NH-alkyl (e.g., NH-methyl, NH-ethyl, NH—$CH_2$-Ph, etc.), alkyl-amine (e.g., $(CH_2)_{1-6}$—$NH_2$), alkyl-amine-alkyl (e.g., $(CH_2)_{1-6}$—$NH_2$—$(CH_2)_{1-5}CH_3$, etc.), $(CH_2)_{1-6}$—$N(CH_3)_2$, alkene-$N(CH_3)_2$, alkyne-$N(CH_3)_2$, $N(CH_3)_2$, O-alkyl (e.g., $OCH_3$, $OCH_2CH_3$, etc.), NH-alcohol (e.g., NH—$CH_2$—$CH_2$—OH), etc.), hydroxy (e.g. —OH), and an alcohol (e.g., methanol, ethanol, butanol, propanol, $CH_2CHOHCH_2OH$, etc.).

In some embodiments, G of any Formula (I) having a -G-$R_{11}$ group is further substituted at one or more additional ring positions (e.g., in addition to the $R_{11}$ substitution). Additional substituents on the G ring may include: Br, Cl, F, I, CN, alkane (e.g., methyl, ethyl, propyl, isopropyl, butyl, etc.), haloalkane (e.g., monohaloalkane (e.g., $CH_2F$, $CH_2CH_2Cl$, $CHBrCH_3$, etc.), dihaloalkane (e.g., $CF_2H$, $CH_2CCl_2H$, etc.), trihaloalkane (e.g., $CBr_3$, $CF_3$, $CCl_3$, $CH_2CBr_3$, $CH_2CF_3$, $CH_2CCl_3$, etc.)), alkene (e.g. $CH=CH_2$, etc.), alkyne (e.g. $C≡CH$, etc), amine (e.g., $NH_2$, NH-alkyl (e.g., NH-methyl, NH-ethyl, NH—$CH_2$-Ph, etc.), alkyl-amine (e.g., $(CH_2)_{1-6}$—$NH_2$), alkyl-amine-alkyl (e.g., $(CH_2)_{1-6}$—$NH_2$—$(CH_2)_{1-5}CH_3$, etc.), $(CH_2)_{1-6}$—$N(CH_3)_2$, alkene-$N(CH_3)_2$, alkyne-$N(CH_3)_2$, $N(CH_3)_2$, O-alkyl (e.g., $OCH_3$, $OCH_2CH_3$, etc.), NH-alcohol (e.g., NH—$CH_2$—$CH_2$—OH), etc.), hydroxy (e.g. —OH), and an alcohol (e.g., methanol, ethanol, butanol, propanol, $CH_2CHOHCH_2OH$, etc.).

In some embodiments, X of Formula (I) is O or S. In some embodiments, A, L, and Y of Formula (I) are independently selected from: C, O, N, and S. In embodiments in which A, L, and/or Y are O or S, the position is not further substituted. In embodiments in which A, L, and/or Y is C or N, the position may comprise, one or two additional substituents selected from: H, D, $CH_3$, $CH_2CH_3$, $CHCH_2$, $NH_2$, OH, COH, $COCH_3$, Br, Cl, F, $N(CH_3)_2$, CN, $CH(CH_3)_2$, $CH(CH_2CH_3)_2$, $CF_3$, $CCl_3$, $CBr_3$, $CHF_2$, $CHCl_2$, $CHBr_2$, $CClH_2$, $CBrH_2$, etc. In some embodiments, X is O.

In some embodiments, M and J of Formula (I) are independently selected from: C and N. In some embodiments, when $R_7$ is not H or D, J is C. In some embodiments, when $R_7$ is H or D, J is C. In some embodiments, when $R_7$ is H or D, M is C or N. In some embodiments, when $R_8$ is not H or D, M is C. In some embodiments, when $R_8$ is H or D, J is C or N. In some embodiments, when $R_8$ is H or D, J is C.

In some embodiments, depending upon the identity of Y, X, A, M, J, L, $R_7$ and $R_8$ of Formula (I), the double bonds of the ring systems are adjusted accordingly to maintain the aromaticity of the terminal rings of the 3-ring system (as is understood by one in the field). In embodiments in which A, M, J, L, and/or Y is N, the A, M, L, J, and/or Y position is not further substituted. In embodiments in which A, M, J, L, and/or Y is C, the A, M, L, J, and/or Y position comprises an substituent selected from: H, D, $CH_3$, $CH_2CH_3$, $CHCH_2$, $NH_2$, OH, COH, $COCH_3$, Br, Cl, F, $N(CH_3)_2$, CN, $CH(CH_3)_2$, $CH(CH_2CH_3)_2$, $CF_3$, $CCl_3$, $CBr_3$, $CHF_2$, $CHCl_2$, $CHBr_2$, $CFH_2$, $CClH_2$, $CBrH_2$, etc. In some embodiments, A, M, L, J, and Y of Formula (I) are independently selected from C and N. In some embodiments, A, M, J, and L are C and Y is N. In some embodiments, A and Y are N and M, J, and L are C. In some embodiments, M and Y are N and J, A and L are C. In some embodiments, J and Y are N and M, A and L are C. In some embodiments, M, L and Y are N and J and A are C. In some embodiments, J, L and Y are N and M and A are C. In some embodiments, J and A are C and M, L, and Y are N. In some embodiments, M and A are C and J, L, and Y are N. Any other suitable combinations of Y, X, A, M, J, and L are within the scope herein.

In some embodiments, any or all hydrogens (e.g., exchangeable hydrogens, non-exchangeable hydrogens, and/or both) on a compound of Formula (I) and substituents thereof may be substituted for deuterium atoms. In some embodiments, any of the hydrogens in the structures, formulas, or substituents described herein, or any subsets thereof, are substituted for deuterium atoms (D).

In certain embodiments, provided herein are compounds represented by a structure of Formula (II):

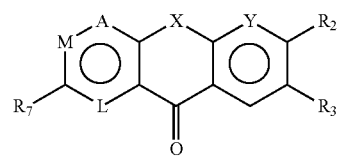

In some embodiments, $R_2$ of Formula (II) is selected from: $CH_3$, $NH_2$, $NHCH_3$, OH, $NH(CH_2)_2OH$, $NH(CH_2)_3OH$, amidino, F, Br, and Cl, and other suitable bioisosters of $NH_2$.

In some embodiments, $R_2$ of Formula (II) is selected from: cycloalkyl, heterocycle, aryl, heteroaryl, NH—$(CH_2)_m$-cycloalkyl, NH—$(CH_2)_m$-heterocycle (e.g., $R_2$ of compound 147), NH—$(CH_2)_m$-aryl, and NH—$(CH_2)_m$-heteroaryl; wherein m is 0-6 (e.g., 0, 1, 2, 3, 4, 5, 6, or any ranges therebetween). In some embodiments, cycloalkyl, heterocycle, aryl, and/or heteroaryl ring groups may be further substituted (e.g., $R_2$ of compound 148), for example, with an alkyl group (e.g., methyl, ethyl, propyl, etc.), an alcohol (e.g., OH, $CH_2OH$, $(CH_2)_2OH$, etc.), amine (e.g., $NH_2$, $CH_2NH_2$, $(CH_2)_2NH_2$, etc.), CN, halogen, etc.

In some embodiments, $R_3$ of a Formula (II) is selected from: a carboxylic acid (e.g., C(O)OH), an alcohol (e.g., OH, $CH_2OH$, $(CH_2)_2OH$, etc.), an ester (e.g., $CO_2CH_3$, $CO_2Et$, etc.), a hydroxamic acid (e.g., C(O)N(OH)H), a phosphoric acid (e.g., $P(O)(OH)_2$), a phosphinic acid (e.g., P(O)(OH)H), a phosphonic acid (e.g., S(O)(O)OH), a sulfonamide (e.g., $S(O)(O)NH_2$), an acylsulfonamide (e.g., C(O)NHS(O)(O)H), $C(O)NHS(O)(O)CH_3$, $C(O)NHS(O)(O)NH_2$), a sulfonylurea (e.g., $NHC(O)NHS(O)(O)CH_3$), a tetrazole, a thiazolidinedione, an oxazolidinedione, 5-oxo-1,2,4-oxadiazole, 5-oxo-1,2,4-thiadiazole, 5-thioxo-1,2,4-thiadiazole, an isothiazole, an isoxazole, a difluorophenol, tetramic acid, tetronic acid, cyclopentane-1,3-dione, a squaric acid, an amide (e.g., C(O)NH-(alkyl) (e.g., C(O)$NHCH_3$, $C(O)NHCH_2CH_3$, etc.), C(O)NH-(cycloalkyl), C(O)NH-(alkyl-cycloalkyl) (e.g., $C(O)NHCH_2(C_6H_{11})$, $C(O)NHCH_2(C_5H_9)$, $C(O)NHCH_2CH_2(C_6H_{11})$, $C(O)NHCH_2CH_2(C_5H_9)$, etc.), C(O)NH-(heteroalkyl) (e.g., $C(O)NHCH_2CH_2N(CH_2)_2$, $C(O)NHCH_2N(CH_2)_2$, $C(O)NHCH_2NHCH_2CH_3$, $C(O)NHCH_2NHCH_3$, $C(O)NHCH_2OCH_2CH_3$, $C(O)NHCH_2CH_2OCH_3$, $C(O)NHCH_2SCH_2CH_3$, $C(O)NHCH_2CH_2SCH_3$, etc.), C(O)NH-(heterocycle), C(O)NH-(alkyl-heterocycle) (e.g., $C(O)NHCH_2(C_5H_9O)$, $C(O)NHCH_2CH_2(C_5H_9O)$, $C(O)NHCH_2(C_5H_9S)$, $C(O)NHCH_2CH_2(C_5H_9S)$, $C(O)NHCH_2(C_5H_{10}N)$, $C(O)NHCH_2CH_2(C_5H_{10}N)$, etc.), and other suitable bioisosteres of a carboxylic acid substituent.

In some embodiments, other suitable bioisosteres of a carboxylic acid substituent include, but are not limited to:

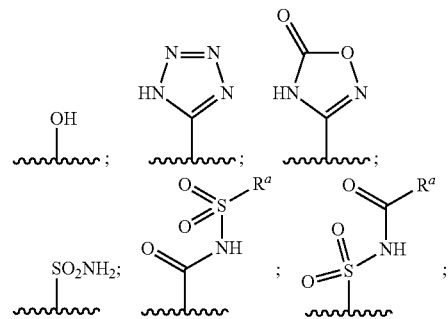

-continued

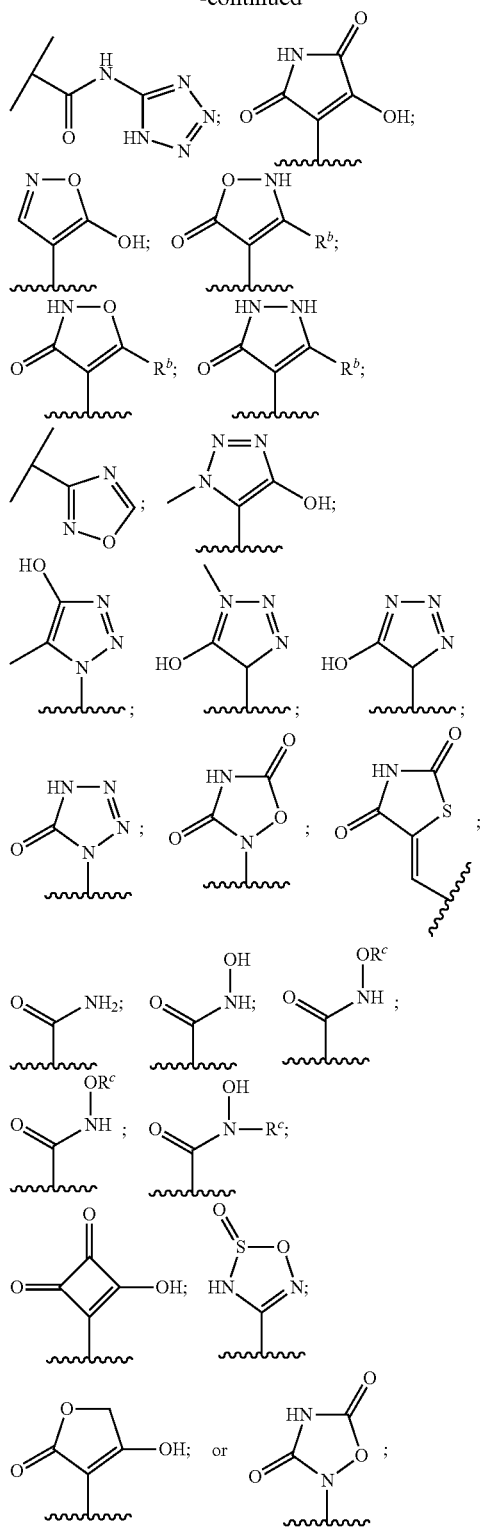

wherein $R^a$, $R^b$ and $R^c$ are independently selected from —$CF_3$, —$CH_3$, phenyl, or benzyl, with the phenyl or benzyl groups being optionally substituted by from 1 to 3 groups selected from $C_6$ alkyl, alkoxy, $C_6$ thioalkyl, $CF_3$, halogen, —OH, or —COOH.

In some embodiments, $R_3$ of a Formula (II) is selected from: cycloalkyl, heterocycle (e.g., tetrazole), aryl, heteroaryl, NH—$(CH_2)_m$-cycloalkyl, NH—$(CH_2)_m$-heterocycle, NH—$(CH_2)_m$-aryl, and NH—$(CH_2)_m$-heteroaryl; wherein m is 0-6 (e.g., 0, 1, 2, 3, 4, 5, 6, or any ranges therebetween). In some embodiments, cycloalkyl, heterocycle, aryl, and/or heteroaryl ring groups may be further substituted, for example, with an alkyl group (e.g., methyl, ethyl, propyl, etc.), an alcohol (e.g., OH, $CH_2OH$, $(CH_2)_2OH$, etc.), amine (e.g., $NH_2$, $CH_2NH_2$, $(CH_2)_2NH_2$, etc.), CN, halogen, etc.

In some embodiments, $R_7$ of Formula (II) is selected from: H, Br, Cl, F, I, D (deuterium), alkane (e.g., methyl, ethyl, propyl, isopropyl, butyl, etc.), haloalkane (e.g., monohaloalkane (e.g., $CH_2F$, $CH_2CH_2Cl$, $CHBrCH_3$, etc.), dihaloalkane (e.g., $CF_2H$, $CH_2CCl_2H$, etc.), trihaloalkane (e.g., $CBr_3$, $CF_3$, $CCl_3$, $CH_2CBr_3$, $CH_2CF_3$, $CH_2CCl_3$, etc.)), trihalomethyl-cycloalkyl (e.g., 1-(trifluoromethyl)cyclopropyl (e.g., $R_7$ of compound 84) 1-(trichloromethyl)cyclohexane, etc.), alkene (e.g. CH=$CH_2$, etc.), alkyne (e.g. C≡CH, etc), amine (e.g., $NH_2$, NH-alkyl (e.g., NH-methyl, NH-ethyl, NH—$CH_2$-Ph, etc.), alkyl-amine (e.g., $(CH_2)_{1-6}$—$NH_2$), alkyl-amine-alkyl (e.g., $(CH_2)_{1-6}$—$NH_2$—$(CH_2)_{1-5}CH_3$, etc.), $(CH_2)_{1-6}$—$N(CH_3)_2$, alkene-$N(CH_3)_2$, alkyne-$N(CH_3)_2$, $N(CH_3)_2$, O-alkyl (e.g., $OCH_3$, $OCH_2CH_3$, etc.), NH-alcohol (e.g., NH—$CH_2$—$CH_2$—OH), etc.), hydroxy (e.g. —OH), an alcohol (e.g., $(CH_2)_{1-6}OH$, $CH_2CHOHCH_2OH$, etc.), cycloalkyl (e.g., cyclopropyl, cyclobutyl, cyclopentyl, cyclohexyl, cycloheptyl, etc.), alkyl-cycloalkyl (e.g., $(CH_2)_{1-6}$-cyclopropyl, $(CH_2)_{1-6}$-cyclobutyl, $(CH_2)_{1-6}$-cyclopentyl, $(CH_2)_{1-6}$-cyclohexyl, $(CH_2)_{1-6}$-cycloheptyl, etc.), alkene-cycloalkyl (e.g., $(CH)_2$-cyclopropyl, $(CH)_2$-cyclobutyl, $(CH)_2$-cyclopentyl, $(CH)_2$-cyclohexyl (e.g., compound 155), $(CH)_2$-cycloheptyl, etc.), cycloalkene (e.g., cyclopropenyl, cyclobutenyl, cyclopentenyl (e.g., $R_7$ of compound 153), cyclohexenyl (e.g., $R_7$ of compound 154), cycloheptenyl, etc.), alkyl-cycloalkenyl (e.g., $(CH_2)_{1-6}$-cyclopropenyl, $(CH_2)_{1-6}$-cyclobutenyl, $(CH_2)_{1-6}$-cyclopentenyl, $(CH_2)_{1-6}$-cyclohexenyl, $(CH_2)_{1-6}$-cycloheptenyl, etc.), alkene-cycloalkenyl (e.g., $(CH)_2$-cyclopropenyl, $(CH)_2$-cyclobutenyl, $(CH)_2$-cyclopentenyl, $(CH)_2$-cyclohexenyl, $(CH)_2$-cycloheptenyl, etc.), and $(CH_2)_{0-6}$-heterocycle (e.g., non-aromatic heterocycle (e.g., aziridine, thiirane, oxirane, oxaziridine, dioxirane, azetidine, oxetane, thietane, diazetidine, dioxetane, dithietane, pyrrolidine, tetrahydrofuran, thiolane, imidazolidine, pyrazolidine, oxazolidine, isoxazolidine, thiazolidine, isothiazolidine, dioxolane, dithiolane, piperdine, oxane, thiane, piperazine, morpholine, thiomorpholine, dioxane, dithiane, trioxane, thithiane, azepane, oxepane, thiepane, homopiperazine, azocane, etc.), heteroaryl (e.g., pyrrole, furan, thiophene, imidazole, oxazole, thiazole, pyrazole, pyridine, pyrazine, pyridazine, pyrimidine, etc.), unsaturated non-aromatic rings, etc.).

In some embodiments, in which $R_7$ of a Formula (II) comprises a cyclic group (e.g., non-aromatic cycloalkane, non-aromatic heterocycle, aryl, heteroaryl, unsaturated non-aromatic, etc) attached directly to $C_7$ or attached to $C_7$ by a linker (e.g., alkane, heteroalkyl, etc.), the cyclic group is further substituted at one or more positions. Suitable substituents off a $R_7$ cyclic group include, but are not limited to: $CH_3$, $CH_2CH_3$, $CHCH_2$, $NH_2$, OH, COH, $COCH_3$, Br, Cl, F, $N(CH_3)_2$, CN, $CH(CH_3)_2$, $CH(CH_2CH_3)_2$, $CF_3$, $CCl_3$, $CBr_3$, $CHF_2$, $CHCl_2$, $CHBr_2$, $CFH_2$, $CClH_2$, $CBrH_2$, etc. In some embodiments, when possible, a single position (e.g., carbon) on a cyclic group at $R_7$ may comprise two non-hydrogen substituents (e.g., two of the aforementioned suitable substituents (e.g., F and F (difluoro), Br and $CH_3$, OH and OH (diol), $CH_3$ and $CH_3$ (dimethyl), etc.)).

In some embodiments, $R_7$ of Formula (II) is $-Z-R_{10}$. In some embodiments, Z of Formula (II) is a cyclic group (e.g., saturated non-aromatic ring, aromatic ring, unsaturated non-aromatic ring, non-aromatic heterocycle, heteroaryl, etc.).

In some embodiments, Z of Formula (II) is selected from:

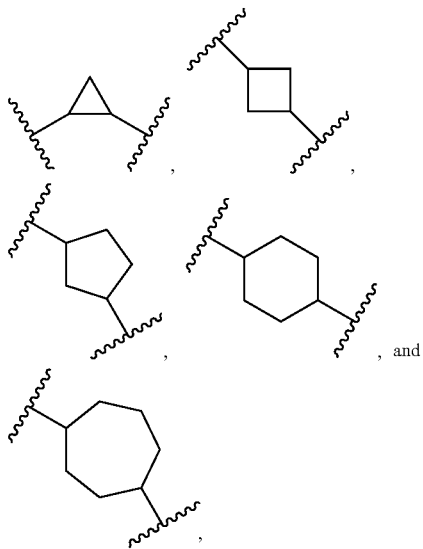

wherein Z connects the formula scaffold to $R_{10}$.

In certain embodiments, Z is a 4-, 5-, 6-, 7- or 8-membered saturated heterocycle. In some embodiments, Z is selected from azetidine, oxetane, piperidine, oxane, piperazine, pyrrolidine, tetrahydrofuran, thiolane, imidazolidine, morpholine, thiomorpholine, azepane, and homopiperazine. In some embodiments, Z is selected from:

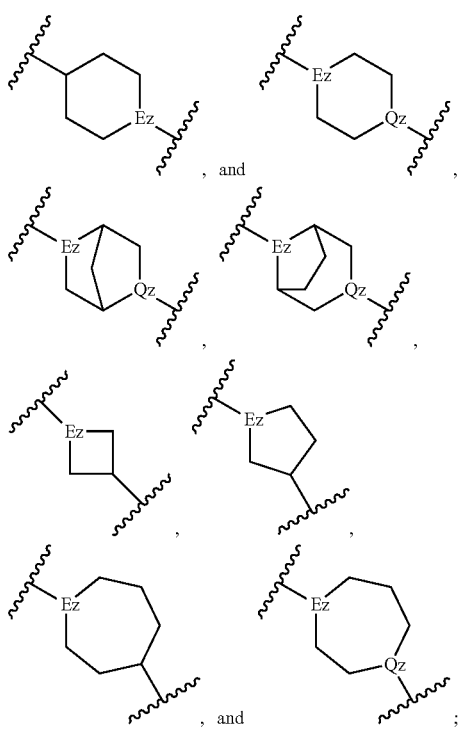

wherein $E_z$ and $Q_z$ are independently selected from C, O, S, and N, and Z may adopt either orientation with respect to connection to $R_{10}$ and the formula scaffold. In some embodiments, $E_z$ and $Q_z$ are independently selected from O, S, and N.

In certain embodiments, for a compound or salt of Formula (II) having a $-Z-R_{10}$ group, Z is selected from an unsaturated, aromatic, or heteroaromatic ring. In particular embodiments, Z is selected from phenyl, pyridine, pyrazine, pyrimidine, pyridazine, naphthalene, anthracene, quinoline, isoquinoline, quinoxaline, acridine, quinazoline, cinnoline, phthalazine, furan, dihydrofuran, thiophene, dihydrothiophene, imidazole, imidazoline, oxazole, oxazoline, pyrrole, dihydropyrrole, thiazole, dihydrothiazole, pyrazole, dihydropyrazole, isoxazole, dihydroisoxazole, isothiazole, dihydroisothiazole, benzofuran, isobenzofuran, indole, isoindole, benzothiophene, benzimidazole, purine, indazole, benzoxazole, benzisoxazole, and benzothiazole. In some embodiments, Z is selected from:

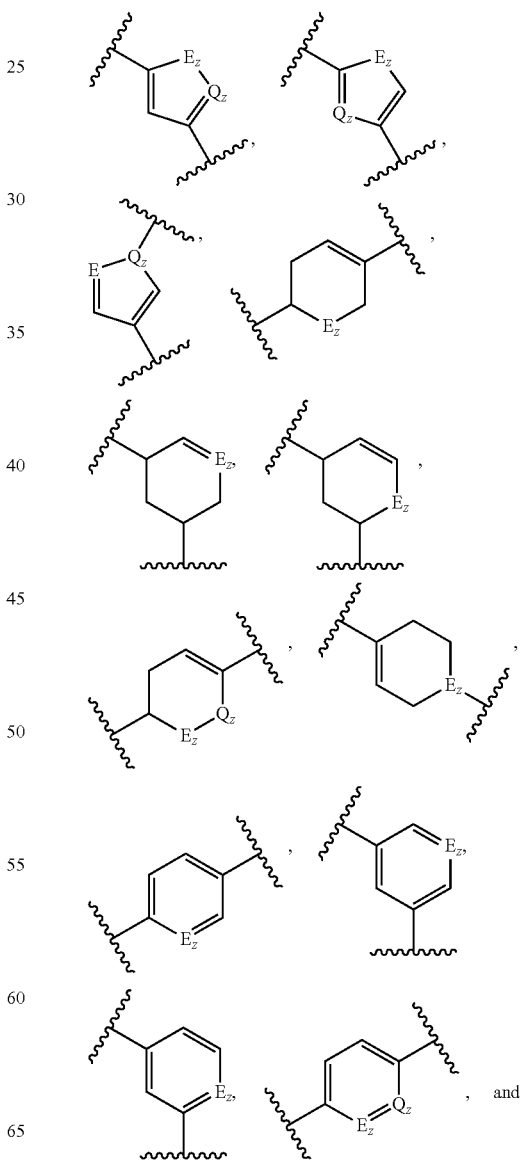

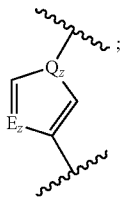

wherein Ez and Gz are independently selected from C, O, S, and N (or O, S, and N, but not C), and Z may adopt either orientation with respect to connection to $R_{10}$ and the scaffold of any Formula (II) having a —Z—$R_{10}$ group.

In some embodiments, $R_{10}$ of any Formula (II) having a —Z—$R_{10}$ group is selected from: H, Br, Cl, F, I, D (deuterium), CN, alkane (e.g., methyl, ethyl, propyl, isopropyl, butyl, etc.), haloalkane (e.g., monohaloalkane (e.g., $CH_2F$, $CH_2CH_2Cl$, $CHBrCH_3$, etc.), dihaloalkane (e.g., $CF_2H$, $CH_2CCl_2H$, etc.), trihaloalkane (e.g., $CBr_3$, $CF_3$, $CCl_3$, $CH_2CBr_3$, $CH_2CF_3$, $CH_2CCl_3$, etc.)), alkene (e.g. $CH=CH_2$, etc.), alkyne (e.g. C≡CH, etc), amine (e.g., $NH_2$, NH-alkyl (e.g., NH-methyl, NH-ethyl, NH—$CH_2$-Ph, etc.), alkyl-amine (e.g., $(CH_2)_{1-6}$—$NH_2$), alkyl-amine-alkyl (e.g., $(CH_2)_{1-6}$—$NH_2$—$(CH_2)_{1-5}CH_3$, etc.), $(CH_2)_{1-6}$—$N(CH_3)_2$, alkene-$N(CH_3)_2$, alkyne-$N(CH_3)_2$, $N(CH_3)_2$, O-alkyl (e.g., $OCH_3$, $OCH_2CH_3$, etc.), NH-alcohol (e.g., NH—$CH_2$—$CH_2$—OH), etc.), hydroxy (e.g. —OH), and an alcohol (e.g., methanol, ethanol, butanol, propanol, $CH_2CHOHCH_2OH$, etc.).

In some embodiments, Z of any Formula (II) having a —Z—$R_{10}$ group is further substituted at one or more additional ring positions (e.g., in addition to the $R_{10}$ substitution). Additional substituents on the Z ring may include: Br, Cl, F, I, CN, alkane (e.g., methyl, ethyl, propyl, isopropyl, butyl, etc.), haloalkane (e.g., monohaloalkane (e.g., $CH_2F$, $CH_2CH_2Cl$, $CHBrCH_3$, etc.), dihaloalkane (e.g., $CF_2H$, $CH_2CCl_2H$, etc.), trihaloalkane (e.g., $CBr_3$, $CF_3$, $CCl_3$, $CH_2CBr_3$, $CH_2CF_3$, $CH_2CCl_3$, etc.)), alkene (e.g. $CH=CH_2$, etc.), alkyne (e.g. C≡CH, etc), amine (e.g., $NH_2$, NH-alkyl (e.g., NH-methyl, NH-ethyl, NH—$CH_2$-Ph, etc.), alkyl-amine (e.g., $(CH_2)_{1-6}$—$NH_2$), alkyl-amine-alkyl (e.g., $(CH_2)_{1-6}$—$NH_2$—$(CH_2)_{1-5}CH_3$, etc.), $(CH_2)_{1-6}$—$N(CH_3)_2$, alkene-$N(CH_3)_2$, alkyne-$N(CH_3)_2$, $N(CH_3)_2$, O-alkyl (e.g., $OCH_3$, $OCH_2CH_3$, etc.), NH-alcohol (e.g., NH—$CH_2$—$CH_2$—OH), etc.), hydroxy (e.g. —OH), and an alcohol (e.g., methanol, ethanol, butanol, propanol, $CH_2CHOHCH_2OH$, etc.).

In some embodiments, X of Formula (I) is O or S. In some embodiments, A, L, and Y of Formula (I) are independently selected from: C, O, N, and S. In embodiments in which A, L, and/or Y are O or S, the position is not further substituted. In embodiments in which A, L, and/or Y is C or N, the position may comprise, one or two additional substituents selected from: H, D, $CH_3$, $CH_2CH_2$, $CHCH_2$, $NH_2$, OH, COH, $COCH_3$, Br, Cl, F, $N(CH_3)_2$, CN, $CH(CH_3)_2$, $CH(CH_2CH_3)_2$, $CF_3$, $CCl_3$, $CBr_3$, $CHF_2$, $CHCl_2$, $CHBr_2$, $CFH_2$, $CClH_2$, $CBrH_2$, etc. In some embodiments, X is O.

In some embodiments, M of Formula (II) is selected from: C, O, S, and N. In some embodiments, M is C. In some embodiments, M is N.

In some embodiments, depending upon the identity of Y, X, A, M, L, and $R_7$ of Formula (II), the double bonds of the ring systems are adjusted accordingly to maintain the aromaticity of the terminal rings of the 3-ring system (as is understood by one in the field). In embodiments in which A, M, L, and/or Y is N, the A, M, L, and/or Y position is not further substituted. In embodiments in which A, M, L, and/or Y is C, the A, M, L, and/or Y position may comprise an substituent selected from: H, D, $CH_3$, $CH_2CH_3$, $CHCH_2$, $NH_2$, OH, COH, $COCH_3$, Br, Cl, F, $N(CH_3)_2$, CN, CH $(CH_3)_2$, —$CH(CH_2CH_3)_2$, $CF_3$, $CCl_3$, $CBr_3$, $CHF_2$, $CHCl_2$, $CHBr_2$, $CFH_2$, $CClH_2$, $CBrH_2$, etc. In some embodiments, A, M, L, and Y of Formula (II) are independently selected from C and N. In some embodiments, A, M, and L are C and Y is N. In some embodiments, A and Y are N and M, and L are C. In some embodiments, M and Y are N and A and L are C. In some embodiments, Y is N and M, A and L are C. In some embodiments, M, L and Y are N and A is C. In some embodiments, L and Y are N and M and A are C. In some embodiments, A is C and M, L, and Y are N. In some embodiments, M and A are C and L, and Y are N. Any other suitable combinations of Y, X, A, M, and L are within the scope herein.

In some embodiments, any or all hydrogens (e.g., exchangeable hydrogens, non-exchangeable hydrogens, and/or both) on a compound of any of Formula (II) and substituents thereof may be substituted for deuterium atoms. In some embodiments, any of the hydrogens in the structures, formulas, or substituents described herein, or any subsets thereof, are substituted for deuterium atoms (D).

In certain embodiments, provided herein are compounds represented by a structure of Formula (III):

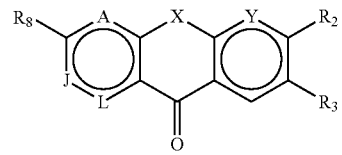

In some embodiments, $R_2$ of Formula (III) is selected from: $CH_3$, $NH_2$, $NHCH_3$, OH, $NH(CH_2)_2OH$, NH $(CH_2)_3OH$, amidino, F, Br, and Cl, and other suitable bioisosters of $NH_2$.

In some embodiments, $R_2$ of Formula (III) is selected from: cycloalkyl, heterocycle, aryl, heteroaryl, NH—(C$H_2)_m$-cycloalkyl, NH—$(CH_2)_m$-heterocycle (e.g., $R_2$ of compound 147), NH—$(CH_2)_m$-aryl, and NH—$(CH_2)_m$-heteroaryl; wherein m is 0-6 (e.g., 0, 1, 2, 3, 4, 5, 6, or any ranges therebetween). In some embodiments, cycloalkyl, heterocycle, aryl, and/or heteroaryl ring groups may be further substituted (e.g., $R_2$ of compound 148), for example, with an alkyl group (e.g., methyl, ethyl, propyl, etc.), an alcohol (e.g., OH, $CH_2OH$, $(CH_2)_2OH$, etc.), amine (e.g., $NH_2$, $CH_2NH_2$, $(CH_2)_2NH_2$, etc.), CN, halogen, etc.

In some embodiments, $R_3$ of a Formula (III) is selected from: a carboxylic acid (e.g., C(O)OH), an alcohol (e.g., OH, $CH_2OH$, $(CH_2)_2OH$, etc.), an ester (e.g., $CO_2CH_3$, $CO_2Et$, etc.), a hydroxamic acid (e.g., C(O)N(OH)H), a phosphoric acid (e.g., P(O)(OH)$_2$), a phosphinic acid (e.g., P(O)(OH)H), a sulphonic acid (e.g., S(O)(O)OH), a sulfonamide (e.g., S(O)(O)NH$_2$), an acylsulfonamide (e.g., C(O)NHS(O)(O)H), C(O)NHS(O)(O)CH$_3$), C(O)NHS(O)(O)NH$_2$), a sulfonylurea (e.g., NHC(O)NHS(O)(O)CH$_3$), a tetrazole, a thiazolidinedione, an oxazolidinedione, 5-oxo-1,2,4-oxadiazole, 5-oxo-1,2,4-thiadiazole, 5-thioxo-1,2,4-thiadiazole, an isothiazole, an isoxazole, a difluorophenol, tetramic acid, tetronic acid, cyclopentane-1,3-dione, a squaric acid, an amide (e.g., C(O)NH-(alkyl) (e.g., C(O)NHCH$_3$, C(O)NHCH$_2$CH$_3$, etc.), C(O)NH-(cycloalkyl), C(O)NH-(alkyl-cycloalkyl) (e.g., C(O)NHCH$_2$(C$_6$H$_{11}$), C(O)NHCH$_2$(C$_5$H$_9$), C(O)NHCH$_2$CH$_2$(C$_6$H$_{11}$), C(O)

NHCH$_2$CH$_2$(C$_5$H$_9$), etc.), C(O)NH-(heteroalkyl) (e.g., C(O)NHCH$_2$CH$_2$N(CH$_2$)$_2$, C(O)NHCH$_2$N(CH$_2$)$_2$, C(O)NHCH$_2$NHCH$_2$CH$_3$, C(O)NHCH$_2$NHCH$_3$, C(O)NHCH$_2$OCH$_2$CH$_3$, C(O)NHCH$_2$CH$_2$OCH$_3$, C(O)NHCH$_2$SCH$_2$CH$_3$, C(O)NHCH$_2$CH$_2$SCH$_3$, etc.), C(O)NH-(heterocycle), C(O)NH-(alkyl-heterocycle) (e.g., C(O)NHCH$_2$(C$_5$H$_9$O), C(O)NHCH$_2$CH$_2$(C$_5$H$_9$O), C(O)NHCH$_2$(C$_5$H$_9$S), C(O)NHCH$_2$CH$_2$(C$_5$H$_9$S), C(O)NHCH$_2$(C$_5$H$_{10}$N), C(O)NHCH$_2$CH$_2$(C$_5$H$_{10}$N), etc.), and other suitable bioisosteres of a carboxylic acid substituent.

In some embodiments, other suitable bioisosteres of a carboxylic acid substituent include, but are not limited to:

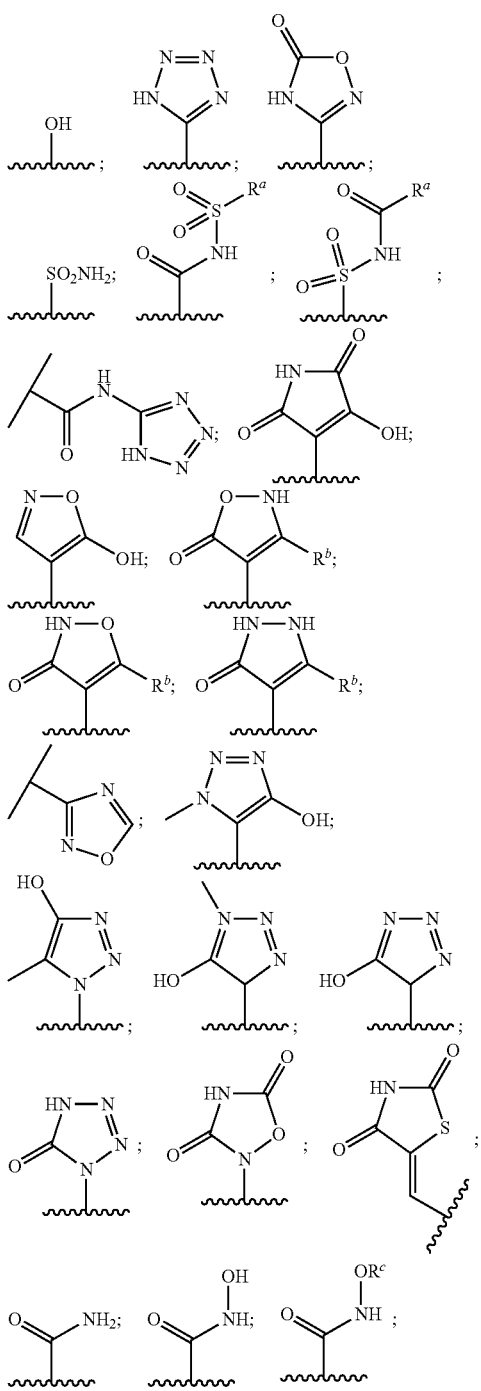

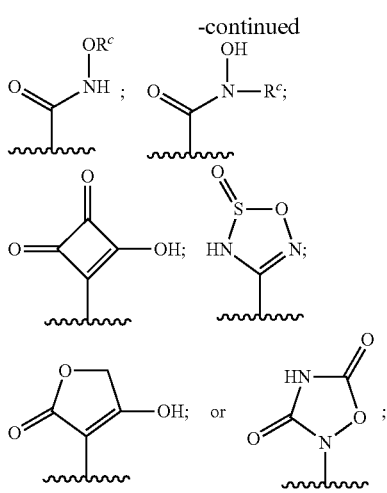

wherein $R^a$, $R^b$ and $R^c$ are independently selected from —CF$_3$, —CH$_3$, phenyl, or benzyl, with the phenyl or benzyl groups being optionally substituted by from 1 to 3 groups selected from C$_6$ alkyl, alkoxy, C$_6$ thioalkyl, CF$_3$, halogen, —OH, or —COOH.

In some embodiments, R$_3$ of a Formula (III) is selected from: cycloalkyl, heterocycle (e.g., tetrazole), aryl, heteroaryl, NH—(CH$_2$)$_m$-cycloalkyl, NH—(CH$_2$)$_m$-heterocycle, NH—(CH$_2$)$_m$-aryl, and NH—(CH$_2$)$_m$-heteroaryl; wherein m is 0-6 (e.g., 0, 1, 2, 3, 4, 5, 6, or any ranges therebetween). In some embodiments, cycloalkyl, heterocycle, aryl, and/or heteroaryl ring groups may be further substituted, for example, with an alkyl group (e.g., methyl, ethyl, propyl, etc.), an alcohol (e.g., OH, CH$_2$OH, (CH$_2$)$_2$OH, etc.), amine (e.g., NH$_2$, CH$_2$NH$_2$, (CH$_2$)$_2$NH$_2$, etc.), CN, halogen, etc.

In some embodiments, R$_8$ of a Formula (III) is selected from: H, Br, Cl, F, I, D (deuterium), alkane (e.g., methyl, ethyl, propyl, isopropyl, butyl, etc.), haloalkane (e.g., monohaloalkane (e.g., CH$_2$F, CH$_2$CH$_2$Cl, CHBrCH$_3$, etc.), dihaloalkane (e.g., CF$_2$H, CH$_2$CCl$_2$H, etc.), trihaloalkane (e.g., CBr$_3$, CF$_3$, CCl$_3$, CH$_2$CBr$_3$, CH$_2$CF$_3$, CH$_2$CCl$_3$, etc.)), trihalomethyl-cycloalkyl (e.g., 1-(trifluoromethyl)cyclopropyl (e.g., R$_7$ of compound 84) 1-(trichloromethyl)cyclohexane, etc.), alkene (e.g. CH═CH$_2$, etc.), alkyne (e.g. C≡CH, etc), amine (e.g., NH$_2$, NH-alkyl (e.g., NH-methyl, NH-ethyl, NH—CH$_2$-Ph, etc.), alkyl-amine (e.g., (CH$_2$)$_{1-6}$—NH$_2$), alkyl-amine-alkyl (e.g., (CH$_2$)$_{1-6}$—NH$_2$—(CH$_2$)$_{1-5}$CH$_3$, etc.), (CH$_2$)$_{1-6}$—N(CH$_3$)$_2$, alkene-N(CH$_3$)$_2$, alkyne-N(CH$_3$)$_2$, N(CH$_3$)$_2$, O-alkyl (e.g., OCH$_3$, OCH$_2$CH$_3$, etc.), NH-alcohol (e.g., NH—CH$_2$—CH$_2$—OH), etc.), hydroxy (e.g. —OH), an alcohol (e.g., (CH$_2$)$_{1-6}$OH, CH$_2$CHOHCH$_2$OH, etc.), cycloalkyl (e.g., cyclopropyl, cyclobutyl, cyclopentyl, cyclohexyl, cycloheptyl, etc.), alkyl-cycloalkyl (e.g., (CH$_2$)$_{1-6}$-cyclopropyl, (CH$_2$)$_{1-6}$-cyclobutyl, (CH$_2$)$_{1-6}$-cyclopentyl, (CH$_2$)$_{1-6}$-cyclohexyl, (CH$_2$)$_{1-6}$-cycloheptyl, etc.), alkene-cycloalkyl (e.g., (CH)$_2$-cyclopropyl, (CH)$_2$-cyclobutyl, (CH)$_2$-cyclopentyl, (CH)$_2$-cyclohexyl (e.g., compound 155), (CH)$_2$-cycloheptyl, etc.), cycloalkene (e.g., cyclopropenyl, cyclobutenyl, cyclopentenyl (e.g., R$_7$ of compound 153), cyclohexenyl (e.g., R$_7$ of compound 154), cycloheptenyl, etc.), alkyl-cycloalkenyl (e.g., (CH$_2$)$_{1-6}$-cyclopropenyl, (CH$_2$)$_{1-6}$-cyclobutenyl, (CH$_2$)$_{1-6}$-cyclopentenyl, (CH$_2$)$_{1-6}$-cyclohexenyl, (CH$_2$)$_{1-6}$-cycloheptenyl, etc.), alkene-cycloalkenyl (e.g., (CH)$_2$-cyclopropenyl, (CH)$_2$-cyclobutenyl, (CH)$_2$-cyclopentenyl, (CH)$_2$-cyclohexenyl, (CH)$_2$-cycloheptenyl, etc.), and (CH$_2$)$_{0-6}$-heterocycle (e.g., non-aromatic heterocycle (e.g., aziridine, thiirane, oxirane, oxaziridine, dioxirane, azetidine, oxetane, thietane, diazetidine, dioxetane, dithietane, pyrrolidine, tetrahydrofuran, thiolane, imidazolidine, pyrazolidine, oxazolidine, isoxazolidine, thiazolidine, isothiazolidine, dioxolane, dithiolane, piperdine, oxane, thiane, piperazine, morpholine, thiomorpholine, dioxane, dithiane, trioxane, thithiane, azepane, oxepane, thiepane, homopiperazine, azocane, etc.), heteroaryl (e.g., pyrrole, furan, thiophene, imidazole, oxazole, thiazole, pyrazole, pyridine, pyrazine, pyridazine, pyrimidine, etc.), unsaturated non-aromatic rings, etc.).

In some embodiments, in which $R_8$ of Formula (III) comprises a cyclic group (e.g., non-aromatic cycloalkane, non-aromatic heterocycle, aryl, heteroaryl, unsaturated non-aromatic, etc.) attached directly to $C_8$ or attached to $C_8$ by a linker (e.g., alkane, heteroalkyl, etc.), the cyclic group is further substituted at one or more positions. Suitable substituents off a $R_8$ cyclic group include, but are not limited to: CH$_3$, CH$_2$CH$_3$, CHCH$_2$, NH$_2$, OH, COH, COCH$_3$, Br, Cl, F, N(CH$_3$)$_2$, CN, CH(CH$_3$)$_2$, CH—(CH$_2$CH$_3$)$_2$, CF$_3$, CCl$_3$, CBr$_3$, CHF$_2$, CHCl$_2$, CHBr$_2$, CFH$_2$, CClH$_2$, CBRH$_2$, etc. In some embodiments, when possible, a single position (e.g., carbon) on a cyclic group at $R_8$ may comprise two non-hydrogen substituents (e.g., two of the aforementioned suitable substituents (e.g., F and F (difluoro), Br and CH$_3$, OH and OH (diol), CH$_3$ and CH$_3$ (dimethyl), etc.)).

In some embodiments, $R_8$ of Formula (III) is -G-$R_{11}$. In some embodiments, G of any Formula (III) having a G-$R_{11}$ is a cyclic group (e.g., saturated non-aromatic ring, aromatic ring, unsaturated non-aromatic ring, non-aromatic heterocycle, heteroaryl, etc.). In some embodiments, G is selected from:

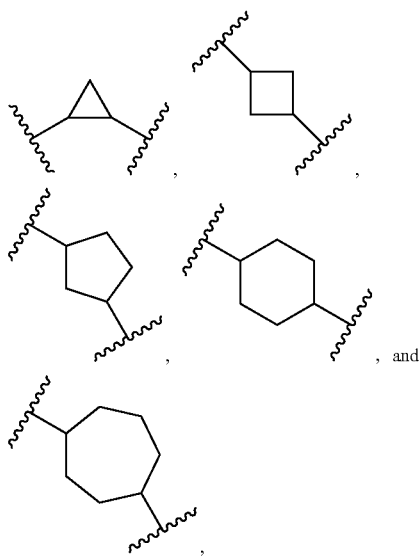

wherein G connects the formula scaffold to $R_{11}$.

In certain embodiments, G is a 4-, 5-, 6-, 7- or 8-membered saturated heterocycle. In some embodiments, G is selected from azetidine, oxetane, piperidine, oxane, piperazine, pyrrolidine, tetrahydrofuran, thiolane, imidazolidine, morpholine, thiomorpholine, azepane, and homopiperazine. In some embodiments, G is selected from:

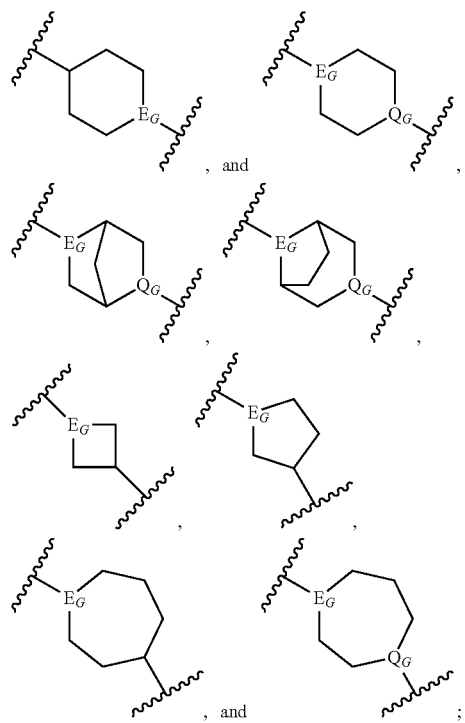

wherein $E_G$ and $Q_G$ are independently selected from C, O, S, and N, and Z may adopt either orientation with respect to connection to $R_{11}$ and the formula scaffold. In some embodiments, $E_G$ and $Q_G$ are independently selected from O, S, and N.

In certain embodiments, for a compound or salt of any Formula (III) having a -G-$R_{11}$ group, G is selected from an unsaturated, aromatic, or heteroaromatic ring. In particular embodiments, G is selected from phenyl, pyridine, pyrazine, pyrimidine, pyridazine, naphthalene, anthracene, quinoline, isoquinoline, quinoxaline, acridine, quinazoline, cinnoline, phthalazine, furan, dihydrofuran, thiophene, dihydrothiophene, imidazole, imidazoline, oxazole, oxazoline, pyrrole, dihydropyrrole, thiazole, dihydrothiazole, pyrazole, dihydropyrazole, isoxazole, dihydroisoxazole, isothiazole, dihydroisothiazole, benzofuran, isobenzofuran, indole, isoindole, benzothiophene, benzimidazole, purine, indazole, benzoxazole, benzisoxazole, and benzothiazole. In some embodiments, G is selected from:

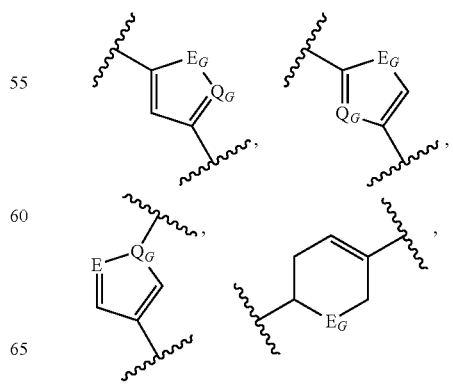

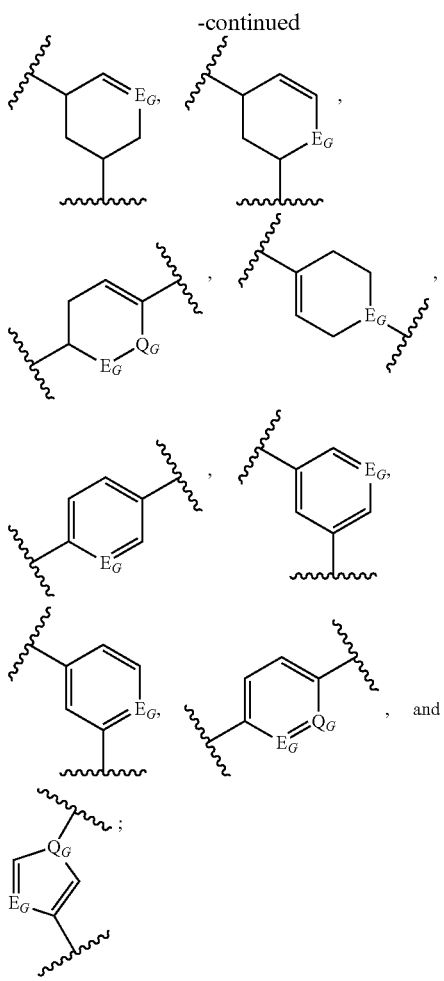

wherein $E_G$ and $G_G$ are independently selected from C, O, S, and N (or O, S, and N, but not C), and G may adopt either orientation with respect to connection to $R_{11}$ and the scaffold of any Formula (III) having a -G-$R_{11}$ group.

In some embodiments, $R_{11}$ of any Formula (III) having a -G-$R_{11}$ group is selected from: H, Br, Cl, F, I, D (deuterium), CN, alkane (e.g., methyl, ethyl, propyl, isopropyl, butyl, etc.), haloalkane (e.g., monohaloalkane (e.g., $CH_2F$, $CH_2CH_2Cl$, $CHBrCH_3$, etc.), dihaloalkane (e.g., $CF_2H$, $CH_2CCl_2H$, etc.), trihaloalkane (e.g., $CBr_3$, $CF_3$, $CCl_3$, $CH_2CBr_3$, $CH_2CF_3$, $CH_2CCl_3$, etc.)), alkene (e.g. $CH=CH_2$, etc.), alkyne (e.g. C≡CH, etc), amine (e.g., $NH_2$, NH-alkyl (e.g., NH-methyl, NH-ethyl, NH—$CH_2$-Ph, etc.), alkyl-amine (e.g., $(CH_2)_{1-6}$—$NH_2$), alkyl-amine-alkyl (e.g., $(CH_2)_{1-6}$—$NH_2$—$(CH_2)_{1-5}CH_3$, etc.), $(CH_2)_{1-6}$—$N(CH_3)_2$, alkene-$N(CH_3)_2$, alkyne-$N(CH_3)_2$, $N(CH_3)_2$, O-alkyl (e.g., $OCH_3$, $OCH_2CH_3$, etc.), NH-alcohol (e.g., NH—$CH_2$—$CH_2$—OH), etc.), hydroxy (e.g. —OH), and an alcohol (e.g., methanol, ethanol, butanol, propanol, $CH_2CHOHCH_2OH$, etc.).

In some embodiments, G of any Formula (III) having a -G-$R_{11}$ group is further substituted at one or more additional ring positions (e.g., in addition to the $R_{11}$ substitution). Additional substituents on the G ring may include: Br, Cl, F, I, CN, alkane (e.g., methyl, ethyl, propyl, isopropyl, butyl, etc.), haloalkane (e.g., monohaloalkane (e.g., $CH_2F$, $CH_2CH_2Cl$, $CHBrCH_3$, etc.), dihaloalkane (e.g., $CF_2H$, $CH_2CCl_2H$, etc.), trihaloalkane (e.g., $CBr_3$, $CF_3$, $CCl_3$, $CH_2CBr_3$, $CH_2CF_3$, $CH_2CCl_3$, etc.)), alkene (e.g. $CH=CH_2$, etc.), alkyne (e.g. C≡CH, etc), amine (e.g., $NH_2$, NH-alkyl (e.g., NH-methyl, NH-ethyl, NH—$CH_2$-Ph, etc.), alkyl-amine (e.g., $(CH_2)_{1-6}$—$NH_2$), alkyl-amine-alkyl (e.g., $(CH_2)_{1-6}$—$NH_2$—$(CH_2)_{1-5}CH_3$, etc.), $(CH_2)_{1-6}$—$N(CH_3)_2$, alkene-$N(CH_3)_2$, alkyne-$N(CH_3)_2$, $N(CH_3)_2$, O-alkyl (e.g., $OCH_3$, $OCH_2CH_3$, etc.), NH-alcohol (e.g., NH—$CH_2$—$CH_2$—OH), etc.), hydroxy (e.g. —OH), and an alcohol (e.g., methanol, ethanol, butanol, propanol, $CH_2CHOHCH_2OH$, etc.).

In some embodiments, A, X, L, and Y of Formula (III) are independently selected from: C, O, N, and S. In embodiments in which any of A, X, L, and/or Y are O or S, the position is not further substituted. In embodiments in which any of A, X, L, and/or Y is C or N, the position may comprise, one or two additional substituents selected from: H, D, $CH_3$, $CH_2CH_3$, $CHCH_2$, $NH_2$, OH, COH, $COCH_3$, Br, Cl, F, $N(CH_3)_2$, CN, $CH(CH_3)_2$, $CH(CH_2CH_3)_2$, $CF_3$, $CCl_3$, $CBr_3$, $CHF_2$, $CHCl_2$, $CHBr_2$, $CFH_2$, $CClH_2$, $CBrH_2$, etc. In some embodiments, X is O.

In some embodiments, J of Formula (III) is selected from: C, O, S, and N. In some embodiments, J is C. In some embodiments, J is N.

In some embodiments, depending upon the identity of Y, X, A, J, L, and $R_8$ of Formula (III), the double bonds of the ring systems are adjusted accordingly to maintain the aromaticity of the terminal rings of the 3-ring system (as is understood by one in the field). In embodiments in which A, J, L, and/or Y is N, the A, L, J, and/or Y position is not further substituted. In embodiments in which A, J, L, and/or Y is C, the A, L, J, and/or Y position comprises an substituent selected from: H, D, $CH_3$, $CH_2CH_3$, $CHCH_2$, $NH_2$, OH, COH, $COCH_3$, Br, Cl, F, $N(CH_3)_2$, CN, $CH(CH_3)_2$, $CH(CH_2CH_3)_2$, $CF_3$, $CCl_3$, $CBr_3$, $CHF_2$, $CHCl_2$, $CHBr_2$, $CFH_2$, $CClH_2$, $CBrH_2$, etc. In some embodiments, A, L, J, and Y of Formula (III) are independently selected from C and N. In some embodiments, A, M, J, and L are C and Y is N. In some embodiments, A and Y are N and J, and L are C. In some embodiments, Y is N and J, A and L are C. In some embodiments, J and Y are N and A and L are C. In some embodiments, L and Y are N and J and A are C. In some embodiments, J, L and Y are N A is C. In some embodiments, J and A are C and L, and Y are N. In some embodiments, A is C and J, L, and Y are N. Any other suitable combinations of Y, X, A, J, and L are within the scope herein.

In some embodiments, any or all hydrogens (e.g., exchangeable hydrogens, non-exchangeable hydrogens, and/or both) on a compound of Formula (III) and substituents thereof may be substituted for deuterium atoms. In some embodiments, any of the hydrogens in the structures, formulas, or substituents described herein, or any subsets thereof, are substituted for deuterium atoms (D).

In certain embodiments, provided herein are compounds represented by a structure of Formula (IV):

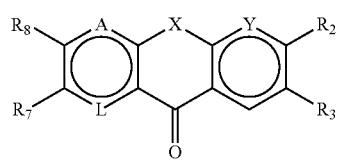

In some embodiments, $R_2$ of Formula (IV) is selected from: $CH_3$, $NH_2$, $NHCH_3$, OH, $NH(CH_2)_2OH$, $NH(CH_2)_3OH$, amidino, F, Br, and Cl, and other suitable bioisosters of $NH_2$.

In some embodiments, $R_2$ of Formula (IV) is selected from: cycloalkyl, heterocycle, aryl, heteroaryl, NH—($CH_2)_m$-cycloalkyl, NH—$(CH_2)_m$-heterocycle (e.g., $R_2$ of compound 147), NH—$(CH_2)_m$-aryl, and NH—$(CH_2)_m$-heteroaryl; wherein m is 0-6 (e.g., 0, 1, 2, 3, 4, 5, 6, or any ranges therebetween). In some embodiments, cycloalkyl, heterocycle, aryl, and/or heteroaryl ring groups may be further substituted (e.g., $R_2$ of compound 148), for example, with an alkyl group (e.g., methyl, ethyl, propyl, etc.), an alcohol (e.g., OH, $CH_2OH$, $(CH_2)_2OH$, etc.), amine (e.g., $NH_2$, $CH_2NH_2$, $(CH_2)_2NH_2$, etc.), CN, halogen, etc.

In some embodiments, $R_3$ of a Formula (IV) is selected from: a carboxylic acid (e.g., C(O)OH), an alcohol (e.g., OH, $CH_2OH$, $(CH_2)_2OH$, etc.), an ester (e.g., $CO_2CH_3$, $CO_2Et$, etc.), a hydroxamic acid (e.g., C(O)N(OH)H), a phosphoric acid (e.g., P(O)(OH)$_2$), a phosphinic acid (e.g., P(O)(OH)H), a sulphonic acid (e.g., S(O)(O)OH), a sulfonamide (e.g., S(O)(O)NH$_2$), an acylsulfonamide (e.g., C(O)NHS(O)(O)H), C(O)NHS(O)(O)CH$_3$), C(O)NHS(O)(O)NH$_2$), a sulfonylurea (e.g., NHC(O)NHS(O)(O)CH$_3$), a tetrazole, a thiazolidinedione, an oxazolidinedione, 5-oxo-1,2,4-oxadiazole, 5-oxo-1,2,4-thiadiazole, 5-thioxo-1,2,4-thiadiazole, an isothiazole, an isoxazole, a difluorophenol, tetramic acid, tetronic acid, cyclopentane-1,3-dione, a squaric acid, an amide (e.g., C(O)NH-(alkyl) (e.g., C(O)NHCH$_3$, C(O)NHCH$_2$CH$_3$, etc.), C(O)NH-(cycloalkyl), C(O)NH-(alkyl-cycloalkyl) (e.g., C(O)NHCH$_2$(C$_6$H$_{11}$), C(O)NHCH$_2$(C$_5$H$_9$), C(O)NHCH$_2$CH$_2$(C$_6$H$_{11}$), C(O)NHCH$_2$CH$_2$(C$_5$H$_9$), etc.), C(O)NH-(heteroalkyl) (e.g., C(O)NHCH$_2$CH$_2$N(CH$_2$)$_2$, C(O)NHCH$_2$N(CH$_2$)$_2$, C(O)NHCH$_2$NHCH$_2$CH$_3$, C(O)NHCH$_2$NHCH$_3$, C(O)NHCH$_2$OCH$_2$CH$_3$, C(O)NHCH$_2$CH$_2$OCH$_3$, C(O)NHCH$_2$SCH$_2$CH$_3$, C(O)NHCH$_2$CH$_2$SCH$_3$, etc.), C(O)NH-(heterocycle), C(O)NH-(alkyl-heterocycle) (e.g., C(O)NHCH$_2$(C$_5$H$_9$O), C(O)NHCH$_2$CH$_2$(C$_5$H$_9$O), C(O)NHCH$_2$(C$_5$H$_9$S), C(O)NHCH$_2$CH$_2$(C$_5$H$_9$S), C(O)NHCH$_2$(C$_5$H$_{10}$N), C(O)NHCH$_2$CH$_2$(C$_5$H$_{10}$N), etc.), and other suitable bioisosteres of a carboxylic acid substituent.

In some embodiments, other suitable bioisosteres of a carboxylic acid substituent include, but are not limited to:

wherein $R^a$, $R^b$ and $R^c$ are independently selected from —CF$_3$, —CH$_3$, phenyl, or benzyl, with the phenyl or benzyl groups being optionally substituted by from 1 to 3 groups selected from C$_6$ alkyl, alkoxy, C$_6$ thioalkyl, CF$_3$, halogen, —OH, or —COOH.

In some embodiments, $R_3$ of a Formula (IV) is selected from: cycloalkyl, heterocycle (e.g., tetrazole), aryl, heteroaryl, NH—$(CH_2)_m$-cycloalkyl, NH—$(CH_2)_m$-heterocycle, NH—$(CH_2)_m$-aryl, and NH—$(CH_2)_m$-heteroaryl; wherein m is 0-6 (e.g., 0, 1, 2, 3, 4, 5, 6, or any ranges therebetween). In some embodiments, cycloalkyl, heterocycle, aryl, and/or heteroaryl ring groups may be further substituted, for example, with an alkyl group (e.g., methyl, ethyl, propyl, etc.), an alcohol (e.g., OH, CH$_2$OH, (CH$_2$)$_2$OH, etc.), amine (e.g., NH$_2$, CH$_2$NH$_2$, (CH$_2$)$_2$NH$_2$, etc.), CN, halogen, etc.

In some embodiments, R$_7$ of Formula (IV) is selected from: H, Br, Cl, F, I, D (deuterium), alkane (e.g., methyl, ethyl, propyl, isopropyl, butyl, etc.), haloalkane (e.g., monohaloalkane (e.g., CH$_2$F, CH$_2$CH$_2$Cl, CHBrCH$_3$, etc.), dihaloalkane (e.g., CF$_2$H, CH$_2$CCl$_2$H, etc.), trihaloalkane (e.g., CBr$_3$, CF$_3$, CCl$_3$, CH$_2$CBr$_3$, CH$_2$CF$_3$, CH$_2$CCl$_3$, etc.)), trihalomethyl-cycloalkyl (e.g., 1-(trifluoromethyl)cyclopropyl (e.g., R$_7$ of compound 84) 1-(trichloromethyl)cyclohexane, etc.), alkene (e.g. CH=CH$_2$, etc.), alkyne (e.g. C≡CH, etc), amine (e.g., NH$_2$, NH-alkyl (e.g., NH-methyl, NH-ethyl, NH—CH$_2$-Ph, etc.), alkyl-amine (e.g., (CH$_2$)$_{1-6}$—NH$_2$), alkyl-amine-alkyl (e.g., (CH$_2$)$_{1-6}$—NH$_2$—(CH$_2$)$_{1-5}$CH$_3$, etc.), (CH$_2$)$_{1-6}$—N(CH$_3$)$_2$, alkene-N(CH$_3$)$_2$, alkyne-N(CH$_3$)$_2$, N(CH$_3$)$_2$, O-alkyl (e.g., OCH$_3$, OCH$_2$CH$_3$, etc.), NH-alcohol (e.g., NH—CH$_2$—CH$_2$—OH), etc.), hydroxy (e.g. —OH), an alcohol (e.g., (CH$_2$)$_{1-6}$OH, CH$_2$CHOHCH$_2$OH, etc.), cycloalkyl (e.g., cyclopropyl, cyclobutyl, cyclopentyl, cyclohexyl, cycloheptyl, etc.), alkyl-cycloalkyl (e.g., (CH$_2$)$_{1-6}$-cyclopropyl, (CH$_2$)$_{1-6}$-cyclobutyl, (CH$_2$)$_{1-6}$-cyclopentyl, (CH$_2$)$_{1-6}$-cyclohexyl, (CH$_2$)$_{1-6}$-cycloheptyl, etc.), alkene-cycloalkyl (e.g., (CH)$_2$-cyclopropyl, (CH)$_2$-cyclobutyl, (CH)$_2$-cyclopentyl, (CH)$_2$-cyclohexyl (e.g., compound 155), (CH)$_2$-cycloheptyl, etc.), cycloalkene (e.g., cyclopropenyl, cyclobutenyl, cyclopentenyl (e.g., R$_7$ of compound 153), cyclohexenyl (e.g., R$_7$ of compound 154), cycloheptenyl, etc.), alkyl-cycloalkenyl (e.g., (CH$_2$)$_{1-6}$-cyclopropenyl, (CH$_2$)$_{1-6}$-cyclobutenyl, (CH$_2$)$_{1-6}$-cyclopentenyl, (CH$_2$)$_{1-6}$-cyclohexenyl, (CH$_2$)$_{1-6}$-cycloheptenyl, etc.), alkene-cycloalkenyl (e.g., (CH)$_2$-cyclopropenyl, (CH)$_2$-cyclobutenyl, (CH)$_2$-cyclopentenyl, (CH)$_2$-cyclohexenyl, (CH)$_2$-cycloheptenyl, etc.), and (CH$_2$)$_{0-6}$-heterocycle (e.g., non-aromatic heterocycle (e.g., aziridine, thiirane, oxirane, oxaziridine, dioxirane, azetidine, oxetane, thietane, diazetidine, dioxetane, dithietane, pyrrolidine, tetrahydrofuran, thiolane, imidazolidine, pyrazolidine, oxazolidine, isoxazolidine, thiazolidine, isothiazolidine, dioxolane, dithiolane, piperdine, oxane, thiane, piperazine, morpholine, thiomorpholine, dioxane, dithiane, trioxane, thithiane, azepane, oxepane, thiepane, homopiperazine, azocane, etc.), heteroaryl (e.g., pyrrole, furan, thiophene, imidazole, oxazole, thiazole, pyrazole, pyridine, pyrazine, pyridazine, pyrimidine, etc.), unsaturated non-aromatic rings, etc.).

In some embodiments, in which R$_7$ of a Formula (IV) comprises a cyclic group (e.g., non-aromatic cycloalkane, non-aromatic heterocycle, aryl, heteroaryl, unsaturated non-aromatic, etc.) attached directly to C$_7$ or attached to C$_7$ by a linker (e.g., alkane, heteroalkyl, etc.), the cyclic group is further substituted at one or more positions. Suitable substituents off a R$_7$ cyclic group include, but are not limited to: CH$_3$, CH$_2$CH$_3$, CHCH$_2$, NH$_2$, OH, COH, COCH$_3$, Br, Cl, F, N(CH$_3$)$_2$, CN, CH(CH$_3$)$_2$, CH(CH$_2$CH$_3$)$_2$, CF$_3$, CCl$_3$, CBr$_3$, CHF$_2$, CHCl$_2$, CHBr$_2$, CFH$_2$, CClH$_2$, CBRH$_2$, etc. In some embodiments, when possible, a single position (e.g., carbon) on a cyclic group at R$_7$ may comprise two non-hydrogen substituents (e.g., two of the aforementioned suitable substituents (e.g., F and F (difluoro), Br and CH$_3$, OH and OH (diol). CH$_3$ and CH$_3$ (dimethyl), etc.)).

In some embodiments, R$_7$ of Formula (IV) is —Z—R$_{10}$. In some embodiments, Z of Formula (IV) is a cyclic group (e.g., saturated non-aromatic ring, aromatic ring, unsaturated non-aromatic ring, non-aromatic heterocycle, heteroaryl, etc.).

In some embodiments, Z of Formula (IV) is selected from:

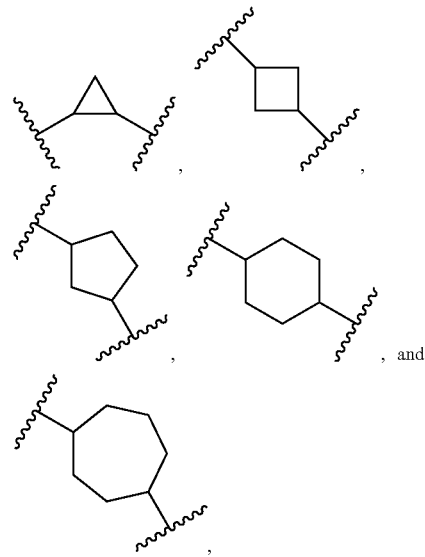

, and wherein Z connects the formula scaffold to R$_{10}$.

In certain embodiments, Z is a 4-, 5-, 6-, 7- or 8-membered saturated heterocycle. In some embodiments, Z is selected from azetidine, oxetane, piperidine, oxane, piperazine, pyrrolidine, tetrahydrofuran, thiolane, imidazolidine, morpholine, thiomorpholine, azepane, and homopiperazine. In some embodiments, Z is selected from:

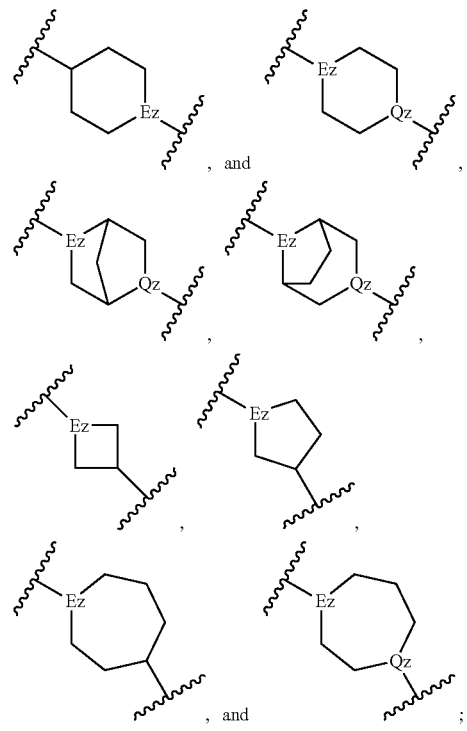

, and wherein Ez and Qz are independently selected from C, O, S, and N, and Z may adopt either orientation with respect to connection to $R_{10}$ and the formula scaffold. In some embodiments, Ez and Qz are independently selected from O, S, and N.

In certain embodiments, for a compound or salt of Formula (IV) having a —Z—$R_{10}$ group, Z is selected from an unsaturated, aromatic, or heteroaromatic ring. In particular embodiments, Z is selected from phenyl, pyridine, pyrazine, pyrimidine, pyridazine, naphthalene, anthracene, quinoline, isoquinoline, quinoxaline, acridine, quinazoline, cinnoline, phthalazine, furan, dihydrofuran, thiophene, dihydrothiophene, imidazole, imidazoline, oxazole, oxazoline, pyrrole, dihydropyrrole, thiazole, dihydrothiazole, pyrazole, dihydropyrazole, isoxazole, dihydroisoxazole, isothiazole, dihydroisothiazole, benzofuran, isobenzofuran, indole, isoindole, benzothiophene, benzimidazole, purine, indazole, benzoxazole, benzisoxazole, and benzothiazole. In some embodiments, Z is selected from:

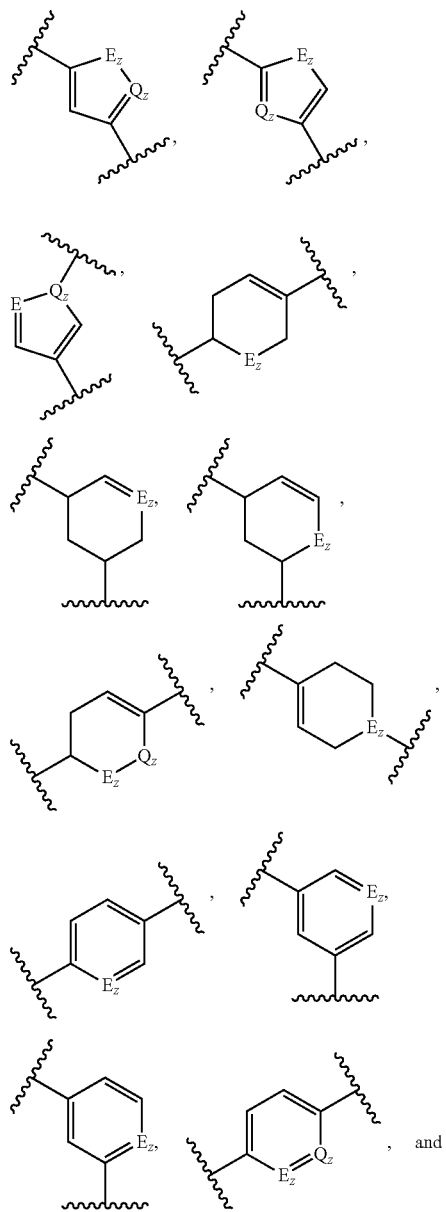

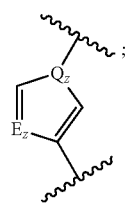

wherein Ez and Gz are independently selected from C, O, S, and N (or O, S, and N, but not C), and Z may adopt either orientation with respect to connection to $R_{10}$ and the scaffold of any Formula (IV) having a —Z—$R_{10}$ group.

In some embodiments, $R_{10}$ of any Formula (IV) having a —Z—$R_{10}$ group is selected from: H, Br, Cl, F, I, D (deuterium), CN, alkane (e.g., methyl, ethyl, propyl, isopropyl, butyl, etc.), haloalkane (e.g., monohaloalkane (e.g., $CH_2F$, $CH_2CH_2Cl$, $CHBrCH_3$, etc.), dihaloalkane (e.g., $CF_2H$, $CH_2CCl_2H$, etc.), trihaloalkane (e.g., $CBr_3$, $CF_3$, $CCl_3$, $CH_2CBr_3$, $CH_2CF_3$, $CH_2CCl_3$, etc.)), alkene (e.g. $CH{=}CH_2$, etc.), alkyne (e.g. $C{\equiv}CH$, etc), amine (e.g., $NH_2$, NH-alkyl (e.g., NH-methyl, NH-ethyl, NH—$CH_2$-Ph, etc.), alkyl-amine (e.g., $(CH_2)_{1-6}$—$NH_2$), alkyl-amine-alkyl (e.g., $(CH_2)_{1-6}$—$NH_2$—$(CH_2)_{1-5}CH_3$, etc.), $(CH_2)_{1-6}$—$N(CH_3)_2$, alkene-$N(CH_3)_2$, alkyne-$N(CH_3)_2$, $N(CH_3)_2$, O-alkyl (e.g., $OCH_3$, $OCH_2CH_3$, etc.), NH-alcohol (e.g., NH—$CH_2$—$CH_2$—OH), etc.), hydroxy (e.g. —OH), and an alcohol (e.g., methanol, ethanol, butanol, propanol, $CH_2CHOHCH_2OH$, etc.).

In some embodiments, Z of any Formula (IV) having a —Z—$R_{10}$ group is further substituted at one or more additional ring positions (e.g., in addition to the $R_{10}$ substitution). Additional substituents on the Z ring may include: Br, Cl, F, I, CN, alkane (e.g., methyl, ethyl, propyl, isopropyl, butyl, etc.), haloalkane (e.g., monohaloalkane (e.g., $CH_2F$, $CH_2CH_2Cl$, $CHBrCH_3$, etc.), dihaloalkane (e.g., $CF_2H$, $CH_2CCl_2H$, etc.), trihaloalkane (e.g., $CBr_3$, $CF_3$, $CCl_3$, $CH_2CBr_3$, $CH_2CF_3$, $CH_2CCl_3$, etc.)), alkene (e.g. $CH{=}CH_2$, etc.), alkyne (e.g. $C{\equiv}CH$, etc), amine (e.g., $NH_2$, NH-alkyl (e.g., NH-methyl, NH-ethyl, NH—$CH_2$-Ph, etc.), alkyl-amine (e.g., $(CH_2)_{1-6}$—$NH_2$), alkyl-amine-alkyl (e.g., $(CH_2)_{1-6}$—$NH_2$—$(CH_2)_{1-5}CH_3$, etc.), $(CH_2)_{1-6}$—$N(CH_3)_2$, alkene-$N(CH_3)_2$, alkyne-$N(CH_3)_2$, $N(CH_3)_2$, O-alkyl (e.g., $OCH_3$, $OCH_2CH_3$, etc.), NH-alcohol (e.g., NH—$CH_2$—$CH_2$—OH), etc.), hydroxy (e.g. —OH), and an alcohol (e.g., methanol, ethanol, butanol, propanol, $CH_2CHOHCH_2OH$, etc.).

In some embodiments, $R_8$ of Formula (IV) is selected from: H, Br, Cl, F, I, D (deuterium), alkane (e.g., methyl, ethyl, propyl, isopropyl, butyl, etc.), haloalkane (e.g., monohaloalkane (e.g., $CH_2F$, $CH_2CH_2Cl$, $CHBrCH_3$, etc.), dihaloalkane (e.g., $CF_2H$, $CH_2CCl_2H$, etc.), trihaloalkane (e.g., $CBr_3$, $CF_3$, $CCl_3$, $CH_2CBr_3$, $CH_2CF_3$, $CH_2CCl_3$, etc.)), trihalomethyl-cycloalkyl (e.g., 1-(trifluoromethyl)cyclopropyl (e.g., $R_7$ of compound 84) 1-(trichloromethyl)cyclohexane, etc.), alkene (e.g. $CH{=}CH_2$, etc.), alkyne (e.g. $C{\equiv}CH$, etc), amine (e.g., $NH_2$, NH-alkyl (e.g., NH-methyl, NH-ethyl, NH—$CH_2$-Ph, etc.), alkyl-amine (e.g., $(CH_2)_{1-6}$—$NH_2$), alkyl-amine-alkyl (e.g., $(CH_2)_{1-6}$—$NH_2$—$(CH_2)_{1-5}CH_3$, etc.), $(CH_2)_{1-6}$—$N(CH_3)_2$, alkene-$N(CH_3)_2$, alkyne-$N(CH_3)_2$, $N(CH_3)_2$, O-alkyl (e.g., $OCH_3$, $OCH_2CH_3$, etc.), NH-alcohol (e.g., NH—$CH_2$—$CH_2$—OH), etc.), hydroxy (e.g. —OH), an alcohol (e.g., $(CH_2)_{1-6}OH$, $CH_2CHOHCH_2OH$, etc.), cycloalkyl (e.g., cyclopropyl, cyclobutyl, cyclopentyl, cyclohexyl, cycloheptyl, etc.), alkyl-cycloalkyl (e.g., $(CH_2)_{1-6}$-cyclopropyl, $(CH_2)_{1-6}$-cyclobutyl, $(CH_2)_{1-6}$-cyclopentyl, $(CH_2)_{1-6}$-cyclohexyl, $(CH_2)_{1-6}$-cycloheptyl, etc.), alkene-cycloalkyl (e.g., $(CH_2)_2$-cyclopropyl, $(CH_2)_2$-cyclobutyl, $(CH_2)_2$-cyclopentyl, $(CH_2)_2$-cyclohexyl (e.g., compound 155), $(CH_2)_2$-cycloheptyl, etc.), cycloalkene (e.g., cyclopropenyl, cyclobutenyl, cyclopentenyl (e.g., $R_7$ of compound 153), cyclohexenyl (e.g., $R_7$ of compound 154), cycloheptenyl, etc.), alkyl-cycloalkenyl (e.g., $(CH_2)_{1-6}$-cyclopropenyl, $(CH_2)_{1-6}$-cyclobutenyl, $(CH_2)_{1-6}$-cyclopentenyl, $(CH_2)_{1-6}$-cyclohexenyl, $(CH_2)_{1-6}$-cycloheptenyl, etc.), alkene-cycloalkenyl (e.g., $(CH_2)_2$-cyclopropenyl, $(CH_2)_2$-cyclobutenyl, $(CH_2)_2$-cyclopentenyl, $(CH_2)_2$-cyclohexenyl, $(CH_2)_2$-cycloheptenyl, etc.), and $(CH_2)_{0-6}$-heterocycle (e.g., non-aromatic heterocycle (e.g., aziridine, thiirane, oxirane, oxaziridine, dioxirane, azetidine, oxetane, thietane, diazetidine, dioxetane, dithietane, pyrrolidine, tetrahydrofuran, thiolane, imidazolidine, pyrazolidine, oxazolidine, isoxazolidine, thiazolidine, isothiazolidine, dioxolane, dithiolane, piperdine, oxane, thiane, piperazine, morpholine, thiomorpholine, dioxane, dithiane, trioxane, thithiane, azepane, oxepane, thiepane, homopiperazine, azocane, etc.), heteroaryl (e.g., pyrrole, furan, thiophene, imidazole, oxazole, thiazole, pyrazole, pyridine, pyrazine, pyridazine, pyrimidine, etc.), unsaturated non-aromatic rings, etc.).

In some embodiments, in which $R_8$ of Formula (IV) comprises a cyclic group (e.g., non-aromatic cycloalkane, non-aromatic heterocycle, aryl, heteroaryl, unsaturated non-aromatic, etc.) attached directly to $C_8$ or attached to $C_8$ by a linker (e.g., alkane, heteroalkyl, etc.), the cyclic group is further substituted at one or more positions. Suitable substituents off a $R_8$ cyclic group include, but are not limited to: $CH_3$, $CH_2CH_3$, $CHCH_2$, $NH_2$, $OH$, $COH$, $COCH_3$, $Br$, $Cl$, $F$, $N(CH_3)_2$, $CN$, $CH(CH_3)_2$, $CH(CH_2CH_3)_2$, $CF_3$, $CCl_3$, $CBr_3$, $CHF_2$, $CHCl_2$, $CHBr_2$, $CFH_2$, $CClH_2$, $CBrH_2$, etc. In some embodiments, when possible, a single position (e.g., carbon) on a cyclic group at $R_8$ may comprise two non-hydrogen substituents (e.g., two of the aforementioned suitable substituents (e.g., F and F (difluoro), Br and $CH_3$, OH and OH (diol), $CH_3$ and $CH_3$ (dimethyl), etc.)).

In some embodiments, R8 of Formula (IV) is -G-$R_{11}$. In some embodiments, G of any Formula (IV) having a G-$R_{11}$ is a cyclic group (e.g., saturated non-aromatic ring, aromatic ring, unsaturated non-aromatic ring, non-aromatic heterocycle, heteroaryl, etc.). In some embodiments, G is selected from:

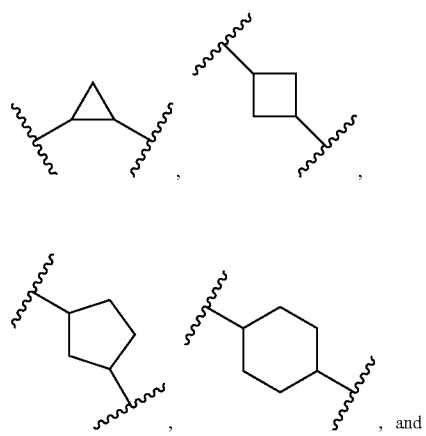

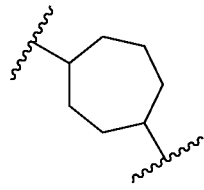

wherein G connects the formula scaffold to $R_{11}$.

In certain embodiments, G is a 4-, 5-, 6-, 7- or 8-membered saturated heterocycle. In some embodiments, G is selected from azetidine, oxetane, piperidine, oxane, piperazine, pyrrolidine, tetrahydrofuran, thiolane, imidazolidine, morpholine, thiomorpholine, azepane, and homopiperazine. In some embodiments, G is selected from:

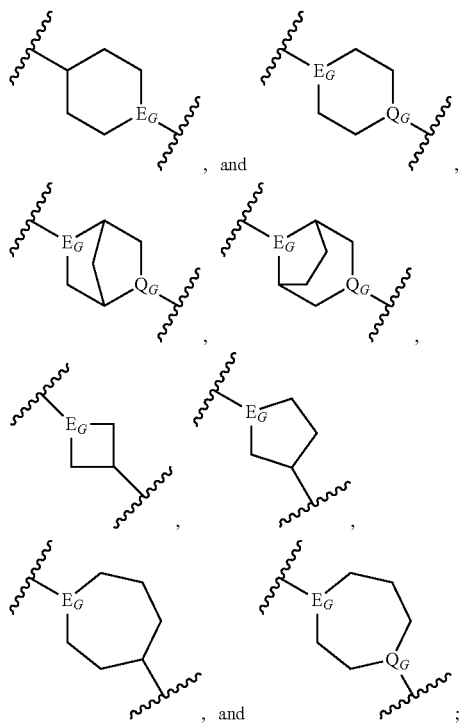

wherein $E_G$ and $Q_G$ are independently selected from C, O, S, and N, and Z may adopt either orientation with respect to connection to $R_{11}$ and the formula scaffold. In some embodiments, $E_G$ and $Q_G$ are independently selected from O, S, and N.

In certain embodiments, for a compound or salt of any Formula (IV) having a -G-$R_{11}$ group, G is selected from an unsaturated, aromatic, or heteroaromatic ring. In particular embodiments, G is selected from phenyl, pyridine, pyrazine, pyrimidine, pyridazine, naphthalene, anthracene, quinoline, isoquinoline, quinoxaline, acridine, quinazoline, cinnoline, phthalazine, furan, dihydrofuran, thiophene, dihydrothiophene, imidazole, imidazoline, oxazole, oxazoline, pyrrole, dihydropyrrole, thiazole, dihydrothiazole, pyrazole, dihydropyrazole, isoxazole, dihydroisoxazole, isothiazole, dihydroisothiazole, benzofuran, isobenzofuran, indole, isoindole, benzothiophene, benzimidazole, purine, indazole, benzoxazole, benzisoxazole, and benzothiazole. In some embodiments, G is selected from:

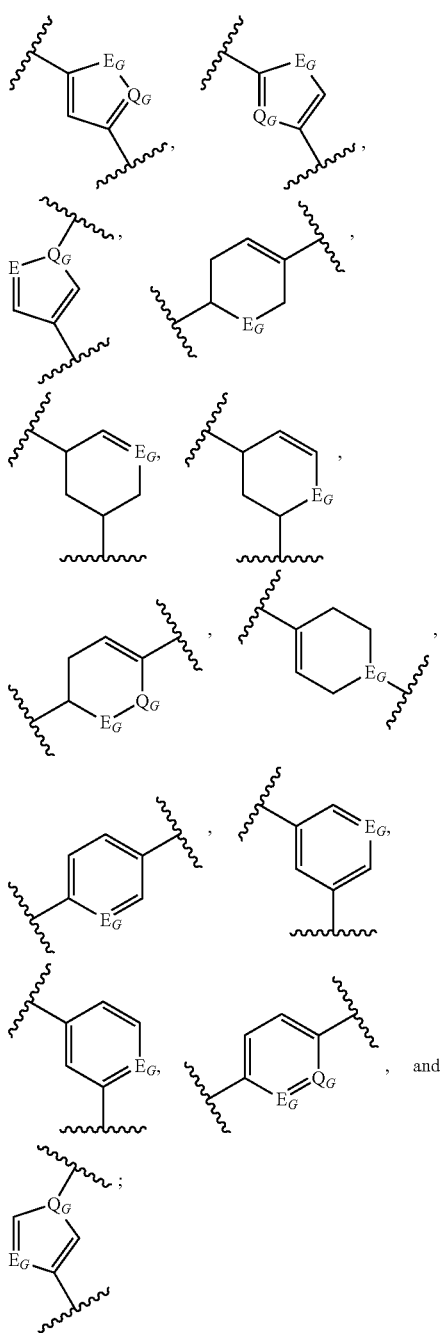

wherein $E_G$ and $G_G$ are independently selected from C, O, S, and N (or O, S, and N, but not C), and G may adopt either orientation with respect to connection to $R_{11}$ and the scaffold of any Formula (IV) having a -G-$R_{11}$ group.

In some embodiments, $R_{11}$ of any Formula (IV) having a -G-$R_{11}$ group is selected from: H, Br, Cl, F, I, D (deuterium), CN, alkane (e.g., methyl, ethyl, propyl, isopropyl, butyl, etc.), haloalkane (e.g., monohaloalkane (e.g., $CH_2F$, $CH_2CH_2Cl$, $CHBrCH_3$, etc.), dihaloalkane (e.g., $CF_2H$, $CH_2CCl_2H$, etc.), trihaloalkane (e.g., $CBr_3$, $CF_3$, $CCl_3$, $CH_2CBr_3$, $CH_2CF_3$, $CH_2CCl_3$, etc.)), alkene (e.g. $CH=CH_2$, etc.), alkyne (e.g. $C\equiv CH$, etc), amine (e.g., $NH_2$, NH-alkyl (e.g., NH-methyl, NH-ethyl, NH—$CH_2$-Ph, etc.), alkyl-amine (e.g., $(CH_2)_{1-6}$—$NH_2$), alkyl-amine-alkyl (e.g., $(CH_2)_{1-6}$—$NH_2$—$(CH_2)_{1-5}CH_3$, etc.), $(CH_2)_{1-6}$—$N(CH_3)_2$, alkene-$N(CH_3)_2$, alkyne-$N(CH_3)_2$, $N(CH_3)_2$, O-alkyl (e.g., $OCH_3$, $OCH_2CH_3$, etc.), NH-alcohol (e.g., NH—$CH_2$—$CH_2$—OH), etc.), hydroxy (e.g. —OH), and an alcohol (e.g., methanol, ethanol, butanol, propanol, $CH_2CHOHCH_2OH$, etc.).

In some embodiments, G of any Formula (IV) having a -G-$R_{11}$ group is further substituted at one or more additional ring positions (e.g., in addition to the $R_{11}$ substitution). Additional substituents on the G ring may include: Br, Cl, F, I, CN, alkane (e.g., methyl, ethyl, propyl, isopropyl, butyl, etc.), haloalkane (e.g., monohaloalkane (e.g., $CH_2F$, $CH_2CH_2Cl$, $CHBrCH_3$, etc.), dihaloalkane (e.g., $CF_2H$, $CH_2CCl_2H$, etc.), trihaloalkane (e.g., $CBr_3$, $CF_3$, $CCl_3$, $CH_2CBr_3$, $CH_2CF_3$, $CH_2CCl_3$, etc.)), alkene (e.g. $CH=CH_2$, etc.), alkyne (e.g. $C\equiv CH$, etc), amine (e.g., $NH_2$, NH-alkyl (e.g., NH-methyl, NH-ethyl, NH—$CH_2$-Ph, etc.), alkyl-amine (e.g., $(CH_2)_{1-6}$—$NH_2$), alkyl-amine-alkyl (e.g., $(CH_2)_{1-6}$—$NH_2$—$(CH_2)_{1-5}CH_3$, etc.), $(CH_2)_{1-6}$—$N(CH_3)_2$, alkene-$N(CH_3)_2$, alkyne-$N(CH_3)_2$, $N(CH_3)_2$, O-alkyl (e.g., $OCH_3$, $OCH_2CH_3$, etc.), NH-alcohol (e.g., NH—$CH_2$—$CH_2$—OH), etc.), hydroxy (e.g. —OH), and an alcohol (e.g., methanol, ethanol, butanol, propanol, $CH_2CHOHCH_2OH$, etc.).

In some embodiments, A, X, L, and Y of Formula (III) are independently selected from: C, O, N, and S. In embodiments in which any of A, X, L, and/or Y are O or S, the position is not further substituted. In embodiments in which any of A, X, L, and/or Y is C or N, the position may comprise, one or two additional substituents selected from: H, D, $CH_3$, $CH_2CH_3$, $CHCH_2$, $NH_2$, OH, COH, $COCH_3$, Br, Cl, F, $N(CH_3)$, CN, $CH(CH_3)_2$, $CH(CH_2CH_3)_2$, $CF_3$, $CCl_3$, $CBr_3$, $CHF_2$, $CHCl_2$, $CHBr_2$, $CFH_2$, $CClH_2$, $CBRH_2$, etc. In some embodiments, X is O.

In some embodiments, depending upon the identity of Y, X, A, L, $R_7$ and $R_8$ of Formula (IV), the double bonds of the ring systems are adjusted accordingly to maintain the aromaticity of the terminal rings of the 3-ring system (as is understood by one in the field). In embodiments in which A, L, and/or Y is N, the A, L, and/or Y position is not further substituted. In embodiments in which A, L, and/or Y is C, the A, M, L, J, and/or Y position comprises an substituent selected from: H, D, $CH_3$, $CH_2CH_3$, $CHCH_2$, $NH_2$, OH, COH, $COCH_3$, Br, Cl, F, $N(CH_3)$, CN, $CH(CH_3)_2$, $CH(CH_2CH_3)_2$, $CF_3$, $CCl_3$, $CBr_3$, $CHF_2$, $CHCl_2$, $CHBr_2$, $CFH_2$, $CClH_2$, $CBRH_2$, etc. In some embodiments, A, L, and Y of Formula (IV) are independently selected from C and N. In some embodiments, A and L are C and Y is N. In some embodiments, A and Y are N and L is C. In some embodiments, Y is N and A and L are C. In some embodiments, L and Y are N and A is C. In some embodiments, J and A are C and Y is N. In some embodiments, A is C and L, and Y are N. Any other suitable combinations of Y, X, A, and L are within the scope herein.

In some embodiments, any or all hydrogens (e.g., exchangeable hydrogens, non-exchangeable hydrogens, and/or both) on a compound of Formula (IV) and substituents thereof may be substituted for deuterium atoms. In some embodiments, any of the hydrogens in the structures, formulas, or substituents described herein, or any subsets thereof, are substituted for deuterium atoms (D).

In certain embodiments, provided herein are compounds represented by a structure of Formula (1):

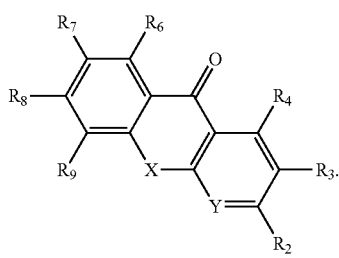

In some embodiments, $R_2$, $R_3$, $R_4$, $R_6$, $R_7$, $R_8$, and $R_9$ of Formula (1) are each independently selected from, for example: H, alkyl, substituted alkyl, hydroxy, alkoxy, amine, thioalkyl, halogen, ketone, amide, cyano, sulfonyl, dialkylphosphine oxide, a carbocyclic ring, an aromatic ring, a substituted aromatic ring, a heterocyclic aromatic ring, a substituted heterocyclic aromatic ring, a substituted or non-substituted heterocyclic non-aromatic ring, carbocyclic or heterocyclic aromatic ring fused to another aromatic ring, a hydrogen bond donor, a hydrogen bond acceptor, and combinations thereof.

In some embodiments, $R_2$ of Formula (1) is selected from: $CH_3$, $NH_2$, $NHCH_3$, OH, $NH(CH_2)_2OH$, $NH(CH_2)_3OH$, amidino, F, Br, and Cl, and other suitable bioisosters of $NH_2$. In some embodiments, $R_2$ of Formula (1) is selected from: cycloalkyl, heterocycle, aryl, heteroaryl, $NH-(CH_2)_m$-cycloalkyl, $NH-(CH_2)_m$-heterocycle (e.g., $R_2$ of compound 147), $NH-(CH_2)_m$-aryl, and $NH-(CH_2)_m$-heteroaryl; wherein m is 0-6 (e.g., 0, 1, 2, 3, 4, 5, 6, or any ranges there between). In some embodiments, cycloalkyl, heterocycle, aryl, and/or heteroaryl ring groups may be further substituted (e.g., $R_2$ of compound 148), for example, with an alkyl group (e.g., methyl, ethyl, propyl, etc.), an alcohol (e.g., OH, $CH_2OH$, $(CH_2)_2OH$, etc.), amine (e.g., $NH_2$, $CH_2NH_2$, $(CH_2)_2NH_2$, etc.), CN, halogen, etc. In some embodiments, $R_2$ is an amidio or substituted (e.g., comprising additional substituent(s) on the terminal nitrogen).

In some embodiments, $R_3$ of Formula (1) is selected from: a carboxylic acid (e.g., COOH), alcohol, tetrazole, ester, amide, heterocycle, etc., or a bioisostere thereof. In some embodiments, $R_3$ of Formula (1) is selected from: a carboxylic acid (e.g., C(O)OH), an alcohol (e.g., $CH_2OH$, $(CH_2)_2OH$, etc.), an ester (e.g., $CO_2CH_3$, $CO_2Et$, etc.) a hydroxamic acid (e.g., C(O)N(OH)H), a phosphoric acid (e.g., $P(O)(OH)_2$), a phosphinic acid (e.g., P(O)(OH)H), a sulphonic acid (e.g., S(O)(O)OH), a sulfonamide (e.g., $S(O)(O)NH_2$), an acylsulfonamide (e.g., C(O)NHS(O)(O)H), $C(O)NHS(O)(O)CH_3$), $C(O)NHS(O)(O)NH_2$), a sulfonylurea (e.g., $NHC(O)NHS(O)(O)CH_3$), a tetrazole, a thiazolidinedione, an oxazolidinedione, 5-oxo-1,2,4-oxadiazole, 5-oxo-1,2,4-thiadiazole, 5-thioxo-1,2,4-thiadiazole, an isothiazole, an isoxazole, a difluorophenol, tetramic acid, tetronic acid, cyclopentane-1,3-dione, a squaric acid, an amide (e.g., C(O)NH-(alkyl) (e.g., $C(O)NHCH_3$, $C(O)NHCH_2CH_3$, etc.), C(O)NH-(cycloalkyl), C(O)NH-(alkyl-cycloalkyl) (e.g., $C(O)NHCH_2(C_6H_{11})$, $C(O)NHCH_2(C_5H_9)$, $C(O)NHCH_2CH_2(C_6H_{11})$, $C(O)NHCH_2CH_2(C_5H_9)$, etc.), C(O)NH-(heteroalkyl) (e.g., $C(O)NHCH_2CH_2N(CH_2)_2$, $C(O)NHCH_2N(CH_2)_2$, $C(O)NHCH_2NHCH_2CH_3$, $C(O)NHCH_2NHCH_3$, $C(O)NHCH_2OCH_2CH_3$, $C(O)NHCH_2CH_2OCH_3$, $C(O)NHCH_2SCH_2CH_3$, $C(O)NHCH_2CH_2SCH_3$, etc.), C(O)NH-(heterocycle), C(O)NH-(alkyl-heterocycle) (e.g., $C(O)NHCH_2(C_5H_9O)$, $C(O)NHCH_2CH_2(C_5H_9O)$, $C(O)NHCH_2(C_5H_9S)$, $C(O)NHCH_2CH_2(C_5H_9S)$, $C(O)NHCH_2$ $(C_5H_{10}N)$, $C(O)NHCH_2CH_2(C_5H_{10}N)$, etc.), and other suitable bioisosteres of a carboxylic acid substituent.

In some embodiments, other suitable bioisosteres of a carboxylic acid substituent include, but are not limited to:

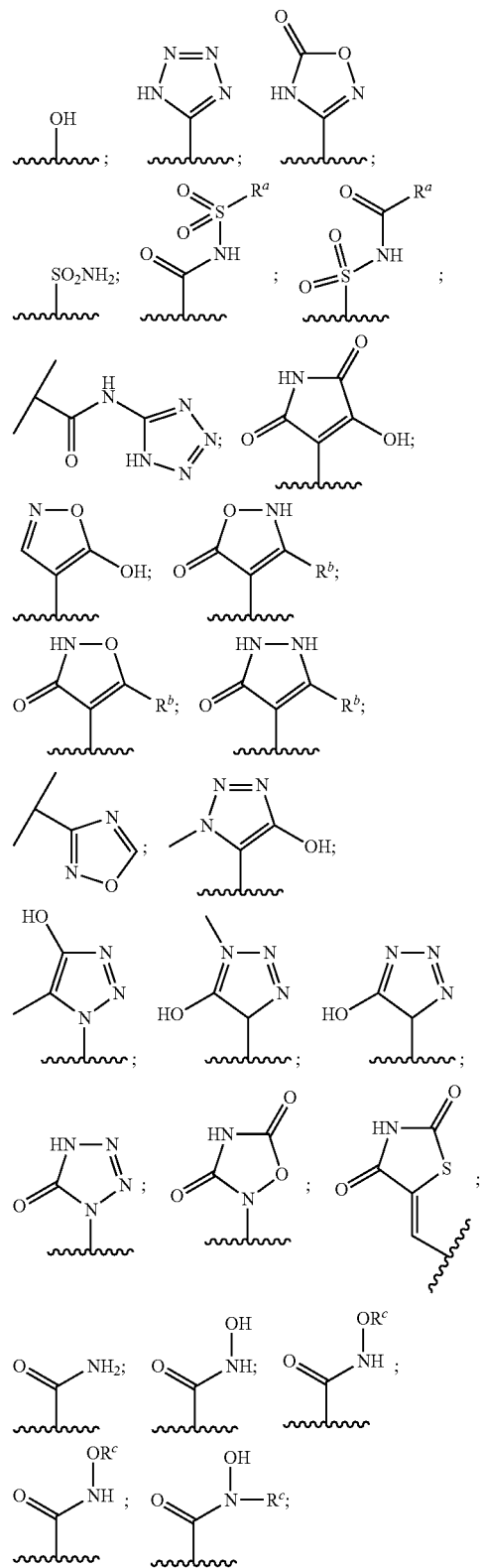

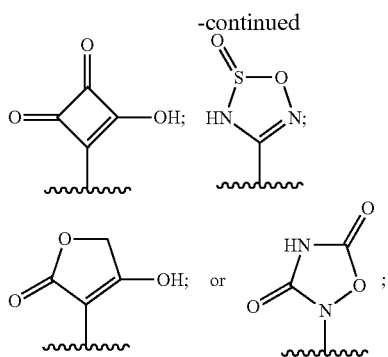

wherein R$^a$, R$^b$ and R$^c$ are independently selected from —CF$_3$, —CH$_3$, phenyl, or benzyl, with the phenyl or benzyl groups being optionally substituted by from 1 to 3 groups selected from C$_6$ alkyl, alkoxy, C$_6$ thioalkyl, CF$_3$, halogen, —OH, or —COOH.

In some embodiments, R$_3$ of Formula (1) is selected from: cycloalkyl, heterocycle (e.g., tetrazole), aryl, heteroaryl, NH—(CH$_2$)$_m$-cycloalkyl, NH—(CH$_2$)$_m$-heterocycle, NH—(CH$_2$)$_m$-aryl, and NH—(CH$_2$)$_m$-heteroaryl; wherein m is 0-6 (e.g., 0, 1, 2, 3, 4, 5, 6, or any ranges therebetween). In some embodiments, cycloalkyl, heterocycle, aryl, and/or heteroaryl ring groups may be further substituted, for example, with an alkyl group (e.g., methyl, ethyl, propyl, etc.), an alcohol (e.g., OH, CH$_2$OH, (CH$_2$)$_2$OH, etc.), amine (e.g., NH$_2$, CH$_2$NH$_2$, (CH$_2$)$_2$NH$_2$, etc.), CN, halogen, etc.

In some embodiments, R$_7$ of Formula (1) is selected from: H, Br, Cl, F, I, D (deuterium), alkane (e.g., methyl, ethyl, propyl, isopropyl, butyl, etc.), haloalkane (e.g., monohaloalkane (e.g., CH$_2$F, CH$_2$CH$_2$Cl, CHBrCH$_3$, etc.), dihaloalkane (e.g., CF$_2$H, CH$_2$CCl$_2$H, etc.), trihaloalkane (e.g., CBr$_3$, CF$_3$, CCl$_3$, CH$_2$CBr$_3$, CH$_2$CF$_3$, CH$_2$CCl$_3$, etc.)), trihalomethyl-cycloalkyl (e.g., 1-(trifluoromethyl)cyclopropyl (e.g., R$_7$ of compound 84) 1-(trichloromethyl)cyclohexane, etc.), alkene (e.g. CH═CH$_2$, etc.), alkyne (e.g. C≡CH, etc), amine (e.g., NH$_2$, NH-alkyl (e.g., NH-methyl, NH-ethyl, NH—CH$_2$-Ph, etc.), alkyl-amine (e.g., (CH$_2$)$_{1-6}$—NH$_2$), alkyl-amine-alkyl (e.g., (CH$_2$)$_{1-6}$—NH$_2$—(CH$_2$)$_{1-5}$CH$_3$, etc.), (CH$_2$)$_{1-6}$—N(CH$_3$)$_2$, alkene-N(CH$_3$)$_2$, alkyne-N(CH$_3$)$_2$, N(CH$_3$)$_2$, O-alkyl (e.g., OCH$_3$, OCH$_2$CH$_3$, etc.), NH-alcohol (e.g., NH—CH$_2$—CH$_2$—OH), etc.), hydroxy (e.g. —OH), an alcohol (e.g., (CH$_2$)$_{1-6}$OH, CH$_2$CHOHCH$_2$OH, etc.), cycloalkyl (e.g., cyclopropyl, cyclobutyl, cyclopentyl, cyclohexyl, cycloheptyl, etc.), alkyl-cycloalkyl (e.g., (CH$_2$)$_{1-6}$-cyclopropyl, (CH$_2$)$_{1-6}$-cyclobutyl, (CH$_2$)$_{1-6}$-cyclopentyl, (CH$_2$)$_{1-6}$-cyclohexyl, (CH$_2$)$_{1-6}$-cycloheptyl, etc.), alkelene-cycloalkyl (e.g., (CH)$_2$-cyclopropyl, (CH)$_2$-cyclobutyl, (CH)$_2$-cyclopentyl, (CH)$_2$-cyclohexyl (e.g., compound 155), (CH)$_2$-cycloheptyl, etc.), cycloalkene (e.g., cyclopropenyl, cyclobutenyl, cyclopentenyl (e.g., R$_7$ of compound 153), cyclohexenyl (e.g., R$_7$ of compound 154), cycloheptenyl, etc.), alkyl-cycloalkenyl (e.g., (CH$_2$)$_{1-6}$-cyclopropenyl, (CH$_2$)$_{1-6}$-cyclobutenyl, (CH$_2$)$_{1-6}$-cyclopentenyl, (CH$_2$)$_{1-6}$-cyclohexenyl, (CH$_2$)$_{1-6}$-cycloheptenyl, etc.), alkene-cycloalkenyl (e.g., (CH)$_2$-cyclopropenyl, (CH)$_2$-cyclobutenyl, (CH)$_2$-cyclopentenyl, (CH)$_2$-cyclohexenyl, (CH)$_2$-cycloheptenyl, etc.), and (CH$_2$)$_{0-6}$-heterocycle (e.g., non-aromatic heterocycle (e.g., aziridine, thiirane, oxirane, oxaziridine, dioxirane, azetidine, oxetan, thietane, diazetidine, dioxetane, dithietane, pyrrolidine, tetrahydrofuran, thiolane, imidazolidine, pyrazolidine, oxazolidine, isoxazolidine, thiazolidine, isothiazolidine, dioxolane, dithiolane, piperdine, oxane, thiane, piperazine, morpholine, thiomorpholine, dioxane, dithiane, trioxane, thithiane, azepane, oxepane, thiepane, homopiperazine, azocane, etc.), heteroaryl (e.g., pyrrole, furan, thiophene, imidazole, oxazole, thiazole, pyrazole, pyridine, pyrazine, pyridazine, pyrimidine, etc.), unsaturated non-aromatic rings, etc.).

In some embodiments, in which R$_7$ of Formula (1) comprises a cyclic group (e.g., non-aromatic cycloalkane, non-aromatic heterocycle, aryl, heteroaryl, unsaturated non-aromatic, etc.) attached directly to C$_7$ or attached to C$_7$ by a linker (e.g., alkane, heteroalkyl, etc.), the cyclic group is further substituted at one or more positions. Suitable substituents off a R$_7$ cyclic group include, but are not limited to: CH$_3$, CH$_2$CH$_3$, CHCH$_2$, NH$_2$, OH, COH, COCH$_3$, Br, Cl, F, N(CH$_3$)$_2$, CN, CH(CH$_3$)$_2$, CH(CH$_2$CH$_3$)$_2$, CF$_3$, CCl$_3$, CBr$_3$, CHF$_2$, CHCl$_2$, CHBr$_2$, CFH$_2$, CClH$_2$, CBrH$_2$, etc. In some embodiments, when possible, a single position (e.g., carbon) on a cyclic group at R$_7$ may comprise two non-hydrogen substituents (e.g., two of the aforementioned suitable substituents (e.g., F and F (difluoro), Br and CH$_3$, OH and OH (diol), CH$_3$ and CH$_3$ (dimethyl), etc.)).

In some embodiments, R$_8$ of Formula (1) is selected from: H, Br, Cl, F, I, D (deuterium), alkane (e.g., methyl, ethyl, propyl, isopropyl, butyl, etc.), haloalkane (e.g., monohaloalkane (e.g., CH$_2$F, CH$_2$CH$_2$Cl, CHBrCH$_3$, etc.), dihaloalkane (e.g., CF$_2$H, CH$_2$CCl$_2$H, etc.), trihaloalkane (e.g., CBr$_3$, CF$_3$, CCl$_3$, CH$_2$CBr$_3$, CH$_2$CF$_3$, CH$_2$CCl$_3$, etc.)), trihalomethyl-cycloalkyl (e.g., 1-(trifluoromethyl)cyclopropyl, 1-(trichloromethyl)cyclohexane, etc.), alkene (e.g. CH═CH$_2$, etc.), alkyne (e.g. C≡CH, etc), amine (e.g., NH$_2$, NH-alkyl (e.g., NH-methyl, NH-ethyl, NH—CH$_2$-Ph, etc.), alkyl-amine (e.g., (CH$_2$)$_{1-6}$—NH$_2$), alkyl-amine-alkyl (e.g., (CH$_2$)$_{1-6}$—NH$_2$—(CH$_2$)$_{1-5}$CH$_3$, etc.), (CH$_2$)$_{1-6}$—N(CH$_3$)$_2$, alkene-N(CH$_3$)$_2$, alkyne-N(CH$_3$)$_2$, N(CH$_3$)$_2$, O-alkyl (e.g., OCH$_3$, OCH$_2$CH$_3$, etc.), NH-alcohol (e.g., NH—CH$_2$—CH$_2$—OH), etc.), hydroxy (e.g. —OH), an alcohol (e.g., (CH$_2$)$_{1-6}$OH, CH$_2$CHOHCH$_2$OH, etc.), cycloalkyl (e.g., cyclopropyl, cyclobutyl, cyclopentyl, cyclohexyl, cycloheptyl, etc.), alkyl-cycloalkyl (e.g., (CH$_2$)$_{1-6}$-cyclopropyl, (CH$_2$)$_{1-6}$-cyclobutyl, (CH$_2$)$_{1-6}$-cyclopentyl, (CH$_2$)$_{1-6}$-cyclohexyl, (CH$_2$)$_{1-6}$-cycloheptyl, etc.), alkelene-cycloalkyl (e.g., (CH)$_2$-cyclopropyl, (CH)$_2$-cyclobutyl, (CH)$_2$-cyclopentyl, (CH)$_2$-cyclohexyl (e.g., compound 155), (CH)$_2$-cycloheptyl, etc.), cycloalkene (e.g., cyclopropenyl, cyclobutenyl, cyclopentenyl, cyclohexenyl, cycloheptenyl, etc.), alkyl-cycloalkenyl (e.g., (CH$_2$)$_{1-6}$-cyclopropenyl, (CH$_2$)$_{1-6}$-cyclobutenyl, (CH$_2$)$_{1-6}$-cyclopentenyl, (CH$_2$)$_{1-6}$-cyclohexenyl, (CH$_2$)$_{1-6}$-cycloheptenyl, etc.), alkene-cycloalkenyl (e.g., (CH)$_2$-cyclopropenyl, (CH)$_2$-cyclobutenyl, (CH)$_2$-cyclopentenyl, (CH)$_2$-cyclohexenyl, (CH)$_2$-cycloheptenyl, etc.), and (CH$_2$)$_{0-6}$-heterocycle (e.g., non-aromatic heterocycle (e.g., aziridine, thiirane, oxirane, oxaziridine, dioxirane, azetidine, oxetan, thietane, diazetidine, dioxetane, dithietane, pyrrolidine, tetrahydrofuran, thiolane, imidazolidine, pyrazolidine, oxazolidine, isoxazolidine, thiazolidine, isothiazolidine, dioxolane, dithiolane, piperdine, oxane, thiane, piperazine, morpholine, thiomorpholine, dioxane, dithiane, trioxane, thithiane, azepane, oxepane, thiepane, homopiperazine, azocane, etc.), heteroaryl (e.g., pyrrole, furan, thiophene, imidazole, oxazole, thiazole, pyrazole, pyridine, pyrazine, pyridazine, pyrimidine, etc.), unsaturated non-aromatic rings, etc.).

In some embodiments, in which R$_8$ of Formula (1) comprises a cyclic group (e.g., non-aromatic cycloalkane, non-aromatic heterocycle, aryl, heteroaryl, unsaturated non-aromatic, etc.) attached directly to C$_7$ or attached to C$_7$ by a linker (e.g., alkane, heteroalkyl, etc.), the cyclic group is further substituted at one or more positions. Suitable substituents off a $R_8$ cyclic group include, but are not limited to: $CH_3$, $CH_2CH_3$, $CHCH_2$, $NH_2$, $OH$, $COH$, $COCH_3$, $Br$, $Cl$, $F$, $N(CH_3)_2$, $CN$, $CH(CH_3)_2$, $CH(CH_2CH_3)_2$, $CF_3$, $CCl_3$, $CBr_3$, $CHF_2$, $CHCl_2$, $CHBr_2$, $CFH_2$, $CClH_2$, $CBrH_2$, etc. In some embodiments, when possible, a single position (e.g., carbon) on a cyclic group at $R_8$ may comprise two non-hydrogen substituents (e.g., two of the aforementioned suitable substituents (e.g., F and F (difluoro), Br and $CH_3$, OH and OH (diol), $CH_3$ and $CH_3$ (dimethyl), etc.)).

In some embodiments, $R_4$, $R_6$, and $R_9$ of Formula (1) are each independently selected from: H, D (deuterium), F, Cl, and Br. In some embodiments, $R_4$, $R_6$, and $R_9$ are each independently selected from: H, D (deuterium), F, or other suitable bioisosters of H.

In some embodiments, X of Formula (1) is selected from: C, O, N, and S. In embodiments in which X is O or S, the X position is not further substituted. In embodiments in which X is C or N, the X position comprises one or two additional substituents selected from: H, D, $CH_3$, $CH_2CH_3$, $CHCH_2$, $NH_2$, $OH$, $COH$, $COCH_3$, $Br$, $Cl$, $F$, $N(CH_3)_2$, $CN$, $CH(CH_3)_2$, $CH(CH_2CH_3)_2$, $CF_3$, $CCl_3$, $CBr_3$, $CHF_2$, $CHCl_2$, $CHBr_2$, $CFH_2$, $CClH_2$, $CBrH_2$, etc. In some embodiments, X is O.

In some embodiments, Y of Formula (1) is selected from: C, O, S, and N. In embodiments in which Y is O or S, the double bonds of the ring systems are adjusted accordingly (as is understood by one in the field). In embodiments in which Y is N, the Y position is not further substituted. In embodiments in which Y is C, the Y position comprises an substituent selected from: H, D, $CH_3$, $CH_2C_3$, $CHCH_2$, $NH_2$, $OH$, $COH$, $COCH_3$, $Br$, $Cl$, $F$, $N(CH_3)_2$, $CN$, $CH(CH_3)_2$, $CH(CH_2CH_3)_2$, $CF_3$, $CCl_3$, $CBr_3$, $CHF_2$, $CHCl_2$, $CHBr_2$, $CFH_2$, $CClH_2$, $CBrH_2$, etc. In some embodiments, Y is N.

In some embodiments, any or all hydrogens (e.g., exchangeable hydrogens, non-exchangeable hydrogens, and/or both) on a compound of Formula (1) and substituents thereof may be substituted for deuterium atoms. In some embodiments, any of the hydrogens in the structures, formulas, or substituents described herein, or any subsets thereof, are substituted for deuterium atoms (D).

In certain embodiments, provided herein are compounds represented by a structure of one or more of Formula (2), Formula (3), Formula (4), Formula (5), Formula (6), Formula (7), Formula (8), Formula (9), Formula (10), Formula (11), Formula (12), Formula (13), Formula (14), Formula (15), Formula (16), Formula (17), Formula (18), Formula (19), Formula (20), Formula (21), Formula (22), Formula (23), Formula (24), Formula (25), Formula (26), Formula (27), Formula (28), Formula (29), Formula (30), Formula (31), Formula (32), Formula (33), Formula (34), Formula (35), Formula (36), Formula (37), Formula (38), Formula (39), Formula (40), Formula (41), Formula (42), Formula (43), Formula (44), Formula (45), Formula (46), Formula (47), Formula (48), Formula (49), Formula (50), Formula (51), Formula (52), Formula (53), Formula (54), Formula (55), Formula (56), Formula (57), Formula (58), Formula (59), Formula (60), Formula (61), Formula (62), Formula (63), Formula (64), Formula (65), Formula (66), Formula (67), Formula (68), Formula (69), Formula (70), Formula (71), Formula (72), and/or Formula (73).

In certain embodiments, provided herein are compounds represented by a structure of one or more of:

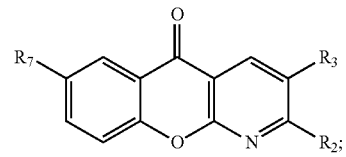

Formula (2)

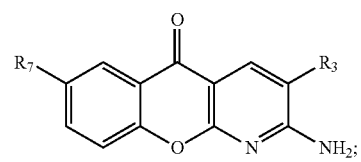

Formula (3)

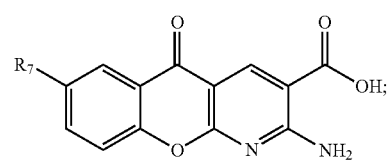

Formula (4)

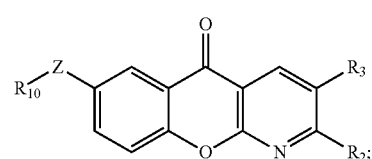

Formula (5)

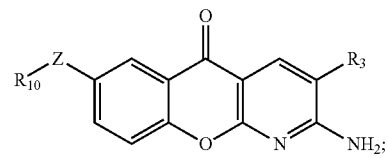

Formula (6)

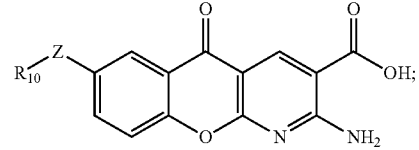

Formula (7)

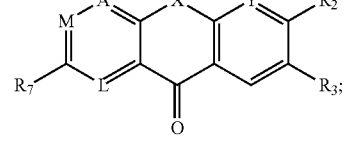

Formula (8)

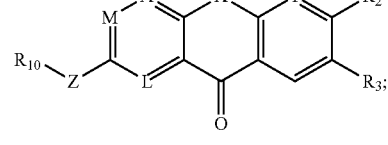

Formula (9)

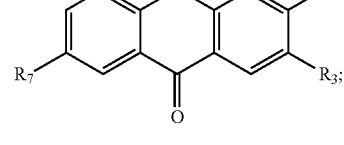

Formula (10)

-continued

Formula (11)
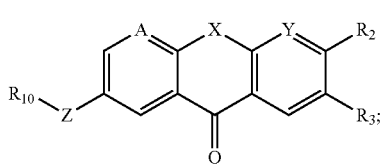

Formula (12)
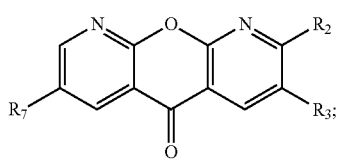

Formula (13)
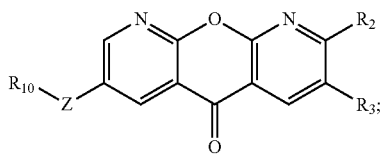

Formula (14)
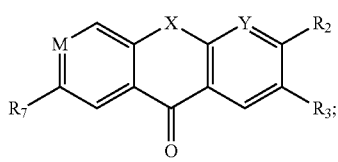

Formula (15)
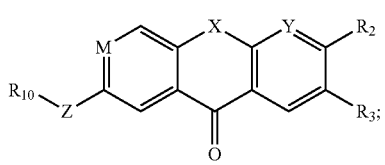

Formula (16)
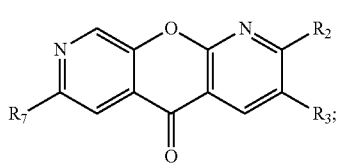

Formula (17)
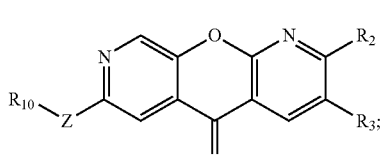

Formula (18)
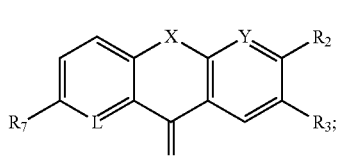

Formula (19)
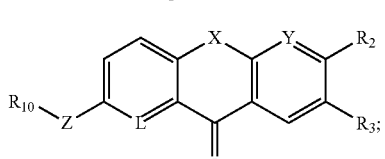

Formula (20)
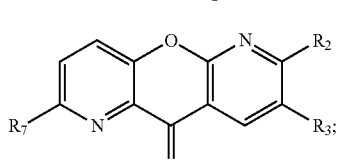

-continued

Formula (21)
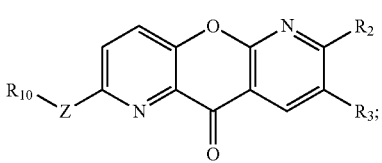

Formula (22)
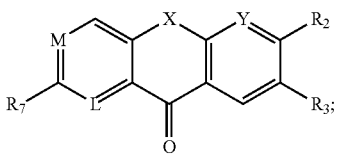

Formula (23)
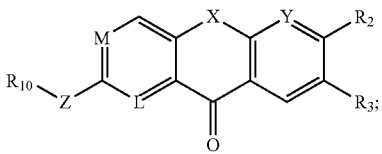

Formula (24)
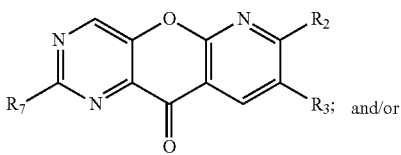

and/or

Formula (25)
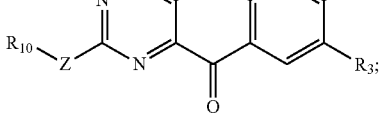

and having substituents (e.g., $R_2$, $R_3$, $R_7$, $R_{10}$, A, G, L, M, X, Y, Z, etc.) as depicted in, for example, Tables 1-3, Examples 1-6, and/or described in the Detailed Description. For example, in particular embodiments: $R_2$ is an amine (e.g., $NH_2$), an amine bioisostere, an amidino, or an amidino bioisostere, $R_3$ is a carboxylic acid (e.g., COOH), alcohol, tetrazole, ester, amide, heterocycle, etc., or a bioisostere thereof; X and Y and are independently N, O, or S; A, M, and L are independently C or N, and $R_7$ (or —Z—$R_{10}$), is a cyclic group (e.g., aromatic, non-aromatic, heterocyclic, heteroaromatic, bicyclic, etc.), substituted cyclic group (e.g., aromatic, non-aromatic, heterocyclic, heteroaromatic, bicyclic, etc.), alkyl-cyclic group (e.g., aromatic, non-aromatic, heterocyclic, heteroaromatic, bicyclic, etc.), alkyl-substituted cyclic group (e.g., aromatic, non-aromatic, heterocyclic, heteroaromatic, bicyclic, etc.), alkyl group, substituted alkyl group (e.g., alkene, alkyne, alcohol, amine, haloalkyl, etc.), halogen, amine, alcohol, or combinations thereof.

In certain embodiments, provided herein are compounds represented by a structure of one or more of Formula (26) through Formula (49), wherein Formulas (26) through (49) correspond to Formulas (2) through (25); however, $R_7$ or —Z—$R_{10}$ is H, M is C, J is C or N (See Formula (III)), and $R_8$ (or G-$R_{11}$) (See Formula (III)) is a cyclic group (e.g., aromatic, non-aromatic, heterocyclic, heteroaromatic, bicyclic, etc.), substituted cyclic group (e.g., aromatic, non-aromatic, heterocyclic, heteroaromatic, bicyclic, etc.), alkyl group, substituted alkyl group (e.g., alkene, alkyne, alcohol, amine, haloalkyl, etc.), halogen, amine, alcohol, or combinations thereof; any $R_7$ or —Z—$R_{10}$ substituents described for Formulas (2) through (25) apply to $R_8$ or -G-$R_{11}$ substituents of Formulas (26) through (49).

In certain embodiments, provided herein are compounds represented by a structure of one or more of Formula (50) through Formula (73), wherein Formulas (50) through (73) correspond to Formulas (2) through (25); however, M is C, and $R_8$ (or G-$R_{11}$) (See Formula (IV)) is a cyclic group (e.g., aromatic, non-aromatic, heterocyclic, heteroaromatic, bicyclic, etc.), substituted cyclic group (e.g., aromatic, non-aromatic, heterocyclic, heteroaromatic, bicyclic, etc.), alkyl group, substituted alkyl group (e.g., alkene, alkyne, alcohol, amine, haloalkyl, etc.), halogen, amine, alcohol, or combinations thereof; any $R_7$ or —Z—$R_{10}$ substituents described for Formulas (2) through (25) also apply to $R_8$ or -G-$R_{11}$ substituents of Formulas (26) through (73).

In some embodiments, $R_2$, $R_3$, $R_7$, and/or $R_8$ of any of Formula (2) through Formula (73), when not otherwise specified in the Formula (e.g., R2 is NH2 in Formulas (3), (27), (51), etc.), are each independently selected from: H, alkyl, substituted alkyl, hydroxy, alkoxy, amine, thioalkyl, halogen, ketone, amide, cyano, sulfonyl, dialkylphosphine oxide, a carbocyclic ring, an aromatic ring, a substituted aromatic ring, a heterocyclic aromatic ring, a substituted heterocyclic aromatic ring, a substituted or non-substituted heterocyclic non-aromatic ring, carbocyclic or heterocyclic aromatic ring fused to another aromatic ring, a hydrogen bond donor, a hydrogen bond acceptor, and combinations thereof.

In some embodiments, $R_2$ of any of Formula (2) through Formula (73), when not otherwise specified in the Formula, is selected from: $CH_3$, $NH_2$, $NHCH_3$, OH, $NH(CH_2)_2OH$, $NH(CH_2)_3OH$, amidino, F, Br, and Cl, and other suitable bioisosters of $NH_2$.

In some embodiments, $R_2$ of any of Formula (2) through Formula (73), when not otherwise specified in the Formula, is selected from: cycloalkyl, heterocycle, aryl, heteroaryl, NH—$(CH_2)_m$-cycloalkyl, NH—$(CH_2)_m$-heterocycle (e.g., $R_2$ of compound 147), NH—$(CH_2)_m$-aryl, and NH—$(CH_2)_m$-heteroaryl; wherein m is 0-6 (e.g., 0, 1, 2, 3, 4, 5, 6, or any ranges therebetween). In some embodiments, cycloalkyl, heterocycle, aryl, and/or heteroaryl ring groups may be further substituted (e.g., $R_2$ of compound 148), for example, with an alkyl group (e.g., methyl, ethyl, propyl, etc.), an alcohol (e.g., OH, $CH_2OH$, $(CH_2)_2OH$, etc.), amine (e.g., $NH_2$, $CH_2NH_2$, $(CH_2)_2NH_2$, etc.), CN, halogen, etc.

In some embodiments, $R_3$ of any of Formula (2) through Formula (73), when not otherwise specified in the Formula (e.g., R3 is COOH in, for example, Formulas (4), (28), (52), etc.), is selected from: a carboxylic acid (e.g., C(O)OH), an alcohol (e.g., OH, $CH_2OH$, $(CH_2)_2OH$, etc.), an ester (e.g., $CO_2CH_3$, $CO_2Et$, etc.), a hydroxamic acid (e.g., C(O)N(OH)H), a phosphoric acid (e.g., $P(O)(OH)_2$), a phosphinic acid (e.g., P(O)(OH)H), a sulphonic acid (e.g., S(O)(O)OH), a sulfonamide (e.g., S(O)(O)$NH_2$), an acylsulfonamide (e.g., C(O)NHS(O)(O)H), C(O)NHS(O)(O)$CH_3$), C(O)NHS(O)(O)$NH_2$), a sulfonylurea (e.g., NHC(O)NHS(O)(O)$CH_3$), a tetrazole, a thiazolidinedione, an oxazolidinedione, 5-oxo-1,2,4-oxadiazole, 5-oxo-1,2,4-thiadiazole, 5-thioxo-1,2,4-thiadiazole, an isothiazole, an isoxazole, a difluorophenol, tetramic acid, tetronic acid, cyclopentane-1,3-dione, a squaric acid, an amide (e.g., C(O)NH-(alkyl) (e.g., C(O)NHCH$_3$, C(O)NHCH$_2$CH$_3$, etc.), C(O)NH-(cycloalkyl), C(O)NH-(alkyl-cycloalkyl) (e.g., C(O)NHCH$_2$(C$_6$H$_{11}$), C(O)NHCH$_2$(C$_5$H$_9$), C(O)NHCH$_2$CH$_2$(C$_6$H$_{11}$), C(O)NHCH$_2$CH$_2$(C$_5$H$_9$), etc.), C(O)NH-(heteroalkyl) (e.g., C(O)NHCH$_2$CH$_2$N(CH$_3$)$_2$, C(O)NHCH$_2$N(CH$_3$)$_2$, C(O)NHCH$_2$NHCH$_2$CH$_3$, C(O)NHCH$_2$NHCH$_3$, C(O)NHCH$_2$OCH$_2$CH$_3$, C(O)NHCH$_2$CH$_2$OCH$_3$, C(O)NHCH$_2$SCH$_2$CH$_3$, C(O)NHCH$_2$CH$_2$SCH$_3$, etc.), C(O)NH-(heterocycle), C(O)NH-(alkyl-heterocycle) (e.g., C(O)NHCH$_2$(C$_5$H$_9$O), C(O)NHCH$_2$CH$_2$(C$_5$H$_9$O), C(O)NHCH$_2$(C$_5$H$_9$S), C(O)NHCH$_2$CH$_2$(C$_5$H$_9$S), C(O)NHCH$_2$(C$_5$H$_{10}$N), C(O)NHCH$_2$CH$_2$(C$_5$H$_{10}$N), etc.), and other suitable bioisosteres of a carboxylic acid substituent.

In some embodiments, other suitable bioisosteres of a carboxylic acid substituent include, but are not limited to:

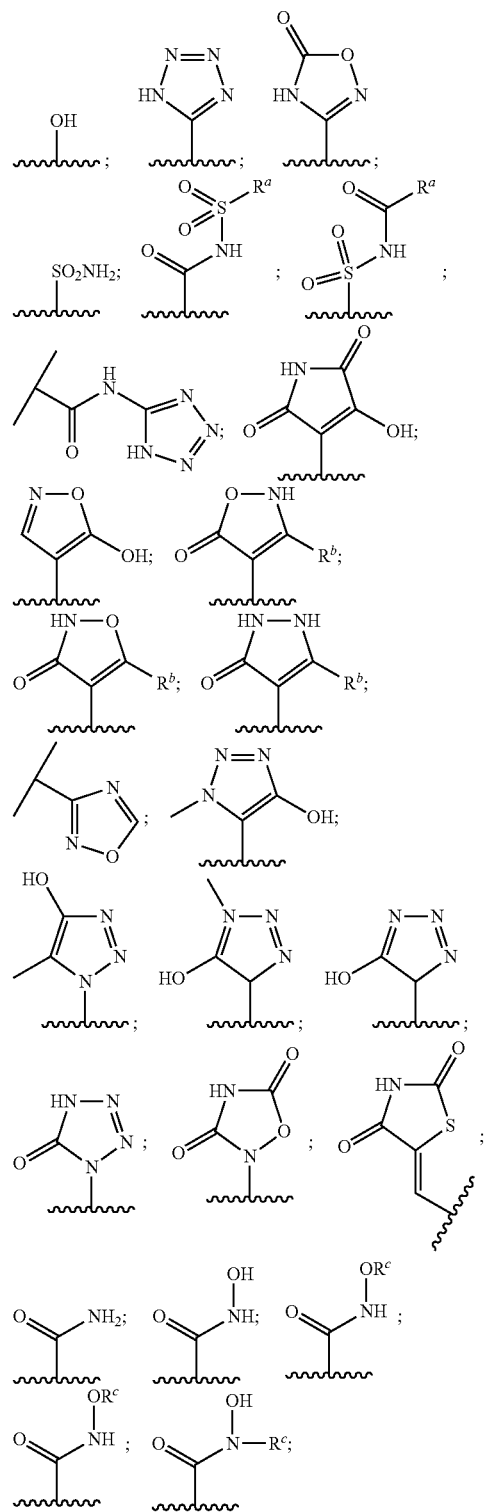

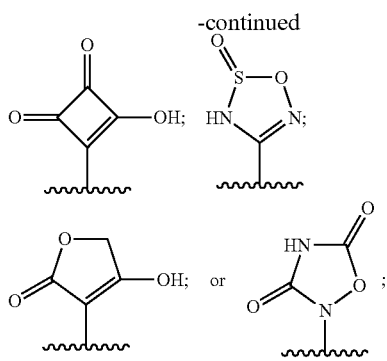

wherein $R^a$, $R^b$ and $R^c$ are independently selected from —$CF_3$, —$CH_3$, phenyl, or benzyl, with the phenyl or benzyl groups being optionally substituted by from 1 to 3 groups selected from $C_6$ alkyl, alkoxy, $C_6$ thioalkyl, $CF_3$, halogen, —OH, or —COOH.

In some embodiments, $R_3$ of any of Formula (2) through Formula (73), when not otherwise specified in the Formula, is selected from: cycloalkyl, heterocycle (e.g., tetrazole), aryl, heteroaryl, NH—$(CH_2)_m$-cycloalkyl, NH—$(CH_2)_m$-heterocycle, NH—$(CH_2)_m$-aryl, and NH—$(CH_2)_m$-heteroaryl; wherein m is 0-6 (e.g., 0, 1, 2, 3, 4, 5, 6, or any ranges therebetween). In some embodiments, cycloalkyl, heterocycle, aryl, and/or heteroaryl ring groups may be further substituted, for example, with an alkyl group (e.g., methyl, ethyl, propyl, etc.), an alcohol (e.g., OH, $CH_2OH$, $(CH_2)_2OH$, etc.), amine (e.g., $NH_2$, $CH_2NH_2$, $(CH_2)_2NH_2$, etc.), CN, halogen, etc.

In some embodiments, $R_7$ of any of Formula (2) through Formula (73), when not otherwise specified in the Formula (e.g., R7 is H (or D) in Formulas (26) through (49)), is selected from: H, Br, Cl, F, I, D (deuterium), alkane (e.g., methyl, ethyl, propyl, isopropyl, butyl, etc.), haloalkane (e.g., monohaloalkane (e.g., $CH_2F$, $CH_2CH_2Cl$, $CHBrCH_3$, etc.), dihaloalkane (e.g., $CF_2H$, $CH_2CCl_2H$, etc.), trihaloalkane (e.g., $CBr_3$, $CF_3$, $CCl_3$, $CH_2CBr_3$, $CH_2CF_3$, $CH_2CCl_3$, etc.)), trihalomethyl-cycloalkyl (e.g., 1-(trifluoromethyl)cyclopropyl (e.g., $R_7$ of compound 84) 1-(trichloromethyl)cyclohexane, etc.), alkene (e.g. CH=$CH_2$, etc.), alkyne (e.g. C≡CH, etc), amine (e.g., $NH_2$, NH-alkyl (e.g., NH-methyl, NH-ethyl, NH—$CH_2$-Ph, etc.), alkyl-amine (e.g., (C$H_2)_{1-6}$—$NH_2$), alkyl-amine-alkyl (e.g., $(CH_2)_{1-6}$—$NH_2$—$(CH_2)_{1-5}CH_3$, etc.), $(CH_2)_{1-6}$—$N(CH_3)_2$, alkene-$N(CH_3)_2$, alkyne-$N(CH_3)_2$, $N(CH_3)_2$, O-alkyl (e.g., $OCH_3$, $OCH_2CH_3$, etc.), NH-alcohol (e.g., NH—$CH_2$—$CH_2$—OH), etc.), hydroxy (e.g. —OH), an alcohol (e.g., $(CH_2)_{1-6}$OH, $CH_2CHOHCH_2OH$, etc.), cycloalkyl (e.g., cyclopropyl, cyclobutyl, cyclopentyl, cyclohexyl, cycloheptyl, etc.), alkyl-cycloalkyl (e.g., $(CH_2)_{1-6}$-cyclopropyl, $(CH_2)_{1-6}$-cyclobutyl, $(CH_2)_{1-6}$-cyclopentyl, $(CH_2)_{1-6}$-cyclohexyl, (C$H_2)_{1-6}$-cycloheptyl, etc.), alkene-cycloalkyl (e.g., $(CH)_2$-cyclopropyl, $(CH)_2$-cyclobutyl, $(CH)_2$-cyclopentyl, $(CH)_2$-cyclohexyl (e.g., compound 155), $(CH)_2$-cycloheptyl, etc.), cycloalkene (e.g., cyclopropenyl, cyclobutenyl, cyclopentenyl (e.g., $R_7$ of compound 153), cyclohexenyl (e.g., $R_7$ of compound 154), cycloheptenyl, etc.), alkyl-cycloalkenyl (e.g., $(CH_2)_{1-6}$-cyclopropenyl, $(CH_2)_{1-6}$-cyclobutenyl, $(CH_2)_{1-6}$-cyclopentenyl, $(CH_2)_{1-6}$-cyclohexenyl, $(CH_2)_{1-6}$-cycloheptenyl, etc.), alkene-cycloalkenyl (e.g., $(CH)_2$-cyclopropenyl, $(CH)_2$-cyclobutenyl, $(CH)_2$-cyclopentenyl, $(CH)_2$-cyclohexenyl, $(CH)_2$-cycloheptenyl, etc.), and (C$H_2)_{0-6}$-heterocycle (e.g., non-aromatic heterocycle (e.g., aziridine, thiirane, oxirane, oxaziridine, dioxirane, azetidine, oxetane, thietane, diazetidine, dioxetane, dithietane, pyrrolidine, tetrahydrofuran, thiolane, imidazolidine, pyrazolidine, oxazolidine, isoxazolidine, thiazolidine, isothiazolidine, dioxolane, dithiolane, piperdine, oxane, thiane, piperazine, morpholine, thiomorpholine, dioxane, dithiane, trioxane, thithiane, azepane, oxepane, thiepane, homopiperazine, azocane, etc.), heteroaryl (e.g., pyrrole, furan, thiophene, imidazole, oxazole, thiazole, pyrazole, pyridine, pyrazine, pyridazine, pyrimidine, etc.), unsaturated non-aromatic rings, etc.).

In some embodiments, in which $R_7$ of any of Formula (2) through Formula (73), when not otherwise specified in the Formula (e.g., $R_7$ is H (or D) in Formulas (26) through (49)), comprises a cyclic group (e.g., non-aromatic cycloalkane, non-aromatic heterocycle, aryl, heteroaryl, unsaturated non-aromatic, etc.) attached directly to $C_7$ or attached to $C_7$ by a linker (e.g., alkane, heteroalkyl, etc.), the cyclic group is further substituted at one or more positions. Suitable substituents off a $R_7$ cyclic group include, but are not limited to: $CH_3$, $CH_2CH_3$, $CHCH_2$, $NH_2$, OH, COH, $COCH_3$, Br, Cl, F, $N(CH_3)_2$, CN, $CH(CH_3)_2$, $CH(CH_2CH_3)_2$, $CF_3$, $CCl_3$, $CBr_3$, $CHF_2$, $CHCl_2$, $CHBr_2$, $CFH_2$, $CClH_2$, $CBrH_2$, etc. In some embodiments, when possible, a single position (e.g., carbon) on a cyclic group at $R_7$ may comprise two non-hydrogen substituents (e.g., two of the aforementioned suitable substituents (e.g., F and F (difluoro), Br and $CH_3$, OH and OH (diol), $CH_3$ and $CH_3$ (dimethyl), etc.)).

In some embodiments, Z of any of Formula (2) through Formula (73), when not specified as $R_7$ or otherwise (e.g., there is no Z—R10 on any of Formulas (26) through (49)), is a cyclic group (e.g., saturated non-aromatic ring, aromatic ring, unsaturated non-aromatic ring, non-aromatic heterocycle, heteroaryl, etc.).

In some embodiments, Z is selected from:

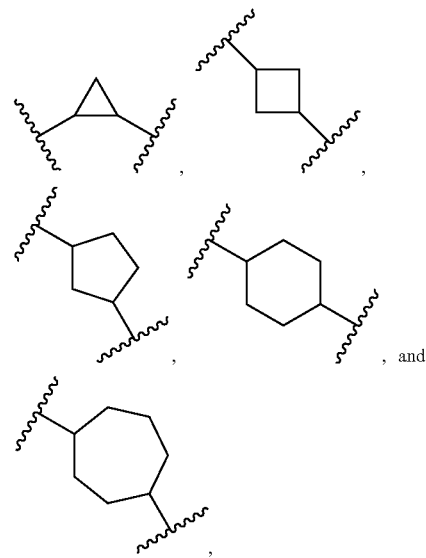

wherein Z connects the formula scaffold to $R_{10}$.

In certain embodiments, Z is a 4-, 5-, 6-, 7- or 8-membered saturated heterocycle. In some embodiments, Z is selected from azetidine, oxetane, piperidine, oxane, piperazine, pyrrolidine, tetrahydrofuran, thiolane, imidazolidine, morpholine, thiomorpholine, azepane, and homopiperazine. In some embodiments, Z is selected from:

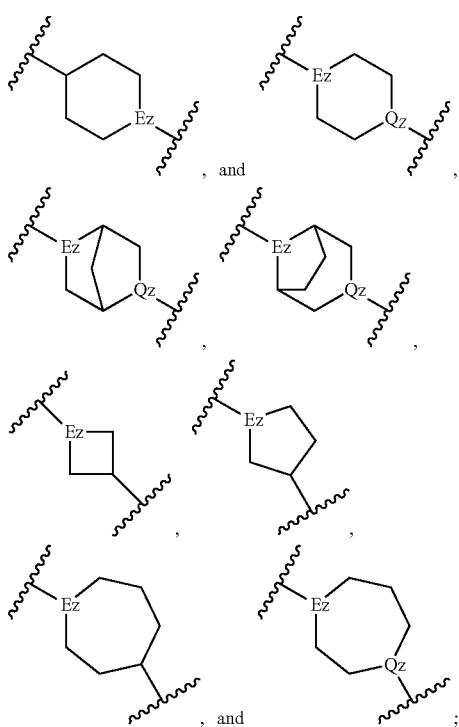

wherein Ez and Qz are independently selected from C, O, S, and N, and Z may adopt either orientation with respect to connection to $R_{10}$ and the formula scaffold. In some embodiments, Ez and Qz are independently selected from O, S, and N.

In certain embodiments, for a compound or salt of any of Formula (2) through Formula (73) having a —Z—$R_{10}$ group, Z is selected from an unsaturated, aromatic, or heteroaromatic ring. In particular embodiments, Z is selected from phenyl, pyridine, pyrazine, pyrimidine, pyridazine, naphthalene, anthracene, quinoline, isoquinoline, quinoxaline, acridine, quinazoline, cinnoline, phthalazine, furan, dihydrofuran, thiophene, dihydrothiophene, imidazole, imidazoline, oxazole, oxazoline, pyrrole, dihydropyrrole, thiazole, dihydrothiazole, pyrazole, dihydropyrazole, isoxazole, dihydroisoxazole, isothiazole, dihydroisothiazole, benzofuran, isobenzofuran, indole, isoindole, benzothiophene, benzimidazole, purine, indazole, benzoxazole, benzisoxazole, and benzothiazole. In some embodiments, Z is selected from:

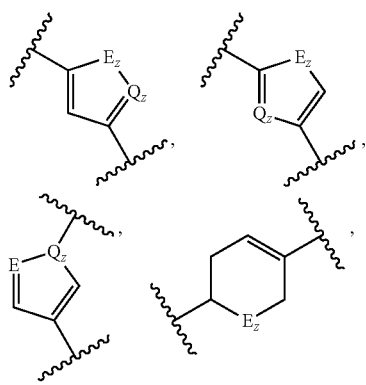

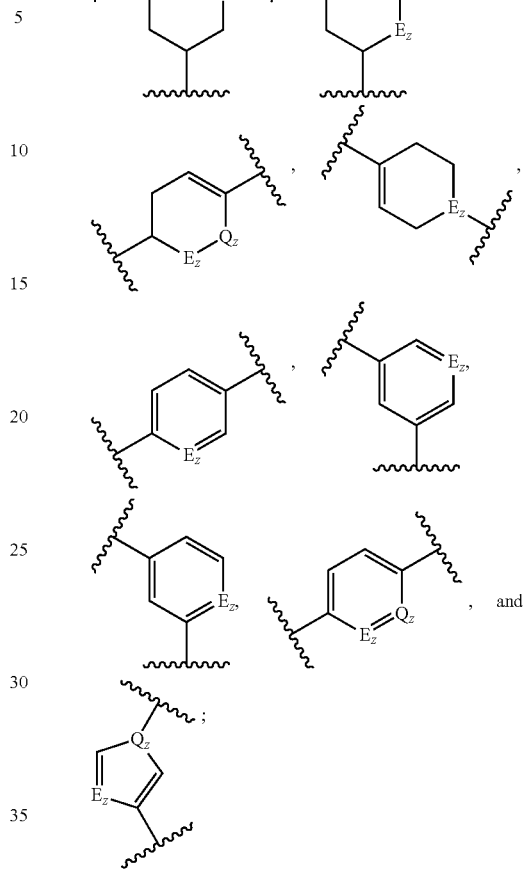

wherein Ez and Gz are independently selected from C, O, S, and N (or O, S, and N, but not C), and Z may adopt either orientation with respect to connection to $R_{10}$ and the scaffold of any of Formula (2) through Formula (73) having a —Z—$R_{10}$ group.

In some embodiments, $R_{10}$ of any of Formula (2) through Formula (73) having a —Z—$R_{10}$ group is selected from: H, Br, Cl, F, I, D (deuterium), CN, alkane (e.g., methyl, ethyl, propyl, isopropyl, butyl, etc.), haloalkane (e.g., monohaloalkane (e.g., $CH_2F$, $CH_2CH_2Cl$, $CHBrCH_3$, etc.), dihaloalkane (e.g., $CF_2H$, $CH_2CCl_2H$, etc.), trihaloalkane (e.g., $CBr_3$, $CF_3$, $CCl_3$, $CH_2CBr_3$, $CH_2CF_3$, $CH_2CCl_3$, etc.)), alkene (e.g. CH=$CH_2$, etc.), alkyne (e.g. C≡CH, etc), amine (e.g., $NH_2$, NH-alkyl (e.g., NH-methyl, NH-ethyl, NH—$CH_2$-Ph, etc.), alkyl-amine (e.g., $(CH_2)_{1-6}$—$NH_2$), alkyl-amine-alkyl (e.g., $(CH_2)_{1-6}$—$NH_2$—$(CH_2)_{1-5}CH_3$, etc.), $(CH_2)_{1-6}$—$N(CH_3)_2$, alkene-$N(CH_3)_2$, alkyne-$N(CH_3)_2$, $N(CH_3)_2$, O-alkyl (e.g., $OCH_3$, $OCH_2CH_3$, etc.), NH-alcohol (e.g., NH—$CH_2$—$CH_2$—OH), etc.), hydroxy (e.g. —OH), and an alcohol (e.g., methanol, ethanol, butanol, propanol, $CH_2CHOHCH_2OH$, etc.).

In some embodiments, Z of any of Formula (2) through Formula (73) having a —Z—$R_{10}$ group is further substituted at one or more additional ring positions (e.g., in addition to the $R_{10}$ substitution). Additional substituents on the Z ring may include: Br, Cl, F, I, CN, alkane (e.g., methyl, ethyl, propyl, isopropyl, butyl, etc.), haloalkane (e.g., monohaloalkane (e.g., $CH_2F$, $CH_2CH_2Cl$, $CHBrCH_3$, etc.), dihaloalkane (e.g., CF$_2$H, CH$_2$CCl$_2$H, etc.), trihaloalkane (e.g., CBr$_3$, CF$_3$, CCl$_3$, CH$_2$CBr$_3$, CH$_2$CF$_3$, CH$_2$CCl$_3$, etc.)), alkene (e.g. CH=CH$_2$, etc.), alkyne (e.g. C≡CH, etc), amine (e.g., NH$_2$, NH-alkyl (e.g., NH-methyl, NH-ethyl, NH—CH$_2$-Ph, etc.), alkyl-amine (e.g., (CH$_2$)$_{1-6}$—NH$_2$), alkyl-amine-alkyl (e.g., (CH$_2$)$_{1-6}$—NH$_2$—(CH$_2$)$_{1-5}$CH$_3$, etc.), (CH$_2$)$_{1-6}$—N(CH$_3$)$_2$, alkene-N(CH$_3$)$_2$, alkyne-N(CH$_3$)$_2$, N(CH$_3$)$_2$, O-alkyl (e.g., OCH$_3$, OCH$_2$CH$_3$, etc.), NH-alcohol (e.g., NH—CH$_2$—CH$_2$—OH), etc.), hydroxy (e.g. —OH), and an alcohol (e.g., methanol, ethanol, butanol, propanol, CH$_2$CHOHCH$_2$OH, etc.).

In some embodiments, R$_8$ of any of Formula (2) through Formula (73), when not otherwise specified in the Formula (e.g., R$_8$ is H (or D) in Formulas (2) through (25)), is selected from: H, Br, Cl, F, I, D (deuterium), alkane (e.g., methyl, ethyl, propyl, isopropyl, butyl, etc.), haloalkane (e.g., monohaloalkane (e.g., CH$_2$F, CH$_2$CH$_2$Cl, CHBrCH$_3$, etc.), dihaloalkane (e.g., CF$_2$H, CH$_2$CCl$_2$H, etc.), trihaloalkane (e.g., CBr$_3$, CF$_3$, CCl$_3$, CH$_2$CBr$_3$, CH$_2$CF$_3$, CH$_2$CCl$_3$, etc.)), trihalomethyl-cycloalkyl (e.g., 1-(trifluoromethyl)cyclopropyl (e.g., R$_7$ of compound 84) 1-(trichloromethyl)cyclohexane, etc.), alkene (e.g. CH=CH$_2$, etc.), alkyne (e.g. C≡CH, etc), amine (e.g., NH$_2$, NH-alkyl (e.g., NH-methyl, NH-ethyl, NH—CH$_2$-Ph, etc.), alkyl-amine (e.g., (CH$_2$)$_{1-6}$—NH$_2$), alkyl-amine-alkyl (e.g., (CH$_2$)$_{1-6}$—NH$_2$—(CH$_2$)$_{1-5}$CH$_3$, etc.), (CH$_2$)$_{1-6}$—N(CH$_3$)$_2$, alkene-N(CH$_3$)$_2$, alkyne-N(CH$_3$)$_2$, N(CH$_3$)$_2$, O-alkyl (e.g., OCH$_3$, OCH$_2$CH$_3$, etc.), NH-alcohol (e.g., NH—CH$_2$—CH$_2$—OH), etc.), hydroxy (e.g. —OH), an alcohol (e.g., (CH$_2$)$_{1-6}$OH, CH$_2$CHOHCH$_2$OH, etc.), cycloalkyl (e.g., cyclopropyl, cyclobutyl, cyclopentyl, cyclohexyl, cycloheptyl, etc.), alkyl-cycloalkyl (e.g., (CH$_2$)$_{1-6}$-cyclopropyl, (CH$_2$)$_{1-6}$-cyclobutyl, (CH$_2$)$_{1-6}$-cyclopentyl, (CH$_2$)$_{1-6}$-cyclohexyl, (CH$_2$)$_{1-6}$-cycloheptyl, etc.), alkene-cycloalkyl (e.g., (CH)$_2$-cyclopropyl, (CH)$_2$-cyclobutyl, (CH)$_2$-cyclopentyl, (CH)$_2$-cyclohexyl (e.g., compound 155), (CH)$_2$-cycloheptyl, etc.), cycloalkene (e.g., cyclopropenyl, cyclobutenyl, cyclopentenyl (e.g., R$_7$ of compound 153), cyclohexenyl (e.g., R$_7$ of compound 154), cycloheptenyl, etc.), alkyl-cycloalkenyl (e.g., (CH$_2$)$_{1-6}$-cyclopropenyl, (CH$_2$)$_{1-6}$-cyclobutenyl, (CH$_2$)$_{1-6}$-cyclopentenyl, (CH$_2$)$_{1-6}$-cyclohexenyl, (CH$_2$)$_{1-6}$-cycloheptenyl, etc.), alkene-cycloalkenyl (e.g., (CH)$_2$-cyclopropenyl, (CH)$_2$-cyclobutenyl, (CH)$_2$-cyclopentenyl, (CH)$_2$-cyclohexenyl, (CH)$_2$-cycloheptenyl, etc.), and (CH$_2$)$_{0-6}$-heterocycle (e.g., non-aromatic heterocycle (e.g., aziridine, thiirane, oxirane, oxaziridine, dioxirane, azetidine, oxetane, thietane, diazetidine, dioxetane, dithietane, pyrrolidine, tetrahydrofuran, thiolane, imidazolidine, pyrazolidine, oxazolidine, isoxazolidine, thiazolidine, isothiazolidine, dioxolane, dithiolane, piperdine, oxane, thiane, piperazine, morpholine, thiomorpholine, dioxane, dithiane, trioxane, thithiane, azepane, oxepane, thiepane, homopiperazine, azocane, etc.), heteroaryl (e.g., pyrrole, furan, thiophene, imidazole, oxazole, thiazole, pyrazole, pyridine, pyrazine, pyridazine, pyrimidine, etc.), unsaturated non-aromatic rings, etc.).

In some embodiments, in which R$_8$ of any of Formula (2) through Formula (73), when not otherwise specified in the Formula (e.g., R$_8$ is H (or D) in Formulas (2) through (25)), comprises a cyclic group (e.g., non-aromatic cycloalkane, non-aromatic heterocycle, aryl, heteroaryl, unsaturated non-aromatic, etc.) attached directly to C$_8$ or attached to C$_8$ by a linker (e.g., alkane, heteroalkyl, etc.), the cyclic group is further substituted at one or more positions. Suitable substituents off a R$_8$ cyclic group include, but are not limited to: CH$_3$, CH$_2$CH$_3$, CHCH$_2$, NH$_2$, OH, COH, COCH$_3$, Br, Cl, F, N(CH$_3$)$_2$, CN, CH(CH$_3$)$_2$, CH(CH$_2$CH$_3$)$_2$, CF$_3$, CCl$_3$, CBr$_3$, CHF$_2$, CHCl$_2$, CHBr$_2$, CFH$_2$, CClH$_2$, CBRH$_2$, etc. In some embodiments, when possible, a single position (e.g., carbon) on a cyclic group at R$_8$ may comprise two non-hydrogen substituents (e.g., two of the aforementioned suitable substituents (e.g., F and F (difluoro), Br and CH$_3$, OH and OH (diol), CH$_3$ and CH$_3$ (dimethyl), etc.)).

In some embodiments, G of any of Formula (2) through Formula (73), when not specified as R$_8$ or otherwise (e.g., there is no G-R$_{11}$ on any of Formulas (2) through (25)), is a cyclic group (e.g., saturated non-aromatic ring, aromatic ring, unsaturated non-aromatic ring, non-aromatic heterocycle, heteroaryl, etc.).

In some embodiments, G is selected from:

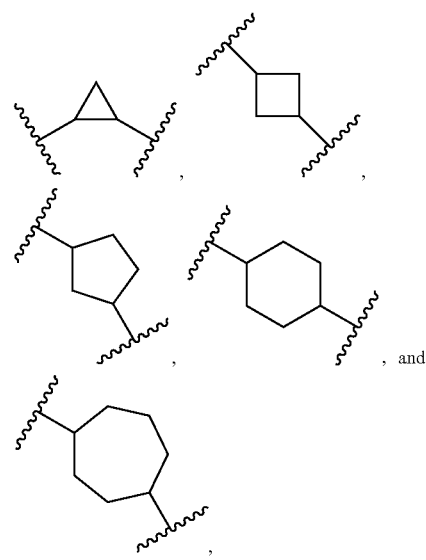

, and wherein G connects the formula scaffold to R$_{11}$.

In certain embodiments, G is a 4-, 5-, 6-, 7- or 8-membered saturated heterocycle. In some embodiments, G is selected from azetidine, oxetane, piperidine, oxane, piperazine, pyrrolidine, tetrahydrofuran, thiolane, imidazolidine, morpholine, thiomorpholine, azepane, and homopiperazine. In some embodiments, G is selected from:

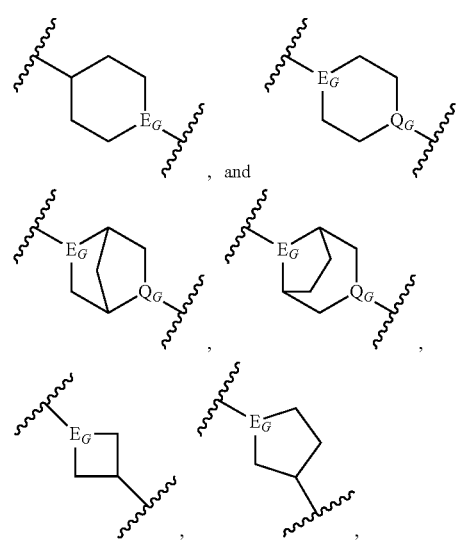

, and

-continued

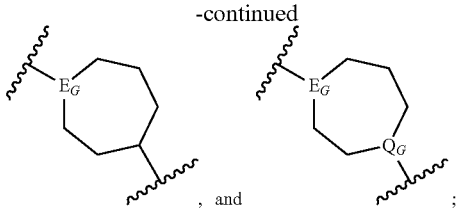

, and ;

wherein $E_G$ and $Q_G$ are independently selected from C, O, S, and N, and Z may adopt either orientation with respect to connection to $R_{11}$ and the formula scaffold. In some embodiments, $E_G$ and $Q_G$ are independently selected from O, S, and N.

In certain embodiments, for a compound or salt of any of Formula (2) through Formula (73) having a -G-$R_{11}$ group, G is selected from an unsaturated, aromatic, or heteroaromatic ring. In particular embodiments, G is selected from phenyl, pyridine, pyrazine, pyrimidine, pyridazine, naphthalene, anthracene, quinoline, isoquinoline, quinoxaline, acridine, quinazoline, cinnoline, phthalazine, furan, dihydrofuran, thiophene, dihydrothiophene, imidazole, imidazoline, oxazole, oxazoline, pyrrole, dihydropyrrole, thiazole, dihydrothiazole, pyrazole, dihydropyrazole, isoxazole, dihydroisoxazole, isothiazole, dihydroisothiazole, benzofuran, isobenzofuran, indole, isoindole, benzothiophene, benzimidazole, purine, indazole, benzoxazole, benzisoxazole, and benzothiazole. In some embodiments, G is selected from:

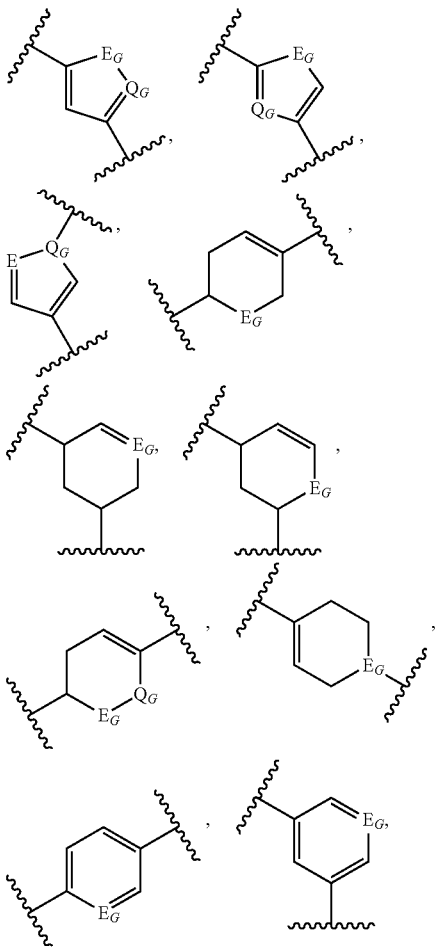

-continued

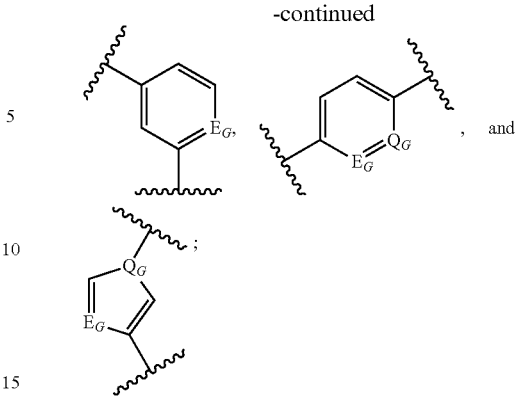

wherein $E_G$ and $G_G$ are independently selected from C, O, S, and N (or O, S, and N, but not C), and G may adopt either orientation with respect to connection to $R_{11}$ and the scaffold of any of Formula (2) through Formula (73) having a -G-$R_{11}$ group.

In some embodiments, $R_{11}$ of any of Formula (2) through Formula (73) having a -G-$R_{11}$ group is selected from: H, Br, Cl, F, I, D (deuterium), CN, alkane (e.g., methyl, ethyl, propyl, isopropyl, butyl, etc.), haloalkane (e.g., monohaloalkane (e.g., $CH_2F$, $CH_2CH_2Cl$, $CHBrCH_3$, etc.), dihaloalkane (e.g., $CF_2H$, $CH_2CCl_2H$, etc.), trihaloalkane (e.g., $CBr_3$, $CF_3$, $CCl_3$, $CH_2CBr_3$, $CH_2CF_3$, $CH_2CCl_3$, etc.)), alkene (e.g. $CH=CH_2$, etc.), alkyne (e.g. C≡CH, etc), amine (e.g., $NH_2$, NH-alkyl (e.g., NH-methyl, NH-ethyl, NH—$CH_2$-Ph, etc.), alkyl-amine (e.g., $(CH_2)_{1-6}$—$NH_2$), alkyl-amine-alkyl (e.g., $(CH_2)_{1-6}$—$NH_2$—$(CH_2)_{1-5}CH_3$, etc.), $(CH_2)_{1-6}$—$N(CH_3)_2$, alkene-$N(CH_3)_2$, alkyne-$N(CH_3)_2$, $N(CH_3)_2$, O-alkyl (e.g., $OCH_3$, $OCH_2CH_3$, etc.), NH-alcohol (e.g., NH—$CH_2$—$CH_2$—OH), etc.), hydroxy (e.g. —OH), and an alcohol (e.g., methanol, ethanol, butanol, propanol, $CH_2CHOHCH_2OH$, etc.).

In some embodiments, G of any of Formula (2) through Formula (73) having a -G-$R_{11}$ group is further substituted at one or more additional ring positions (e.g., in addition to the $R_{11}$ substitution). Additional substituents on the G ring may include: Br, Cl, F, I, CN, alkane (e.g., methyl, ethyl, propyl, isopropyl, butyl, etc.), haloalkane (e.g., monohaloalkane (e.g., $CH_2F$, $CH_2CH_2Cl$, $CHBrCH_3$, etc.), dihaloalkane (e.g., $CF_2H$, $CH_2CCl_2H$, etc.), trihaloalkane (e.g., $CBr_3$, $CF_3$, $CCl_3$, $CH_2CBr_3$, $CH_2CF_3$, $CH_2CCl_3$, etc.)), alkene (e.g. $CH=CH_2$, etc.), alkyne (e.g. C≡CH, etc), amine (e.g., $NH_2$, NH-alkyl (e.g., NH-methyl, NH-ethyl, NH—$CH_2$-Ph, etc.), alkyl-amine (e.g., $(CH_2)_{1-6}$—$NH_2$), alkyl-amine-alkyl (e.g., $(CH_2)_{1-6}$—$NH_2$—$(CH_2)_{1-5}CH_3$, etc.), $(CH_2)_{1-6}$—$N(CH_3)_2$, alkene-$N(CH_3)_2$, alkyne-$N(CH_3)_2$, $N(CH_3)_2$, O-alkyl (e.g., $OCH_3$, $OCH_2CH_3$, etc.), NH-alcohol (e.g., NH—$CH_2$—$CH_2$—OH), etc.), hydroxy (e.g. —OH), and an alcohol (e.g., methanol, ethanol, butanol, propanol, $CH_2CHOHCH_2OH$, etc.).

In some embodiments, X of any of Formula (2) through Formula (73), when not otherwise specified in the Formula (e.g., X is O in, for example, Formulas (3), (27), (51), etc.), is selected from: C, O, N, and S. In embodiments in which X is O or S, the X position is not further substituted. In embodiments in which X is C or N, the X position comprises one or two additional substituents selected from: H, D, $CH_3$, $CH_2C_3$, $CHCH_2$, $NH_2$, OH, COH, $COCH_3$, Br, Cl, F, $N(CH_3)_2$, CN, $CH(CH_3)_2$, $CH(CH_2CH_3)_2$, $CF_3$, $CCl_3$, $CBr_3$, $CHF_2$, $CHCl_2$, $CHBr_2$, $CFH_2$, $CClH_2$, $CBrH_2$, etc. In some embodiments, X is O.

In some embodiments, A, M, L, and Y of any of Formula (2) through Formula (73), when not otherwise specified in the Formula, are independently selected from: C, O, S, and N. In embodiments in which A, M, L, and/or Y is O or S, the double bonds of the ring systems are adjusted accordingly (as is understood by one in the field). In embodiments in which A, M, L, and/or Y is N, the A, M, L, and/or Y position is not further substituted. In embodiments in which A, M, L, and/or Y is C, the A, M, L, and/or Y position comprises an substituent selected from: H, D, $CH_3$, $CH_2CH_3$, $CHCH_2$, $NH_2$, OH, COH, $COCH_3$, Br, Cl, F, $N(CH_3)_2$, CN, CH $(CH_3)_2$, $CH(CH_2CH_3)_2$, $CF_3$, $CCl_3$, $CBr_3$, $CHF_2$, $CHCl_2$, $CHBr_2$, $CFH_2$, $CClH_2$, $CBRH_2$, etc. In some embodiments, A, M, L, and Y of any of Formula (2) through Formula (73), when not otherwise specified in the Formula, are independently selected from C and N. In some embodiments, A, M, and L are C and Y is N. In some embodiments, A and Y are N and M and L are C. In some embodiments, M and Y are N and A and L are C. In some embodiments, L and Y are N and M and A are C. In some embodiments, A is C and M, L, and Y are N.

In some embodiments, any or all hydrogens (e.g., exchangeable hydrogens, non-exchangeable hydrogens, and/or both) on a compound of any of Formula (2) through Formula (73) and substituents thereof may be substituted for deuterium atoms. In some embodiments, any of the hydrogens in the structures, formulas, or substituents described herein, or any subsets thereof, are substituted for deuterium atoms (D).

In some embodiments, $R_7$, $R_8$, —Z—$R_{10}$, and/or -G-$R_{11}$ of any of Formulas (I) through (IV) and/or (1) through (73) are selected from:

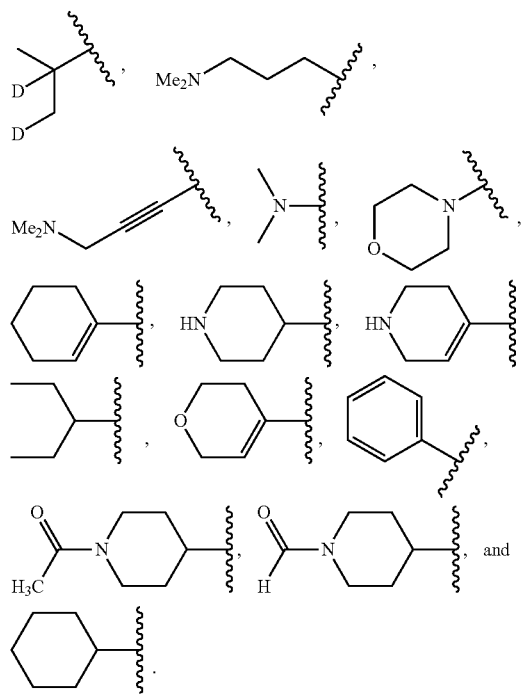

In some embodiments, $R_7$, $R_8$, —Z—$R_{10}$, and/or -G-$R_{11}$ of any of Formulas (I) through (IV) and/or (1) through (73) are selected from the corresponding substituents in the compounds of Table 1, Table 2, Table, 3, and/or Example 5.

In some embodiments, for any amlexanox analogs comprising one or more chiral centers, a racemic mixture, or racemate, is provided. In other embodiments, a single enantiomer (e.g., at one or more chiral centers, at all chiral centers, at some chiral centers, etc.) of an amlexanox analog is provided (e.g., R or S, right- or left-handed, L or D, + or −, etc.) In some embodiments, deuterated analogs of any amlexanox analogs may also be provided. Deuteration of amlexanox is described, for example, in U.S. Pat. No. 8,946,424; herein incorporated by reference in its entirety.

III. Pharmaceutical Formulation

Amlexanox analogs may be used to treat a variety of disease and conditions, particularly those related to improper insulin-insulin receptor signaling (e.g., those caused by increased phosphorylation of the insulin receptor by IKKi, thereby attenuating the ability of insulin to bind to this receptor for normal glucose metabolism). In particular embodiments, an amlexanox analog is administered to a subject in order to reduce body fat or increase lead body mass in the subject. In other embodiments, an amlexanox analog is administered to a subject to reduce the symptoms of (or eliminate the symptoms of) obesity, insulin resistance, diabetes, and related disorders. In some embodiments, an amlexanox analog is administered to lower cholesterol or lipid in a subject or to prevent elevated cholesterol or lipids in a subject. In some embodiments, an amlexanox analog is used to treat the symptoms of obesity or type 2 diabetes.

Both Types 1 and 2 diabetes mellitus are disorders of dysregulated energy metabolism, due to inadequate action and/or secretion of insulin. Although it is more common in Type 2, patients with both forms of diabetes exhibit insulin resistance, resulting from a defect in insulin-stimulated glucose transport in muscle and fat and suppression of hepatic glucose output. Obesity is a crucial determinant in the development of most cases of Type 2 diabetes, and is associated with increased circulating levels of pro-inflammatory cytokines that impair glucose tolerance, such as TNFα, IL-6, IL-18, IL-1β, and CRP. Weight loss decreases the circulating levels of these cytokines, suggesting a direct role of adipose tissue in regulating systemic inflammation. The inflammatory signaling cascade leading to NFκB activation contributes to the development of insulin resistance in obese animal models. Haploinsufficiency of IκB Kinase-β (IKK β) protects mice from high fat diet-induced insulin resistance, but does not protect against obesity. High dose salicylates, which inhibit IKK β activity, improve glucose tolerance in obese mice.

Provided herein are pharmaceutical compositions comprising an amlexanox analog, alone or in combination with at least one other agent, such as a stabilizing compound, and may be administered in any sterile, biocompatible pharmaceutical carrier, including, but not limited to, saline, buffered saline, dextrose, and water.

As is well known in the medical arts, dosages for any one patient depends upon many factors, including the patient's size, body surface area, age, the particular compound to be administered, sex, time and route of administration, general health, and interaction with other drugs being concurrently administered.

Depending on the condition being treated, these pharmaceutical compositions may be formulated and administered systemically or locally. Techniques for formulation and administration may be found in the latest edition of "Remington's Pharmaceutical Sciences" (Mack Publishing Co, Easton Pa.). Suitable routes may, for example, include oral or transmucosal administration; as well as parenteral delivery, including intramuscular, subcutaneous, intramedullary, intrathecal, intraventricular, intravenous, intraperitoneal, or intranasal administration.

For injection, the amlexanox analog pharmaceutical compositions may be formulated in aqueous solutions, preferably in physiologically compatible buffers such as Hanks' solution, Ringer's solution, or physiologically buffered saline. For tissue or cellular administration, penetrants appropriate to the particular barrier to be permeated are used in the formulation. Such penetrants are generally known in the art.

In other embodiments, the pharmaceutical compositions are formulated using pharmaceutically acceptable carriers well known in the art in dosages suitable for oral administration. Such carriers enable the pharmaceutical compositions to be formulated as tablets, pills, capsules, liquids, gels, syrups, slurries, suspensions and the like, for oral or nasal ingestion by a patient to be treated.

Pharmaceutical compositions include compositions wherein the active ingredients (e.g., an amlexanox analog) are contained in an effective amount to achieve the intended purpose. For example, an effective amount of an amlexanox analog may be that amount that restores a normal (non-diseased) rate of insulin mediated glucose metabolism. Determination of effective amounts is well within the capability of those skilled in the art, especially in light of the disclosure provided herein.

In addition to the active ingredients (e.g., an amlexanox analog) pharmaceutical compositions may contain suitable pharmaceutically acceptable carriers comprising excipients and auxiliaries that facilitate processing of the active compounds into preparations that can be used pharmaceutically. The preparations formulated for oral administration may be in the form of tablets, dragees, capsules, or solutions. The pharmaceutical compositions of the present invention may be manufactured in a manner that is itself known (e.g., by means of conventional mixing, dissolving, granulating, dragee-making, levigating, emulsifying, encapsulating, entrapping or lyophilizing processes).

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances that increase the viscosity of the suspension, such as sodium carboxymethyl cellulose, sorbitol, or dextran. Optionally, the suspension may also contain suitable stabilizers or agents that increase the solubility of the compounds to allow for the preparation of highly concentrated solutions.

Pharmaceutical preparations for oral use can be obtained by combining the active compounds with solid excipient, optionally grinding a resulting mixture, and processing the mixture of granules, after adding suitable auxiliaries, if desired, to obtain tablets or dragee cores. Suitable excipients are carbohydrate or protein fillers such as sugars, including lactose, sucrose, mannitol, or sorbitol; starch from corn, wheat, rice, potato, etc; cellulose such as methyl cellulose, hydroxypropylmethyl-cellulose, or sodium carboxymethylcellulose; and gums including arabic and tragacanth; and proteins such as gelatin and collagen. If desired, disintegrating or solubilizing agents may be added, such as the cross-linked polyvinyl pyrrolidone, agar, alginic acid or a salt thereof such as sodium alginate.

Dragee cores are provided with suitable coatings such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, (e.g., dosage).

Pharmaceutical preparations for oral administration include push-fit capsules made of gelatin, as well as soft, sealed capsules made of gelatin and a coating such as glycerol or sorbitol. The push-fit capsules can contain the active ingredients mixed with a filler or binders such as lactose or starches, lubricants such as talc or magnesium stearate, and, optionally, stabilizers. In soft capsules, the active compounds may be dissolved or suspended in suitable liquids, such as fatty oils, liquid paraffin, or liquid polyethylene glycol with or without stabilizers.

Compositions comprising amlexanox analog formulated in a pharmaceutical acceptable carrier may be prepared, placed in an appropriate container, and labeled for treatment of an indicated condition. Conditions indicated on the label may include treatment of obesity, diabetes, insulin resistance, or weight loss.

The pharmaceutical composition may be provided as a salt and can be formed with many acids, including but not limited to hydrochloric, sulfuric, acetic, lactic, tartaric, malic, succinic, etc. Salts tend to be more soluble in aqueous or other protonic solvents that are the corresponding free base forms. In other cases, the preferred preparation may be a lyophilized powder in 1 mM-50 mM histidine, 0.1%-2% sucrose, 2%-7% mannitol at a pH range of 4.5 to 5.5 that is combined with buffer prior to use.

In some embodiments, a therapeutically effective dose may be estimated initially from cell culture assays and/or animal models (particularly murine models). A therapeutically effective dose refers to that amount of an amlexanox analog that ameliorates symptoms of the disease state or unwanted condition. Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index, and it can be expressed as the ratio $LD_{50}/ED_{50}$. Compounds that exhibit large therapeutic indices are preferred. Data obtained from these cell culture assays and additional animal studies can be used in formulating a range of dosage for human use. The dosage of such compounds lies preferably within a range of circulating concentrations that include the $ED_{50}$ with little or no toxicity. The dosage varies within this range depending upon the dosage form employed, sensitivity of the patient, and the route of administration. The exact dosage is chosen by the individual clinician in view of the patient to be treated. Dosage and administration are adjusted to provide sufficient levels of the active moiety or to maintain the desired effect. Additional factors which may be taken into account include the severity of the disease state; age, weight, and gender of the patient; diet, time and frequency of administration, drug combination (s), reaction sensitivities, and tolerance/response to therapy. Long acting pharmaceutical compositions might be administered every 3 to 4 days, every week, or once every two weeks depending on half-life and clearance rate of the particular formulation.

Typical dosage amounts may vary from 0.1 to 100,000 micrograms, up to a total dose of about 1 g, depending upon the route of administration. Guidance as to particular dosages and methods of delivery is provided in the literature (See, U.S. Pat. Nos. 4,657,760; 5,206,344; 5,225,212; WO2004/097009, or WO2005/075465, each of which are herein incorporated by reference).

IV. Combination Therapy

In some embodiments, the compounds disclosed herein are combined or used in combination with other agents useful in the treatment of kinase-mediated disorders. Or, by way of example only, the therapeutic effectiveness of one of the compounds described herein may be enhanced by administration of an adjuvant (e.g., by itself the adjuvant may only have minimal therapeutic benefit, but in combination with another therapeutic agent, the overall therapeutic benefit to the patient is enhanced).

Such other agents, adjuvants, or drugs, may be administered, by a route and in an amount commonly used therefor, simultaneously or sequentially with a compound as disclosed herein. When a compound as disclosed herein is used contemporaneously with one or more other drugs, a pharmaceutical composition containing such other drugs in addition to the compound disclosed herein may be utilized, but is not required.

In some embodiments, a compound provided herein is combined with an anti-obesity and/or an anti-diabetes therapy. For example, in some embodiments a compound described herein is provided with a meglitinide, e.g., to stimulate the release of insulin. Exemplary meglitinides are repaglinide (Prandin) and nateglinide (Starlix). In some embodiments, a compound described herein is provided with a sulfonylurea, e.g., to stimulate the release of insulin. Exemplary sulfonylureas are glipizide (Glucotrol), glimepiride (Amaryl), and glyburide (DiaBeta, Glynase).

In some embodiments, a compound described herein is provided with a dipeptidyl peptidase-4 (DPP-4) inhibitor, e.g., to stimulate the release of insulin and/or to inhibit the release of glucose from the liver. Exemplary dipeptidyl peptidase-4 (DPP-4) inhibitors are saxagliptin (Onglyza), sitagliptin (Januvia), and linagliptin (Tradjenta). In some embodiments, a compound described herein is provided with a biguanide, e.g., to inhibit the release of glucose from the liver and/or to improve sensitivity to insulin. An exemplary biguanide is metformin (Fortamet, Glucophage). In some embodiments, a compound described herein is provided with a thiazolidinedione, e.g., to improve sensitivity to insulin and/or to inhibit the release of glucose from the liver. Exemplary thiazolidinediones include but are not limited to rosiglitazone (Avandia) and pioglitazone (Actos). In some embodiments a compound described herein is provided with an alpha-glucosidase inhibitor, e.g., to slow the breakdown of starches and some sugars. Exemplary alpha-glucosidase inhibitors include acarbose (Precose) and miglitol (Glyset). In some embodiments, a compound as described herein is provided with an injectable medication such as an amylin mimetic or an incretin memetic, e.g., to stimulate the release of insulin. An exemplary amylin mimetic is pramlintide (Symlin); exemplary incretin mimetics include exenatide (Byetta) and liraglutide (Victoza). In some embodiments a compound described herein is provided with insulin. The technology is not limited to any particular form of insulin, but encompasses providing the compounds described with any form of insulin. In some embodiments, the compounds described are used with an insulin injection. In some embodiments, a compound described herein is provided with more than one additional therapy (e.g., drug or other biologically active composition or compound), e.g., two, three, four or more compounds.

In certain embodiments, the compounds disclosed herein are combined with one or more non-steroidal anti-inflammatory agents, anilide analgesics, glucocorticoids, and immunosuppressants.

In certain embodiments, the compounds disclosed herein are combined with one or more non-steroidal anti-inflammatory agents, including, but not limited to, aceclofenac, acemetacin, amoxiprin, aspirin, azapropazone, benorilate, bromfenac, carprofen, celecoxib, choline magnesium salicylate, diclofenac, diflunisal, etodolac, etoracoxib, faislamine, fenbuten, fenoprofen, flurbiprofen, ibuprofe, ketoprofen, ketorolac, lornoxicam, loxoprofen, lumiracoxib, meloxicam, meclofenamic acid, mefenamic acid, meloxicam, metamizole, methyl salicylate, magnesium salicylate, nabumetone, naproxen, nimesulide, oxyphenbutazone, parecoxib, phenylbutazone, piroxicam, salicyl salicylate, sulindac, 89yridine89amine, suprofen, tenoxicam, tiaprofenic acid, and tolmetin. In certain embodiments, the compounds disclosed herein can be combined with one or more anilide analgesics, including, but not limited to, acetaminophen and phenacetin.

In certain embodiments, the compounds disclosed herein can be combined with one or more glucocorticoids, including, but not limited to, budesonide, flunisolide, betamethasone, fluticasone, triamcinolone, mometasone, ciclesonide, hydrocortisone, cortisone acetate, prednisone, prednisolone, methylprednisolone, and dexamethasone.

Certain embodiments, the compounds disclosed herein are combined with one or more immunosuppressants, including, but not limited to, fingolimod, cyclosporine A, azathioprine, dexamethasone, tacrolimus, sirolimus, pimecrolimus, mycophenolate salts, everolimus, basiliximab, daclizumab, anti-thymocyte globulin, anti-lymphocyte globulin, and CTLA4IgG.

In some embodiments, an amlexanox analog, or derivative thereof, or a pharmaceutically acceptable salt thereof, is co-administered with one or more additional therapeutic agents or medical interventions. In some embodiments, co-administration involves co-formulation of two or more agents together into the same medicament. In other embodiments, the agents are in separate formulations but are administered together, either simultaneously or in sequence (e.g., separated by one or more minutes, hours, days, etc.). In some embodiments, where a synergistic or additive benefit is achieved, the co-administered agent may be provided at a lower dose than would normally be administered if that agent were being used in isolation to treat the disease or condition.

The compounds disclosed herein can also be administered in combination with other classes of compounds, including, but not limited to, norepinephrine reuptake inhibitors (NRIs) such as atomoxetine; dopamine reuptake inhibitors (DARIs), such as methylphenidate; serotonin-norepinephrine reuptake inhibitors (SNRIs), such as milnacipran; sedatives, such as diazepham; norepinephrine-dopamine reuptake inhibitor (NDRIs), such as bupropion; serotonin-norepinephrine-dopamine-reuptake-inhibitors (SNDRIs), such as venlafaxine; monoamine oxidase inhibitors, such as selegiline; hypothalamic phospholipids; endothelin converting enzyme (ECE) inhibitors, such as phosphoramidon; opioids, such as tramadol; thromboxane receptor antagonists, such as ifetroban; potassium channel openers; thrombin inhibitors, such as hirudin; hypothalamic phospholipids; growth factor inhibitors, such as modulators of PDGF activity; platelet activating factor (PAF) antagonists; anti-platelet agents, such as GPIIb/IIIa blockers (e.g., abdximab, eptifibatide, and tirofiban), P2Y(AC) antagonists (e.g., clopidogrel, ticlopidine and CS-747), and aspirin; anticoagulants, such as warfarin; low molecular weight heparins, such as enoxaparin; Factor VIIa Inhibitors and Factor Xa Inhibitors; renin inhibitors; neutral endopeptidase (NEP) inhibitors; vasopepsidase inhibitors (dual NEP-ACE inhibitors), such as omapatrilat and gemopatrilat; HMG CoA reductase inhibitors, such as pravastatin, lovastatin, atorvastatin, simvastatin, NK-104 (a.k.a. itavastatin, nisvastatin, or nisbastatin), and ZD-4522 (also known as rosuvastatin, or atavastatin or visastatin); squalene synthetase inhibitors; fibrates; bile acid sequestrants, such as questran; niacin; anti-atherosclerotic agents, such as ACAT inhibitors; MTP Inhibitors; calcium channel blockers, such as amlodipine besylate; potassium channel activators; alpha-muscarinic agents; beta-muscarinic agents, such as carvedilol and metoprolol; antiarrhythmic agents; diuretics, such as chlorothlazide, hydrochlorothiazide, flumethiazide, hydroflumethiazide, bendroflumethiazide, methylchlorothiazide, trichloromethiazide, polythiazide, benzothlazide, ethacrynic acid, tricrynafen, chlorthalidone, furosenilde, musolimine, bumetanide, triamterene, amiloride, and spironolactone; thrombolytic agents, such as tissue plasminogen activator (tPA), recombinant tPA, streptokinase, urokinase, prourokinase, and anisoylated plasminogen streptokinase activator complex (APSAC); anti-diabetic agents, such as biguanides (e.g. metformin), glucosidase inhibitors (e.g., acarbose), insulins, meglitinides (e.g., repaglinide), sulfonylureas (e.g., glimepiride, glyburide, and glipizide), thiozolidinediones (e.g. troglitazone, rosiglitazone and pioglitazone), and PPAR-gamma agonists; mineralocorticoid receptor antagonists, such as spironolactone and eplerenone; growth hormone secretagogues; aP2 inhibitors; phosphodiesterase inhibitors, such as PDE III inhibitors (e.g., cilostazol) and PDE V inhibitors (e.g., sildenafil, tadalafil, vardenafil); protein tyrosine kinase inhibitors; antiinflammatories; antiproliferatives, such as methotrexate, FK506 (tacrolimus, Prograf), mycophenolate mofetil; chemotherapeutic agents; anticancer agents and cytotoxic agents (e.g., alkylating agents, such as nitrogen mustards, alkyl sulfonates, nitrosoureas, ethylenimines, and triazenes); antimetabolites, such as folate antagonists, purine analogues, and 91yridine analogues; antibiotics, such as anthracyclines, bleomycins, mitomycin, dactinomycin, and plicamycin; enzymes, such as L-asparaginase; farnesyl-protein transferase inhibitors; hormonal agents, such as estrogens/antiestrogens, androgens/antiandrogens, progestins, and luteinizing hormone-releasing hormone anatagonists, and octreotide acetate; microtubule-disruptor agents, such as ecteinascidins; microtubule-stabilizing agents, such as pacitaxel, docetaxel, and epothilones A-F; plant-derived products, such as vinca alkaloids, epipodophyllotoxins, and taxanes; topoisomerase inhibitors; prenyl-protein transferase inhibitors; cyclosporins; steroids, such as prednisone and dexamethasone; cytotoxic drugs, such as azathiprine and cyclophosphamide; TNF-alpha inhibitors, such as tenidap; anti-TNF antibodies or soluble TNF receptor, such as etanercept, rapamycin, and leflunimide; and cyclooxygenase-2 (COX-2) inhibitors, such as celecoxib and rofecoxib; and miscellaneous agents such as, hydroxyurea, procarbazine, mitotane, hexamethylmelamine, gold compounds, platinum coordination complexes, such as cisplatin, satraplatin, and carboplatin.

Thus, some embodiments provide methods for treating kinase-mediated disorders in a human or animal subject in need of such treatment comprising administering to said subject an amount of a compound disclosed herein effective to reduce or prevent said disorder in the subject, in combination with at least one additional agent for the treatment of said disorder that is known in the art. Some embodiments provide therapeutic compositions comprising at least one compound disclosed herein in combination with one or more additional agents for the treatment of kinase-mediated disorders.

V. Kits

The technology provided herein also includes kits for use in the instant methods. Kits of the technology comprise one or more containers comprising an amlexanox analog, a derivative thereof, or a pharmaceutically acceptable salt thereof, and/or a second agent, and in some variations further comprise instructions for use in accordance with any of the methods provided herein. The kit may further comprise a description of selecting an individual suitable treatment. Instructions supplied in the kits of the technology are typically written instructions on a label or package insert (e.g., a paper insert included with the kit), but machine-readable instructions (e.g., instructions carried on a magnetic or optical storage disk) are also contemplated. In some embodiments, the kit is a package containing a sealed container comprising any one of the preparations described above, together with instructions for use. The kit can also include a diluent container containing a pharmaceutically acceptable diluent. The kit can further comprise instructions for mixing the preparation and the diluent. The diluent can be any pharmaceutically acceptable diluent. Well known diluents include 5% dextrose solution and physiological saline solution. The container can be an infusion bag, a sealed bottle, a vial, a vial with a septum, an ampoule, an ampoule with a septum, an infusion bag, or a syringe. The containers can optionally include indicia indicating that the containers have been autoclaved or otherwise subjected to sterilization techniques. The kit can include instructions for administering the various solutions contained in the containers to subjects.

VI. Methods of Treatment

The technology also relates to methods of treatment with an amlexanox analog. According to another aspect of the technology, a method is provided for treating a subject in need of such treatment with an effective amount of an amlexanox analog or a salt thereof. For example, some subjects in need of compositions according to the technology have diabetes, insulin resistance, steatosis, hepatitis, obesity, allergic rhinitis, conjunctivitis, allergy, asthma, immune disorder, atherosclerosis, canker sore, ulcer (e.g., aphthous ulcer, symptoms of Behcet's Disease, etc.), or inflammation (e.g., inflammatory bowel disease, Crohn's disease, osteoarthritis, etc.). The method involves administering to the subject an effective amount of an amlexanox analog or salt thereof in any one of the pharmaceutical preparations described above, detailed herein, and/or set forth in the claims. The subject can be any subject in need of such treatment. In the foregoing description, the technology is in connection with an amlexanox analog or salts thereof. Such salts include, but are not limited to, bromide salts, chloride salts, iodide salts, carbonate salts, and sulfate salts. It should be understood, however, that an amlexanox analog is a member of a class of compounds and the technology is intended to embrace pharmaceutical preparations, methods, and kits containing related derivatives within this class.

In some embodiments, provided herein are methods of treatment comprising: administering a pharmaceutically effective amount of an amlexanox analog, a derivative thereof, or a pharmaceutically acceptable salt thereof, alone or in combination with another agent, to a subject having a condition in need of treatment. In some embodiments, the administration causes one or more of: a reduction in or elimination of one or more symptoms of the condition, prevention of increased severity of one or more symptoms of the condition, and/or reduction, prevention, or elimination of further diseases or conditions.

In some embodiments, the methods provided comprise testing a subject for a disease or condition followed by administering an amlexanox analog, a derivative thereof, or a pharmaceutically acceptable salt thereof, alone or in combination with other agents. In some embodiments, methods comprise administering to a subject an amlexanox analog, a derivative thereof, or a pharmaceutically acceptable salt thereof, alone or in combination with other agents, followed by testing the subject for a disease or a condition. In some embodiments, methods comprise testing a subject for a disease or condition followed by administering an amlexanox analog, a derivative thereof, or a pharmaceutically acceptable salt thereof, alone or in combination with other agents, followed by a second round of testing for a disease or condition (e.g., to monitor the effect of the treatment). In some embodiments, methods comprise testing a subject for a disease or condition followed by administering an amlexanox analog, a derivative thereof, or a pharmaceutically acceptable salt thereof, alone or in combination with other agents, followed by a second round of testing for a disease or condition and a second administration of an amlexanox analog, a derivative thereof, or a pharmaceutically acceptable salt thereof, alone or in combination with other agents, with this second administration being modified in dose, duration, frequency, or administration route in a manner dependent upon the results of the prior testing. In some embodiments, a subject is tested to assess the presence, the absence, or the level of a disease, e.g., by assaying or measuring a biomarker, a metabolite, a physical symptom, an indication, etc., to determine the risk of or the presence of the disease and thereafter the subject is treated with an amlexanox analog based on the outcome of the test. In some embodiments, a patient is tested, treated, and then tested again to monitor the response to therapy. In some embodiments, cycles of testing and treatment may occur without limitation to the pattern of testing and treating (e.g., test/treat, test/treat/test, test/treat/test/treat, test/treat/test/treat/test, test/treat/treat/test/treat/treat, etc.), the periodicity, or the duration of the interval between each testing and treatment phase.

In some embodiments, the technology provided comprises use of an amlexanox analog, a derivative thereof, or a pharmaceutically acceptable salt thereof, alone or in combination with other agents in the manufacture of a medicament for the treatment of a condition. In some embodiments, the technology provides an amlexanox analog, a derivative thereof, or a pharmaceutically acceptable salt thereof, for the treatment of a condition.

EXPERIMENTAL

Example 1

Exemplary Synthesized Compounds

Table 1 provides a list of exemplary synthesized compounds.

TABLE 1

| Compound # | structure | MW | cLogP | tPSA |
|---|---|---|---|---|
| 5 | *(structure)* | 296.28 | 2.59 | 101.98 |
| 24 | *(structure)* | 341.32 | 1.201 | 114.45 |
| 11 | *(structure)* | 324.34 | 3.71 | 101.98 |
| 26 | *(structure)* | 365.32 | 0.359 | 126.26 |

TABLE 1-continued

| Compound # | structure | MW | cLogP | tPSA |
|---|---|---|---|---|
| 28 | 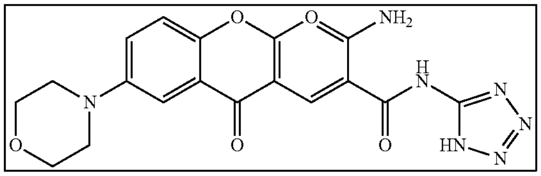 | 408.38 | 0.0401 | 155.36 |
| 34 | HCl salt | 375.81 | −0.425 | 114.01 |
| 42 | 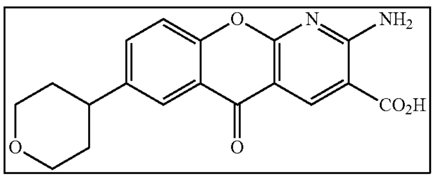 [SMILES: Nc1nc2oc3ccc(C4CCOCC4)cc3c(=O)c2cc1C(=O)O] | 340.33 | 1.87 | 111.21 |
| 15 | 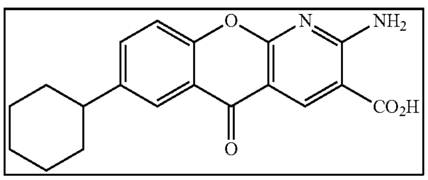 [SMILES: Nc1nc2oc3ccc(C4CCCCC4)cc3c(=O)c2cc1C(=O)O] | 338.36 | 4.26 | 101.98 |
| 40 | 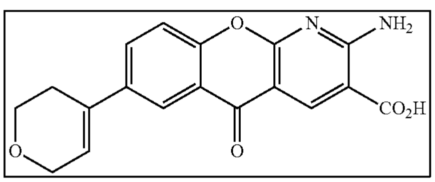 [SMILES: Nc1nc2oc3ccc(C4=CCOCC4)cc3c(=O)c2cc1C(=O)O] | 338.32 | 1.76 | 111.21 |
| 36 | 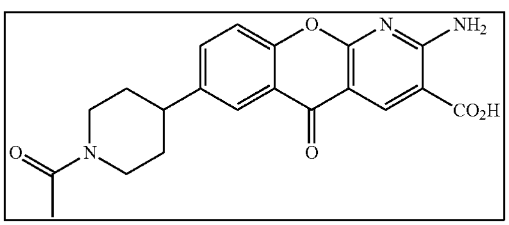 [SMILES: CC(=O)N1CCC(c2ccc3oc4nc(N)c(C(=O)O)cc4c(=O)c3c2)CC1] | 381.39 | 0.891 | 122.29 |
| 13 | 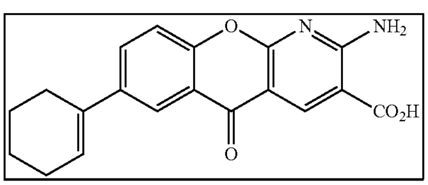 | 336.35 | 3.96 | 101.98 |
| 30 | 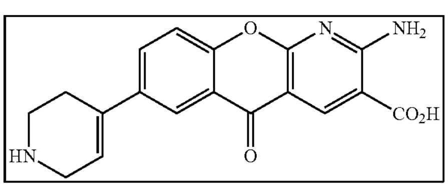 [SMILES: Nc1nc2oc3ccc(C4=CCNCC4)cc3c(=O)c2cc1C(=O)O] | 337.33 | −0.529 | 114.01 |

TABLE 1-continued

| Compound # | structure | MW | cLogP | tPSA |
|---|---|---|---|---|
| 38 | 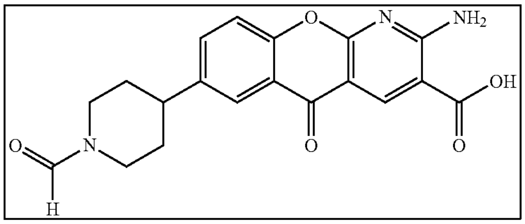 [SMILES: Nc1nc2oc3ccc(C4CCN(C=O)CC4)cc3c(=O)c2cc1C(=O)O] | 367.36 | 0.945 | 122.29 |
| 51 | 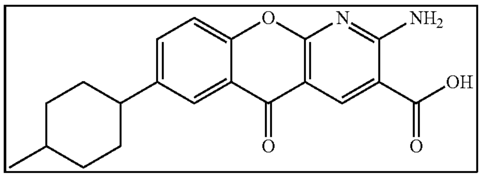 [SMILES: CC1CCC(c2ccc3oc4nc(N)c(C(=O)O)cc4c(=O)c3c2)CC1] | 352.39 | 4.783 | 101.98 |
| 67 | 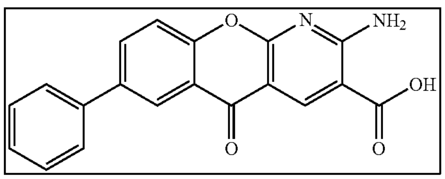 [SMILES: Nc1nc2oc3ccc(-c4ccccc4)cc3c(=O)c2cc1C(=O)O] | 332.31 | 3.532 | 101.98 |
| 8 | 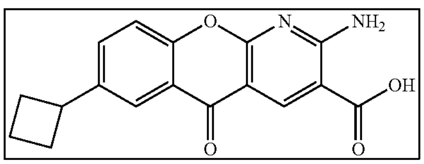 [SMILES: Nc1nc2oc3ccc(C4CCC4)cc3c(=O)c2cc1C(=O)O] | 310.31 | 3.146 | 101.98 |
| 19 | 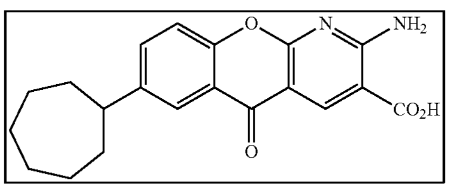 [SMILES: Nc1nc2oc3ccc(C4CCCCCC4)cc3c(=O)c2cc1C(=O)O] | 352.39 | 4.823 | 101.98 |
| 61 | 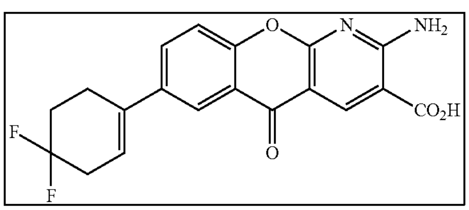 [SMILES: Nc1nc2oc3ccc(C4=CCC(F)(F)CC4)cc3c(=O)c2cc1C(=O)O] | 372.33 | 3.346 | 101.98 |
| 65 | 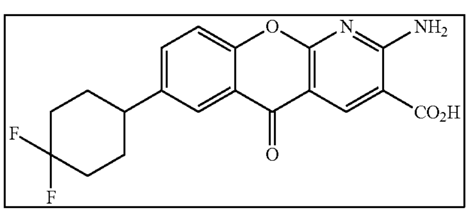 [SMILES: Nc1nc2oc3ccc(C4CCC(F)(F)CC4)cc3c(=O)c2cc1C(=O)O] | 374.34 | 3.65 | 101.98 |
| 45 | 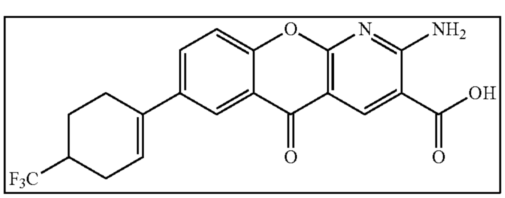 [SMILES: Nc1nc2oc3ccc(C4=CCC(C(F)(F)F)CC4)cc3c(=O)c2cc1C(=O)O] | 404.35 | 3.75 | 101.98 |

TABLE 1-continued
| Compound # | structure | MW | cLogP | tPSA |
|---|---|---|---|---|
| 52 | 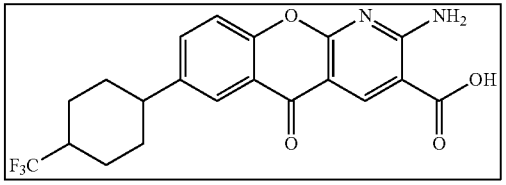 [SMILES: Nc1nc2oc3ccc(C4CCC(C(F)(F)F)CC4)cc3c(=O)c2cc1C(=O)O] | 406.36 | 4.06 | 101.98 |
| 74 | 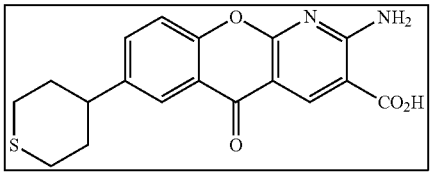 [SMILES: Nc1nc2oc3ccc(C4CCSCC4)cc3c(=O)c2cc1C(=O)O] | 356.4 | 2.92 | 101.98 |
| 47 | 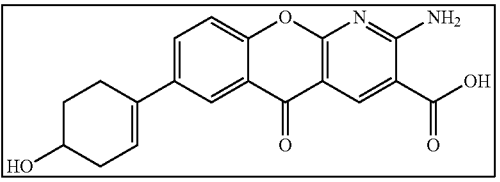 [SMILES: Nc1nc2oc3ccc(C4=CCC(O)CC4)cc3c(=O)c2cc1C(=O)O] | 352.35 | 1.87 | 122.21 |
| 53 | 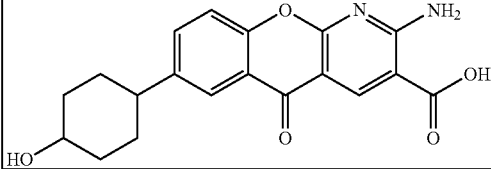 | 354.36 | 2.18 | 122.21 |
| 54a | 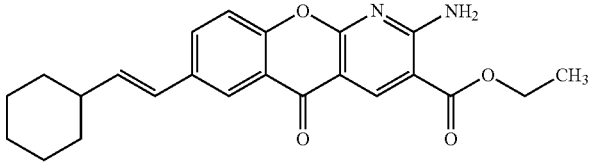 [SMILES: CCOC(=O)c1cc2c(=O)c3cc(/C=C/C4CCCCC4)ccc3oc2nc1N] | | | |
| 54b | 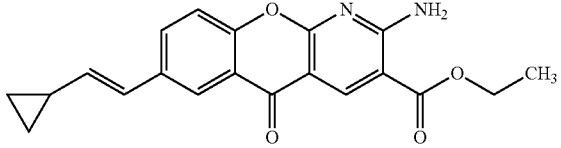 [SMILES: CCOC(=O)c1cc2c(=O)c3cc(/C=C/C4CC4)ccc3oc2nc1N] | | | |
| 54c | 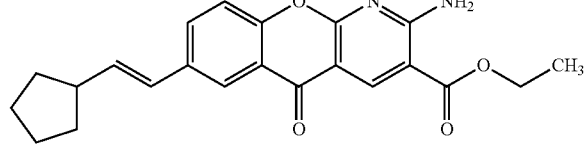 | | | |
| 55a | 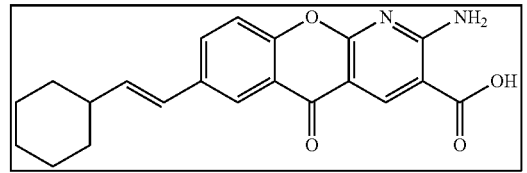 [SMILES: Nc1nc2oc3ccc(/C=C/C4CCCCC4)cc3c(=O)c2cc1C(=O)O] | 364.4 | 5.02 | 101.98 |

TABLE 1-continued

| Compound # | structure | MW | cLogP | tPSA |
|---|---|---|---|---|
| 55b | 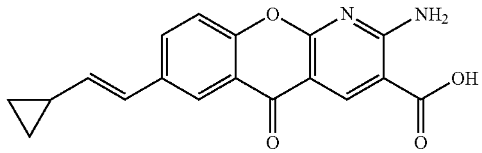 [SMILES: Nc1nc2oc3ccc(/C=C/C4CC4)cc3c(=O)c2cc1C(=O)O] | | | |
| 55c | 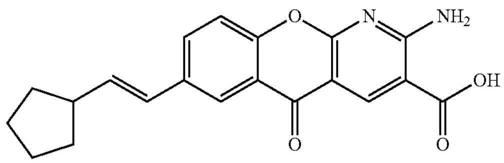 [SMILES: Nc1nc2oc3ccc(/C=C/C4CCCC4)cc3c(=O)c2cc1C(=O)O] | | | |
| 56a | 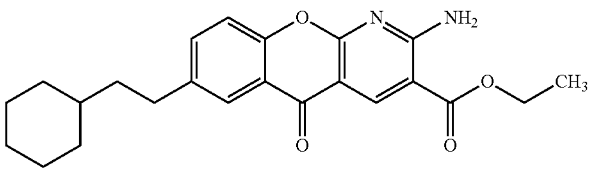 [SMILES: CCOC(=O)c1cc2c(=O)c3cc(CCC4CCCCC4)ccc3oc2nc1N] | | | |
| 56b | 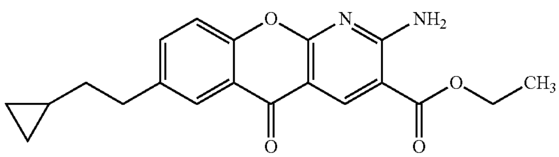 [SMILES: CCOC(=O)c1cc2c(=O)c3cc(CCC4CC4)ccc3oc2nc1N] | | | |
| 56c | 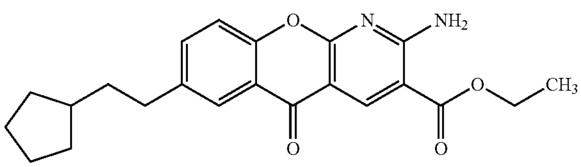 [SMILES: CCOC(=O)c1cc2c(=O)c3cc(CCC4CCCC4)ccc3oc2nc1N] | | | |
| 57a | 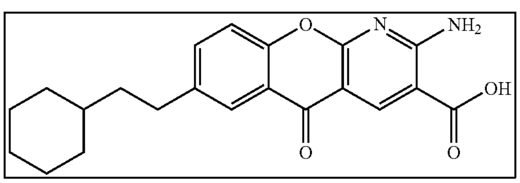 [SMILES: Nc1nc2oc3ccc(CCC4CCCCC4)cc3c(=O)c2cc1C(=O)O] | 366.42 | 5.32 | 101.98 |
| 57b | 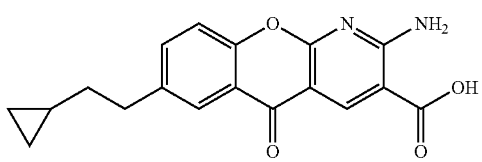 [SMILES: Nc1nc2oc3ccc(CCC4CC4)cc3c(=O)c2cc1C(=O)O] | | | |
| 57c | 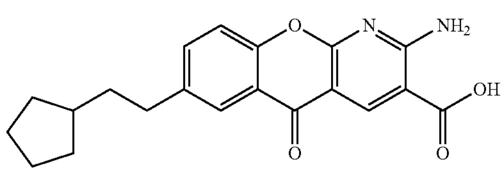 [SMILES: Nc1nc2oc3ccc(CCC4CCCC4)cc3c(=O)c2cc1C(=O)O] | | | |
| 78 | 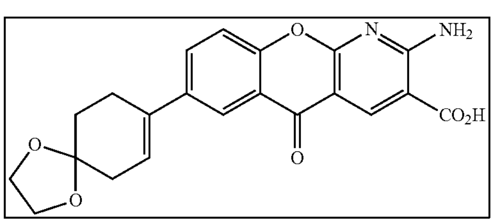 [SMILES: Nc1nc2oc3ccc(C4=CCC5(CC4)OCCO5)cc3c(=O)c2cc1C(=O)O] | 394.38 | 2.5 | 120.44 |

TABLE 1-continued

| Compound # | structure | MW | cLogP | tPSA |
|---|---|---|---|---|
| 80 | 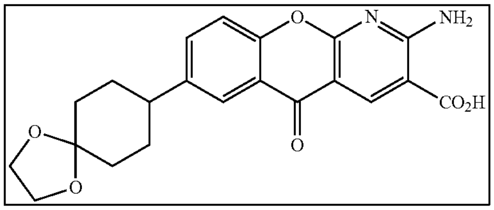 [SMILES: Nc1nc2oc3ccc(C4CCC5(CC4)OCCO5)cc3c(=O)c2cc1C(=O)O] | 396.4 | 2.8 | 120.44 |
| 69 | 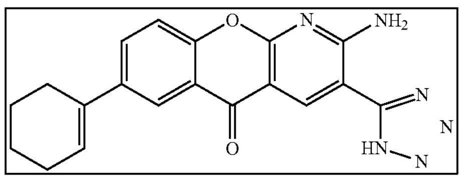 | 360.38 | 3.13 | 113.79 |
| 71 | 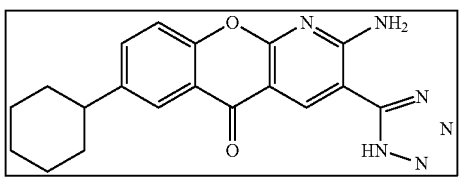 | 362.39 | 3.43 | 113.79 |
| 76 | 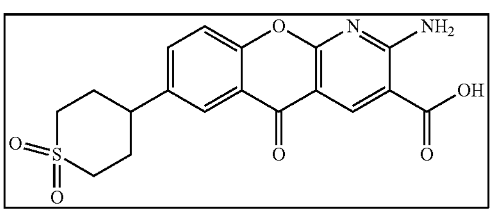 [SMILES: Nc1nc2oc3ccc(C4CCS(=O)(=O)CC4)cc3c(=O)c2cc1C(=O)O] | 388.39 | 0.485 | 136.12 |
| 81 | 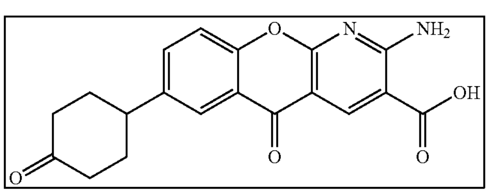 [SMILES: Nc1nc2oc3ccc(C4CCC(=O)CC4)cc3c(=O)c2cc1C(=O)O] | 352.35 | 1.78 | 119.05 |

Example 2

Synthesis Schemes for Exemplary Compounds

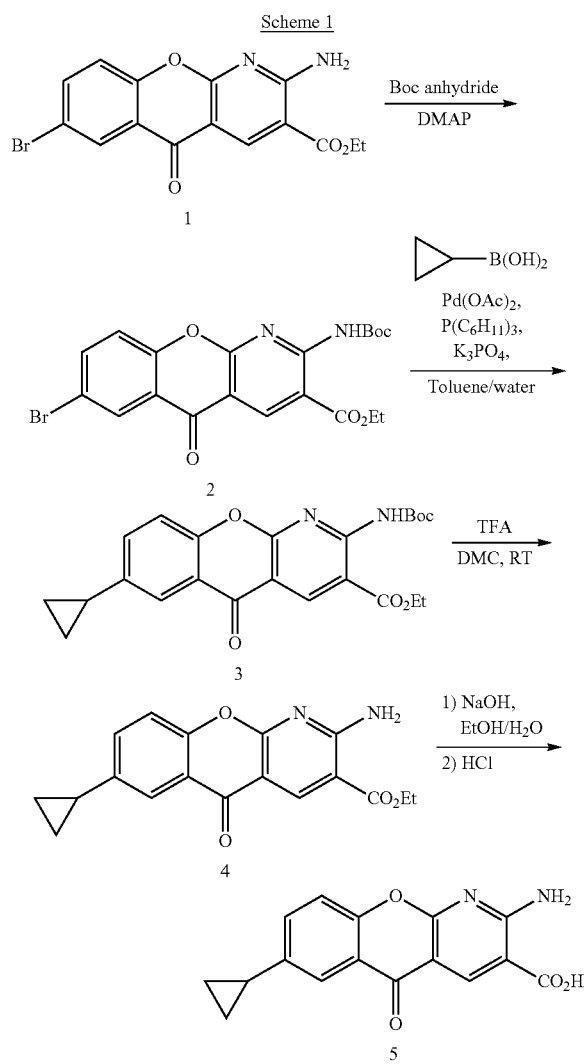

Ethyl 7-bromo-2-((tert-butoxycarbonyl)amino)-5-oxo-5H-chromeno[2,3-b]pyridine-3-carboxylate (2)

To a suspension of ethyl 2-amino-7-bromo-5-oxo-5H-chromeno[2,3-b]pyridine-3-carboxylate (1) (50 mg, 0.14 mmol, prepared by the method of C. Ghosh et al., J. Chem. Soc. Perkin Trans. 1, 1979, 1964-8) and 4-dimethylaminopyridine (1 mg, 8.2 umol) in dichloromethane (5 mL) was added di-tert-butyl dicarbonate (33 mg, 0.15 mmol) portionwise. The mixture was stirred at room temperature for 16 h. The solid was collected by filtration, washed with dichloromethane (2 mL) and dried to afford 2 (53 mg, 83%) as a white solid. $^1$H NMR (400 MHz, chloroform-d): δ 10.91 (s, 1H), 9.28 (d, J=0.9 Hz, 1H), 8.41 (d, J=2.4 Hz, 1H), 7.83 (dd, J=8.9, 2.5 Hz, 1H), 7.51 (d, J=8.9 Hz, 1H), 4.46 (q, J=7.1 Hz, 2H), 1.58 (d, J=0.9 Hz, 9H), 1.47 (t, J=7.1 Hz, 3H). MS TOFES$^-$: m/z 461, 463 (M−H)$^-$.

Ethyl 2-((tert-butoxycarbonyl)amino)-7-cyclopropyl-5-oxo-5H-chromeno[2,3-b]pyridine-3-carboxylate (3)

To a nitrogen-degassed suspension of compound 2 (100 mg, 0.22 mmol), cyclopropyl boronic acid (37 mg, 0.43 mmol), tripotassium phosphate (160 mg, 0.76 mmol) and tricyclohexylphosphine (9.1 mg, 0.03 mmol) in toluene (7 mL) and water (0.7 mL) was added Pd(Oac)$_2$ (3.6 mg, 0.02 mmol). The mixture was heated at 100° C. for 4 h, cooled, and distributed between water and dichloromethane. The organic phase was concentrated to a residual solid that was purified by flash silica gel chromatography (elution with 0.5-1.0% methanol in dichloromethane) to give 3 (62 mg, 68%). $^1$H NMR (400 MHz, chloroform-d): δ 10.88 (s, 1H), 9.29 (s, 1H), 7.94 (d, J=2.1 Hz, 1H), 7.60-7.42 (m, 2H), 4.46 (q, J=7.1 Hz, 2H), 2.03 (ddd, J=13.5, 8.6, 5.0 Hz, 1H), 1.47 (t, J=7.1 Hz, 3H), 1.08-0.97 (m, 2H), 0.80 (dt, J=6.6, 4.8 Hz, 2H). MS TOFES$^+$: m/z 425.2 (M+H)$^+$.

Ethyl 2-amino-7-cyclopropyl-5-oxo-5H-chromeno[2,3-b]pyridine-3-carboxylate (4)

To a solution of compound 3 (59 mg, 0.14 mmol) in dichloromethane (20 mL) was added 0.5 mL trifluoroacetic acid and the mixture was stirred for 15 min at room temperature. The mixture was washed with saturated aq NaHCO$_3$, dried (Na$_2$SO$_4$), and concentrated to give 4 (45 mg, 100%) as a white solid. $^1$H NMR (400 MHz, DMSO-d$_6$): δ 8.80 (s, 1H), 8.34 (s, 1H), 8.09 (s, 1H), 7.77 (d, J=2.2 Hz, 1H), 7.58-7.42 (m, 2H), 4.35 (q, J=7.1 Hz, 2H), 2.11 (dt, J=8.5, 3.7 Hz, 1H), 1.36 (t, J=7.1 Hz, 3H), 1.07-0.92 (m, 2H), 0.79-0.65 (m, 2H). MS TOFES$^+$: m/z 325.0 (M+H)$^+$.

2-Amino-7-cyclopropyl-5-oxo-5H-chromeno[2,3-b]pyridine-3-carboxylic acid (5)

To a suspension of 4 (43 mg, 0.13 mmol) in ethanol (10 mL) and water (1.3 mL) was added 1N aq NaOH (1.3 mL) and the mixture was stirred for 50 min at 50° C. The mixture was concentrated to a residue that was dissolved in water (25 mL) and acidified with 10% aq HCl to pH 2-3. The fine suspension was stirred at room temperature for 2 h and then let stand overnight. The formed precipitate was collected by filtration, washed with water and dried to give 5 (30 mg, 76%). $^1$H NMR (400 MHz, DMSO-d$_6$): δ 13.47 (s, 1H), 8.79 (s, 1H), 8.26 (d, J=13.4 Hz, 2H), 7.76 (d, J=2.2 Hz, 1H), 7.60-7.41 (m, 2H), 2.10 (dt, J=8.5, 3.8 Hz, 1H), 1.09-0.92 (m, 2H), 0.74 (dd, J=4.9, 2.0 Hz, 2H). MS TOFES$^+$: m/z 297.0 (M+H)$^+$.

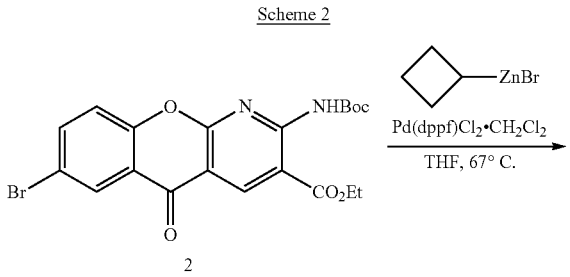

Scheme 2

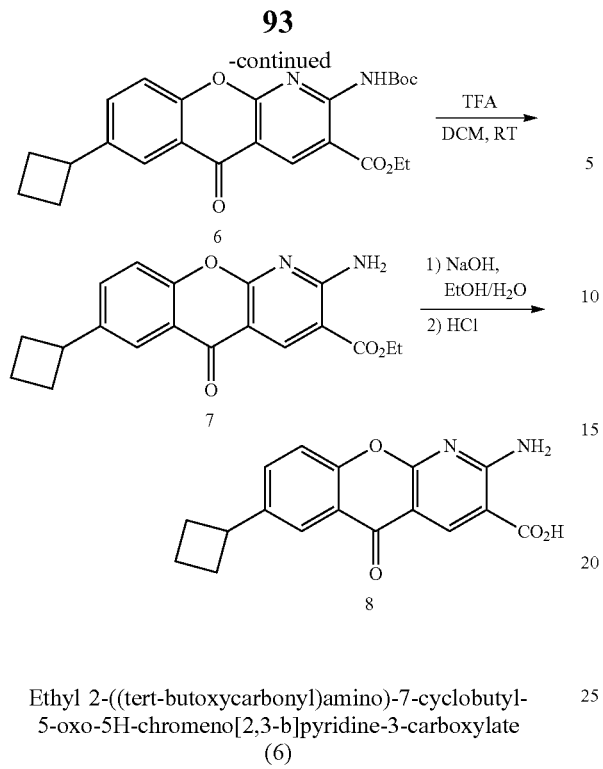

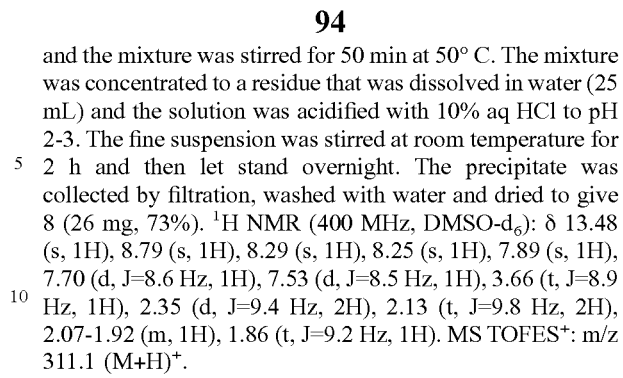

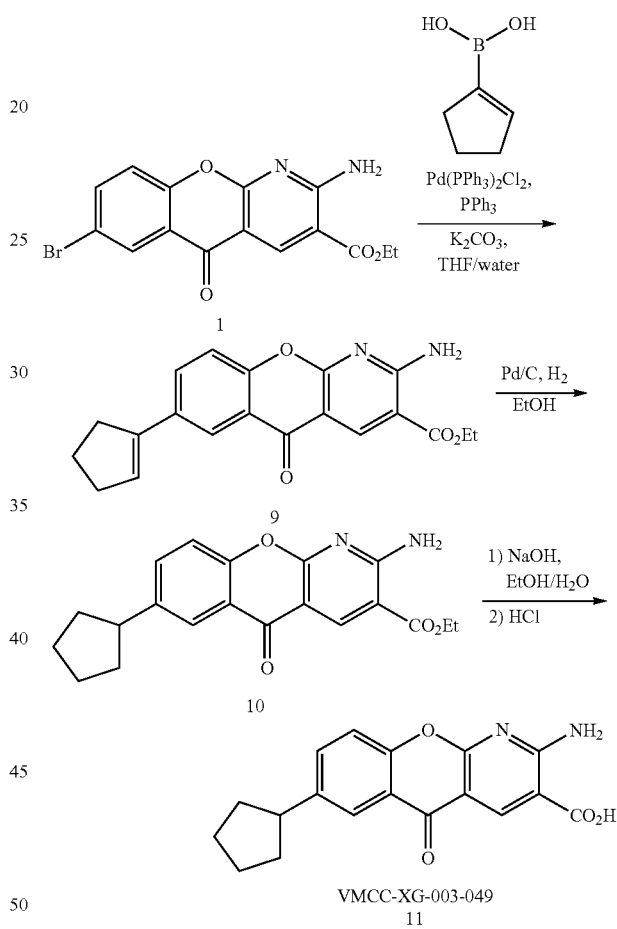

and the mixture was stirred for 50 min at 50° C. The mixture was concentrated to a residue that was dissolved in water (25 mL) and the solution was acidified with 10% aq HCl to pH 2-3. The fine suspension was stirred at room temperature for 2 h and then let stand overnight. The precipitate was collected by filtration, washed with water and dried to give 8 (26 mg, 73%). $^1$H NMR (400 MHz, DMSO-$d_6$): δ 13.48 (s, 1H), 8.79 (s, 1H), 8.29 (s, 1H), 8.25 (s, 1H), 7.89 (s, 1H), 7.70 (d, J=8.6 Hz, 1H), 7.53 (d, J=8.5 Hz, 1H), 3.66 (t, J=8.9 Hz, 1H), 2.35 (d, J=9.4 Hz, 2H), 2.13 (t, J=9.8 Hz, 2H), 2.07-1.92 (m, 1H), 1.86 (t, J=9.2 Hz, 1H). MS TOFES$^+$: m/z 311.1 (M+H)$^+$.

Scheme 3

Ethyl 2-((tert-butoxycarbonyl)amino)-7-cyclobutyl-5-oxo-5H-chromeno[2,3-b]pyridine-3-carboxylate (6)

Cyclobutylzinc(II) bromide (5.0 ml of 0.5 M solution in tetrahydrofuran, 2.5 mmol) was added to compound 2 (200 mg, 0.43 mmol) and Pd(dppf)Cl$_2$·CH$_2$Cl$_2$ (35.3 mg, 0.04 mmol) under nitrogen. The suspension was degassed with nitrogen and the vial capped. The mixture was stirred at 67° C. for 16 h, cooled, and distributed between water and dichloromethane. The organic phase was washed successively with 5% aq NaHCO$_3$ and brine, dried (Na$_2$SO$_4$), and concentrated to a solid that was purified by preparative plate chromatography (elution with 0.2% methanol in dichloromethane) to give 6 (50 mg, 26%). $^1$H NMR (400 MHz, chloroform-d): δ 10.89 (s, 1H), 9.30 (d, J=0.9 Hz, 1H), 8.10 (d, J=2.3 Hz, 1H), 7.68-7.57 (m, 1H), 7.54 (d, J=8.6 Hz, 1H), 4.47 (q, J=7.1 Hz, 2H), 3.66 (t, J=8.9 Hz, 1H), 2.42 (dtd, J=10.4, 7.9, 2.4 Hz, 2H), 2.27-2.14 (m, 2H), 2.14-1.98 (m, 1H), 1.95-1.84 (m, 1H), 1.58 (s, 9H), 1.47 (t, J=7.1 Hz, 3H). MS TOFES$^+$: m/z 439.1 (M+H)$^+$.

Ethyl 2-amino-7-cyclobutyl-5-oxo-5H-chromeno[2,3-b]pyridine-3-carboxylate (7)

A solution of compound 6 (50 mg, 0.11 mmol) in dichloromethane (20 mL) was treated with trifluoroacetic acid (0.5 mL) and stirred at room temperature for 1 h. The mixture was washed with saturated aq NaHCO$_3$, dried (Na$_2$SO$_4$), and concentrated to give 7 (39 mg, 100%) as a white solid. $^1$H NMR (400 MHz, chloroform-d): δ 9.15 (s, 1H), 8.36 (s, 1H), 8.09 (d, J=2.2 Hz, 1H), 7.56 (ddd, J=8.5, 2.3, 0.7 Hz, 1H), 7.43 (d, J=8.5 Hz, 1H), 5.91 (s, 1H), 4.41 (q, J=7.1 Hz, 2H), 3.65 (p, J=8.8 Hz, 1H), 2.41 (dtd, J=10.5, 8.0, 2.4 Hz, 2H), 2.21 (pd, J=9.6, 2.0 Hz, 2H), 2.12-2.01 (m, 1H), 1.95-1.82 (m, 1H), 1.44 (t, J=7.1 Hz, 3H). MS TOFES$^+$: m/z 339.1 (M+H)$^+$.

2-Amino-7-cyclobutyl-5-oxo-5H-chromeno[2,3-b]pyridine-3-carboxylic acid (8)

To a suspension of 7 (39 mg, 0.12 mmol) in ethanol (10 mL) and water (1.3 mL) was added 1N aq NaOH (1.3 mL)

Ethyl 2-amino-7-(cyclopent-1-en-1-yl)-5-oxo-5H-chromeno[2,3-b]pyridine-3-carboxylate (9)

A solution of potassium carbonate (228 mg, 1.65 mmol) in water (3 mL) was added to a nitrogen-degassed mixture of compound 1 (200 mg, 0.55 mmol), cyclopent-1-en-1-ylboronic acid (68 mg, 0.61 mmol), triphenylphosphine (8.7 mg, 0.03 mmol), and PdCl$_2$(PPh$_3$)$_2$ (7.7 mg, 0.01 mmol) in tetrahydrofuran (9 mL). The reaction vessel was sealed with a screw cap and heated at 100° C. for 19 h. The mixture was cooled and distributed between water and dichloromethane. The organic phase was washed with brine, dried (Na$_2$SO$_4$), and concentrated to give 9 (160 mg, 83%). $^1$H NMR (400 MHz, chloroform-d): δ 9.16 (d, J=1.7 Hz, 1H), 8.36 (s, 1H), 8.21 (d, J=2.3 Hz, 1H), 7.84 (dd, J=8.7, 2.3 Hz, 1H), 7.44 (d, J=8.7 Hz, 1H), 6.30 (m, 1H), 5.86 (s, 1H), 4.41 (q, J=7.1 Hz, 2H), 2.87-2.73 (m, 2H), 2.66-2.50 (m, 2H), 2.07 (p, J=7.6 Hz, 2H), 1.44 (t, J=7.1 Hz, 3H). MS TOFES$^+$: m/z 351.1 (M+H)$^+$.

Ethyl 2-amino-7-cyclopentyl-5-oxo-5H-chromeno[2,3-b]pyridine-3-carboxylate (10)

A flask with compound 9 (110 mg, 0.31 mmol) dissolved in ethanol (150 mL) was purged with nitrogen, and 10% palladium on carbon (70 mg) was added. The mixture was then purged with nitrogen and hydrogen, and hydrogenated at 14 PSI using a Parr shaker at room temperature for 16 h. The mixture was filtered over celite and concentrated to a residue that was purified by silica gel preparative plate chromatography (elution with 0.35% methanol in dichloromethane) to give 10 (50 mg, 45%). $^1$H NMR (400 MHz, chloroform-d): δ 9.15 (s, 1H), 8.36 (s, 1H), 8.11 (d, J=2.2 Hz, 1H), 7.59 (dd, J=8.6, 2.3 Hz, 1H), 7.42 (d, J=8.6 Hz, 1H), 5.93 (s, 1H), 4.40 (t, J=7.1 Hz, 2H), 3.23-3.05 (m, 1H), 2.22-2.06 (m, 2H), 1.85 (qd, J=6.1, 4.1 Hz, 2H), 1.80-1.54 (m, 4H), 1.44 (t, J=7.1 Hz, 3H). MS TOFES$^+$: m/z 353.1 (M+H)$^+$.

2-Amino-7-cyclopentyl-5-oxo-5H-chromeno[2,3-b]pyridine-3-carboxylic acid (11)

To compound 10 (50 mg, 0.14 mmol) in ethanol (20 mL) and water (2.5 mL) was added 1N aq NaOH (2.5 mL) and the mixture was stirred for 45 min at 50° C. The mixture was concentrated to a solid that was diluted with water (60 mL) and acidified with 1N aq HCl to pH~3. The fine suspension was stirred at room temperature for 3 h and then let stand for 30 min. The precipitate was collected by filtration, washed with water and dried to give 11 (37 mg, 80%) as a white solid. $^1$H NMR (400 MHz, DMSO-d$_6$): δ 13.46 (s, 1H), 8.80 (s, 1H), 8.26 (d, J=12.9 Hz, 2H), 7.92 (d, J=2.3 Hz, 1H), 7.72 (dd, J=8.6, 2.3 Hz, 1H), 7.52 (d, J=8.6 Hz, 1H), 3.22-3.03 (m, 1H), 2.17-1.98 (m, 2H), 1.80 (t, J=5.4 Hz, 2H), 1.68 (dt, J=8.9, 4.4 Hz, 2H), 1.64-1.48 (m, 2H). MS TOFES$^+$: m/z 325.1 (M+H)$^+$.

Scheme 4

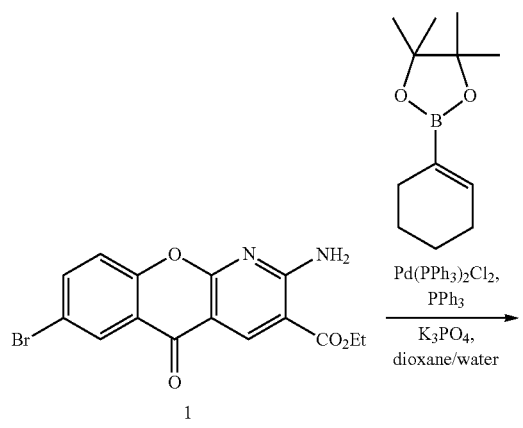

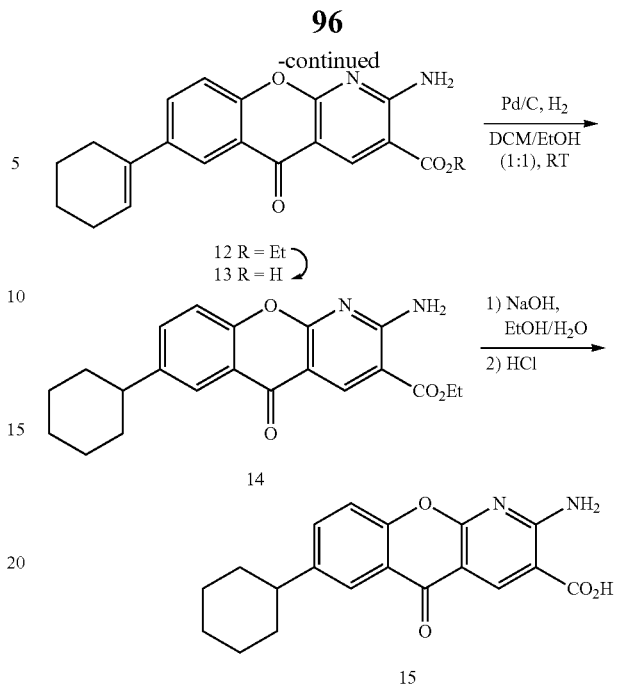

Ethyl 2-amino-7-(cyclohex-1-en-1-yl)-5-oxo-5H-chromeno[2,3-b]pyridine-3-carboxylate (12)

A solution of tripotassium phosphate (1.403 g, 6.61 mmol) in water (2.6 mL) was added to a nitrogen degassed suspension of compound 1 (400 mg, 1.10 mmol), 1-cyclohexen-yl-boronic acid pinacol ester (252 mg, 1.21 mmol), triphenylphosphine (144 mg, 0.55 mmol), Pd(OAc)$_2$ (24.7 mg, 0.11 mmol) and p-dioxane (26 mL). The reaction was heated under nitrogen at 100-110° C. for 20 min, resulting in a clear orange solution, and continued at 70° C. for 1 h. The mixture was concentrated and diluted with water. The precipitate was collected by filtration, washed successively with water and dichloromethane and dried to give 12 (250 mg) as a white solid. The biphasic filtrate was extracted with dichloromethane (2×), and the combined organic phases were dried (Na$_2$SO$_4$) and concentrated to an orange solid that was triturated in dichloromethane to give a second crop of 12 (80 mg). Total yield=330 mg (82%). $^1$H NMR (400 MHz, chloroform-d): δ 9.16 (s, 1H), 8.36 (s, 1H), 8.22 (d, J=2.4 Hz, 1H), 7.76 (dd, J=8.8, 2.4 Hz, 1H), 7.44 (d, J=8.8 Hz, 1H), 6.25 (s, 1H), 5.84 (s, 1H), 4.41 (q, J=7.1 Hz, 2H), 2.48 (s, 2H), 2.25 (q, J=3.0 Hz, 2H), 1.86-1.78 (m, 2H), 1.72-1.65 (m, 2H), 1.44 (t, J=7.1 Hz, 3H). MS TOFES$^+$: m/z 365.1 (M+H)$^+$.

2-Amino-7-(cyclohex-1-en-1-yl)-5-oxo-5H-chromeno[2,3-b]pyridine-3-carboxylic acid (13)

To a suspension of compound 12 (68 mg, 0.19 mmol) in ethanol (10 mL) and water (1.3 mL) was added 1N aq NaOH (1.3 mL) and the mixture was stirred for 50 min at 50° C. and then concentrated. The residue was diluted with water (80 mL) and acidified with 1N aq HCl to pH 3-4. The fine suspension was stirred at room temperature overnight and then let stand for a day. The precipitate was collected by filtration, washed with water and dried to give 13 (50 mg, 80%) as a white solid. $^1$H NMR (400 MHz, DMSO-d$_6$): δ 13.45 (s, 1H), 8.79 (s, 1H), 8.25 (d, J=13.2 Hz, 2H), 7.99 (d, J=2.4 Hz, 1H), 7.89 (dd, J=8.8, 2.4 Hz, 1H), 7.53 (d, J=8.8

Hz, 1H), 6.29 (s, 1H), 2.42 (s, 2H), 2.24-2.18 (m, 2H), 1.75 (q, J=5.9 Hz, 2H), 1.67-1.58 (m, 2H). MS TOFES⁺: m/z 337.1 (M+H)⁺.

Ethyl 2-amino-7-cyclohexyl-5-oxo-5H-chromeno[2,3-b]pyridine-3-carboxylate (14)

A flask with compound 12 (165 mg, 0.45 mmol) in dichloromethane (85 mL) and ethanol (100 mL) was purged with nitrogen, and 10% palladium on carbon (200 mg) was added. The mixture was then purged with nitrogen and hydrogen, and hydrogenated at 55 PSI using a Parr shaker at room temperature for 19 h. The mixture was filtered over celite and concentrated to a residue that was purified by silica gel preparative plate chromatography (elution with 1% methanol in dichloromethane) to give 14 (125 mg, 75%) as a white solid. $^1$H NMR (400 MHz, chloroform-d): δ 9.15 (s, 1H), 8.35 (s, 1H), 8.09 (d, J=2.3 Hz, 1H), 7.57 (dd, J=8.6, 2.3 Hz, 1H), 7.42 (d, J=8.6 Hz, 1H), 5.90 (s, 1H), 4.40 (q, J=7.1 Hz, 2H), 2.63 (td, J=11.4, 3.3 Hz, 1H), 1.90 (dd, J=17.0, 12.3 Hz, 4H), 1.78 (d, J=12.4 Hz, 1H), 1.55-1.35 (m, 7H), 1.34-1.24 (m, 1H). MS TOFES⁺: m/z 367.3 (M+H)⁺.

2-Amino-7-cyclohexyl-5-oxo-5H-chromeno[2,3-b]pyridine-3-carboxylic acid (15)

To a suspension of 14 (233 mg, 0.64 mmol) in ethanol (40 mL) and water (4.5 mL) was added 1N aq NaOH (4.5 mL) and the mixture was stirred for 90 min at 50° C. The mixture was filtered and the filtrate was concentrated to a residue that was dissolved in water (70 mL). The solution was acidified with 1N aq HCl to pH~3 and the fine suspension was stirred at room temperature overnight and then let stand for 1 h. The precipitate was collected by filtration, washed with water and dried to give 15 (204 mg, 95%) as a white solid. $^1$H NMR (400 MHz, DMSO-d$_6$): δ 13.46 (s, 1H), 8.79 (s, 1H), 8.27 (s, 1H), 8.24 (s, 1H), 7.89 (d, J=2.3 Hz, 1H), 7.70 (dd, J=8.6, 2.3 Hz, 1H), 7.51 (d, J=8.6 Hz, 1H), 2.65 (t, J=10.7 Hz, 1H), 1.83 (d, J=11.2 Hz, 4H), 1.71 (d, J=12.6 Hz, 1H), 1.42 (q, J=12.5, 12.1 Hz, 4H), 1.26 (q, J=11.1, 10.3 Hz, 1H). MS TOFES⁺: m/z 339.0 (M+H)⁺.

Scheme 5

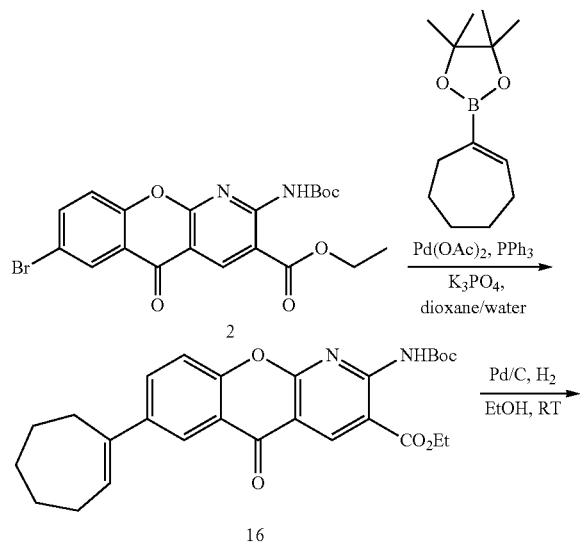

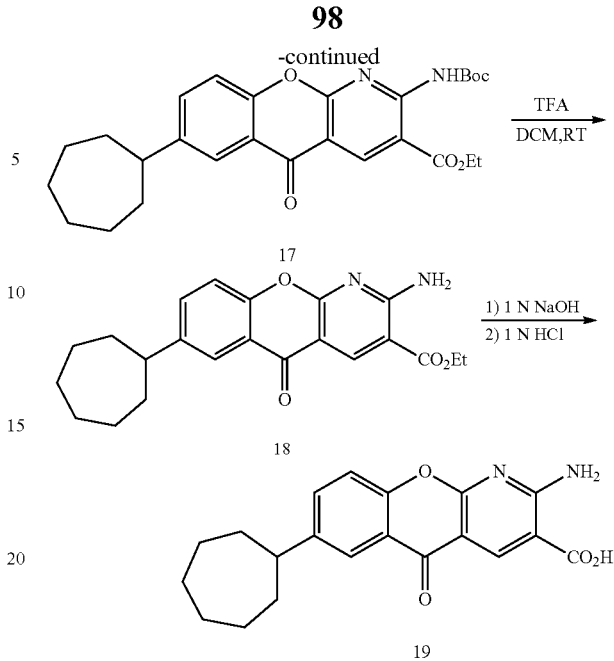

Ethyl 2-((tert-butoxycarbonyl)amino)-7-(cyclohept-1-en-1-yl)-5-oxo-5H-chromeno[2,3-b]pyridine-3-carboxylate (16)

A solution of tripotassium phosphate (495 mg, 2.33 mmol) in water (0.75 mL) was added to a nitrogen-degassed suspension of compound 2 (180 mg, 0.39 mmol), 2-(cyclohept-1-en-1-yl)-4,4,5,5-tetramethyl-1,3,2-dioxaborolane (173 mg, 0.78 mmol), triphenylphosphine (51 mg, 0.19 mmol), and Pd(Oac)$_2$ (8.7 mg, 0.04 mmol) in p-dioxane (7.5 mL). The reaction vessel was sealed with a screw cap and heated at 110° C. for 5 min, becoming a clear light orange solution, and then at 75° C. for 1 h. The mixture was concentrated to a residue that was distributed between water and dichloromethane. The organic phase was dried (Na$_2$SO$_4$) and concentrated to a residue that purified by flash silica gel chromatography (elution with 0.4% methanol in dichloromethane) to give 16 (145 mg, 78%). $^1$H NMR (400 MHz, chloroform-d): δ 10.89 (s, 1H), 9.30 (s, 1H), 8.17 (d, J=2.3 Hz, 1H), 7.72 (dd, J=8.7, 2.4 Hz, 1H), 7.53 (d, J=8.7 Hz, 1H), 6.21 (t, J=6.7 Hz, 1H), 4.47 (q, J=7.1 Hz, 2H), 2.70-2.61 (m, 2H), 2.37-2.26 (m, 2H), 1.92-1.79 (m, 2H), 1.72-1.66 (m, 2H), 1.58 (m, 11H), 1.48 (t, J=7.1 Hz, 3H). MS TOFES⁺: m/z 479.1 (M+H)⁺.

Ethyl 2-((tert-butoxycarbonyl)amino)-7-cycloheptyl-5-oxo-5H-chromeno[2,3-b]pyridine-3-carboxylate (17)

A flask with a solution of compound 16 (145 mg, 0.30 mmol) in dichloromethane (10 mL) and ethanol (15 mL) was purged with nitrogen and 10% palladium on carbon (50 mg) was added. The mixture was then purged with nitrogen and hydrogen, and hydrogenated at 23 PSI using a Parr shaker at room temperature for 19 h. The mixture was filtered over celite and concentrated to a residue that was purified by silica gel preparative plate chromatography (elution with 0.3% methanol in dichloromethane) to give 17 (112 mg, 77%). $^1$H NMR (400 MHz, chloroform-d): δ 10.89 (s, 1H), 9.30 (s, 1H), 8.08 (d, J=2.3 Hz, 1H), 7.60 (dd, J=8.6, 2.3 Hz, 1H), 7.53 (d, J=8.6 Hz, 1H), 4.46 (q, J=7.2 Hz, 2H), 2.82 (tt, J=10.6, 3.6 Hz, 1H), 1.95 (dq, J=11.5, 3.5 Hz, 2H), 1.83 (ddq, J=12.3, 6.2, 3.1 Hz, 2H), 1.78-1.59 (m, 8H), 1.58 (s, 9H), 1.47 (t, J=7.1 Hz, 3H). MS TOFES⁺: m/z 481.1 (M+H)⁺.

Ethyl 2-amino-7-cycloheptyl-5-oxo-5H-chromeno[2,3-b]pyridine-3-carboxylate (18)

A solution of compound 17 (105 mg, 0.23 mmol) in dichloromethane (20 mL) was treated with trifluoroacetic acid (0.5 mL) and stirred for 30 min at room temperature. The mixture was washed with saturated aq NaHCO₃, dried (Na₂SO₄) and concentrated to give 18 (82 mg, 94%) as a solid. ¹H NMR (400 MHz, chloroform-d): δ 9.15 (s, 1H), 8.35 (s, 1H), 8.06 (d, J=2.3 Hz, 1H), 7.55 (dd, J=8.6, 2.3 Hz, 1H), 7.41 (d, J=8.6 Hz, 1H), 5.88 (s, 1H), 4.40 (q, J=7.2 Hz, 2H), 2.87-2.74 (m, 1H), 1.97-1.88 (m, 2H), 1.82 (dt, J=9.5, 3.3 Hz, 2H), 1.72 (td, J=10.3, 3.4 Hz, 4H), 1.61 (d, J=6.5 Hz, 4H), 1.44 (t, J=7.1 Hz, 3H). MS TOFES⁺: m/z 381.1 (M+H)⁺.

2-Amino-7-cycloheptyl-5-oxo-5H-chromeno[2,3-b]pyridine-3-carboxylic acid (19)

To a suspension of compound 18 (82 mg, 0.22 mmol) in ethanol (20 mL) and water (2.5 mL) was added 1N aq NaOH (2.5 mL) and the mixture was stirred for 1 h at 50° C. and then concentrated. The residue was diluted with water (150 mL) and acidified with 1N aq HCl to pH 3-4. The fine suspension was stirred at room temperature overnight and then let stand for 2 h. The precipitate was collected by filtration, washed with water and dried to give 19 as a white solid. ¹H NMR (500 MHz, DMSO-d₆): δ 13.46 (s, 1H), 8.79 (s, 1H), 8.36-8.17 (m, 2H), 7.88 (d, J=2.5 Hz, 1H), 7.68 (dd, J=8.6, 2.5 Hz, 1H), 7.50 (d, J=8.4 Hz, 1H), 2.84 (ddd, J=10.6, 7.1, 3.8 Hz, 1H), 1.86-1.49 (m, 12H). MS TOFES⁺: m/z 353.0 (M+H)⁺.

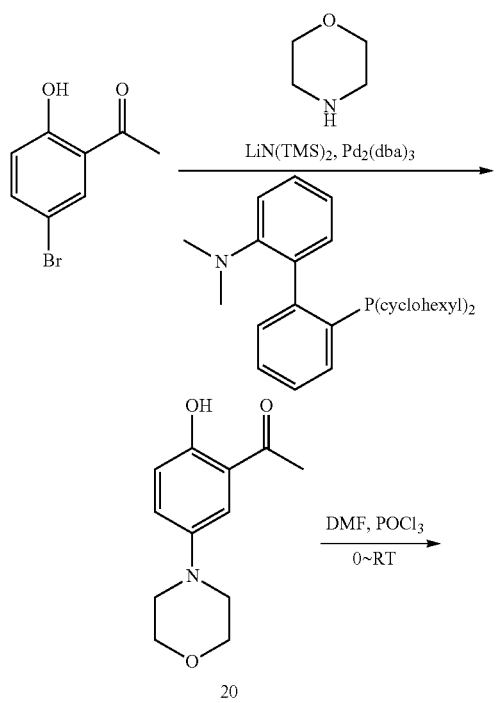

Scheme 6

1-(2-Hydroxy-5-morpholinophenyl)ethan-1-one (20)

To a nitrogen-degassed solution of 5'-bromo-2'-hydroxyacetophenone (2.0 g, 9.3 mmol) in tetrahydrofuran (15 mL) was added morpholine (1.3 g, 14.9 mmol), lithium hexamethyldisilazide (32.6 mL, 1 M in tetrahydrofuran, 32.6 mmol), Pd₂(dba)₃ (136 mg, 0.15 mmol), and 2-dicyclohexylphosphino-2'-N,N-(dimethylamino)biphenyl (117 mg, 0.30 mmol). The mixture was degassed again with nitrogen and sealed in a capped vial and stirred at 75° C. for 1 h. After cooling the mixture was concentrated to a residue that was distributed between dichloromethane and saturated aq ammonium chloride solution. The organic phase was washed with brine and concentrated to an oil that was purified by flash silica gel chromatography, eluting with 0.5:1:100 trimethylamine solution (25% w/w solution in methanol)/methanol/dichloromethane to give 20 (1.67 g, 81%) as a solid. ¹H NMR (400 MHz, chloroform-d): δ 11.92 (s, 1H), 7.22-7.18 (m, 2H), 6.97-6.92 (m, 1H), 3.93-3.82 (m, 4H), 3.10-3.01 (m, 4H), 2.63 (s, 3H). MS TOFES⁺: m/z 222.1 (M+H)⁺.

6-Morpholino-4-oxo-4H-chromene-3-carbaldehyde (21)

To a cooled (0-5° C.) and well stirred mixture of compound 20 (1.67 g, 7.55 mmol) and N,N-dimethylformamide (7.17 g, 98 mmol) was added slowly POCl₃ (5.8 g, 37.7 mmol) under nitrogen over 10 min. After stirring at room temperature for 16 h, the mixture was poured onto crushed ice. After melting, the mixture was adjusted to pH-8.5 with saturated aq Na$_2$CO$_3$ and extracted with dichloromethane (3×). The combined extracts were washed with saturated aq NaHCO$_3$ and brine, dried (Na$_2$SO$_4$), and concentrated to give crude 21 (1.66 g, 68%) as a red-brown solid. $^1$H NMR (400 MHz, chloroform-d): δ 10.40 (s, 1H), 8.52 (s, 1H), 7.61 (d, J=3.1 Hz, 1H), 7.47 (d, J=9.2 Hz, 1H), 7.34 (dd, J=9.2, 3.1 Hz, 1H), 3.92-3.88 (m, 4H), 3.29-3.23 (m, 4H). MS TOFES$^+$: m/z 260.0 (M+H)$^+$.

Ethyl 2-amino-7-morpholino-5-oxo-5H-chromeno[2,3-b]pyridine-3-carboxylate (23)

A mixture of compound 21 (2.95 g, 11.38 mmol), hydroxylamine hydrochloride (0.949 g, 13.65 mmol) and sodium iodide (0.853 g, 5.69 mmol) in acetonitrile (50 mL) was heated at reflux for 3 h. The mixture was cooled and filtered through celite and the pad washed by dichloromethane. The filtrate was concentrated and the residue was diluted with water and adjusted to pH~9 with 5% aq Na$_2$CO$_3$. The aqueous mixture was extracted with dichloromethane (3×) and the combined organic phases were washed successively with 5% aq sodium sulfite, water, and brine, dried (Na$_2$SO$_4$), and concentrated to leave crude 6-morpholino-4-oxo-4H-chromene-3-carbonitrile (22) (1.68 g) as a brown solid. MS TOFES$^+$: m/z 257.0 (M+H)$^+$. A mixture of compound 22 (1.06 g), piperidine (0.353 g, 4.14 mmol), ethyl cyanoacetate (0.609 g, 5.38 mmol) and ethanol (10 mL) was heated at reflux for 4 h. The mixture was maintained at room temperature overnight, and the precipitated solids were collected by filtration, washed with ethanol, and dried to afford 23 (0.235 g, 9% over two steps). $^1$H NMR (400 MHz, chloroform-d): δ 9.15 (s, 1H), 7.65 (d, J=3.1 Hz, 1H), 7.44 (d, J=9.1 Hz, 1H), 7.34 (dd, J=9.2, 3.1 Hz, 1H), 4.41 (q, J=7.1 Hz, 2H), 3.94-3.84 (m, 4H), 3.27-3.20 (m, 4H), 1.44 (t, J=7.1 Hz, 3H). MS TOFES$^+$: m/z 370.0 (M+H)$^+$.

2-Amino-7-morpholino-5-oxo-5H-chromeno[2,3-b]pyridine-3-carboxylic acid (24)

To a suspension of 23 (0.23 g, 0.62 mmol) in ethanol (24 mL) and water (3.0 mL) was added 1N aq NaOH (3.0 mL) and the mixture was stirred for 50 min at 50° C. The mixture was filtered and the filtrate was concentrated to a residue that was dissolved in water (20 mL) and acidified with 1N aq HCl to pH~3.0. The fine suspension was stirred at room temperature for 2 h and then let stand overnight. The precipitate was collected by filtration, washed with water, and dried to give 24 (180 mg, 85%). $^1$H NMR (400 MHz, DMSO-d$_6$): δ 13.44 (s, 1H), 8.80 (d, J=3.8 Hz, 1H), 8.22 (s, 2H), 7.60-7.47 (m, 2H), 7.41 (d, J=3.3 Hz, 1H), 3.77 (t, J=4.7 Hz, 4H), 3.18 (d, J=5.1 Hz, 4H). MS TOFES$^+$: m/z 342.0 (M+H)$^+$.

Scheme 7

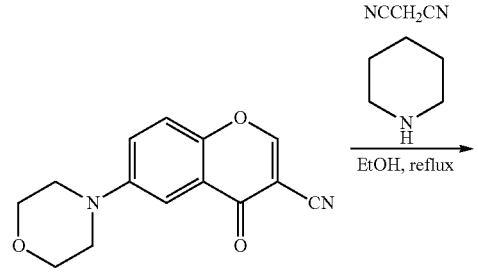

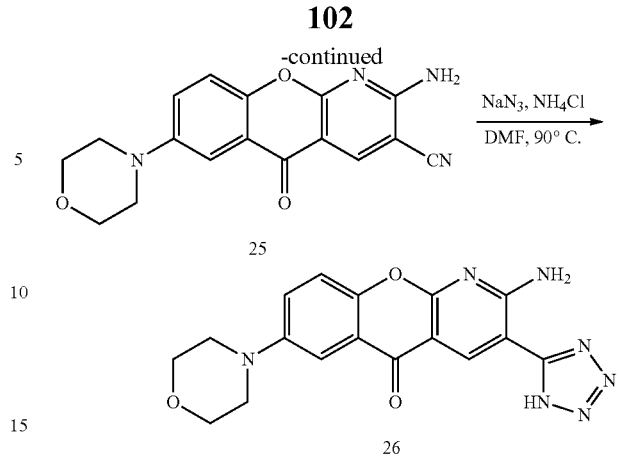

2-Amino-7-morpholino-5-oxo-5H-chromeno[2,3-b]pyridine-3-carbonitrile (25)

A suspension of compound 22 (0.6 g, 1.76 mmol), piperidine (0.199 g, 2.34 mmol), malononitrile (0.309 g, 4.67 mmol) and ethanol (12 mL) was heated at reflux for 3 h. After standing at room temperature overnight, the separated solids were collected by filtration, washed with ethanol (4×), and dried to afford 25 (0.37 g, 65%). $^1$H NMR (400 MHz, DMSO-d$_6$): δ 8.62 (s, 1H), 7.54 (d, J=2.8 Hz, 1H), 7.52 (s, 1H), 7.50 (s, 1H), 7.39 (d, J=2.9 Hz, 1H), 3.76 (d, J=5.0 Hz, 4H), 3.18 (d, J=4.8 Hz, 4H). MS TOFES$^+$: m/z 323.1 (M+H)$^+$.

2-Amino-7-morpholino-3-(1H-tetrazol-5-yl)-5H-chromeno[2,3-b]110yridine-5-one (26)

A mixture of compound 25 (90 mg, 0.28 mmol), sodium azide (54.5 mg, 0.84 mmol), and ammonium chloride (45.0 mg, 0.84 mmol) in N,N-dimethylformamide (1 mL) was stirred for 16 h at 90° C. in a sealed tube. After cooling, the mixture was diluted with water, acidified with 10% aq HCl to pH 2-3, and the formed precipitate stirred for 15 min. The solids were collected, washed with water, air dried, and then triturated in methanol (1 mL) with sonication. This cycle was repeated and the solids were collected and dried to give 26 (58 mg, 58%). $^1$H NMR (400 MHz, DMSO-d$_6$): δ 9.02 (s, 1H), 8.41 (s, 1H), 7.55 (s, 1H), 7.45 (s, 1H), 3.78 (m, 4H), 3.19 (m, 4H). MS TOFES$^+$: m/z 366.1 (M+H)$^+$.

Scheme 8

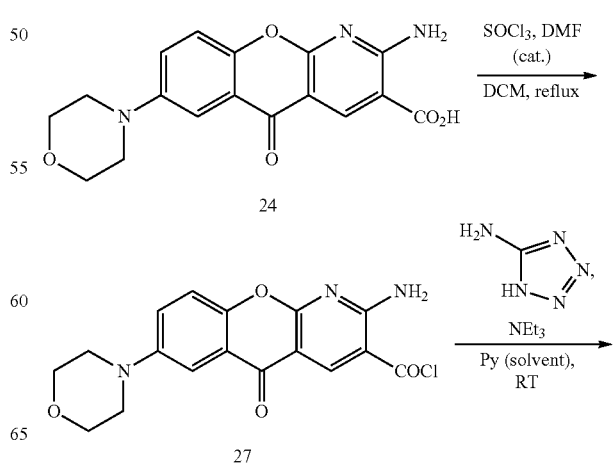

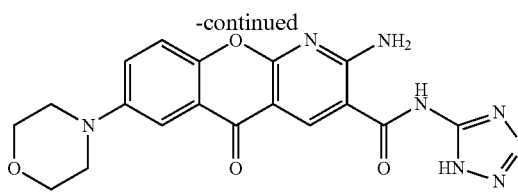

28

2-Amino-7-morpholino-5-oxo-N-(1H-tetrazol-5-yl)-5H-chromeno[2,3-b]pyridine-3-carboxamide (28)

To a stirred suspension of compound 24 (100 mg, 0.29 mmol) and N,N-dimethylformamide (2 mg, catalytic) in dry dichloromethane (10 mL) at room temperature was added drop-wise thionyl chloride (4 mL, 55.7 mmol), and the resulting mixture was heated at reflux for 3 h. The cooled mixture was concentrated and dried in vacuo to give crude 2-amino-7-morpholino-5-oxo-5H-chromeno[2,3-b]pyridine-3-carbonyl chloride (27) (154 mg) as an orange solid. A solution of compound 27 (105 mg, 0.29 mmol), tetrazole-5-amine (37 mg, 0.44 mmol), triethylamine (178 mg, 1.76 mmol) and pyridine (5 mL) was stirred at room temperature for 4 h. The mixture was diluted with acetonitrile (10 mL), stirred for 5 min and filtered. The filtrate was concentrated to a residue that was diluted with water (5 mL) and dichloromethane (5 mL). The biphasic mixture was sonicated for 5 min, let stand at room temperature for 16 h and filtered. The collected solids were washed successively with water and dichloromethane, and dried to give 28 (45 mg, 38%). $^1$H NMR (400 MHz, DMSO-$d_6$): δ 9.10 (s, 1H), 8.24 (s, 2H), 7.56 (d, J=2.9 Hz, 1H), 7.54 (s, 1H), 7.45 (d, J=2.8 Hz, 1H), 3.79-3.76 (m, 4H), 3.19 (m, 4H). MS TOFES$^+$: m/z 409.0 (M+H)$^+$.

Scheme 9

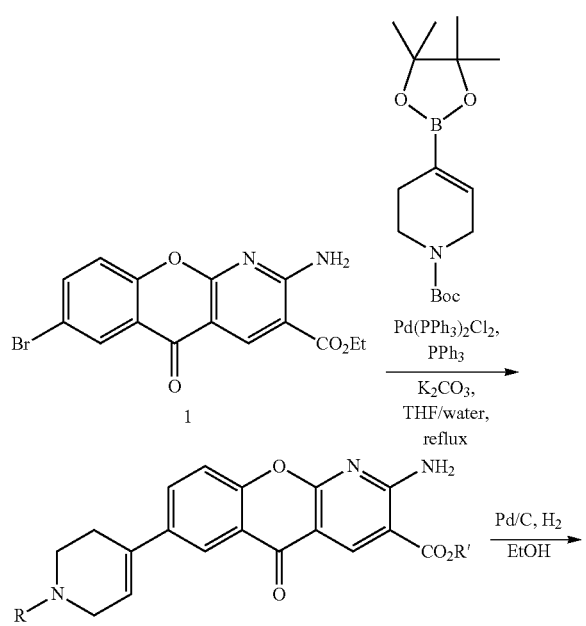

29 R = Boc, R' = Et
30 R = H, R' = H

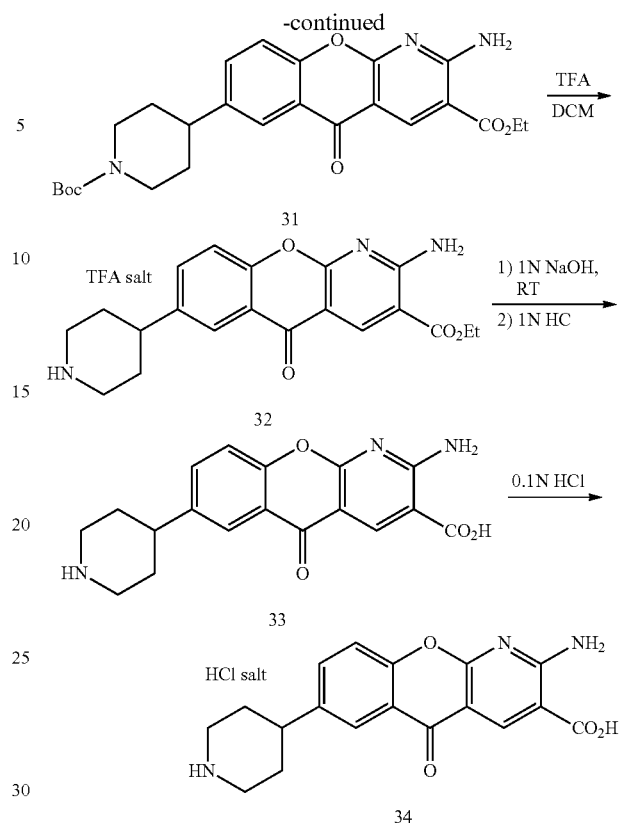

Ethyl 2-amino-7-(1-(tert-butoxycarbonyl)-1,2,3,6-tetrahydropyridin-4-yl)-5-oxo-5H-chromeno[2,3-b]pyridine-3-carboxylate (29)

A solution of potassium carbonate (1.712 g, 12.3 mmol) in water (22 mL) was added to a nitrogen-degassed suspension of compound 1 (1.5 g, 4.13 mmol), tert-butyl 4-(4,4,5,5-tetramethyl-1,3,2-dioxaborolan-2-yl)-3,6-dihydropyridine-1(2H)-carboxylate (1.405 g, 4.54 mmol), triphenylphosphine (65 mg, 0.25 mmol), PdCl$_2$(PPh$_3$)$_2$ (58 mg, 0.08 mmol) in tetrahydrofuran (67 mL). After heating at reflux under nitrogen for 18 h, the cooled mixture was concentrated and distributed between 5% aq NaHCO$_3$ and dichloromethane. The organic phase was washed with brine, dried (Na$_2$SO$_4$), and concentrated to a residue that was purified by flash silica gel chromatography (elution with 1-2% methanol in dichloromethane) to give 29 (1.44 g, 75%) as a white solid. $^1$H NMR (400 MHz, chloroform-d): δ 9.16 (s, 1H), 8.38 (s, 1H), 8.23 (d, J=2.4 Hz, 1H), 7.75 (dd, J=8.8, 2.4 Hz, 1H), 7.47 (d, J=8.7 Hz, 1H), 6.17 (s, 1H), 5.86 (s, 1H), 4.41 (q, J=7.1 Hz, 2H), 4.12 (s, 2H), 3.68 (t, J=5.7 Hz, 2H), 2.61 (s, 2H), 1.51 (s, 9H), 1.44 (t, J=7.1 Hz, 3H). MS TOFES$^+$: m/z 466.0 (M+H)$^+$.

2-Amino-5-oxo-7-(1,2,3,6-tetrahydropyridin-4-yl)-5H-chromeno[2,3-b]pyridine-3-carboxylic acid (30)

To a solution of compound 29 (90 mg, 0.19 mmol) in dichloromethane (10 mL) was added trifluoroacetic acid (0.25 mL) and the mixture was stirred for 5 h at 40° C. The mixture was concentrated to a residue that was diluted with ethanol (20 mL), water (2.5 mL), and 1N aq NaOH (2.5 mL). After stirring for 30 min at 50° C., the mixture was concentrated to a residue that was dissolved in water and acidified with 1N aq HCl to pH 6-7. The resulting fine suspension was stirred at room temperature for 24 h and then let stand for 24 h. The precipitate was collected, washed with water and dried to give 30 (46 mg, 70%). $^1$H NMR (400 MHz, deuterium oxide): δ 7.87 (s, 1H), 6.96 (d, J=8.8 Hz, 1H), 6.72 (s, 1H), 6.54 (d, J=8.5 Hz, 1H), 5.69 (s, 1H), 3.10 (m, 2H), 2.76 (m, 2H), 1.76 (m, 2H). MS TOFES$^+$: m/z 338.1 (M+H)$^+$.

Ethyl 2-amino-7-(1-(tert-butoxycarbonyl)piperidin-4-yl)-5-oxo-5H-chromeno[2,3-b]pyridine-3-carboxylate (31)

A flask with a solution of compound 29 (650 mg, 1.40 mmol) in ethanol (255 mL) was purged with nitrogen and 10% palladium on carbon (250 mg) was added. The mixture was then purged with nitrogen and hydrogen, and hydrogenated at 17 PSI using a Parr shaker at room temperature for 19 h. The mixture was filtered over celite and concentrated to a residue that was purified by flash silica gel chromatography (0.7% MeOH in dichloromethane) to give 31 (510 mg, 78%) as a white solid. $^1$H NMR (400 MHz, chloroform-d): δ 9.15 (s, 1H), 8.37 (s, 1H), 8.09 (d, J=2.2 Hz, 1H), 7.56 (dd, J=8.7, 2.3 Hz, 1H), 7.45 (d, J=8.6 Hz, 1H), 5.86 (s, 1H), 4.41 (q, J=7.1 Hz, 2H), 4.28 (s, 2H), 2.94-2.65 (m, 3H), 1.88 (d, J=13.1 Hz, 2H), 1.70 (td, J=12.6, 4.3 Hz, 2H), 1.50 (s, 9H), 1.44 (t, J=7.1 Hz, 3H). MS TOFES$^+$: m/z 468.2 (M+H)$^+$.

Ethyl 2-amino-5-oxo-7-(piperidin-4-yl)-5H-chromeno[2,3-b]pyridine-3-carboxylate, trifluoroacetic acid salt (32)

A solution of compound 31 (100 mg, 0.21 mmol) in dichloromethane (10 mL) was treated with trifluoroacetic acid (0.25 mL) and stirred for 5 h at 40° C. The mixture was concentrated to leave crude 32 (124 mg) as an off-white solid. It was used directly in the next step. $^1$H NMR (400 MHz, chloroform-d): δ 9.17 (s, 1H), 8.70 (s, 1H), 8.62 (s, 1H), 8.20 (s, 1H), 8.13 (d, J=2.2 Hz, 1H), 7.63 (d, J=2.3 Hz, 1H), 7.55 (s, 1H), 4.42 (q, J=7.1 Hz, 2H), 3.70 (d, J=12.7 Hz, 2H), 3.18 (d, J=12.0 Hz, 2H), 3.00 (d, J=10.9 Hz, 1H), 2.15 (d, J=22.9 Hz, 4H), 1.44 (t, J=7.1 Hz, 3H). MS TOFES$^+$: m/z 368.1 (M+H)$^+$.

2-Amino-5-oxo-7-(piperidin-1-ium-4-yl)-5H-chromeno[2,3-b]pyridine-3-carboxylate (33)

To a solution of compound 32 (103 mg, 0.21 mmol) in ethanol (20 mL) and water (2.5 mL) was added 1N aq NaOH (2.5 mL), and the mixture was stirred for 10 min at 50° C. and concentrated. The residue was diluted with water (8 mL) and the suspension was acidified with 1 N aq. HCl to pH 5-6. The precipitate was maintained for 1 h at room temperature, collected, washed with water and dried to give 33 (54 mg, 75%). $^1$H NMR (400 MHz, DMSO-d$_6$): δ 9.55 (s, 1H), 8.81 (d, J=20.5 Hz, 1H), 8.74 (s, 1H), 7.93 (d, J=2.3 Hz, 1H), 7.91-7.80 (m, 1H), 7.67 (dd, J=8.6, 2.3 Hz, 1H), 7.56 (d, J=8.6 Hz, 1H), 3.42 (d, J=13.3 Hz, 3H), 3.08-2.97 (m, 2H), 2.01 (d, J=13.5 Hz, 2H), 1.87 (qd, J=13.2, 3.8 Hz, 2H). MS TOFES$^+$: m/z 340.1 (M+H)$^+$. The hydrochloride salt was prepared as follows: Compound 33 (51 mg, 0.15 mmol) was dissolved in 15 mL of 0.1 N aq HCl at 50° C. The clear solution was concentrated to a white solid that was dried to give 34 (51 mg, 90%). $^1$H NMR (400 MHz, deuterium oxide): δ 8.00 (s, 1H), 7.44 (d, J=2.1 Hz, 1H), 7.40 (d, J=9.0 Hz, 1H), 6.96 (d, J=8.5 Hz, 1H), 3.58 (d, J=12.5 Hz, 2H), 3.16 (t, J=12.8 Hz, 2H), 2.83 (t, J=12.5 Hz, 1H), 2.11 (d, J=14.0 Hz, 2H), 1.82 (q, J=13.4 Hz, 2H).

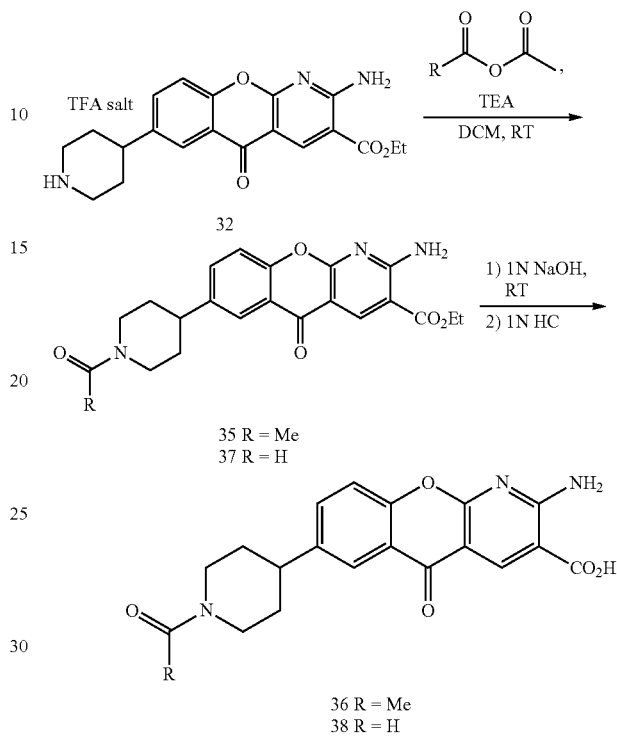

Scheme 10

Ethyl 7-(1-acetylpiperidin-4-yl)-2-amino-5-oxo-5H-chromeno[2,3-b]pyridine-3-carboxylate (35)

A solution of compound 32 (103 mg, 0.21 mmol), triethylamine (0.21 mL, 1.5 mmol), acetic anhydride (33 mg, 0.32 mmol) and dichloromethane (25 mL) was stirred at room temperature for 10 min and concentrated to leave crude 35 (170 mg) that was used directly in the next step. $^1$H NMR (500 MHz, chloroform-d): δ 9.15 (d, J=1.5 Hz, 1H), 8.37 (s, 1H), 8.09 (t, J=1.8 Hz, 1H), 7.56 (dt, J=8.6, 1.9 Hz, 1H), 7.46 (dd, J=8.6, 1.4 Hz, 1H), 6.00 (s, 1H), 4.87-4.76 (m, 1H), 4.41 (qd, J=7.1, 1.5 Hz, 2H), 4.04-3.92 (m, 1H), 3.24-3.18 (m, 1H), 2.93-2.84 (m, 1H), 2.66 (dd, J=14.2, 11.5 Hz, 1H), 2.16 (d, J=1.4 Hz, 3H), 2.01-1.88 (m, 2H), 1.70 (ddd, J=24.7, 12.3, 4.3 Hz, 2H), 1.44 (td, J=7.1, 1.5 Hz, 3H). MS TOFES$^+$: m/z 410.1 (M+H)$^+$.

7-(1-Acetylpiperidin-4-yl)-2-amino-5-oxo-5H-chromeno[2,3-b]pyridine-3-carboxylic acid (36)

To a solution of compound 35 (170 mg) in ethanol (20 mL) and water (2.5 mL) was added 1N aq NaOH (2.5 mL). The mixture was stirred for 30 min at 50° C. and then concentrated. The residue was diluted with water (10 mL) and acidified with 1N aq HCl to pH 3-4. The fine suspension was maintained at room temperature overnight and the precipitate was collected by filtration, washed with water and dried to give 36 (50 mg, 61% over two steps). $^1$H NMR (400 MHz, DMSO-d$_6$): δ 13.45 (s, 1H), 8.80 (s, 1H), 8.26 (s, 2H), 7.93 (d, J=2.3 Hz, 1H), 7.74 (dd, J=8.7, 2.3 Hz, 1H), 7.54 (d, J=8.6 Hz, 1H), 4.55 (d, J=12.9 Hz, 1H), 3.94 (d, J=13.4 Hz, 1H), 3.15 (t, J=12.9 Hz, 1H), 2.94 (t, J=12.2 Hz, 1H), 2.60 (t, J=12.6 Hz, 1H), 2.04 (s, 3H), 1.84 (t, J=12.7 Hz, 2H), 1.74-1.56 (m, 1H), 1.55-1.37 (m, 1H). MS TOFES$^+$: m/z 382.1 (M+H)$^+$.

Ethyl 2-amino-7-(1-formylpiperidin-4-yl)-5-oxo-5H-chromeno[2,3-b]pyridine-3-carboxylate (37)

A solution of compound 32 (103 mg, 0.21 mmol), triethylamine (0.21 ml, 1.5 mmol), formic acetic anhydride (28.3 mg, 0.32 mmol) and dichloromethane (25 mL) was stirred at room temperature for 10 min and concentrated to a white solid that was triturated in diethyl ether and dried to give 37 (66 mg, 78%). $^1$H NMR (400 MHz, chloroform-d): δ 9.16 (d, J=2.1 Hz, 1H), 8.39 (s, 1H), 8.10 (q, J=2.4 Hz, 2H), 7.56 (d, J=8.5 Hz, 1H), 7.47 (dd, J=8.6, 2.3 Hz, 1H), 5.91 (s, 1H), 4.62 (d, J=13.5 Hz, 1H), 4.47-4.34 (m, 2H), 3.79 (d, J=13.6 Hz, 1H), 3.25 (t, J=13.3 Hz, 1H), 2.94 (t, J=12.7 Hz, 1H), 2.76 (t, J=13.0 Hz, 1H), 2.04-1.91 (m, 2H), 1.69 (dd, J=16.7, 10.8 Hz, 2H), 1.44 (td, J=7.2, 2.2 Hz, 3H). MS TOFES$^+$: m/z 396.1 (M+H)$^+$.

2-Amino-7-(1-formylpiperidin-4-yl)-5-oxo-5H-chromeno[2,3-b]pyridine-3-carboxylic acid (38)

To a solution of compound 37 (66 mg, 0.17 mmol) in EtOH (10 mL) and water (1.3 mL) was added 1N aq NaOH (1.3 mL) and the mixture was stirred for 30 min at 50° C. and then concentrated. The residue was diluted with water (10 mL) and acidified with 1N aq HCl to pH 3-4. The fine suspension was maintained at room temperature overnight and the precipitate was collected, washed with water and dried to give 38 (52 mg, 85%) as a white solid. $^1$H NMR (400 MHz, DMSO-d$_6$): δ 8.78 (s, 1H), 8.29 (d, J=17.1 Hz, 2H), 8.04 (s, 1H), 7.92 (d, J=2.3 Hz, 1H), 7.74 (dd, J=8.7, 2.3 Hz, 1H), 7.54 (d, J=8.6 Hz, 1H), 4.33 (d, J=12.8 Hz, 1H), 3.81 (d, J=13.1 Hz, 1H), 3.16 (t, J=12.0 Hz, 1H), 2.98 (t, J=12.7 Hz, 1H), 2.76-2.64 (m, 1H), 1.87 (t, J=13.7 Hz, 2H), 1.61 (td, J=12.5, 4.3 Hz, 1H), 1.53-1.37 (m, 1H). MS TOFES$^+$: m/z 368.1 (M+H)$^+$.

Scheme 11

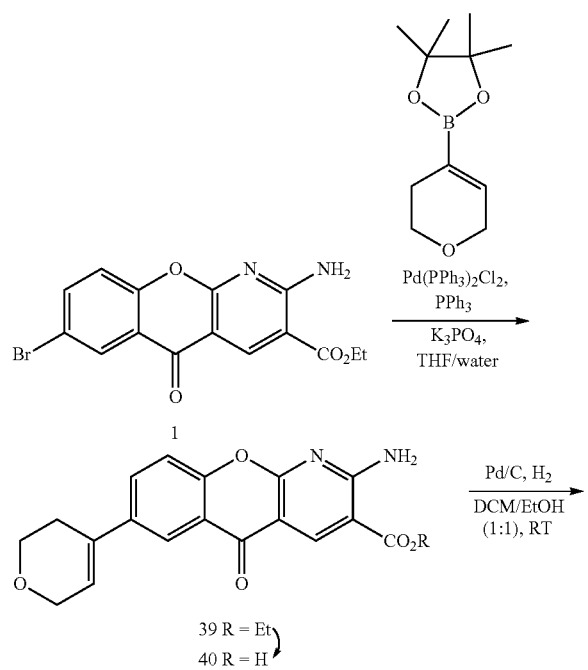

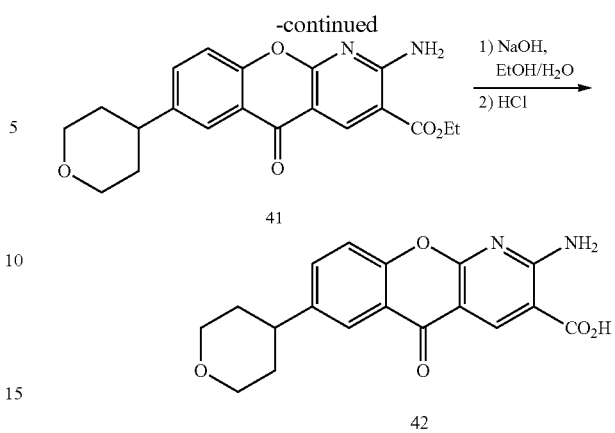

Ethyl 2-amino-7-(3,6-dihydro-2H-pyran-4-yl)-5-oxo-5H-chromeno[2,3-b]pyridine-3-carboxylate (39)

A solution of potassium carbonate (171 mg, 1.24 mmol)) in water (2.2 mL) was added to a nitrogen-degassed suspension of compound 1 (150 mg, 0.41 mmol), 2-(3,6-dihydro-2H-pyran-4-yl)-4,4,5,5-tetramethyl-1,3,2-dioxaborolane (95 mg, 0.45 mmol), triphenylphosphine (6.5 mg, 0.03 mmol), Pd(PPh$_3$)$_2$Cl$_2$ (5.8 mg, 0.08 mmol) in tetrahydrofuran (6.7 mL). The reaction vessel was sealed with a screw cap and heated at 100° C. for 19 h. The mixture was cooled and distributed between dichloromethane and water. The organic phase was washed with brine, dried (Na$_2$SO$_4$), and concentrated to a residue that was purified by silica gel preparative plate chromatography (elution with 3% methanol in dichloromethane) to give 39 (93 mg, 61%) as a solid. $^1$H NMR (400 MHz, chloroform-d): δ 9.16 (s, 1H), 8.38 (s, 1H), 8.24 (d, J=2.4 Hz, 1H), 7.78 (dd, J=8.7, 2.4 Hz, 1H), 7.47 (s, 1H), 6.27 (s, 1H), 5.86 (s, 1H), 4.45-4.39 (m, 2H), 4.38 (dd, J=5.2, 2.4 Hz, 2H), 3.98 (t, J=5.4 Hz, 2H), 2.67-2.53 (m, 2H), 1.44 (t, J=7.1 Hz, 3H). MS TOFES$^+$: m/z 367.1 (M+H)$^+$.

2-Amino-7-(3,6-dihydro-2H-pyran-4-yl)-5-oxo-5H-chromeno[2,3-b]pyridine-3-carboxylic acid (40)

To a solution of compound 39 (30 mg, 0.08 mmol) in ethanol (12 mL) and water (1.5 mL) was added 1N aq NaOH (1.5 mL), and the mixture was stirred for 45 min at 50° C. and then concentrated. The residue was diluted with water (5 mL) and the solution was acidified with 1N aq HCl to pH 3. The fine suspension was stirred at room temperature for 3 h, and then let stand for 30 min. The precipitate was collected by filtration, washed with water and dried to give 40 (20 mg, 72%). $^1$H NMR (400 MHz, DMSO-d$_6$): δ 13.47 (s, 1H), 8.79 (s, 1H), 8.31-8.21 (m, 2H), 8.04 (d, J=2.3 Hz, 1H), 7.96 (d, J=8.9 Hz, 1H), 7.58 (d, J=8.8 Hz, 1H), 6.41 (s, 1H), 4.36-4.14 (m, 2H), 3.85 (t, J=5.5 Hz, 2H), 3.31 (s, 2H). MS TOFES$^+$: m/z 339.1 (M+H)$^+$.

Ethyl 2-amino-5-oxo-7-(tetrahydro-2H-pyran-4-yl)-5H-chromeno[2,3-b]pyridine-3-carboxylate (41)

A flask with a suspension of compound 39 (65 mg, 0.18 mmol) in ethanol (150 mL) was purged with nitrogen and 10% palladium on carbon (75 mg) was added. The mixture was then purged with nitrogen and hydrogen, and hydrogenated at 20 PSI using a Parr shaker at room temperature for 24 h. The mixture was filtered over celite and concentrated to a residue that was purified by silica gel preparative plate chromatography (elution with 2% methanol in dichloromethane) to give 41 (54 mg, 83%) as a solid. $^1$H NMR (400 MHz, chloroform-d): δ 9.16 (s, 1H), 8.37 (s, 1H), 8.12 (d, J=2.2 Hz, 1H), 7.59 (dd, J=8.6, 2.3 Hz, 1H), 7.47 (d, J=8.6 Hz, 1H), 5.86 (s, 1H), 4.41 (q, J=7.1 Hz, 2H), 4.12 (dd, J=10.5, 3.7 Hz, 2H), 3.56 (td, J=11.4, 2.9 Hz, 2H), 2.90 (td, J=11.2, 5.2 Hz, 1H), 1.97-1.75 (m, 4H), 1.49-1.35 (m, 3H). MS TOFES$^+$: m/z 369.1 (M+H)$^+$.

2-Amino-5-oxo-7-(tetrahydro-2H-pyran-4-yl)-5H-chromeno[2,3-b]pyridine-3-carboxylic acid (42)

To a suspension of 41 (52 mg, 0.14 mmol) in ethanol (20 mL) and water (2.5 mL) was added 1N aq NaOH (2.5 mL) and the mixture was stirred for 45 min at 50° C. and then concentrated. The residue was diluted with water (5 mL) and was acidified with 1N aq HCl to pH 3-4. The fine suspension was stirred at room temperature overnight and then let stand for 20 h. The precipitate was collected by filtration, washed with water and dried to give 42 (42 mg, 87%) as a white solid. $^1$H NMR (400 MHz, DMSO-d$_6$): δ 13.47 (s, 1H), 8.80 (s, 1H), 8.28 (s, 1H), 8.25 (s, 1H), 7.92 (d, J=2.3 Hz, 1H), 7.76 (dd, J=8.6, 2.3 Hz, 1H), 7.56 (d, J=8.6 Hz, 1H), 4.07-3.90 (m, 2H), 3.46 (td, J=11.5, 2.4 Hz, 2H), 3.03-2.83 (m, 1H), 1.88-1.55 (m, 4H). MS TOFES$^+$: m/z 341.1 (M+H)$^+$.

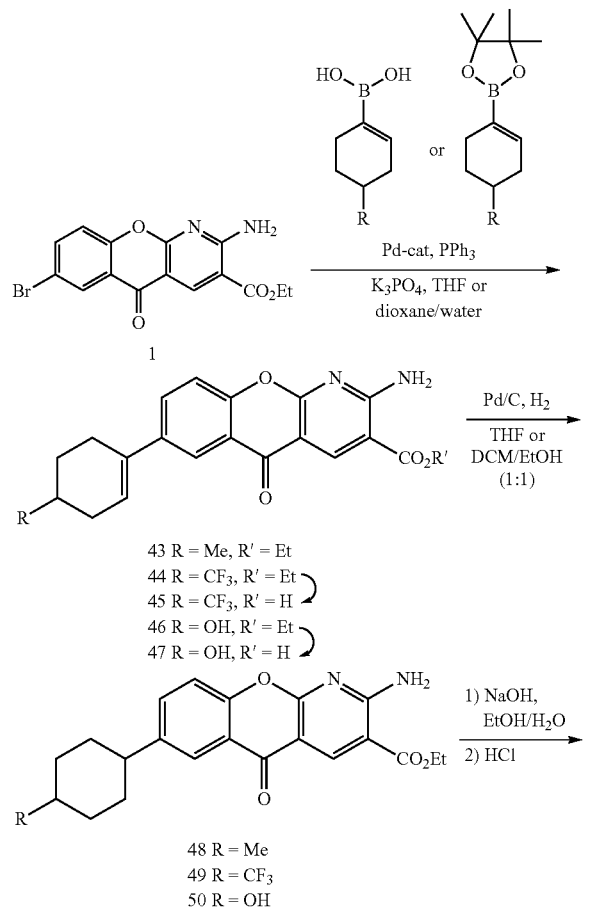

Scheme 12

43 R = Me, R' = Et
44 R = CF$_3$, R' = Et
45 R = CF$_3$, R' = H
46 R = OH, R' = Et
47 R = OH, R' = H
48 R = Me
49 R = CF$_3$
50 R = OH

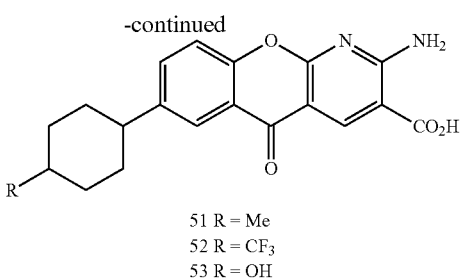

51 R = Me
52 R = CF$_3$
53 R = OH

Ethyl 2-amino-7-(4-methylcyclohex-1-en-1-yl)-5-oxo-5H-chromeno[2,3-b]pyridine-3-carboxylate (43)

A solution of potassium carbonate (400 mg, 2.89 mmol) in water (5.3 mL) was added to a nitrogen-degassed suspension of compound 1 (350 mg, 0.96 mmol), 4-methylcyclohex-1-en-1-ylboronic acid (236 mg, 1.69 mmol), triphenylphosphine (15.2 mg, 0.06 mmol), and PdCl$_2$(PPh$_3$)$_2$ (13.5 mg, 0.02 mmol) in tetrahydrofuran (16 mL). The reaction vessel was sealed with a screw cap and heated at 100° C. for 18 h. The mixture was cooled and distributed between dichloromethane and water. The organic phase was dried (Na$_2$SO$_4$) and concentrated to a solid that was collected by filtration and washed sparingly with dichloromethane to give 43 (290 mg, 80%) as a white solid. $^1$H NMR (400 MHz, chloroform-d): δ 9.16 (s, 1H), 8.36 (s, 1H), 8.22 (d, J=2.4 Hz, 1H), 7.77 (dd, J=8.7, 2.4 Hz, 1H), 7.43 (d, J=8.7 Hz, 1H), 6.22 (s, 1H), 5.83 (s, 1H), 4.41 (q, J=7.1 Hz, 2H), 2.53 (s, 2H), 2.34 (d, J=18.0 Hz, 1H), 1.94-1.70 (m, 3H), 1.44 (t, J=7.1 Hz, 3H), 1.42-1.31 (m, 1H), 1.03 (d, J=6.5 Hz, 3H). MS TOFES$^+$: m/z 379.2 (M+H)$^+$.

Ethyl 2-amino-5-oxo-7-(4-(trifluoromethyl)cyclohex-1-en-1-yl)-5H-chromeno[2,3-b]pyridine-3-carboxylate (44)

A solution of tripotassium phosphate (701 mg, 3.30 mmol) in water (1.35 mL) was added to a nitrogen-degassed suspension of compound 1 (200 mg, 0.55 mmol), 4,4,5,5-tetramethyl-2-(4-(trifluoromethyl)cyclohex-1-en-1-yl)-1,3,2-dioxaborolane (175 mg, 0.63 mmol), triphenylphosphine (72.2 mg, 0.28 mmol), and Pd(Oac)$_2$ (12.4 mg, 0.06 mmol) in p-dioxane (13.5 mL). The reaction vessel was sealed with a screw cap and heated at 100-110° C. for 20 min and then stirred at 70° C. for 2 h. After cooling, the mixture was concentrated to a residue that was distributed between dichloromethane and water. The organic phase was washed with brine, dried (Na$_2$SO$_4$), and concentrated to leave a solid that was triturated, first with dichloromethane and then ether, and dried to give 44 (176 mg, 74%) as a white solid. $^1$H NMR (400 MHz, DMSO-d$_6$): δ 8.81 (s, 1H), 8.41 (s, 1H), 8.12 (s, 1H), 8.03 (d, J=2.4 Hz, 1H), 7.93 (dd, J=8.8, 2.4 Hz, 1H), 7.58 (d, J=8.8 Hz, 1H), 6.30 (s, 1H), 4.35 (q, J=7.1 Hz, 2H), 2.60 (s, 3H), 2.46 (s, 1H), 2.25 (t, J=13.5 Hz, 1H), 2.12 (d, J=13.0 Hz, 1H), 1.67-1.57 (m, 1H), 1.36 (t, J=7.1 Hz, 3H). MS TOFES$^+$: m/z 433.0 (M+H)$^+$.

2-Amino-5-oxo-7-(4-(trifluoromethyl)cyclohex-1-en-1-yl)-5H-chromeno[2,3-b]pyridine-3-carboxylic acid (45)

To a suspension of compound 44 (32 mg, 0.07 mmol) in ethanol (8 mL) and water (1 mL) was added 1N aq NaOH (1 mL) and the mixture was stirred for 2 h at 50° C. and concentrated. The residue was diluted with water (150 mL) and acidified with 1N aq. HCl to pH 3-4. The fine suspension was stirred at room temperature for 3 d and then let stand over the weekend. The precipitate was collected by filtration, washed with water, and dried to give 45 (28 mg, 94%) as a white solid. $^1$H NMR (400 MHz, DMSO-$d_6$): δ 8.78 (s, 1H), 8.31 (s, 1H), 8.27 (s, 1H), 8.01 (d, J=2.3 Hz, 1H), 7.91 (d, J=8.8 Hz, 1H), 7.56 (d, J=8.7 Hz, 1H), 6.29 (s, 1H), 2.59 (s, 3H), 2.46 (s, 1H), 2.24 (t, J=15.0 Hz, 1H), 2.17-2.06 (m, 1H), 1.60 (tt, J=12.1, 6.5 Hz, 1H). MS TOFES$^+$: m/z 405.0 (M+H)$^+$.

Ethyl 2-amino-7-(4-hydroxycyclohex-1-en-1-yl)-5-oxo-5H-chromeno[2,3-b]pyridine-3-carboxylate (46)

A solution of tripotassium phosphate (701 mg, 3.3 mmol) in water (1.35 mL) was added to a nitrogen-degassed suspension of compound 1 (200 mg, 0.55 mmol), 4-(4,4,5,5-tetramethyl-1,3,2-dioxaborolan-2-yl)cyclohex-3-en-1-ol (136 mg, 0.61 mmol), triphenylphosphine (72.2 mg, 0.28 mmol), and Pd(OAc)$_2$ (12.4 mg, 0.06 mmol) in p-dioxane (13.5 mL). The reaction vessel was sealed with a screw cap and heated at 100-110° C. for 20 min, and then stirred at 70° C. for 1 h. After cooling, the mixture was concentrated and the residue was treated with a biphasic mixture of dichloromethane (150 mL) and water (30 mL). Precipitated solids were collected by filtration, washed with water and dried to give a first crop of product (137 mg). The dichloromethane phase of the filtrate was dried (Na$_2$SO$_4$) and concentrated to a solid that was triturated in dichloromethane and dried to give a second crop (42 mg). Total yield of 46=179 mg (85%). $^1$H NMR (400 MHz, chloroform-d): δ 9.16 (s, 1H), 8.37 (s, 1H), 8.23 (d, J=2.4 Hz, 1H), 7.77 (dd, J=8.8, 2.4 Hz, 1H), 7.45 (d, J=8.8 Hz, 1H), 6.13 (s, 1H), 5.84 (s, 1H), 4.41 (q, J=7.1 Hz, 2H), 4.11 (s, 1H), 2.75-2.57 (m, 3H), 2.31-2.22 (m, 1H), 2.05 (s, 1H), 1.97-1.77 (m, 2H), 1.44 (t, J=7.1 Hz, 3H). MS TOFES$^+$: m/z 381.0 (M+H)$^+$.

2-Amino-7-(4-hydroxycyclohex-1-en-1-yl)-5-oxo-5H-chromeno[2,3-b]pyridine-3-carboxylic acid (47)

To a suspension of compound 46 (35 mg, 0.09 mmol) in ethanol (12 mL) and water (1.5 mL) was added 1N aq NaOH (1.5 mL) and the mixture was stirred for 3 h at 50° C. and then concentrated. The residue was diluted with water (30 mL) and acidified with 1N aq HCl to pH 3-4. The fine suspension was stirred at room temperature for 48 h and then let stand for 1 d. The precipitate was collected by filtration, washed with water, and dried to give 47 (27 mg, 83%) as a white solid. $^1$H NMR (400 MHz, DMSO-$d_6$): δ 13.47 (s, 1H), 8.78 (s, 1H), 8.31 (s, 1H), 8.24 (s, 1H), 7.99 (s, 1H), 7.90 (d, J=8.8 Hz, 1H), 7.53 (d, J=8.7 Hz, 1H), 6.17 (s, 1H), 4.72 (s, 1H), 3.80 (d, J=8.7 Hz, 1H), 2.44 (s, 3H), 2.08 (d, J=18.0 Hz, 1H), 1.90 (s, 1H), 1.63 (s, 1H). MS TOFES$^+$: m/z 353.0 (M+H)$^+$.

Ethyl 2-amino-7-(4-methylcyclohexyl)-5-oxo-5H-chromeno[2,3-b]pyridine-3-carboxylate (48)

A flask with a solution of compound 43 (290 mg, 0.77 mmol) in tetrahydrofuran (100 mL) and EtOH (90 mL) was purged with nitrogen and 10% palladium on carbon (100 mg) was added. The mixture was then purged with nitrogen and hydrogen, and hydrogenated at 22 PSI using a Parr shaker at room temperature for 19 h. The mixture was filtered over celite and concentrated to a residue that was purified by flash silica gel chromatography (elution with 0.5% methanol in dichloromethane) to give a 3:2 mixture (by $^1$H NMR) of isomers of 48 (227 mg, 78%) as a white solid. $^1$H NMR (400 MHz, chloroform-d): δ 9.16 (s, 1H), 8.35 (s, 1H), 8.10 (dd, J=11.2, 2.3 Hz, 1H), 7.59 (ddd, J=13.9, 8.6, 2.3 Hz, 1H), 7.43 (dd, J=8.6, 4.5 Hz, 1H), 5.84 (s, 1H), 4.45-4.33 (m, 2H), 2.64 (dt, J=39.4, 11.5 Hz, 1H), 1.96 (d, J=13.8 Hz, 1H), 1.81 (d, J=11.6 Hz, 1H), 1.73-1.50 (m, 6H), 1.11 (d, J=12.3 Hz, 1H), 1.00 (dd, J=36.9, 6.8 Hz, 3H). MS TOFES$^+$: m/z 381.3 (M+H)$^+$.

Ethyl 2-amino-5-oxo-7-(4-(trifluoromethyl)cyclohexyl)-5H-chromeno[2,3-b]pyridine-3-carboxylate (49)

A flask with a solution of compound 44 (135 mg, 0.31 mmol) in dichloromethane (90 mL) and ethanol (90 mL) was purged with nitrogen and 10% palladium on carbon (100 mg) was added. The mixture was then purged with nitrogen and hydrogen, and hydrogenated at 30 PSI using a Parr shaker at room temperature for 22 h. The mixture was filtered over celite and concentrated to a residue that was triturated in ethanol and dried to give a 2:1 mixture (by $^1$H NMR) of isomers of 49 (110 mg, 81%) as a white solid. $^1$H NMR (500 MHz, chloroform-d): δ 9.15 (s, 1H), 8.36 (s, 1H), 8.10 (dd, J=16.0, 2.3 Hz, 1H), 7.58 (ddd, J=25.6, 8.6, 2.3 Hz, 1H), 7.45 (dd, J=8.6, 5.6 Hz, 1H), 5.83 (s, 1H), 4.41 (q, J=7.1 Hz, 2H), 2.85-2.63 (m, 1H), 2.34 (tt, J=10.4, 5.4 Hz, 1H), 2.19-2.04 (m, 2H), 1.98 (dd, J=14.0, 7.5 Hz, 3H), 1.89-1.69 (m, 3H), 1.44 (t, J=7.1 Hz, 3H). MS TOFES$^+$: m/z 435.0 (M+H)$^+$.

Ethyl 2-amino-7-(4-hydroxycyclohexyl)-5-oxo-5H-chromeno[2,3-b]pyridine-3-carboxylate (50)

A flask with a solution of compound 46 (137 mg, 0.36 mmol) in dichloromethane (50 mL) and ethanol (50 mL) was purged with nitrogen and 10% palladium on carbon (180 mg) was added. The mixture was then purged with nitrogen and hydrogen, and hydrogenated at 42 PSI using a Parr shaker at room temperature for 24 h. The mixture was filtered over celite and concentrated to a residue that was triturated in ethanol and dried to give a 3:2 mixture (by $^1$H NMR) of isomers of 50 (108 mg, 78%) as a white solid. $^1$H NMR (400 MHz, chloroform-d): δ 9.16 (d, J=2.6 Hz, 1H), 8.36 (s, 1H), 8.13 (d, J=2.3 Hz, 1H), 8.09 (d, J=2.3 Hz, 1H), 7.65-7.58 (m, 1H), 7.58-7.50 (m, OH), 7.44 (dd, J=8.6, 3.2 Hz, 1H), 5.84 (s, 1H), 4.41 (q, J=7.1 Hz, 2H), 4.17 (s, 1H), 3.73 (dt, J=11.1, 5.7 Hz, 1H), 2.78-2.56 (m, 1H), 2.18-2.05 (m, 1H), 2.06-1.86 (m, 4H), 1.73 (d, J=12.2 Hz, 3H), 1.44 (t, J=7.1 Hz, 3H). MS TOFES$^+$: m/z 383.0 (M+H)$^+$.

2-Amino-7-(4-methylcyclohexyl)-5-oxo-5H-chromeno[2,3-b]pyridine-3-carboxylic acid (51)

To a suspension of compound 48 (85 mg, 0.22 mmol) in ethanol (20 mL) and water (2.5 mL) was added 1N aq NaOH (2.5 mL) and the mixture was stirred for 45 min at 50° C. and then concentrated. The residue was dissolved in water (180 mL) by warming to 60° C. and acidified with 1N aq HCl to pH 3-4. The fine suspension was stirred at room temperature for 2 h and then let stand overnight. The precipitate was collected by filtration, washed successively with water and acetonitrile and dried to give a 3:2 mixture (by $^1$H NMR) of isomers of 51 (65 mg, 83%) as a white solid. $^1$H NMR (400 MHz, DMSO-$d_6$): δ 13.47 (s, 1H), 8.79 (s, 1H), 8.26 (d, J=17.4 Hz, 2H), 7.91 (d, J=11.4 Hz, 1H), 7.73 (dd, J=17.2, 8.7 Hz, 1H), 7.52 (dd, J=8.7, 4.1 Hz, 1H), 2.65 (d, J=38.8

Hz, 1H), 1.98-1.57 (m, 6H), 1.49 (d, J=12.6 Hz, 2H), 1.16-1.05 (m, 1H), 0.97 (dd, J=40.2, 6.8 Hz, 3H). MS TOFES⁺: m/z 353.1 (M+H)⁺.

2-Amino-5-oxo-7-(4-(trifluoromethyl)cyclohexyl)-5H-chromeno[2,3-b]pyridine-3-carboxylic acid (52)

To a suspension of compound 49 (110 mg, 0.25 mmol) in ethanol (24 mL) and water (3 mL) was added 1N aq NaOH (3 mL) and the mixture was stirred for 50 min at 50° C. and then concentrated. The residue was dissolved in water (100 mL) and ethanol (20 mL) and acidified with 1N aq HCl to pH 3-4. The fine suspension was stirred at room temperature for 2 h and then let stand over weekend. The precipitate was collected by filtration, washed with water, and dried to give 52 (96 mg, 93%) as a white solid. ¹H NMR (400 MHz, DMSO-d₆): δ 8.79 (s, 1H), 8.30 (s, 1H), 8.25 (s, 1H), 7.93 (s, 1H), 7.73 (t, J=9.5 Hz, 1H), 7.55 (dd, J=8.5, 4.0 Hz, 1H), 2.92 (s, 1H), 2.69 (d, J=13.5 Hz, 1H), 1.87 (dt, J=58.6, 11.6 Hz, 6H), 1.67-1.52 (m, 1H), 1.45 (t, J=12.4 Hz, 1H). MS TOFES⁺: m/z 407.0 (M+H)⁺.

2-Amino-7-(4-hydroxycyclohexyl)-5-oxo-5H-chromeno[2,3-b]pyridine-3-carboxylic acid (53)

To a suspension of compound 50 (106 mg, 0.28 mmol) in ethanol (24 mL) and water (3 mL) was added 1N aq NaOH (3 mL) and the mixture was stirred for 1 h at 50° C. The solution was filtered and the filtrate was concentrated to a residue that was diluted with water (30 mL) and acidified with 1 N aq. HCl to pH 3-4. The fine suspension was stirred at room temperature for 2 d and then let stand for 2 h. The precipitate was collected by filtration, washed with water, and dried to give a 3:2 mixture (by ¹H NMR) of isomers of 53 (85 mg, 87%) as a white solid. ¹H NMR (400 MHz, DMSO-d₆): δ 13.47 (s, 1H), 8.79 (d, J=3.2 Hz, 1H), 8.26 (d, J=16.1 Hz, 2H), 7.91 (dd, J=9.7, 2.2 Hz, 1H), 7.70 (dt, J=8.5, 2.7 Hz, 1H), 7.51 (dd, J=8.6, 4.9 Hz, 1H), 4.61 (s, OH), 4.44 (s, 1H), 3.90 (s, 1H), 2.65 (q, J=9.7, 7.5 Hz, 1H), 1.94-1.69 (m, 3H), 1.64-1.42 (m, 3H), 1.31 (d, J=12.0 Hz, 1H). MS TOFES⁺: m/z 355.0 (M+H)⁺.

Scheme 13

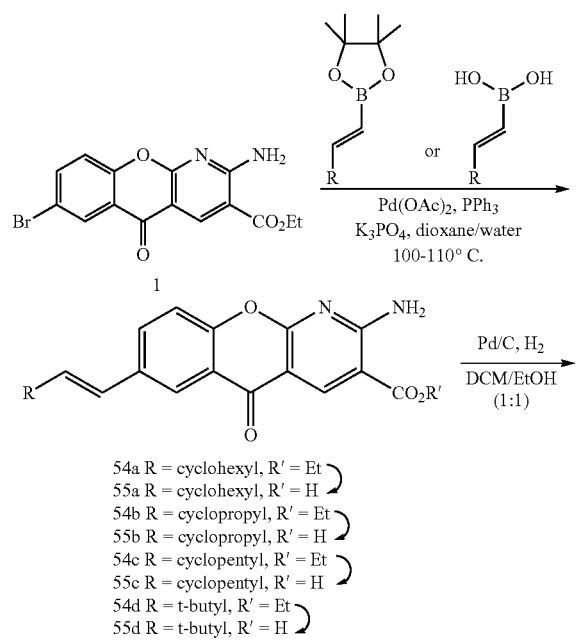

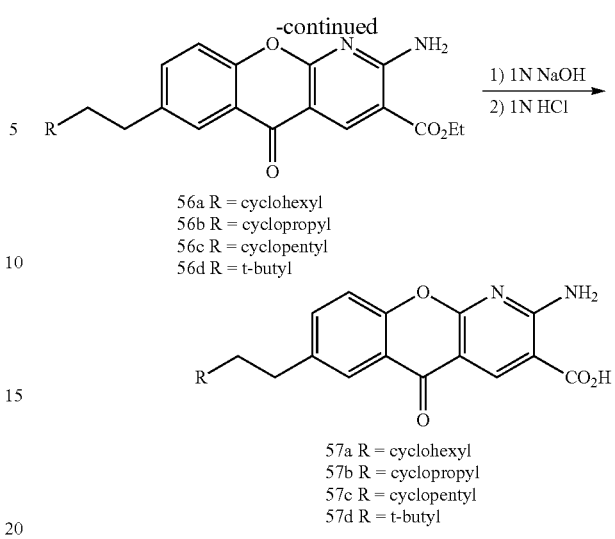

Ethyl (E)-2-amino-7-(2-cyclohexylvinyl)-5-oxo-5H-chromeno[2,3-b]pyridine-3-carboxylate (54a)

A solution of tripotassium phosphate (701 mg, 3.30 mmol) in water (1.35 mL) was added to a nitrogen-degassed suspension of compound 1 (200 mg, 0.55 mmol), (E)-(2-cyclohexylvinyl)boronic acid (93 mg, 0.61 mmol), triphenylphosphine (72.2 mg, 0.28 mmol), Pd(OAc)₂ (12.4 mg, 0.06 mmol) in p-dioxane (13.5 mL). The reaction vessel was sealed with a screw cap and heated at 100-110° C. for 20 min and then stirred at 70° C. for 2 h. After cooling, the mixture was concentrated and diluted with water (30 mL) and dichloromethane (150 mL). The solids from the biphasic mixture were collected by filtration and the organic phase of the filtrate was concentrated to leave additional solids. The combined solids were triturated in dichloromethane and dried to give 54a (180 mg, 83%) as an off-white solid. ¹H NMR (400 MHz, chloroform-d): δ 9.15 (s, 1H), 8.37 (s, 1H), 8.19 (d, J=2.2 Hz, 1H), 7.70 (dd, J=8.7, 2.3 Hz, 1H), 7.42 (d, J=8.6 Hz, 1H), 6.42 (d, J=16.0 Hz, 1H), 6.29 (dd, J=15.9, 6.8 Hz, 1H), 5.86 (s, 1H), 4.41 (q, J=7.1 Hz, 2H), 2.17 (d, J=6.1 Hz, 1H), 1.81 (t, J=15.0 Hz, 4H), 1.70 (d, J=12.5 Hz, 1H), 1.44 (t, J=7.1 Hz, 3H), 1.40-1.28 (m, 2H), 1.28-1.07 (m, 3H). MS TOFES⁺: m/z 393.0 (M+H)⁺.

Ethyl (E)-2-amino-7-(2-cyclopropylvinyl)-5-oxo-5H-chromeno[2,3-b]pyridine-3-carboxylate (54b)

A solution of tripotassium phosphate (2104 mg, 9.91 mmol) in water (4 mL) was added to a suspension of compound 1 (600 mg, 1.65 mmol), (E)-(2-cyclopropylvinyl) boronic acid pinacol ester (401 mg, 2.07 mmol), triphenylphosphine (217 mg, 0.83 mmol), Pd(OAc)₂ (37.1 mg, 1.17 mmol) and p-dioxane (40 mL) under an atmosphere of nitrogen. The reaction vessel was heated at 100-110° C. for 40 min. The reaction mixture was diluted with water and extracted with dichloromethane (2×). The combined organic phases were dried (Na₂SO₄) and concentrated to a solid that was triturated in a small volume of dichloromethane and dried to give 54b (489 mg, 84%) as a white solid. ¹H NMR (400 MHz, chloroform-d) δ 9.15 (s, 1H), 8.36 (s, 1H), 8.14 (d, J=2.3 Hz, 1H), 7.64 (dd, J=8.7, 2.3 Hz, 1H), 7.41 (d, J=8.7 Hz, 1H), 6.54 (d, J=15.7 Hz, 1H), 5.87 (s, 1H), 5.82 (d, J=9.1 Hz, 1H), 4.40 (q, J=7.1 Hz, 2H), 1.61 (d, J=4.4 Hz, 1H), 1.44 (t, J=7.1 Hz, 3H), 0.93-0.82 (m, 2H), 0.56 (dt, J=6.5, 4.5 Hz, 2H). MS m/z 351.1335 (M+H)+.

Ethyl (E)-2-amino-7-(2-cyclopentylvinyl)-5-oxo-5H-chromeno[2,3-b]pyridine-3-carboxylate (54c)

A solution of tripotassium phosphate (701 mg, 3.30 mmol) in water (1.35 mL) was added to a nitrogen-degassed suspension of compound 1 (200 mg, 0.55 mmol), (E)-(2-cyclopentylvinyl)boronic acid (96 mg, 0.69 mmol), triphenylphosphine (72.2 mg, 0.28 mmol), Pd(OAc)$_2$ (12.4 mg, 0.06 mmol) and p-dioxane (13.5 mL) under an atmosphere of nitrogen. The reaction vessel was sealed with a screw cap and heated at 100-110° C. for 25 min and then at 70° C. for 2 h. Workup as described above for the synthesis of 54b gave 54c (158 mg, 76%) as white solid. $^1$H NMR (400 MHz, chloroform-d) δ 9.15 (s, 1H), 8.36 (s, 1H), 8.18 (d, J=2.3 Hz, 1H), 7.69 (dd, J=8.7, 2.3 Hz, 1H), 7.42 (d, J=8.6 Hz, 1H), 6.45 (d, J=15.8 Hz, 1H), 6.32 (dd, J=15.8, 7.7 Hz, 1H), 5.89 (s, 1H), 4.40 (q, J=7.1 Hz, 2H), 2.64 (q, J=8.1 Hz, 1H), 1.87 (dd, J=12.2, 7.5 Hz, 2H), 1.73 (dq, J=7.4, 4.5, 4.1 Hz, 2H), 1.69-1.61 (m, 2H), 1.44 (t, J=7.2 Hz, 5H). MS m/z 379.1650 (M+1)+.

Ethyl (E)-2-amino-7-(3,3-dimethylbut-1-en-1-yl)-5-oxo-5H-chromeno[2,3-b]pyridine-3-carboxylate (54d)

A solution of tripotassium phosphate (701 mg, 3.30 mmol) in water (1.35 mL) was added to a suspension of compound 1 (200 mg, 0.55 mmol), (E)-(2-cyclopentylvinyl) boronic acid (88 mg, 0.69 mmol), triphenylphosphine (72.2 mg, 0.28 mmol), Pd(OAc)$_2$ (12.4 mg, 0.06 mmol) and p-dioxane (13.5 mL) under an atmosphere of nitrogen. The reaction vessel was sealed with a screw cap and heated at 100-110° C. for 2 h. Workup as described above for the synthesis of 54b gave 54d (152 mg, 75%) as a white solid. $^1$H NMR (400 MHz, chloroform-d) δ 9.16 (s, 1H), 8.37 (s, 1H), 8.21 (d, J=2.2 Hz, 1H), 7.71 (dd, J=8.6, 2.2 Hz, 1H), 7.43 (d, J=8.6 Hz, 1H), 6.38 (s, 2H), 5.87 (s, 1H), 4.41 (q, J=7.1 Hz, 2H), 1.44 (t, J=7.1 Hz, 3H), 1.15 (s, 9H). MS m/z 367.1656 (M+1)+.

(E)-2-amino-7-(2-cyclohexylvinyl)-5-oxo-5H-chromeno[2,3-b]pyridine-3-carboxylic acid (55a)

To a suspension of compound 54a (35 mg, 0.09 mmol) in ethanol (12 mL) and water (1.5 mL) was added 1N aq NaOH (1.5 mL) and the mixture was stirred for 3 h at 50° C. The solution was filtered and the filtrate concentrated to a residue that was dissolved in water (30 mL) and acidified with 1N aq HCl to pH 3-4. The fine suspension was stirred at room temperature for 48 h and then let stand for 1 d. The precipitate was collected, washed with water, and dried to give 55a (28 mg, 86%) as a white solid. $^1$H NMR (400 MHz, DMSO-d$_6$): δ 13.49 (s, 1H), 8.79 (s, 1H), 8.29 (d, J=11.1 Hz, 2H), 8.00 (d, J=2.2 Hz, 1H), 7.88 (dd, J=8.7, 2.3 Hz, 1H), 7.53 (d, J=8.6 Hz, 1H), 6.50 (d, J=16.1 Hz, 1H), 6.36 (dd, J=16.1, 6.8 Hz, 1H), 2.15 (d, J=9.8 Hz, 1H), 1.92-1.46 (m, 5H), 1.24 (dt, J=35.6, 12.4 Hz, 5H). MS m/z 365.1 (M+H)+.

(E)-2-amino-7-(2-cyclopropylvinyl)-5-oxo-5H-chromeno[2,3-b]pyridine-3-carboxylic acid (55b)

To a suspension of compound 54b (125 mg, 0.36 mmol) in ethanol (32 mL) and water (4 mL) was added 1N aq NaOH (4 mL). After stirring for 3 h at 50° C., the resulting solution was filtered. The filtrate was concentrated, diluted with water (30 mL) and acidified with 1N aq HCl to pH 3-4. The formed suspension was stirred at room temperature for 18 h, collected, washed with water, and dried to give 55b (105 mg, 91%) as a solid. $^1$H NMR (400 MHz, DMSO-d$_6$) δ 13.48 (s, 1H), 8.79 (s, 1H), 8.31 (s, 1H), 8.25 (s, 1H), 7.96 (d, J=2.2 Hz, 1H), 7.52 (d, J=8.7 Hz, 1H), 6.61 (d, J=15.8 Hz, 1H), 5.96 (dd, J=15.9, 9.2 Hz, 1H), 1.61 (tt, J=8.4, 4.4 Hz, 1H), 0.88-0.74 (m, 2H), 0.64-0.48 (m, 2H). MS m/z 323.1027 (M+H)+.

(E)-2-amino-7-(2-cyclopentylvinyl)-5-oxo-5H-chromeno[2,3-b]pyridine-3-carboxylic acid (55c)

Similar reaction of compound 54c (35 mg, 0.09 mmol) and 1N aq NaOH (1.5 mL) in ethanol (12 mL) and water (1.5 mL) followed by workup (stirring of precipitate at room temperature for 24 h and then storage at room temperature for 2 d) gave 55c (28 mg, 86%) as a solid. $^1$H NMR (400 MHz, DMSO-d$_6$) δ 13.49 (s, 1H), 8.80 (s, 1H), 8.30 (s, 1H), 8.28 (s, 1H), 8.01 (d, J=2.2 Hz, 1H), 7.89 (dd, J=8.7, 2.3 Hz, 1H), 7.54 (d, J=8.6 Hz, 1H), 6.54 (d, J=15.9 Hz, 1H), 6.40 (dd, J=15.9, 7.7 Hz, 1H), 2.64 (dt, J=16.0, 7.9 Hz, 1H), 1.83 (d, J=8.8 Hz, 2H), 1.69 (dd, J=7.9, 3.6 Hz, 2H), 1.59 (dq, J=7.8, 3.2 Hz, 2H), 1.47-1.37 (m, 2H). MS m/z 351.1354 (M+1)+.

(E)-2-Amino-7-(3,3-dimethylbut-1-en-1-yl)-5-oxo-5H-chromeno[2,3-b]pyridine-3-carboxylic acid (55d)

Similar reaction of compound 54d (45 mg, 0.12 mmol) and 1N aq NaOH (1.5 mL) in ethanol (12 mL) and water (1.5 mL) followed by workup (stirring of precipitate at room temperature for 24 h and then storage at room temperature for 2 d) gave 55d (37 mg, 89%) as a solid. $^1$H NMR (400 MHz, DMSO-d$_6$) δ 13.47 (s, 1H), 8.80 (s, 1H), 8.32 (s, 1H), 8.25 (s, 1H), 8.04 (d, J=2.2 Hz, 1H), 7.90 (dd, J=8.8, 2.2 Hz, 1H), 7.54 (d, J=8.7 Hz, 1H), 6.46 (s, 2H), 1.12 (s, 9H). MS m/z 339.1338 (M+H)+.

Ethyl 2-amino-7-(2-cyclohexylethyl)-5-oxo-5H-chromeno[2,3-b]pyridine-3-carboxylate (56a)

A flask with a solution of compound 54a (140 mg, 0.36 mmol) in dichloromethane (50 mL) and ethanol (50 mL) was purged with nitrogen and 10% palladium on carbon (180 mg) was added. The mixture was then purged with nitrogen and hydrogen, and hydrogenated at 45 PSI using a Parr shaker at room temperature for 22 h. The mixture was filtered over celite and concentrated to a residue that was triturated in ethanol and dried to give 56a (109 mg, 77%) as a white solid. $^1$H NMR (400 MHz, chloroform-d): δ 9.16 (s, 1H), 8.36 (s, 1H), 8.06 (d, J=2.2 Hz, 1H), 7.53 (dd, J=8.5, 2.3 Hz, 1H), 7.41 (d, J=8.5 Hz, 1H), 5.84 (s, 1H), 4.41 (q, J=7.1 Hz, 2H), 2.80-2.62 (m, 2H), 1.72 (td, J=24.5, 22.4, 11.9 Hz, 5H), 1.54 (d, J=7.2 Hz, 2H), 1.44 (t, J=7.1 Hz, 3H), 1.33-1.09 (m, 4H), 0.95 (q, J=11.9, 11.4 Hz, 2H). MS m/z 395.1 (M+H)+.

Ethyl 2-amino-7-(2-cyclopropylethyl)-5-oxo-5H-chromeno[2,3-b]pyridine-3-carboxylate (56b)

Similar reaction of compound 54b (360 mg, 1.03 mmol) in dichloromethane (90 mL) and ethanol (135 mL) over 10% palladium on carbon (350 mg) at 30 PSI for 16 h gave on workup a solid that was recrystallized 3× from a mixture of dichloromethane and ethanol to give 56b (40 mg, 11%) as a white solid. $^1$H NMR (500 MHz, chloroform-d) δ 9.15 (s, 1H), 8.35 (s, 1H), 8.07 (d, J=2.2 Hz, 1H), 7.55 (dd, J=8.5, 2.3 Hz, 1H), 7.41 (d, J=8.5 Hz, 1H), 5.87 (s, 1H), 4.41 (q, J=7.1 Hz, 2H), 2.83 (dd, J=8.6, 6.8 Hz, 2H), 1.56 (dd, J=8.5, 6.6 Hz, 2H), 1.44 (t, J=7.1 Hz, 3H), 0.70 (ddt, J=10.2, 7.6, 3.8 Hz, 1H), 0.48-0.37 (m, 2H), 0.10-0.02 (m, 2H). MS m/z 353.1494 (M+H)$^+$.

Ethyl 2-amino-7-(2-cyclopentylethyl)-5-oxo-5H-chromeno[2,3-b]pyridine-3-carboxylate (56c)

Similar reaction of compound 54c (120 mg, 0.32 mmol) in dichloromethane (30 mL) and ethanol (45 mL) over 10% palladium on carbon (120 mg) at 45 PSI for 22 h gave 195 mg of solid that was triturated in ethanol and dried to leave 56c (94 mg, 78%) as a white solid. $^1$H NMR (400 MHz, chloroform-d) δ 9.15 (s, 1H), 8.35 (s, 1H), 8.06 (d, J=2.2 Hz, 1H), 7.53 (dd, J=8.6, 2.3 Hz, 1H), 7.41 (d, J=8.5 Hz, 1H), 5.85 (s, 1H), 4.41 (q, J=7.2 Hz, 2H), 2.73 (dd, J=9.1, 6.7 Hz, 2H), 1.80 (s, 3H), 1.72-1.65 (m, 2H), 1.62 (q, J=3.5, 3.1 Hz, 2H), 1.52 (dd, J=7.8, 4.4 Hz, 2H), 1.44 (t, J=7.1 Hz, 3H), 1.15 (d, J=4.1 Hz, 2H). MS m/z 381.1810 (M+1)$^+$.

Ethyl 2-Amino-7-(3,3-dimethylbutyl)-5-oxo-5H-chromeno[2,3-b]pyridine-3-carboxylate (56d)

Similar reaction of compound 54d (95 mg, 0.26 mmol) in dichloromethane (25 mL) and ethanol (50 mL) over 10% palladium on carbon (90 mg) at 42 PSI for 18 h gave a solid that was triturated in ethanol and dried to give 56d (77 mg, 81%) as a white solid. $^1$H NMR (400 MHz, chloroform-d) δ 9.16 (s, 1H), 8.36 (s, 1H), 8.07 (d, J=2.2 Hz, 1H), 7.54 (dd, J=8.5, 2.3 Hz, 1H), 7.41 (d, J=8.5 Hz, 1H), 5.84 (s, 1H), 4.41 (q, J=7.1 Hz, 2H), 2.73-2.65 (m, 2H), 1.58-1.50 (m, 2H), 1.44 (t, J=7.1 Hz, 3H), 0.99 (s, 9H). MS m/z 369.1816 (M+H)$^+$.

2-Amino-7-(2-cyclohexylethyl)-5-oxo-5H-chromeno[2,3-b]pyridine-3-carboxylic acid (57a)

To a suspension of compound 56a (105 mg, 0.27 mmol) in ethanol (24 mL) and water (3 mL) was added 1N aq NaOH (3 mL) and the mixture was stirred for 3 h at 50° C. and then filtered. The filtrate was concentrated to a residue was diluted with water (40 mL) and acidified with 1N aq HCl to pH 3-4. The fine suspension was stirred at room temperature for 3 h and then let stand for 2 h. The precipitate was collected, washed successively with water and acetonitrile, and dried to give 57a (80 mg, 82%) as a white solid. $^1$H NMR (400 MHz, DMSO-d$_6$): δ 13.47 (s, 1H), 8.79 (s, 1H), 8.26 (d, J=18.8 Hz, 2H), 7.86 (d, J=2.3 Hz, 1H), 7.65 (dd, J=8.5, 2.2 Hz, 1H), 7.50 (d, J=8.5 Hz, 1H), 2.70 (t, J=8.1 Hz, 2H), 1.84-1.69 (m, 2H), 1.63 (d, J=15.0 Hz, 3H), 1.49 (q, J=7.5 Hz, 2H), 1.30-1.16 (m, 2H), 1.16 (m, 2H), 0.93 (t, J=11.8 Hz, 2H). MS m/z 367.1 (M+H)$^+$.

2-Amino-7-(2-cyclopropylethyl)-5-oxo-5H-chromeno[2,3-b]pyridine-3-carboxylic acid (57b)

Similar reaction of compound 56b (40 mg, 0.11 mmol) and 1N aq NaOH (1.5 mL) in ethanol (12 mL) and water (1.5 mL) was followed by the same workup (stirring the formed precipitate at room temperature for 24 h and then storage at room temperature for 5 h) gave 57b (30 mg, 81%) as a solid. $^1$H NMR (500 MHz, DMSO-d$_6$) δ 13.46 (s, 1H), 8.79 (s, 1H), 8.26 (s, 2H), 7.90 (d, J=2.2 Hz, 1H), 7.68 (dd, J=8.5, 2.3 Hz, 1H), 7.51 (d, J=8.5 Hz, 1H), 2.79 (t, J=7.7 Hz, 2H), 1.51 (dt, J=9.3, 7.1 Hz, 2H), 0.69 (ddt, J=9.8, 7.3, 4.1 Hz, 1H), 0.45-0.31 (m, 2H), 0.11-0.00 (m, 2H). MS m/z 325.1200 (M+H)$^+$.

2-Amino-7-(2-cyclopentylethyl)-5-oxo-5H-chromeno[2,3-b]pyridine-3-carboxylic acid (57c)

Similar reaction of compound 56c (94 mg, 0.25 mmol) and 1N aq NaOH (3 mL) in ethanol (24 mL) and water (3 mL) for 2 h at 50° C. was followed by the same workup (stirring the formed precipitate at room temperature for 24 h and then storage at room temperature for 2 d) to give 57c (83 mg, 95%) as a solid. $^1$H NMR (400 MHz, DMSO-d$_6$) δ 13.54-13.34 (m, 1H), 8.79 (s, 1H), 8.27 (s, 1H), 8.24 (s, 1H), 7.87 (d, J=2.2 Hz, 1H), 7.66 (dd, J=8.6, 2.3 Hz, 1H), 7.50 (d, J=8.5 Hz, 1H), 2.70 (t, J=7.9 Hz, 2H), 1.73 (d, J=8.9 Hz, 3H), 1.60 (tt, J=10.4, 5.8 Hz, 4H), 1.47 (dd, J=7.7, 4.6 Hz, 2H), 1.13 (s, 2H). MS m/z 353.1491 (M+1)$^+$.

2-Amino-7-(3,3-dimethylbutyl)-5-oxo-5H-chromeno[2,3-b]pyridine-3-carboxylic acid (57d)

Reaction of 56d (75 mg, 0.20 mmol) and 1N aq NaOH (1.5 mL) ethanol (16 mL) and water (2 mL) was carried out exactly as described above for the synthesis of 57c to give 57d (60 mg, 87%) as a solid. $^1$H NMR (400 MHz, DMSO-d$_6$) δ 8.79 (s, 1H), 8.28 (s, 1H), 8.24 (s, 1H), 7.88 (d, J=2.2 Hz, 1H), 7.67 (dd, J=8.5, 2.2 Hz, 1H), 7.50 (d, J=8.5 Hz, 1H), 2.72-2.60 (m, 2H), 1.54-1.39 (m, 2H), 0.96 (s, 9H). MS m/z 341.1498 (M+H)$^+$.

Scheme 14

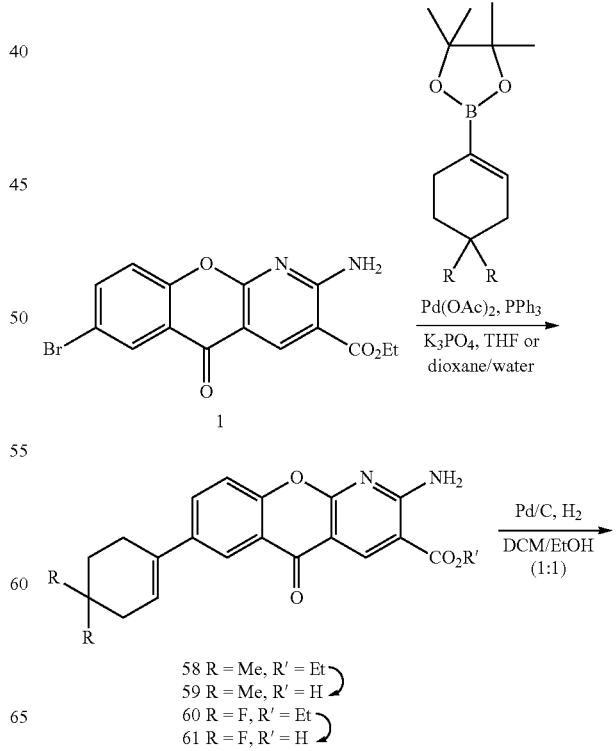

58 R = Me, R' = Et
59 R = Me, R' = H
60 R = F, R' = Et
61 R = F, R' = H

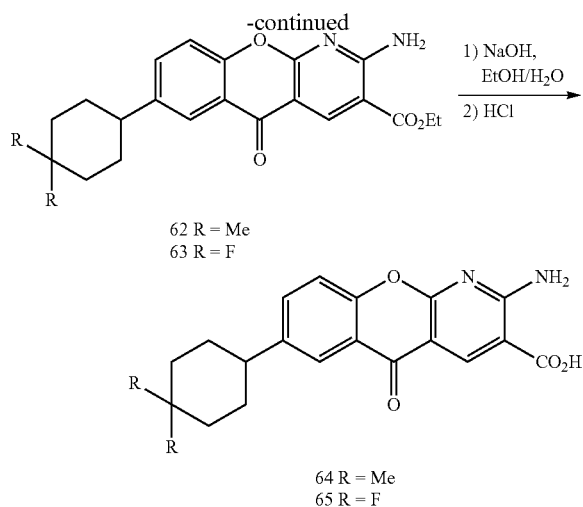

62 R = Me
63 R = F

64 R = Me
65 R = F

Ethyl 2-amino-7-(4,4-dimethylcyclohex-1-en-1-yl)-5-oxo-5H-chromeno[2,3-b]pyridine-3-carboxylate (58)

A solution of tripotassium phosphate (701 mg, 3.30 mmol) in water (1.35 mL) was added to a nitrogen-degassed suspension of compound 1 (200 mg, 0.55 mmol), 2-(4,4-dimethylcyclohex-1-en-1-yl)-4,4,5,5-tetramethyl-1,3,2-dioxaborolane (150 mg, 0.66 mmol), triphenylphosphine (72.2 mg, 0.28 mmol), Pd(Oac)$_2$ (12.4 mg, 0.06 mmol) in p-dioxane (13.5 mL). The reaction vessel was sealed with a screw cap and heated at 100-110° C. for 20 min and then stirred at 70° C. for 2 h. After cooling, the mixture was concentrated and distributed between water and dichloromethane. The organic phase was washed with brine, dried (Na$_2$SO$_4$), and concentrated to a residue that was purified by silica gel preparative plate chromatography (elution with 0.4% methanol in dichloromethane) to give 58 (170 mg, 79%) as a white solid. $^1$H NMR (400 MHz, chloroform-d): δ 9.16 (s, 1H), 8.36 (s, 1H), 8.23 (d, J=2.4 Hz, 1H), 7.78 (dd, J=8.7, 2.4 Hz, 1H), 7.43 (d, J=8.8 Hz, 1H), 6.24-6.13 (m, 1H), 5.94-5.80 (m, 1H), 4.41 (q, J=7.1 Hz, 2H), 2.50 (ddt, J=6.6, 4.5, 2.3 Hz, 2H), 2.11-1.98 (m, 2H), 1.57 (t, J=6.4 Hz, 2H), 1.44 (t, J=7.1 Hz, 3H), 0.99 (s, 6H). MS TOFES$^+$: m/z 393.2 (M+H)$^+$.

2-Amino-7-(4,4-dimethylcyclohex-1-en-1-yl)-5-oxo-5H-chromeno[2,3-b]pyridine-3-carboxylic acid (59)

To a suspension of compound 58 (45 mg, 0.12 mmol) in ethanol (12 mL) and water (1.5 mL) was added 1N aq NaOH (1.5 mL) and the mixture was stirred for 1 h at 50° C. and then filtered. The filtrate was concentrated to a residue that was diluted with water (30 mL) and acidified with 1N aq. HCl to pH 3-4. The fine suspension was stirred at room temperature for 18 h and then let stand for 2 h. The precipitate was collected by filtration, washed with water, and dried to give 59 (26 mg, 62%). $^1$H NMR (400 MHz, DMSO-d$_6$): δ 13.47 (s, 1H), 8.79 (s, 1H), 8.30 (s, 1H), 8.24 (s, 1H), 8.01 (d, J=2.4 Hz, 1H), 7.91 (dd, J=8.8, 2.4 Hz, 1H), 7.53 (d, J=8.8 Hz, 1H), 6.22 (d, J=4.3 Hz, 1H), 2.45 (d, J=6.2 Hz, 2H), 2.01 (d, J=3.8 Hz, 2H), 1.51 (t, J=6.4 Hz, 2H), 0.95 (s, 6H). MS TOFES$^+$: m/z 365.1 (M+H)$^+$.

Ethyl 2-amino-7-(4,4-difluorocyclohex-1-en-1-yl)-5-oxo-5H-chromeno[2,3-b]pyridine-3-carboxylate (60)

A solution of tripotassium phosphate (701 mg, 3.3 mmol) in water (1.35 mL) was added to a nitrogen-degassed suspension of 1 (200 mg, 0.55 mmol), 2-(4,4-difluorocyclohex-1-en-1-yl)-4,4,5,5-tetramethyl-1,3,2-dioxaborolane (155 mg, 0.63 mmol), triphenylphosphine (72.2 mg, 0.28 mmol), Pd(Oac)$_2$ (12.4 mg, 0.06 mmol) in p-dioxane (13.5 mL). The reaction vessel was sealed with a screw cap and heated at 100-110° C. for 20 min and then stirred at 70° C. for 2 h. After cooling, the mixture was concentrated and the residue distributed between water and dichloromethane. The organic phase was washed with brine, dried (Na$_2$SO$_4$), and concentrated to a solid that was triturated first in dichloromethane and then ether, and dried to give 60 (180 mg, 82%) as a white solid. $^1$H NMR (500 MHz, chloroform-d): δ 9.15 (s, 1H), 8.38 (s, 1H), 8.23 (d, J=2.4 Hz, 1H), 7.74 (dd, J=8.7, 2.4 Hz, 1H), 7.47 (d, J=8.7 Hz, 1H), 6.04 (d, J=3.9 Hz, 1H), 5.88 (s, 1H), 4.41 (q, J=7.1 Hz, 2H), 2.83-2.71 (m, 4H), 2.22 (tq, J=13.8, 6.9 Hz, 2H), 1.44 (t, J=7.1 Hz, 3H). MS TOFES$^+$: m/z 401.0 (M+H)$^+$.

2-Amino-7-(4,4-difluorocyclohex-1-en-1-yl)-5-oxo-5H-chromeno[2,3-b]pyridine-3-carboxylic acid (61)

To a suspension of compound 60 (38 mg, 0.1 mmol) in ethanol (8 mL) and water (1 mL) was added 1N aq NaOH (1 mL) and the mixture was stirred for 45 min at 50° C. and concentrated. The residue was dissolved in water (40 mL) and acidified with 1N aq HCl to pH 3~4. The fine suspension was stirred at room temperature overnight and then let stand for 1 h. The precipitate was collected by filtration, washed with water, and dried to give 61 (30 mg, 85%) as a white solid. $^1$H NMR (500 MHz, DMSO-d$_6$): δ 13.48 (s, 1H), 8.80 (d, J=1.1 Hz, 1H), 8.31 (s, 1H), 8.26 (s, 1H), 8.05 (d, J=2.5 Hz, 1H), 7.94 (dt, J=8.8, 1.6 Hz, 1H), 7.58 (dd, J=8.8, 1.1 Hz, 1H), 6.16 (s, 1H), 2.85-2.64 (m, 5H), 2.22 (dt, J=14.2, 7.3 Hz, 2H). MS TOFES$^+$: m/z 373.0 (M+H)$^+$.

Ethyl 2-amino-7-(4,4-dimethylcyclohexyl)-5-oxo-5H-chromeno[2,3-b]pyridine-3-carboxylate (62)

A flask with compound 58 (125 mg, 0.32 mmol) in ethanol (180 mL) was purged with nitrogen and 10% palladium on carbon (200 mg) was added. The mixture was then purged with nitrogen and hydrogen, and hydrogenated at 54 PSI using a Parr shaker at room temperature for 19 h. The mixture was filtered over celite and concentrated to a residue that was purified by silica gel preparative plate chromatography (elution with 0.6% methanol in dichloromethane) to give 62 (63 mg, 50%) as a white solid. $^1$H NMR (400 MHz, chloroform-d): δ 9.16 (s, 1H), 8.36 (s, 1H), 8.10 (d, J=2.3 Hz, 1H), 7.59 (dd, J=8.6, 2.3 Hz, 1H), 7.43 (d, J=8.6 Hz, 1H), 5.92 (s, 1H), 4.41 (q, J=7.1 Hz, 2H), 2.60-2.50 (m, 1H), 1.78-1.66 (m, 4H), 1.53 (d, J=13.2 Hz, 2H), 1.44 (t, J=7.1 Hz, 3H), 1.40-1.31 (m, 2H), 0.99 (d, J=11.3 Hz, 6H). MS TOFES$^+$: m/z 395.1 (M+H)$^+$.

Ethyl 2-amino-7-(4,4-difluorocyclohexyl)-5-oxo-5H-chromeno[2,3-b]pyridine-3-carboxylate (63)

A flask with a solution of compound 60 (140 mg, 0.35 mmol) in dichloromethane (90 mL) and ethanol (90 mL) was purged with nitrogen and 10% palladium on carbon (100 mg) was added. The mixture was then purged with nitrogen and hydrogen, and hydrogenated at 30 PSI using a Parr shaker at room temperature for 22 h. The mixture was filtered over celite and concentrated to a residue that was triturated in ethanol and dried to give 63 (112 mg, 80%) as a white solid. $^1$H NMR (500 MHz, chloroform-d): δ 9.15 (s, 1H), 8.37 (s, 1H), 8.11 (d, J=2.3 Hz, 1H), 7.58 (dd, J=8.6, 2.4

Hz, 1H), 7.46 (d, J=8.7 Hz, 1H), 5.83 (s, 1H), 4.41 (q, J=7.2 Hz, 2H), 2.76 (s, 1H), 2.25 (d, J=5.7 Hz, 2H), 1.99 (d, J=10.2 Hz, 2H), 1.94-1.83 (m, 4H), 1.44 (t, J=7.1 Hz, 3H). MS TOFES$^+$: m/z 403.0 (M+H)$^+$.

2-Amino-7-(4,4-dimethylcyclohexyl)-5-oxo-5H-chromeno[2,3-b]pyridine-3-carboxylic acid (64)

To a suspension of 62 (63 mg, 0.16 mmol) in ethanol (12 mL) and water (1.5 mL) was added 1N aq NaOH (1.5 mL) and the mixture was stirred for 1 h at 50° C. and filtered. The filtrate was concentrated to a residue that was diluted with water (30 mL) and acidified with 1N aq HCl to pH~3. The fine suspension was stirred at room temperature for 5 h and then stored for 48 h. The precipitate was collected by filtration, washed with water, and dried to give 64 (52 mg, 89%). $^1$H NMR (400 MHz, DMSO-d$_6$): δ 13.47 (s, 1H), 8.79 (s, 1H), 8.28 (s, 1H), 8.25 (s, 1H), 7.91 (d, J=2.3 Hz, 1H), 7.74 (dd, J=8.6, 2.3 Hz, 1H), 7.52 (d, J=8.6 Hz, 1H), 2.58 (dt, J=10.8, 5.7 Hz, 1H), 1.71-1.55 (m, 4H), 1.48 (d, J=12.8 Hz, 2H), 1.35 (td, J=12.5, 5.3 Hz, 2H), 0.99 (s, 3H), 0.95 (s, 3H). MS TOFES$^+$: m/z 367.1 (M+H)$^+$.

2-Amino-7-(4,4-difluorocyclohexyl)-5-oxo-5H-chromeno[2,3-b]pyridine-3-carboxylic acid (65)

To a suspension of compound 63 (112 mg, 0.28 mmol) in ethanol (24 mL) and water (3 mL) was added 1N aq NaOH (3 mL) and the mixture was stirred at 50° C. for 90 min and concentrated. The residue was dissolved in water (100 mL) and acidified with 1N aq HCl to pH 3-4. The resulting fine suspension was stirred at room temperature overnight and then let stand for 2 h. The precipitate was collected by filtration, washed with water, and dried to give 65 (85 mg, 82%) as a white solid. $^1$H NMR (400 MHz, DMSO-d$_6$): δ 13.48 (s, 1H), 8.79 (s, 1H), 8.29 (s, 1H), 8.25 (s, 1H), 7.92 (s, 1H), 7.74 (d, J=8.7 Hz, 1H), 7.54 (d, J=8.6 Hz, 1H), 2.89 (s, 1H), 2.22-1.85 (m, 6H), 1.70 (d, J=13.6 Hz, 2H). MS TOFES$^+$: m/z 375.0 (M+H)$^+$.

Scheme 15

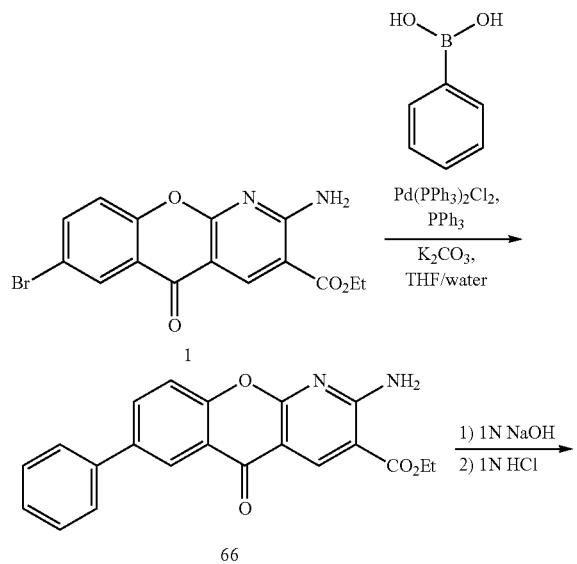

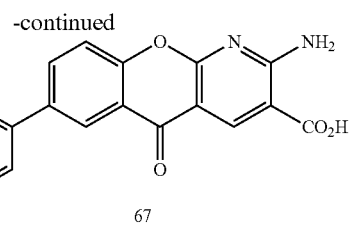

67

Ethyl 2-amino-5-oxo-7-phenyl-5H-chromeno[2,3-b]pyridine-3-carboxylate (66)

A solution of potassium carbonate (171 mg, 1.24 mmol) in water (7 mL) was added to a nitrogen degassed suspension of compound 1 (150 mg, 0.41 mmol), phenylboronic acid (60.4 mg, 0.50 mmol), triphenylphosphine (6.5 mg, 0.03 mmol), and PdCl$_2$(PPh$_3$)$_2$ (5.8 mg, 0.01 mmol) in tetrahydrofuran (7 mL). The reaction vessel was sealed with a screw cap and heated at 100° C. for 18 h, and then cooled and distributed between water and dichloromethane. The organic phase was concentrated to a residue that was purified by silica gel preparative plate chromatography (elution with 1.5% methanol in dichloromethane) to give 66 (110 mg, 74%) as an light orange solid. $^1$H NMR (400 MHz, DMSO-d$_6$): δ 8.82 (s, 1H), 8.41 (s, 1H), 8.28 (d, J=2.4 Hz, 1H), 8.15 (d, J=2.4 Hz, 1H), 8.13 (d, J=2.5 Hz, 1H), 7.80-7.71 (m, 2H), 7.70 (d, J=8.7 Hz, 1H), 7.52 (t, J=7.6 Hz, 2H), 7.45-7.39 (m, 1H), 4.35 (q, J=7.1 Hz, 2H), 1.37 (t, J=7.1 Hz, 3H). MS TOFES$^+$: m/z 361.2 (M+H)$^+$.

2-Amino-5-oxo-7-phenyl-5H-chromeno[2,3-b]pyridine-3-carboxylic acid (67)

To a suspension of compound 66 (110 mg, 0.31 mmol) in ethanol (20 mL) and water (2.5 mL) was added 1N aq NaOH (2.5 mL) and the mixture was stirred at 50° C. for 2 h and concentrated. The residue was dissolved in ethanol/water (1:1, 120 mL) and acidified with 1N aq HCl to pH 3~4. The fine suspension was stirred at room temperature for 2 d and then let stand over the weekend. The precipitate was collected by filtration, washed successively with water and acetonitrile, and dried to give 67 (73 mg, 72%) as a white solid. $^1$H NMR (400 MHz, DMSO-d$_6$): δ 13.51 (s, 1H), 8.82 (s, 1H), 8.36 (s, 1H), 8.29 (d, J=2.5 Hz, 2H), 8.14 (dd, J=8.6, 2.4 Hz, 1H), 7.76 (d, J=7.7 Hz, 2H), 7.70 (d, J=8.7 Hz, 1H), 7.52 (t, J=7.5 Hz, 2H), 7.42 (t, J=7.4 Hz, 1H). MS TOFES$^+$: m/z 333.1 (M+H)$^+$.

Scheme 16

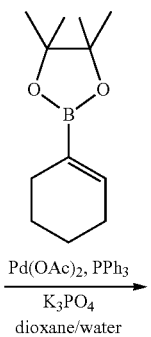

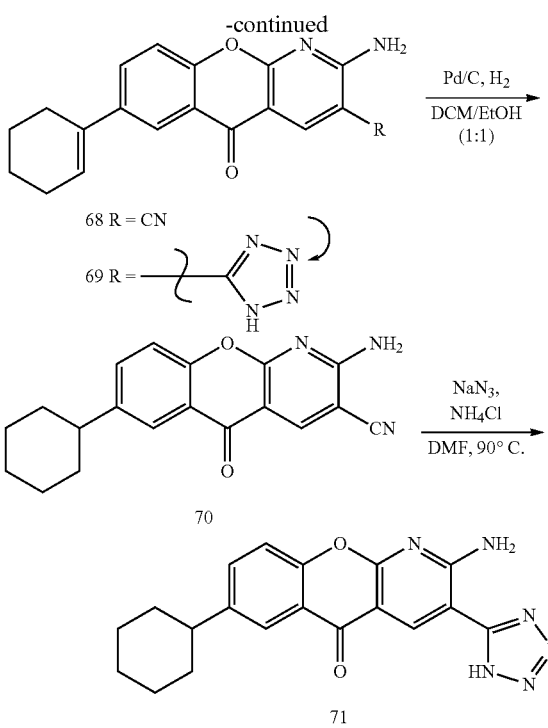

2-Amino-7-(cyclohex-1-en-1-yl)-5-oxo-5H-chromeno[2,3-b]pyridine-3-carbonitrile (68)

A solution of tripotassium phosphate (701 mg, 3.3 mmol) in water (1.5 mL) was added to a nitrogen-degassed suspension of 2-amino-7-bromo-5-oxo-5H-chromeno[2,3-b]pyridine-3-carbonitrile (174 mg, 0.55 mmol), 2-(cyclohex-1-en-1-yl)-4,4,5,5-tetramethyl-1,3,2-dioxaborolane (252 mg, 1.21 mmol), triphenylphosphine (72.2 mg, 0.28 mmol), and Pd(Oac)$_2$ (12.4 mg, 0.06 mmol) in p-dioxane (13 mL). The reaction vessel was sealed with a screw cap and heated at 100-110° C. for 30 min and then stirred at 70° C. for 1.5 h. After cooling, the mixture was concentrated and the residue was diluted with a mixture of water and dichloromethane. Precipitated solids were collected by filtration and the organic phase of the biphasic filtrate was dried (Na$_2$SO$_4$) and concentrated to leave additional solids. The combined solids were triturated in dichloromethane and dried to give 68 (136 mg, 78%) as an orange solid. $^1$H NMR (400 MHz, DMSO-d$_6$): δ 8.61 (s, 1H), 8.13 (s, 2H), 7.97 (d, J=2.3 Hz, 1H), 7.89 (dd, J=8.8, 2.4 Hz, 1H), 7.52 (d, J=8.7 Hz, 1H), 6.29 (s, 1H), 2.41 (s, 2H), 2.21 (s, 2H), 1.82-1.70 (m, 2H), 1.62 (t, J=5.8 Hz, 2H). MS TOFES$^+$: m/z 318.0 (M+H)$^+$.

2-Amino-7-(cyclohex-1-en-1-yl)-3-(1H-tetrazol-5-yl)-5H-chromeno[2,3-b]132yridine-5-one (69)

A mixture of compound 68 (50 mg, 0.16 mmol), sodium azide (30.7 mg, 0.47 mmol), and ammonium chloride (25.3 mg, 0.47 mmol) in N,N-dimethylformamide (0.5 mL) was stirred at 90° C. in a capped vial for 18 h. After cooling, the mixture was poured into water (5 mL) and the suspension was acidified with 10% aq HCl to pH 2-3 followed by stirring at room temperature for 10 min. The precipitate was collected by filtration, washed successively with water, acetonitrile, and dichloromethane, and dried to give 69 (45 mg, 79%). $^1$H NMR (400 MHz, DMSO-d$_6$): δ 8.99 (s, 1H), 8.44 (s, 2H), 8.01 (d, J=2.4 Hz, 1H), 7.89 (dd, J=8.8, 2.4 Hz, 1H), 7.55 (d, J=8.8 Hz, 1H), 6.29 (s, 1H), 2.42 (s, 2H), 2.21 (d, J=4.6 Hz, 2H), 1.76 (dd, J=7.2, 4.6 Hz, 2H), 1.68-1.55 (m, 2H). MS TOFES$^+$: m/z 361.0 (M+H)$^+$.

2-Amino-7-cyclohexyl-5-oxo-5H-chromeno[2,3-b]pyridine-3-carbonitrile (70)

A flask with a solution of compound 68 (58 mg, 0.18 mmol) in dichloromethane (90 mL) and ethanol (80 mL) was purged with nitrogen and 10% palladium on carbon (80 mg) was added. The mixture was then purged with nitrogen and hydrogen, and hydrogenated at 42 PSI using a Parr shaker at room temperature for 22 h. The mixture was filtered over celite and concentrated to a residue that was triturated in ethanol and dried to give 70 (44 mg, 75%) as a white solid. $^1$H NMR (500 MHz, chloroform-d): δ 8.75 (s, 1H), 8.08 (d, J=2.3 Hz, 1H), 7.60 (dd, J=8.6, 2.3 Hz, 1H), 7.44 (d, J=8.6 Hz, 1H), 5.76 (s, 2H), 2.63 (d, J=3.4 Hz, 1H), 1.90 (dd, J=19.2, 12.5 Hz, 4H), 1.78 (d, J=13.2 Hz, 1H), 1.52-1.36 (m, 4H), 1.29 (m, 1H). MS TOFES$^+$: m/z 320.0 (M+H)$^+$.

2-Amino-7-cyclohexyl-3-(1H-tetrazol-5-yl)-5H-chromeno[2,3-b]133yridine-5-one (71)

A mixture of compound 70 (40 mg, 0.13 mmol), sodium azide (24.4 mg, 0.38 mmol), and ammonium chloride (20.1 mg, 0.38 mmol) in N,N-dimethylformamide (0.5 mL) was stirred at 90° C. in a capped vial for 18 h. After cooling, the mixture was poured into water (5 mL) and the suspension was acidified with 10% aq HCl acid to pH 2-3 followed by stirring at room temperature for 24 h and standing for 2 h. The precipitate was collected by filtration, washed successively with water, 1:1 ether/acetonitrile, dichloromethane, and dried to give 71 (38 mg, 84%) as an orange solid. $^1$H NMR (400 MHz, DMSO-d$_6$): δ 9.02 (s, 1H), 8.44 (s, 2H), 7.93 (d, J=2.2 Hz, 1H), 7.76-7.67 (m, 1H), 7.55 (d, J=8.5 Hz, 1H), 2.67 (t, J=11.0 Hz, 1H), 1.82 (d, J=11.0 Hz, 4H), 1.72 (d, J=12.5 Hz, 1H), 1.43 (q, J=13.6, 13.0 Hz, 4H), 1.27 (d, J=12.0 Hz, 1H). MS TOFES$^+$: m/z 363.1 (M+H)$^+$.

Scheme 17

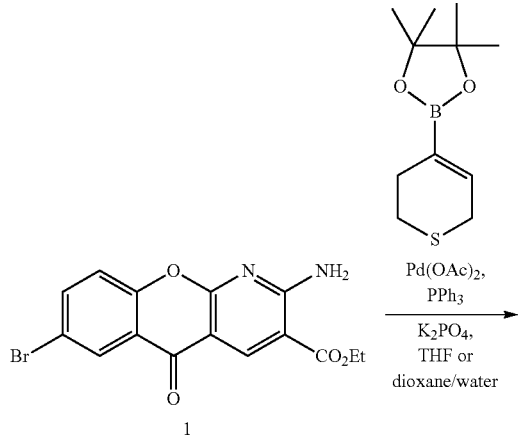

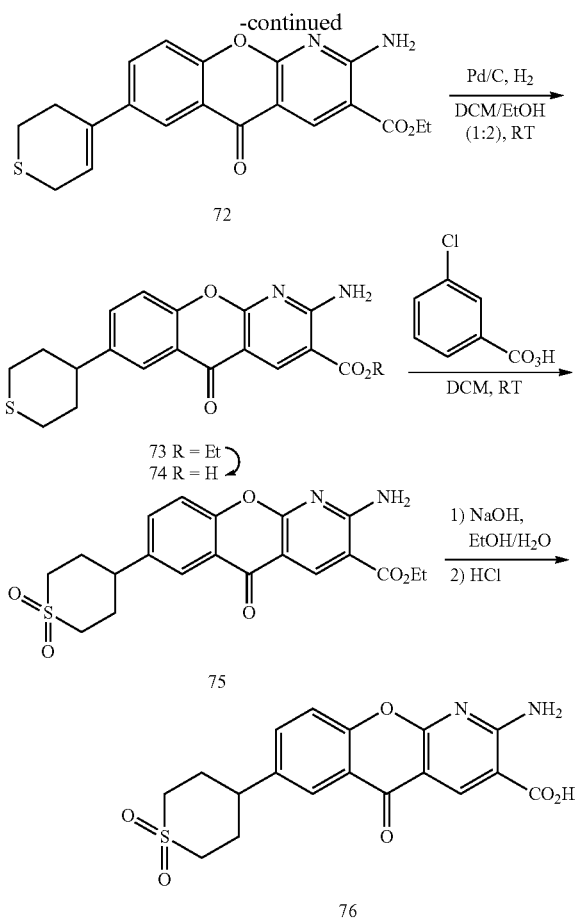

Ethyl 2-amino-7-(3,6-dihydro-2H-thiopyran-4-yl)-5-oxo-5H-chromeno[2,3-b]pyridine-3-carboxylate (72)

A solution of tripotassium phosphate (701 mg, 3.3 mmol) in water (1.4 mL) was added to a nitrogen-degassed mixture of compound 1 (200 mg, 0.55 mmol), 2-(3,6-dihydro-2H-thiopyran-4-yl)-4,4,5,5-tetramethyl-1,3,2-dioxaborolane (143 mg, 0.63 mmol), triphenylphosphine (72.2 mg, 0.28 mmol), Pd(Oac)$_2$ (12.4 mg, 0.06 mmol) in p-dioxane (13.5 mL). The reaction vessel was sealed with a screw cap and heated at 100-110° C. for 15 min and then stirred at 70° C. for 40 min. After cooling, the mixture was concentrated and the residue was distributed between dichloromethane and water. The organic phase was washed with brine, dried (Na$_2$SO$_4$), and concentrated to a solid that was triturated in dichloromethane and dried to give 72 (156 mg, 74%) as an off-white solid. $^1$H NMR (400 MHz, chloroform-d): δ 9.15 (s, 1H), 8.37 (s, 1H), 8.20 (d, J=2.4 Hz, 1H), 7.71 (dd, J=8.7, 2.4 Hz, 1H), 7.46 (d, J=8.7 Hz, 1H), 6.31 (dt, J=4.5, 2.6 Hz, 1H), 5.87 (s, 1H), 4.40 (q, J=7.1 Hz, 2H), 3.38 (dt, J=4.6, 2.4 Hz, 2H), 2.92 (t, J=5.7 Hz, 2H), 2.81-2.73 (m, 2H), 1.44 (t, J=7.1 Hz, 3H). MS TOFES$^+$: m/z 383.0 (M+H)$^+$.

Ethyl 2-amino-5-oxo-7-(tetrahydro-2H-thiopyran-4-yl)-5H-chromeno[2,3-b]pyridine-3-carboxylate (73)

A flask with a solution of compound 72 (110 mg, 0.29 mmol) in dichloromethane (50 mL) and ethanol (100 mL) was purged with nitrogen and 10% palladium on carbon (100 mg) was added. The mixture was then purged with nitrogen and hydrogen, and hydrogenated at 38 PSI using a Parr shaker at room temperature for 72 h. The mixture was filtered over celite and concentrated to a residue that triturated in ethanol and dried to give 73 (61 mg, 55%) as a white solid. $^1$H NMR (400 MHz, chloroform-d): δ 9.16 (s, 1H), 8.37 (s, 1H), 8.09 (d, J=2.3 Hz, 1H), 7.56 (dd, J=8.6, 2.3 Hz, 1H), 7.45 (d, J=8.6 Hz, 1H), 5.86 (s, 1H), 4.41 (q, J=7.1 Hz, 2H), 2.95-2.82 (m, 2H), 2.78-2.62 (m, 3H), 2.24-2.15 (m, 2H), 1.93 (qd, J=12.5, 3.2 Hz, 2H), 1.44 (t, J=7.1 Hz, 3H). MS TOFES$^+$: m/z 385.0 (M+H)$^+$.

2-Amino-5-oxo-7-(tetrahydro-2H-thiopyran-4-yl)-5H-chromeno[2,3-b]pyridine-3-carboxylic acid (74)

To a suspension of compound 73 (61 mg, 0.16 mmol) in ethanol (12 mL) and water (1.5 mL) was added 1N aq NaOH (1.5 mL). The mixture was stirred at 50° C. for 1 h and concentrated. The residue was diluted with water (40 mL) and acidified with 1N aq HCl to pH 3-4. The fine suspension was stirred at room temperature for 4 h and then let stand over the weekend. The precipitate was collected by filtration, washed with water, and dried to give 74 (46 mg, 81%) as a white solid. $^1$H NMR (500 MHz, DMSO-d$_6$): δ 13.46 (s, 1H), 8.79 (d, J=1.5 Hz, 1H), 8.26 (d, J=16.7 Hz, 2H), 7.89 (d, J=2.4 Hz, 1H), 7.72 (dd, J=8.7, 2.4 Hz, 1H), 7.58-7.51 (m, 1H), 2.82 (t, J=12.9 Hz, 2H), 2.75 (d, J=3.0 Hz, 1H), 2.68 (d, J=13.3 Hz, 2H), 2.10 (dd, J=13.0, 3.4 Hz, 2H), 1.76 (qd, J=12.6, 3.2 Hz, 2H). MS TOFES$^+$: m/z 357.0 (M+H)$^+$.

Ethyl 2-amino-7-(1,1-dioxidotetrahydro-2H-thiopyran-4-yl)-5-oxo-5H-chromeno[2,3-b]pyridine-3-carboxylate (75)

An ice-cold solution of compound 73 (55 mg, 0.14 mmol) in dichloromethane (10 mL) was treated portion-wise with 3-chlorobenzoperoxoic acid (106 mg of 70% purity, 0.43 mmol) and the mixture was stirred for 30 min at room temperature with TLC (3% MeOH in dichloromethane) showing complete reaction. The mixture was washed successively with 5% aq. Na$_2$CO$_3$, water, and brine, dried (Na$_2$SO$_4$), and purified by silica gel preparative plate chromatography (elution with 3.5% methanol in dichloromethane) to give 75 (33 mg, 55%) as a solid. $^1$H NMR (400 MHz, chloroform-d): δ 9.16 (s, 1H), 8.41 (s, 1H), 8.14 (d, J=2.3 Hz, 1H), 7.60 (dd, J=8.6, 2.4 Hz, 1H), 7.49 (d, J=8.6 Hz, 1H), 5.91 (s, 1H), 4.41 (q, J=7.1 Hz, 2H), 3.19 (dd, J=8.8, 3.3 Hz, 4H), 2.96 (t, J=12.3 Hz, 1H), 2.49 (dt, J=13.7, 6.1 Hz, 2H), 2.28 (d, J=14.4 Hz, 2H), 1.44 (t, J=7.1 Hz, 3H). MS TOFES$^+$: m/z 417.0 (M+H)$^+$.

2-Amino-7-(1,1-dioxidotetrahydro-2H-thiopyran-4-yl)-5-oxo-5H-chromeno[2,3-b]pyridine-3-carboxylic acid (76)

To a suspension of compound 75 (33 mg, 0.08 mmol) in ethanol (12 mL) and water (1.5 mL) was added 1N aq NaOH (1.5 mL) and the mixture was stirred for 2 h at 50° C. and concentrated. The residue was diluted with water (40 mL) and acidified with 1N aq HCl to pH 3-4. The fine suspension was stirred at room temperature over the weekend and then let stand for 2 h. The precipitate was collected by filtration, washed successively with water, 1:1 ether/acetonitrile, and dichloromethane, and dried to give 76 (26 mg, 84%) as a white solid. $^1$H NMR (400 MHz, DMSO-d$_6$): δ 8.79 (s, 1H), 8.28 (d, J=18.3 Hz, 2H), 7.93 (s, 1H), 7.75 (d, J=8.8 Hz, 1H), 7.57 (d, J=8.6 Hz, 1H), 3.14 (d, J=13.6 Hz, 5H), 2.16 (d, J=9.0 Hz, 4H). MS TOFES$^+$: m/z 389.0 (M+H)$^+$.

Scheme 18

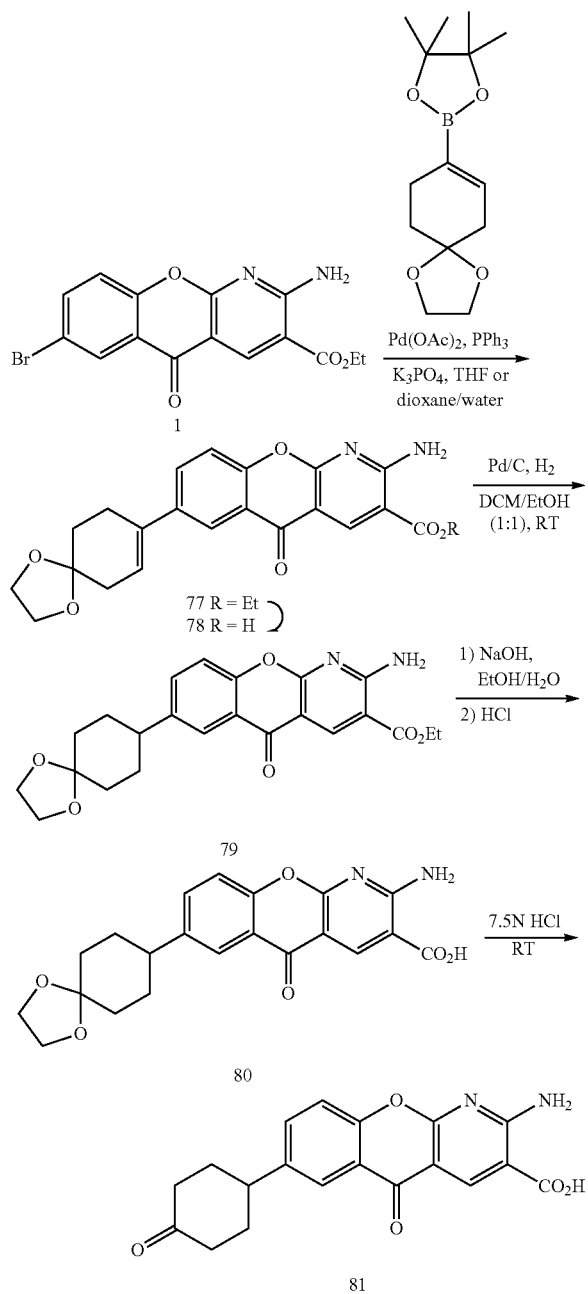

Ethyl 2-amino-5-oxo-7-(1,4-dioxaspiro[4.5]dec-7-en-8-yl)-5H-chromeno[2,3-b]pyridine-3-carboxylate (77)

A solution of tripotassium phosphate (701 mg, 3.3 mmol) in water (1.4 mL) was added to a nitrogen-degassed suspension of compound 1 (200 mg, 0.55 mmol), 4,4,5,5-tetramethyl-2-(1,4-dioxaspiro[4.5]dec-7-en-8-yl)-1,3,2-dioxaborolane (161 mg, 0.61 mmol), triphenylphosphine (72.2 mg, 0.28 mmol), and Pd(OAc)$_2$ (12.4 mg, 0.06 mmol) in p-dioxane (13.5 mL). The reaction vessel was sealed with a screw cap and heated at 100-110° C. for 15 min and then stirred at 70° C. for 1.5 h. The cooled mixture was concentrated and the residue was distributed between water and dichloromethane. The organic phase was dried (Na$_2$SO$_4$) and concentrated to a solid that was triturated in ethanol, collected, and dried to give 77 (205 mg, 88%). $^1$H NMR (400 MHz, chloroform-d): δ 9.16 (s, 1H), 8.37 (s, 1H), 8.25 (d, J=2.4 Hz, 1H), 7.78 (dd, J=8.7, 2.4 Hz, 1H), 7.44 (d, J=8.7 Hz, 1H), 6.16-6.08 (m, 1H), 5.87 (s, 1H), 4.40 (q, J=7.1 Hz, 2H), 4.04 (s, 4H), 2.81-2.69 (m, 2H), 2.52 (t, J=2.5 Hz, 2H), 1.97 (t, J=6.5 Hz, 2H), 1.44 (t, J=7.1 Hz, 3H). MS TOFES$^+$: m/z 423.0 (M+H)$^+$.

2-Amino-5-oxo-7-(1,4-dioxaspiro[4.5]dec-7-en-8-yl)-5H-chromeno[2,3-b]pyridine-3-carboxylic acid (78)

To a suspension of compound 77 (40 mg, 0.1 mmol) in ethanol (12 mL) and water (1.5 mL) was added 1N aq NaOH (1.5 mL) and the mixture was stirred for 3 h at 50° C. The mixture was filtered and the filtrate was concentrated to a residue that was dissolved in water (30 mL) and acidified with 1N aq HCl to pH 3-4. The fine suspension was stirred at room temperature for 18 h and then let stand for 4 h. The precipitate was collected by filtration, washed successively with water, acetonitrile, and dichloromethane, and dried to give 78 (18 mg, 48%) as a white solid. $^1$H NMR (400 MHz, DMSO-d$_6$): δ 8.79 (s, 1H), 8.29 (s, 2H), 8.02 (d, J=2.4 Hz, 1H), 7.92 (dd, J=8.9, 2.4 Hz, 1H), 7.55 (d, J=8.7 Hz, 1H), 6.16 (s, 1H), 3.93 (s, 4H), 2.60 (d, J=7.3 Hz, 2H), 2.41 (s, 2H), 1.86 (d, J=6.5 Hz, 2H). MS TOFES$^+$: m/z 395.0 (M+H)$^+$.

Ethyl 2-amino-5-oxo-7-(1,4-dioxaspiro[4.5]decan-8-yl)-5H-chromeno[2,3-b]pyridine-3-carboxylate (79)

A flask with a solution of compound 77 (116 mg, 0.28 mmol) in dichloromethane (30 mL) and ethanol (30 mL) was purged with nitrogen and 10% palladium on carbon (120 mg) was added. The mixture was then purged with nitrogen and hydrogen, and hydrogenated at 40 PSI using a Parr shaker at room temperature for 22 h. The mixture was filtered over celite and concentrated to a residue that was purified by silica gel preparative plate chromatography (elution with 0.3% methanol in dichloromethane) to give 79 (74 mg, 64%) as a white solid. $^1$H NMR (400 MHz, chloroform-d): δ 9.14 (s, 1H), 8.40-8.31 (m, 1H), 8.13 (d, J=2.3 Hz, 1H), 7.59 (dd, J=8.6, 2.4 Hz, 1H), 7.42 (d, J=8.6 Hz, 1H), 6.16 (s, 1H), 4.40 (q, J=7.1 Hz, 2H), 4.00 (s, 4H), 2.71 (ddt, J=11.2, 8.1, 3.9 Hz, 1H), 1.95-1.81 (m, 6H), 1.79-1.65 (m, 2H), 1.44 (t, J=7.1 Hz, 3H). MS TOFES$^+$: m/z 425.0 (M+H)$^+$.

2-Amino-5-oxo-7-(1,4-dioxaspiro[4.5]decan-8-yl)-5H-chromeno[2,3-b]pyridine-3-carboxylic acid (80)

To a suspension of compound 79 (74 mg, 0.17 mmol) in ethanol (12 mL) and water (1.5 mL) was added 1N aq NaOH (1.5 mL) and the mixture was stirred at 50° C. for 3 h. The mixture was filtered and the filtrate was concentrated to a residue that was dissolved in water (30 mL) and acidified with 1N aq HCl to pH 3-4. The fine suspension was stirred at room temperature for 18 h and then let stand for 2 h. The precipitate was collected by filtration, washed successively with water, 1:1 acetonitrile/ether, and dichloromethane, and dried to give 80 (54 mg, 78%) as a white solid. $^1$H NMR (400 MHz, DMSO-d$_6$): δ 8.79 (s, 1H), 8.26 (d, J=16.6 Hz, 2H), 7.90 (d, J=2.4 Hz, 1H), 7.70 (dd, J=8.7, 2.4 Hz, 1H), 7.52 (d, J=8.6 Hz, 1H), 3.90 (s, 4H), 2.76 (s, 1H), 1.87-1.72 (m, 4H), 1.67 (q, J=9.9, 7.4 Hz, 4H). MS TOFES⁺: m/z 397.0 (M+H)⁺.

2-Amino-5-oxo-7-(4-oxocyclohexyl)-5H-chromeno [2,3-b]pyridine-3-carboxylic acid (81)

A suspension of compound 80 (29 mg, 0.07 mmol) in 7.5N aq HCl (4 mL) was sonicated for 1 min and then stirred at room temperature for 48 h. The precipitate was collected by filtration, washed with water, and dried to give 81 (25 mg, 97%) as a white solid. ¹H NMR (400 MHz, DMSO-d₆): δ 8.79 (s, 1H), 8.28 (s, 2H), 7.98 (d, J=2.3 Hz, 1H), 7.80 (dd, J=8.6, 2.3 Hz, 1H), 7.56 (d, J=8.6 Hz, 1H), 3.30-3.18 (m, 1H), 2.61 (td, J=14.2, 6.0 Hz, 2H), 2.29 (d, J=14.5 Hz, 2H), 2.10 (d, J=2.9 Hz, 2H), 1.94 (qd, J=13.0, 4.0 Hz, 2H). MS TOFES⁺: m/z 353.1 (M+H)⁺.

Example 3

Exemplary Compounds

Table 2 provides a list of exemplary synthesized compounds.

TABLE 2-continued
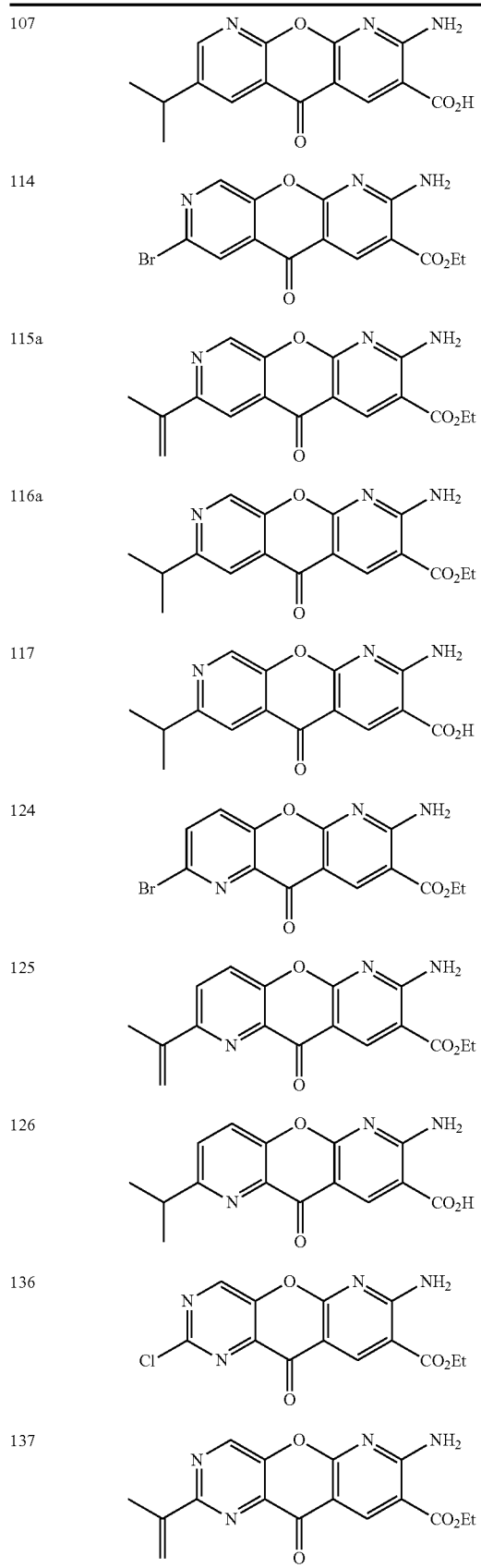
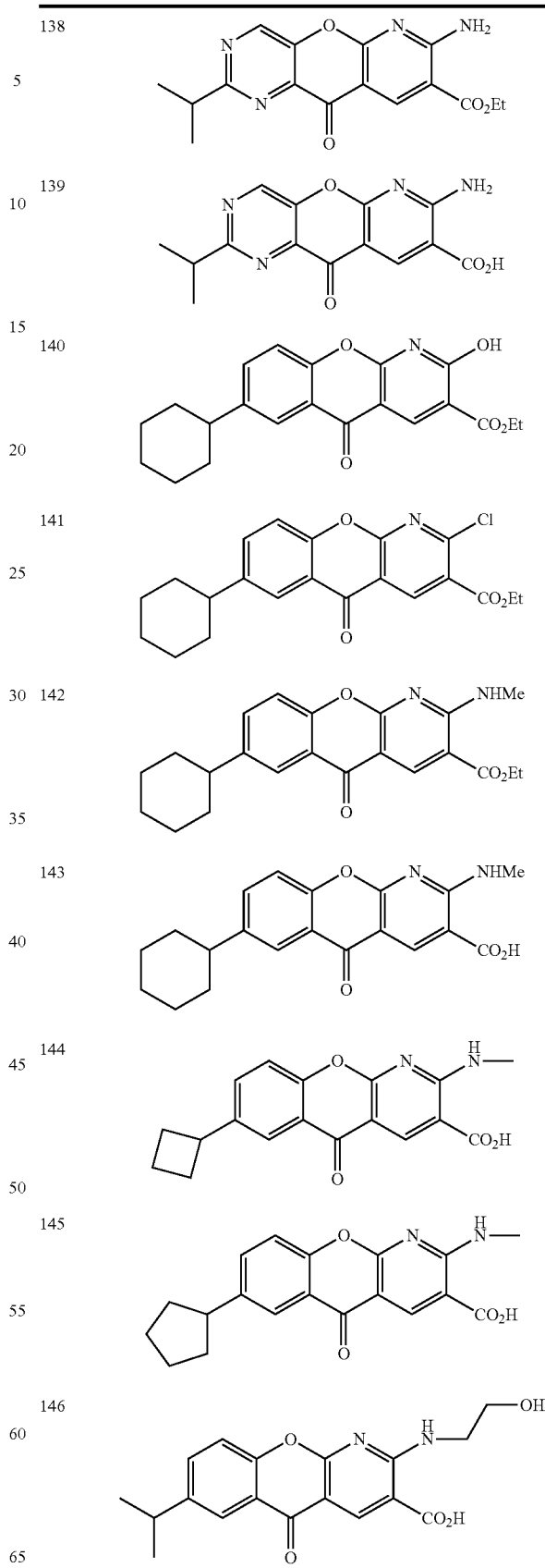

TABLE 2-continued
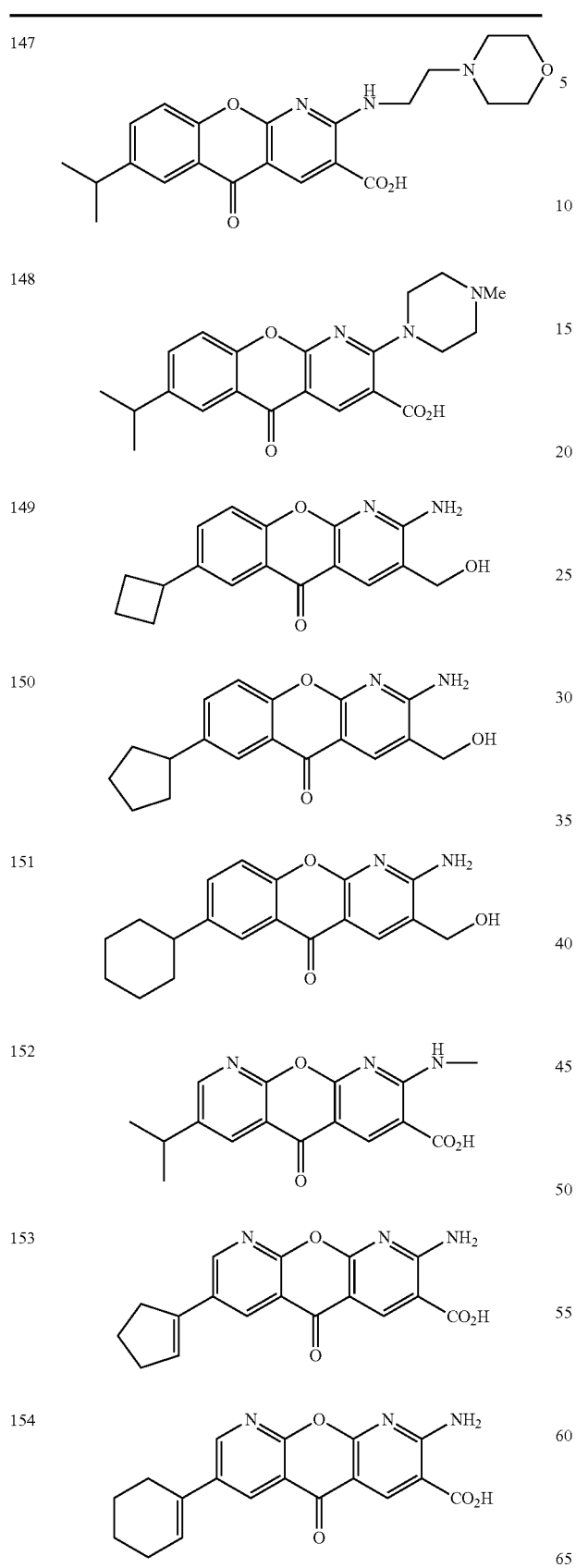
TABLE 2-continued
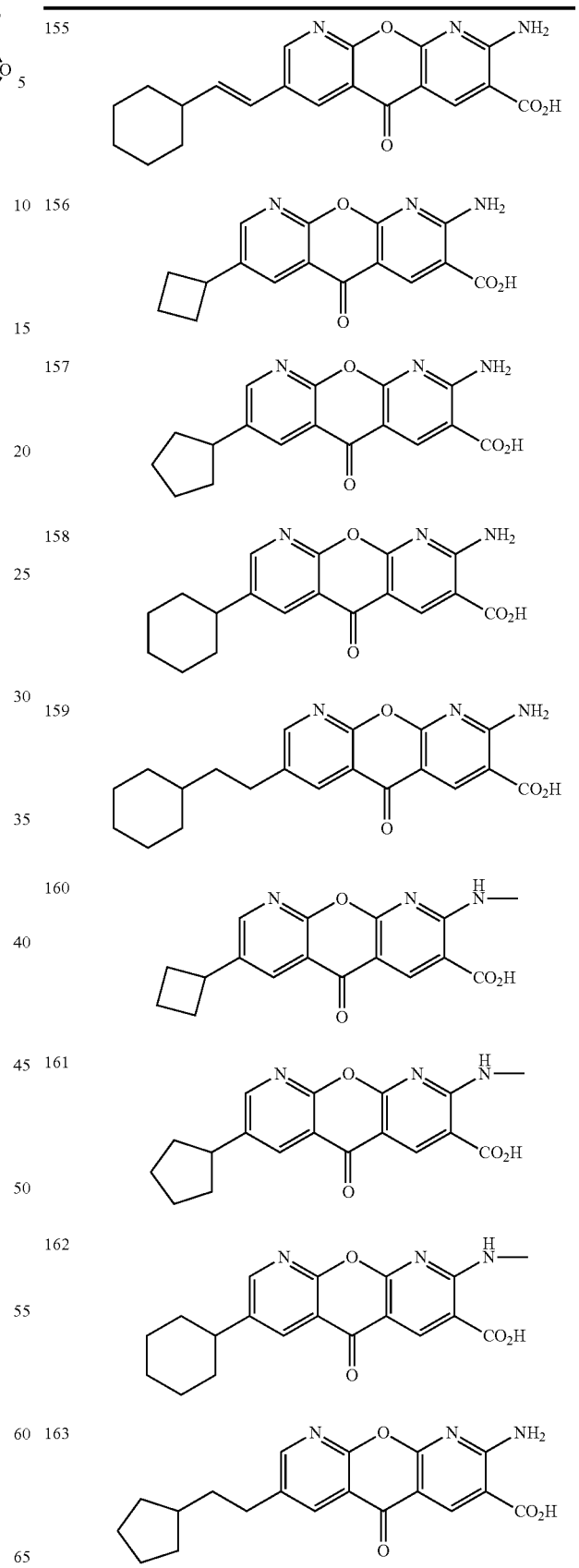

TABLE 2-continued
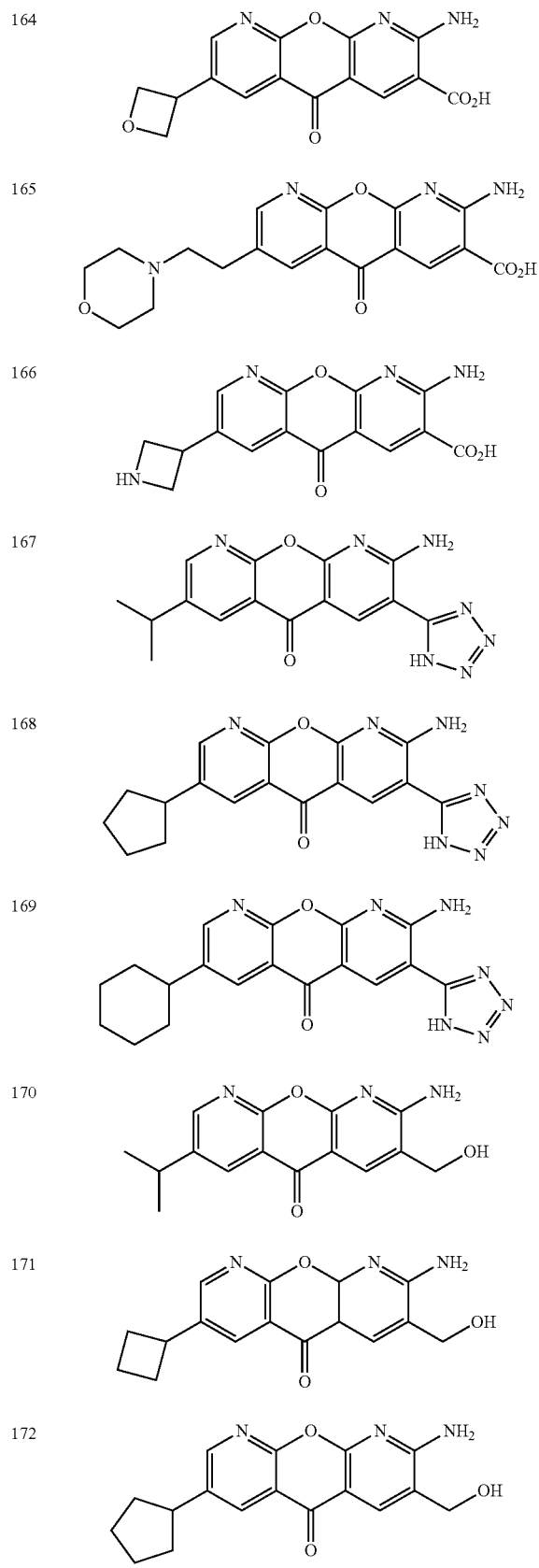
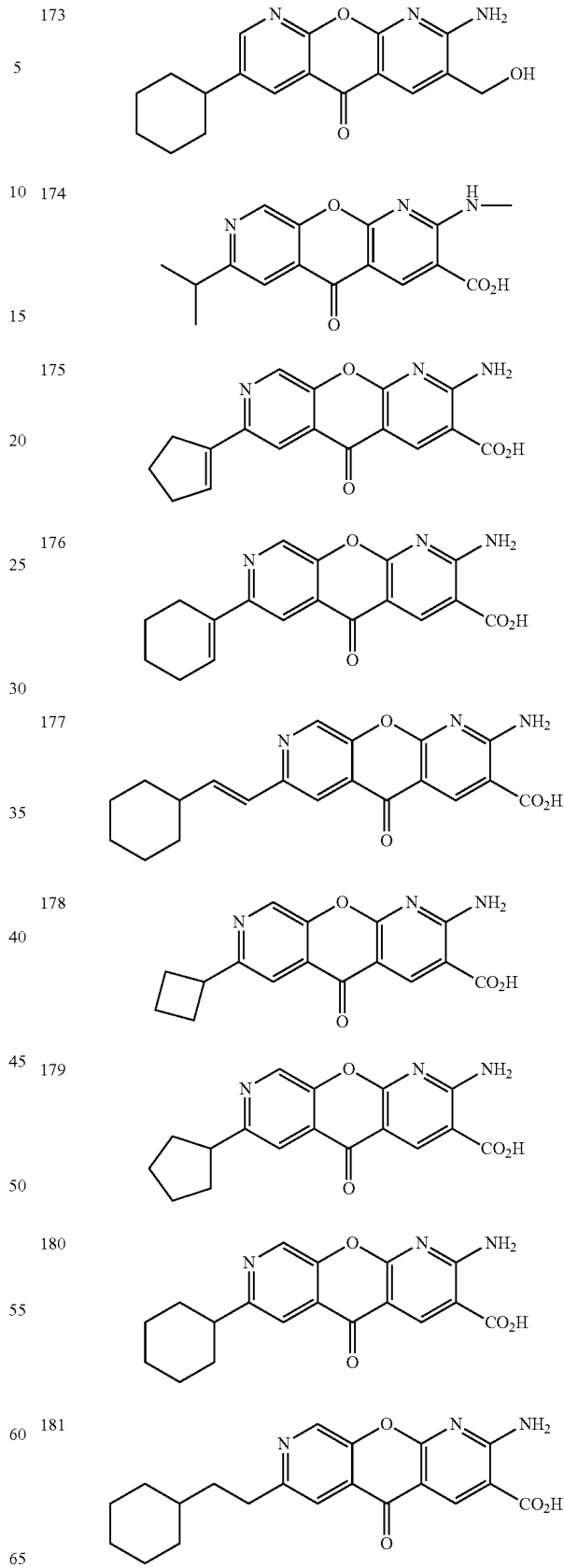

TABLE 2-continued
| | |
|---|---|
| 182 | 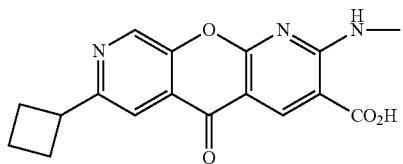 [SMILES: CNc1nc2oc3ccc(C4CCC4)cc3c(=O)c2cc1C(=O)O] |
| 183 | 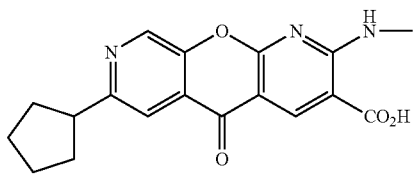 [SMILES: CNc1nc2oc3cnc(C4CCCC4)cc3c(=O)c2cc1C(=O)O] |
| 184 | 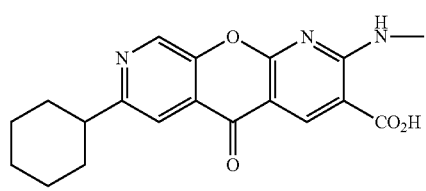 [SMILES: CNc1nc2oc3cnc(C4CCCCC4)cc3c(=O)c2cc1C(=O)O] |
| 185 | 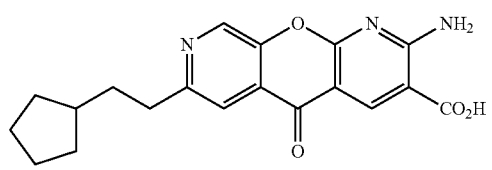 [SMILES: Nc1nc2oc3cnc(CCC4CCCC4)cc3c(=O)c2cc1C(=O)O] |
| 186 | 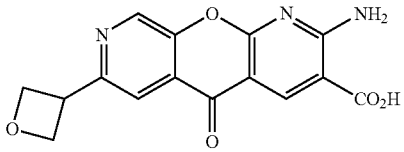 [SMILES: Nc1nc2oc3cnc(C4COC4)cc3c(=O)c2cc1C(=O)O] |
| 187 | 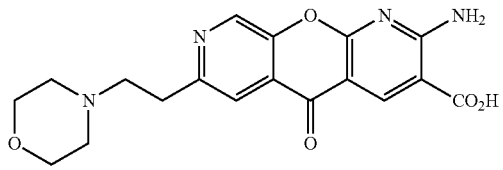 [SMILES: Nc1nc2oc3cnc(CCN4CCOCC4)cc3c(=O)c2cc1C(=O)O] |
| 188 | 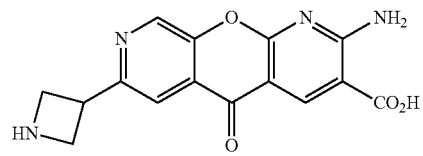 [SMILES: Nc1nc2oc3cnc(C4CNC4)cc3c(=O)c2cc1C(=O)O] |
| 189 | 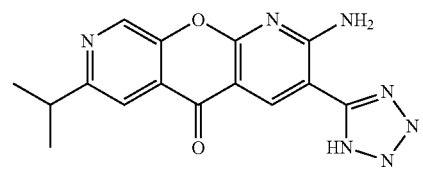 |
| 190 | 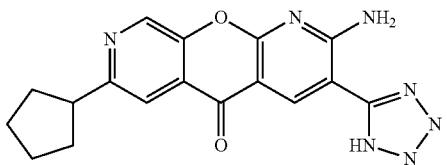 [SMILES: Nc1nc2oc3cnc(C4CCCC4)cc3c(=O)c2cc1C1=NNNN1] |
TABLE 2-continued
| | |
|---|---|
| 191 | 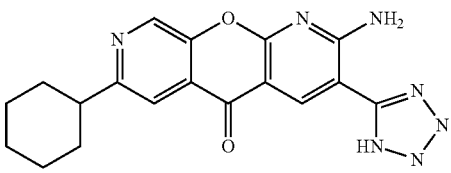 [SMILES: Nc1nc2oc3cnc(C4CCCCC4)cc3c(=O)c2cc1C1=NNNN1] |
| 192 | 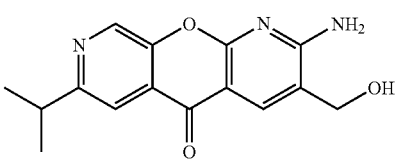 [SMILES: CC(C)c1cc2c(=O)c3cc(CO)c(N)nc3oc2cn1] |
| 193 | 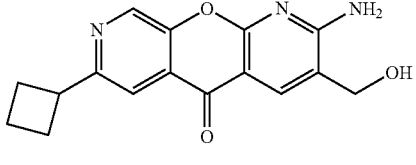 [SMILES: Nc1nc2oc3cnc(C4CCC4)cc3c(=O)c2cc1CO] |
| 194 | 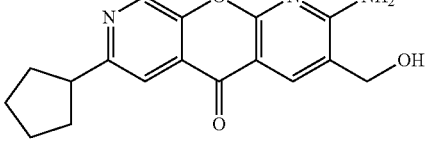 |
| 195 | 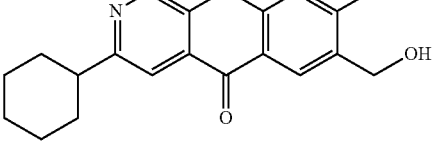 |
| 196 | 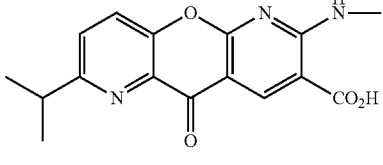 |
| 197 | 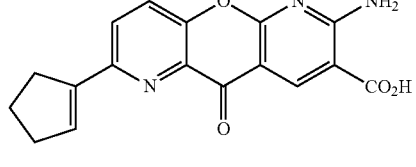 |
| 198 | 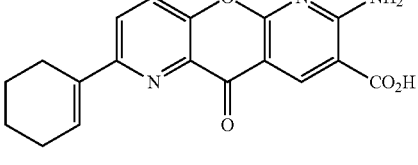 |
| 199 | 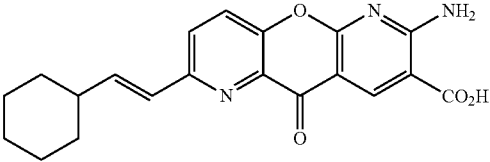 [SMILES: Nc1nc2oc3ccc(/C=C/C4CCCCC4)nc3c(=O)c2cc1C(=O)O] |

TABLE 2-continued
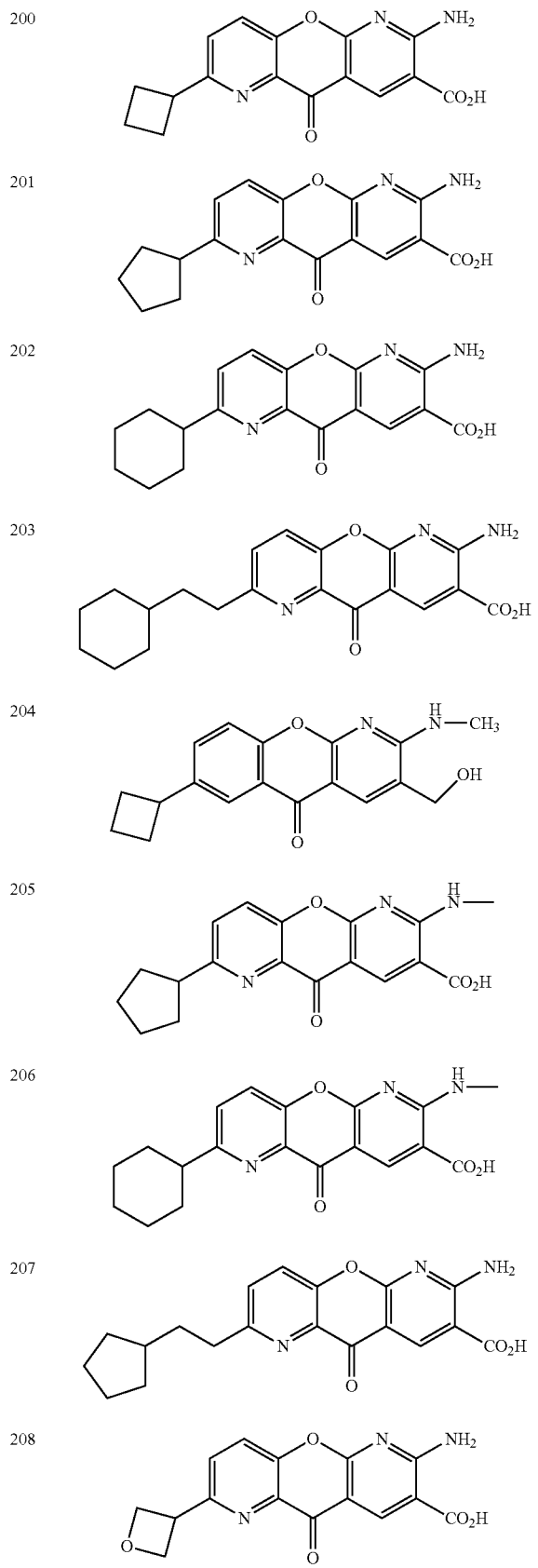
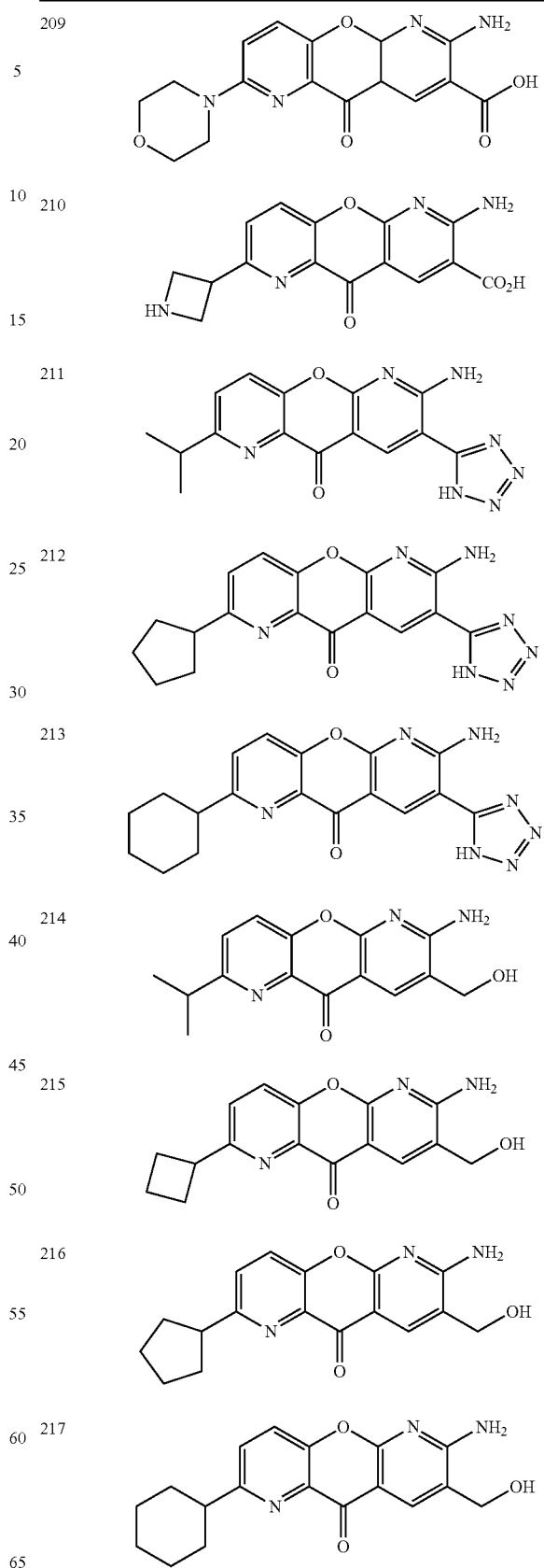

TABLE 2-continued
| 218 | 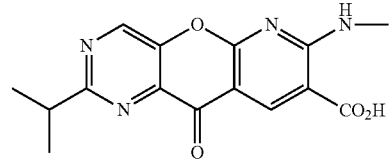 [SMILES: CNc1nc2oc3cnc(C(C)C)nc3c(=O)c2cc1C(=O)O] |
| --- | --- |
| 219 | 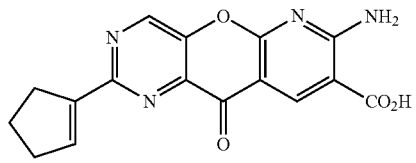 |
| 220 | 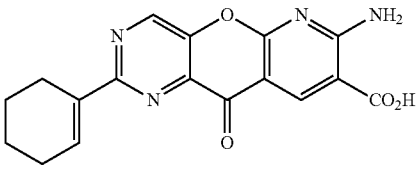 [SMILES: Nc1nc2oc3cnc(C4=CCCCC4)nc3c(=O)c2cc1C(=O)O] |
| 221 | 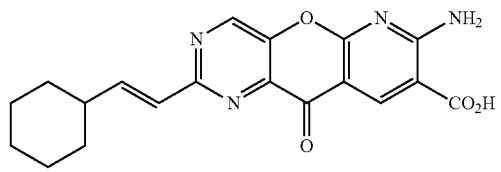 [SMILES: Nc1nc2oc3cnc(/C=C/C4CCCCC4)nc3c(=O)c2cc1C(=O)O] |
| 222 | 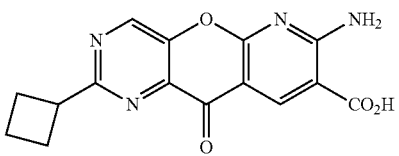 |
| 223 | 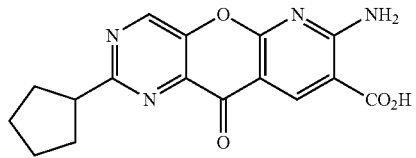 [SMILES: Nc1nc2oc3cnc(C4CCCC4)nc3c(=O)c2cc1C(=O)O] |
| 224 | 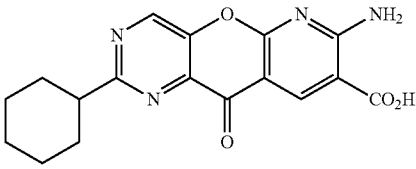 |
| 225 | 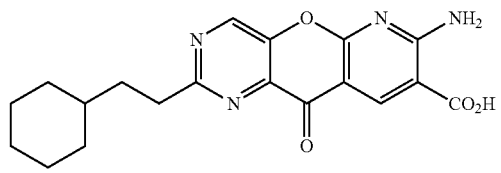 |
| 226 | 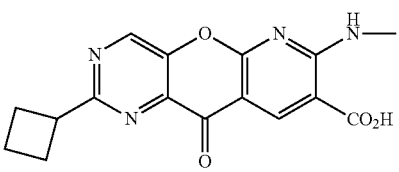 [SMILES: CNc1nc2oc3cnc(C4CCC4)nc3c(=O)c2cc1C(=O)O] |
TABLE 2-continued
| 227 | 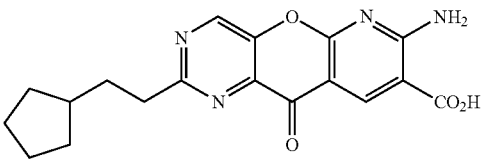 [SMILES: Nc1nc2oc3cnc(CCC4CCCC4)nc3c(=O)c2cc1C(=O)O] |
| --- | --- |
| 228 | 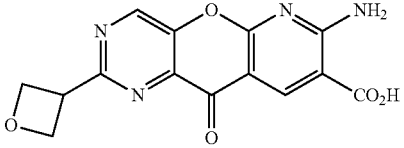 [SMILES: Nc1nc2oc3cnc(C4COC4)nc3c(=O)c2cc1C(=O)O] |
| 229 | 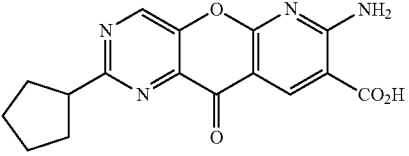 [SMILES: Nc1nc2oc3cnc(C4CCCC4)nc3c(=O)c2cc1C(=O)O] |
| 230 | 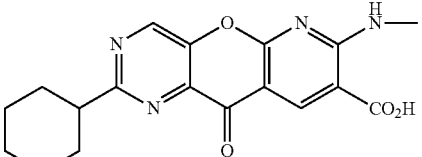 |
| 231 | 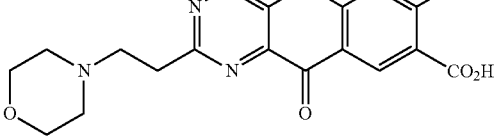 |
| 232 | 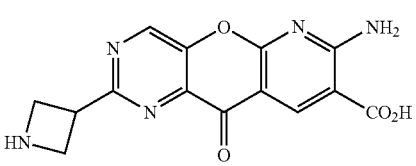 [SMILES: Nc1nc2oc3cnc(C4CNC4)nc3c(=O)c2cc1C(=O)O] |
| 233 | 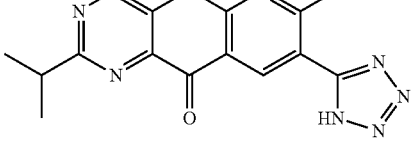 |
| 234 | 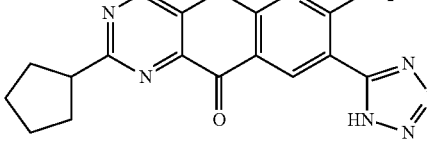 |
| 235 | 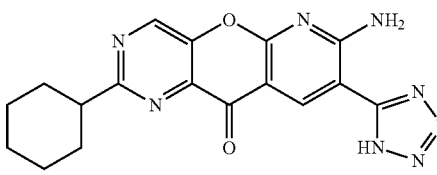 |

TABLE 2-continued

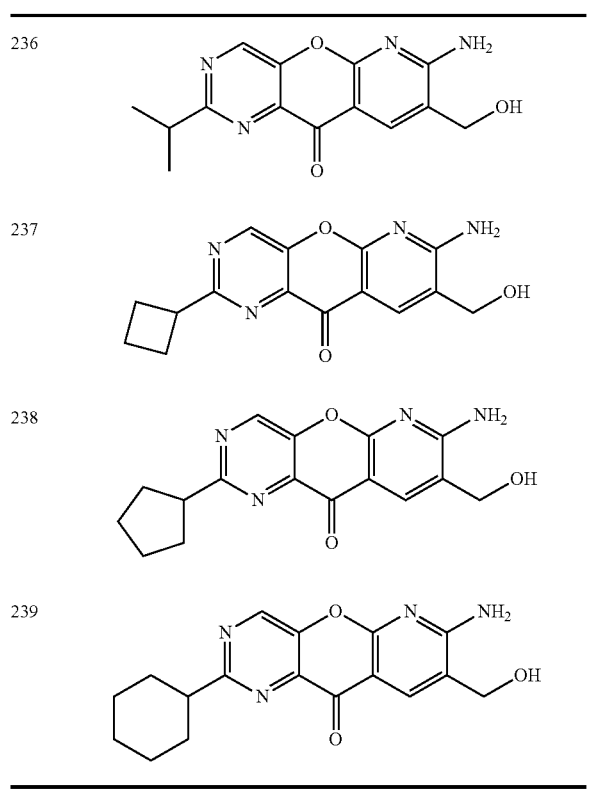

236, 237, 238, 239

Example 4

Synthesis Schemes for Exemplary Compounds

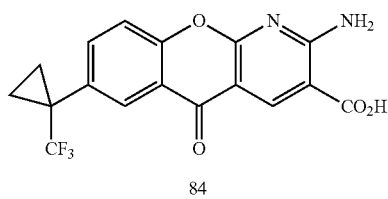

84

Ethyl 2-amino-5-oxo-7-(3,3,3-trifluoroprop-1-en-2-yl)-5H-chromeno[2,3-b]pyridine-3-carboxylate (82) is obtained starting from compound 1 as shown in Scheme 19.

ethyl 2-amino-5-oxo-7-(1-(trifluoromethyl)cyclopropyl)-5H-chromeno[2,3-b]pyridine-3-carboxylate (83) is obtained starting from compound 82 as shown in Scheme 19.

2-Amino-5-oxo-7-(1-(trifluoromethyl)cyclopropyl)-5H-chromeno[2,3-b]pyridine-3-carboxylic acid (84) is obtained starting from compound 83 as shown in Scheme 19.

Scheme 20

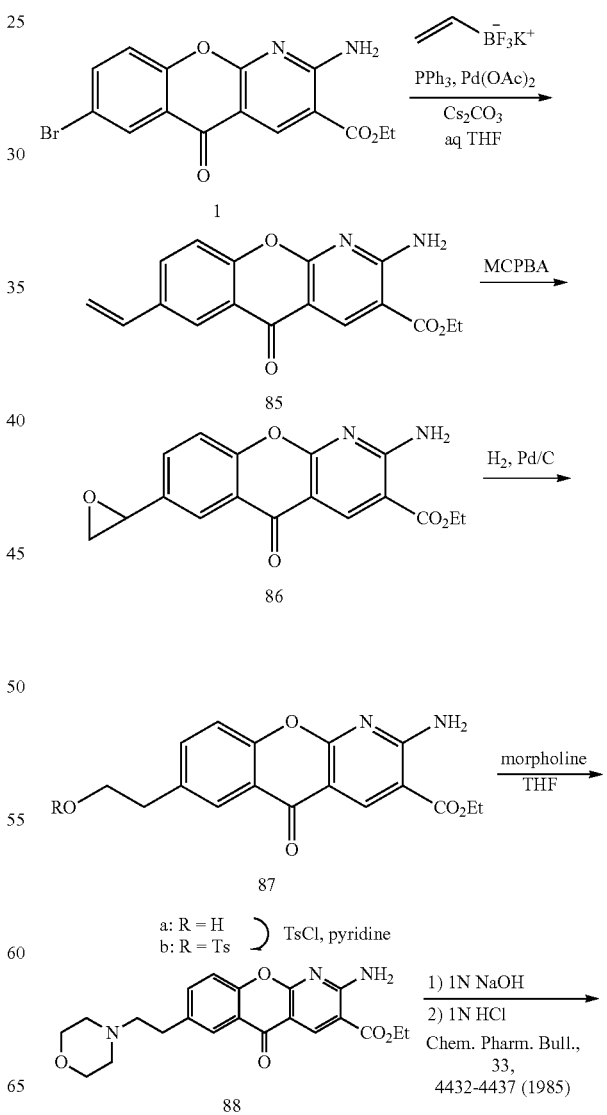

Scheme 19

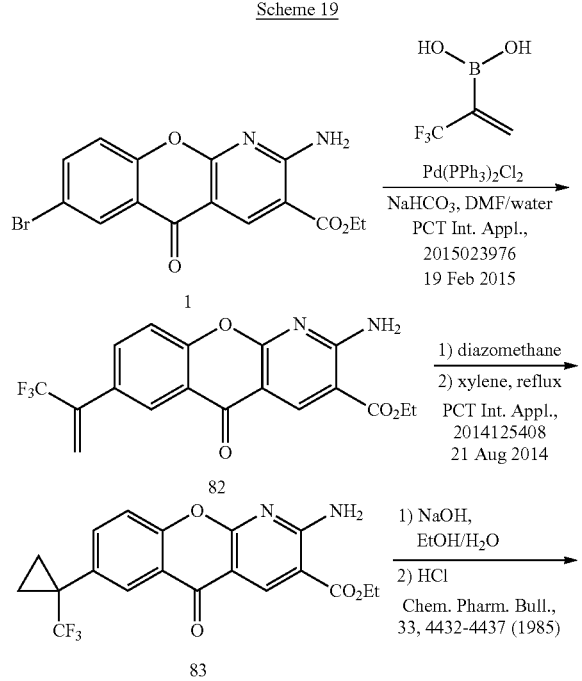

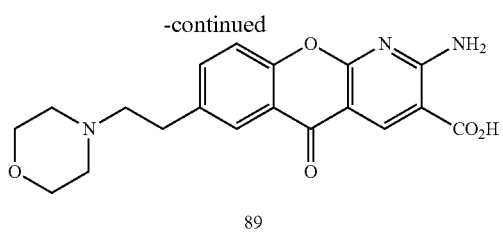

89

Ethyl 2-amino-5-oxo-7-vinyl-5H-chromeno[2,3-b]pyridine-3-carboxylate (85) is obtained starting from compound 1 as shown in Scheme 20.

Ethyl 2-amino-7-(oxiran-2-yl)-5-oxo-5H-chromeno[2,3-b]pyridine-3-carboxylate (86) is obtained starting from compound 85 as shown in Scheme 20.

Ethyl 2-amino-7-(2-hydroxyethyl)-5-oxo-5H-chromeno[2,3-b]pyridine-3-carboxylate (87a) is obtained starting from compound 86 as shown in Scheme 20.

Ethyl 2-amino-5-oxo-7-(2-(tosyloxy)ethyl)-5H-chromeno[2,3-b]pyridine-3-carboxylate (87b) is obtained starting from compound 87a as shown in Scheme 20.

Ethyl 2-amino-7-(2-morpholinoethyl)-5-oxo-5H-chromeno[2,3-b]pyridine-3-carboxylate (88) is obtained starting from compound 87b as shown in Scheme 20.

2-Amino-7-(2-morpholinoethyl)-5-oxo-5H-chromeno[2,3-b]pyridine-3-carboxylic acid (89) is obtained starting from compound 88 as shown in Scheme 20.

Scheme 21

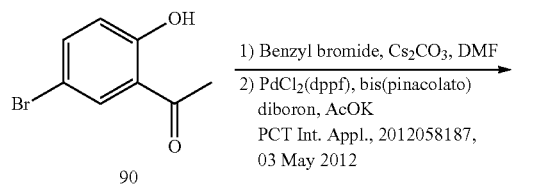

90

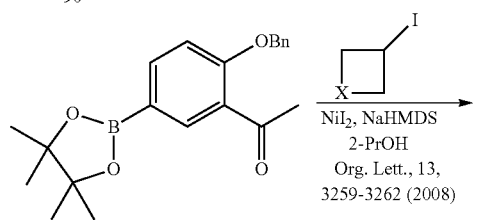

91

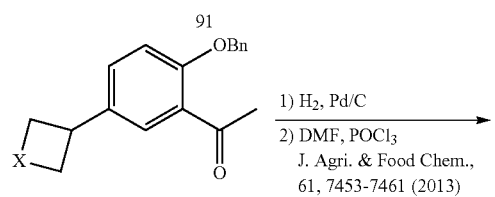

92
a: X = O
b: X = NBoc

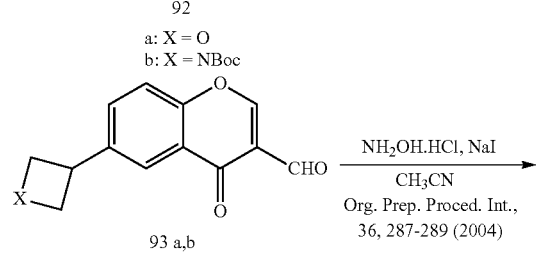

93 a,b

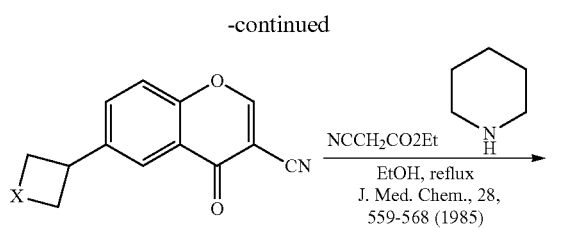

94 a,b

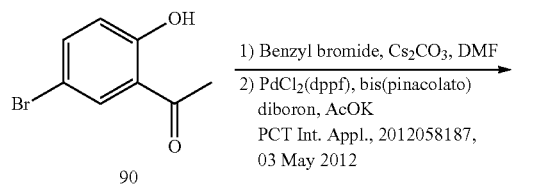

95 a,b 96
a: X = O
b: X = NBoc
c: X = NH

Ethyl 2-amino-7-(oxetan-3-yl)-5-oxo-5H-chromeno[2,3-b]pyridine-3-carboxylate (95a) is obtained starting from compound 90 and proceeding through the steps shown in Scheme 21.

Ethyl 2-amino-7-(1-(tert-butoxycarbonyl)azetidin-3-yl)-5-oxo-5H-chromeno[2,3-b]pyridine-3-carboxylate (95b) is obtained starting from compound 90 and proceeding through the steps shown in Scheme 21.

2-Amino-7-(oxetan-3-yl)-5-oxo-5H-chromeno[2,3-b]pyridine-3-carboxylic acid (96a) was obtained starting from compound 95a as shown in Scheme 21.

2-Amino-7-(1-(tert-butoxycarbonyl)azetidin-3-yl)-5-oxo-5H-chromeno[2,3-b]pyridine-3-carboxylic acid (96b) is obtained starting from compound 95b as shown in Scheme 21.

2-Amino-7-(azetidin-3-yl)-5-oxo-5H-chromeno[2,3-b]pyridine-3-carboxylic acid (96c) is obtained starting from compound 96c as shown in Scheme 21.

Scheme 22

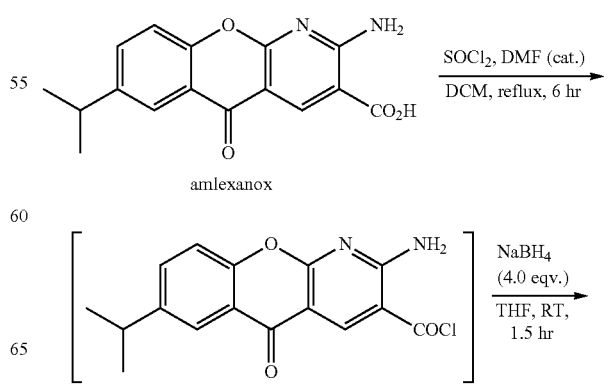

-continued

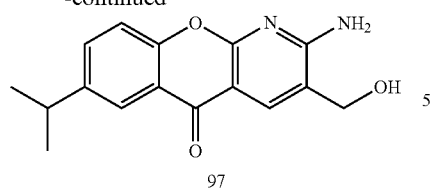

97

2-Amino-3-(hydroxymethyl)-7-isopropyl-5H-chromeno[2,3-b]pyridin-5-one (97)

To a stirred suspension of amlexanox (300 mg, 1.0 mmol), N,N-dimethylformamide (8 mg, 0.11 mmol) and dichloromethane (30 mL) was added thionyl chloride (15 mL, 206 mmol) at room temperature. The resulting mixture was refluxed for 5 h and then concentrated to leave 325 mg of an orange solid. A portion (150 mg, 0.47 mmol) was diluted with tetrahydrofuran (20 mL) and the suspension was treated with sodium borohydride (72 mg, 1.9 mmol) and stirred for 1.5 h at room temperature. The mixture was quenched with water and the resultant clear orange solution was stirred for 10 min and extracted with dichloromethane (2×). The organic phase was dried (Na$_2$SO$_4$) and concentrated to a solid that was triturated in a small amount of dichloromethane and dried to give 97 (105 mg, 78%) as a light orange solid. $^1$H NMR (400 MHz, DMSO-d6) δ 8.16 (s, 1H), 7.93 (d, J=2.3 Hz, 1H), 7.69 (dd, J=8.6, 2.3 Hz, 1H), 7.51 (d, J=8.6 Hz, 1H), 7.21 (s, 2H), 5.37 (t, J=5.6 Hz, 1H), 4.47-4.36 (m, 2H), 3.05 (p, J=6.9 Hz, 1H), 1.26 (d, J=6.9 Hz, 6H). MS m/z 285.12 (M+H)$^+$.

Scheme 23

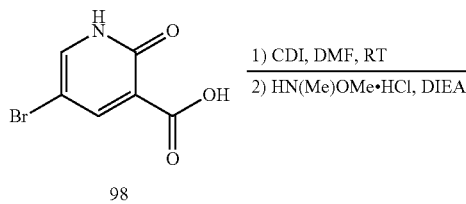
98

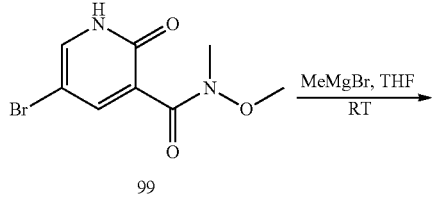
99

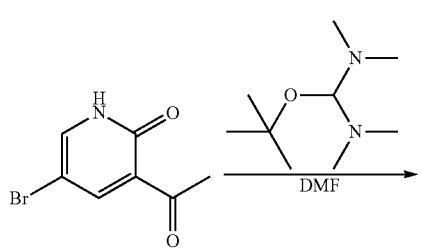
100

-continued

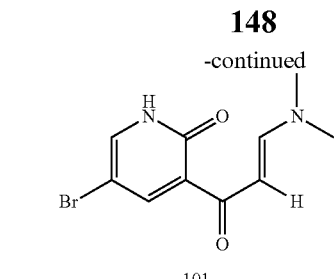
101

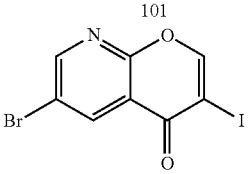
102

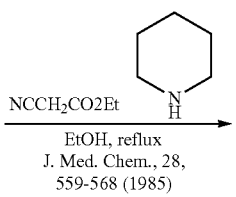
103

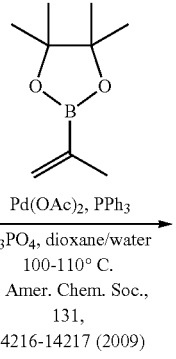
104

105

106

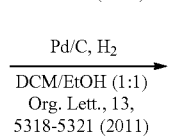
107

5-Bromo-N-methoxy-N-methyl-2-oxo-1,2-dihydropyridine-3-carboxamide (99)

A solution of 5-bromo-2-oxo-1,2-dihydropyridine-3-carboxylic acid (98) (5.50 g, 25.2 mmol) in dry N,N-dimethylformamide (50 mL) was treated in four portions with carbonyl diimidazole (4.50 g, 27.8 mmol). The mixture was stirred at room temperature for 1 h and then charged with N,O-dimethylhydroxylamine hydrochloride (2.71 g, 27.8 mmol) followed by triethylamine (3.9 mL, 27.8 mmol). After stirring at 45° C. for 1 h and at room temperature for 18 h, the mixture was concentrated in vacuo to a residue that was diluted with water and extracted with dichloromethane (3×). The combined organic phases were dried (Na$_2$SO$_4$) and concentrated to an oil that was purified by flash silica gel chromatography (elution with 3% methanol in dichloromethane) to give 99 (5.3 g, 80%) as a solid. $^1$H NMR (400 MHz, chloroform-d): δ 7.65 (d, J=2.7 Hz, 1H), 7.63 (d, J=2.7 Hz, 1H), 3.67 (s, 3H), 3.35 (s, 3H). MS TOFES$^+$: m/z 260.9, 262.9 (M+H)$^+$.

3-Acetyl-5-bromopyridin-2(1H)-one (100)

To a 0° C. solution of compound 99 (5.0 g, 19.2 mmol) in dry tetrahydrofuran (140 mL) was added methyl magnesium bromide (80 mL of 1M in THF) over 50 min. The mixture was stirred at 0° C. for 30 min and then at room temperature for 18 h, quenched with saturated aq ammonium chloride and extracted with dichloromethane (4×). The insoluble white precipitate between the two phases was collected. The combined organic phases were dried (Na$_2$SO$_4$) and concentrated to an orange solid that was combined with the collected precipitate and dissolved in 100 mL of 10% methanol in dichloromethane. The solution was mixed with 50 g of flash silica gel. The solvent was evaporated and the silica gel charge was placed on top of a flash silica gel column, which was eluted with 5% methanol in dichloromethane. Workup of product fractions gave 100 (2.7 g, 65%) as a solid. $^1$H NMR (400 MHz, DMSO-d$_6$): δ 12.59 (s, 1H), 8.02 (d, J=3.0 Hz, 1H), 7.98 (d, J=3.0 Hz, 1H), 2.53 (s, 3H). MS TOFES$^+$: m/z 215.9, 217.9 (M+H)$^+$.

1-tert-Butoxy-N,N,N',N'-tetramethylmethanediamine (101)

A solution of compound 100 (300 mg, 1.4 mmol), tert-butoxybis(dimethylamino)methane (726 mg, 4.2 mmol) and N,N-dimethylformamide (8 mL) was heated at 40° C. for 16 h. Additional tert-butoxybis(dimethylamino)methane (363 mg, 2.1 mmol) was added and the mixture was heated for an additional 24 h. The solution was concentrated in vacuo and the residue was diluted with water. The mixture was extracted with dichloromethane (7×) and the combined organic phases were dried (Na$_2$SO$_4$) and concentrated to give 101 (300 mg, 80%) as an orange solid. $^1$H NMR (400 MHz, chloroform-d): δ 8.28 (d, J=2.6 Hz, 1H), 8.09 (d, J=2.5 Hz, 1H), 7.94 (d, J=12.0 Hz, 1H), 5.70 (d, J=12.0 Hz, 1H), 3.24 (s, 3H), 3.02 (s, 3H). MS TOFES$^+$: m/z 271.0, 273.0 (M+H)$^+$.

6-Bromo-3-iodo-4H-pyrano[2,3-b]pyridin-4-one (102)

A solution of compound 101 (1.63 g, 6.0 mmol), pyridine (1.52 g, 19.2 mmol) and dichloromethane (70 mL) was treated at room temperature with a solution of iodine (7.32 g, 28.8 mmol) in dichloromethane (280 mL). After stirring for 5 h, the solution was washed with saturated aq. Na$_2$SO$_3$. The organic phase was separated, and the aqueous phase was extracted further with dichloromethane (2×). The combined organic phases were washed with brine, dried (Na$_2$SO$_4$), and concentrated to a residue that was purified by flash silica gel column chromatography (elution with 0.1-0.2% methanol in dichloromethane) to give 102 (1.36 g, 64%) as a white solid. $^1$H NMR (400 MHz, chloroform-d): δ 8.77 (dd, J=2.6, 0.7 Hz, 1H), 8.73 (dd, J=2.6, 0.7 Hz, 1H), 8.42 (d, J=0.7 Hz, 1H). MS TOFES$^+$: m/z 351.8, 353.8 (M+H)$^+$.

Ethyl 2-amino-7-bromo-5-oxo-5H-pyrano[2,3-b:6,5-b']dipyridine-3-carboxylate (104) is obtained starting from compound 102 and proceeding through the steps shown in Scheme 23.

Ethyl 2-amino-5-oxo-7-(prop-1-en-2-yl)-5H-pyrano[2,3-b:6,5-b']dipyridine-3-carboxylate (105) is obtained starting from compound 104 as shown in Scheme 23.

Ethyl 2-amino-7-isopropyl-5-oxo-5H-pyrano[2,3-b:6,5-b']dipyridine-3-carboxylate (106) is obtained starting from compound 105 as shown in Scheme 23.

2-Amino-7-isopropyl-5-oxo-5H-pyrano[2,3-b:6,5-b']dipyridine-3-carboxylic acid (107) is obtained starting from compound 106 as shown in Scheme 23.

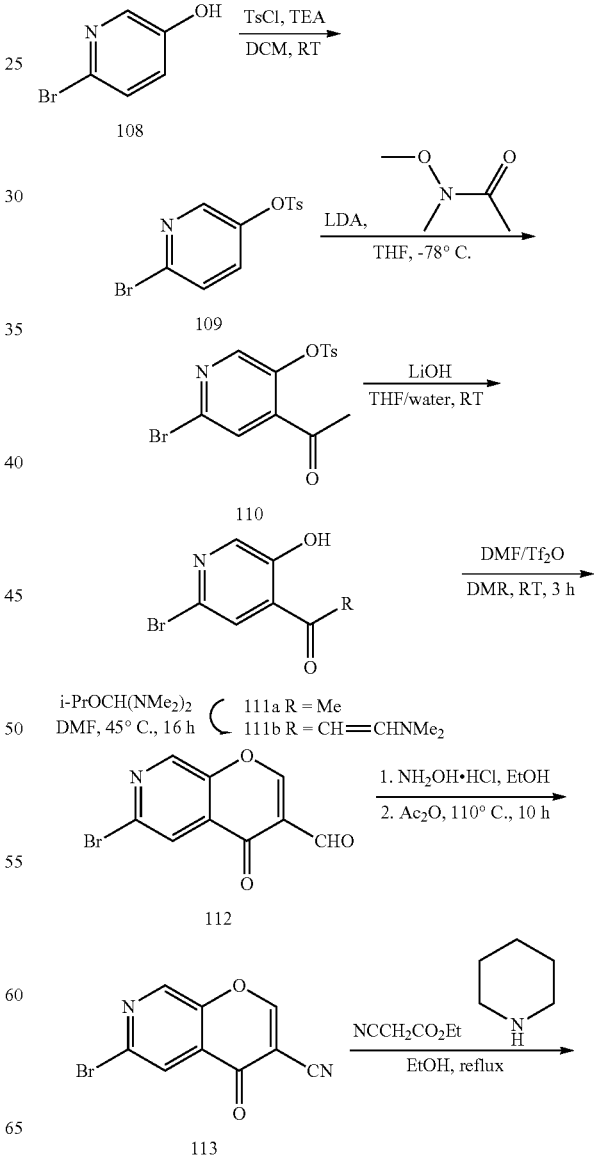

Scheme 24

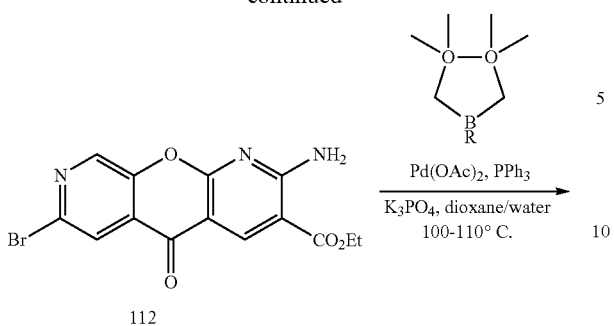

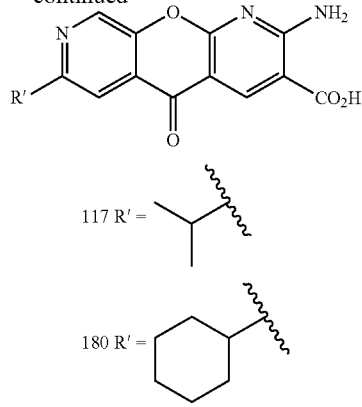

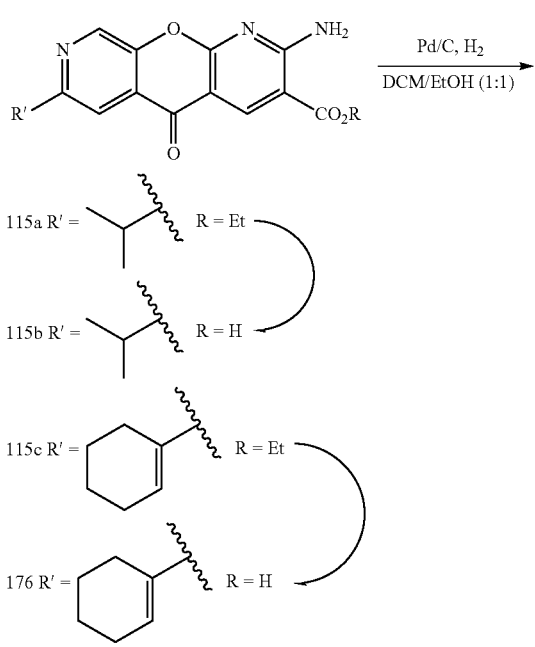

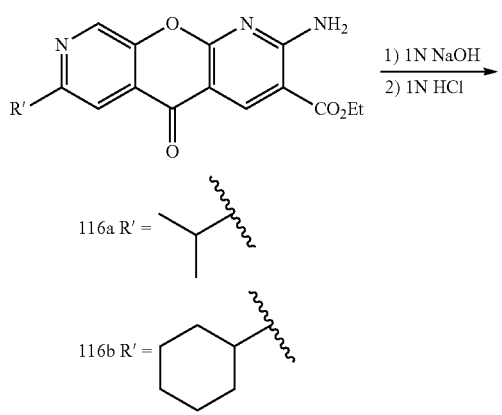

6-Bromopyridin-3-yl 4-methylbenzenesulfonate (109)

A solution of 4-methylbenzene-1-sulfonyl chloride (27.4 g, 144 mmol) in dichloromethane (150 mL) was added to a solution of 6-bromopyridin-3-ol (108; 25 g, 144 mmol) and triethylamine (30.1 mL, 216 mmol) in dichloromethane (300 mL) at 0° C. under nitrogen. The mixture was stirred at 0° C. for 90 min and then at room temperature for 18 h. The mixture was ice-cooled, treated cautiously with a saturated aq NaHCO$_3$ solution (130 mL), stirred at room temperature for 30 min and then the phases were separated. The aqueous layer phase was further extracted with dichloromethane, the combined phases dried (Na$_2$SO$_4$), and concentrated to leave a solid residue. Crystallization from ethyl acetate/hexanes gave 109 (46.3 g, 98%) as a solid. $^1$H NMR (400 MHz, chloroform-d) δ 7.90 (d, J=2.9 Hz, 1H), 7.73-7.66 (m, 2H), 7.49-7.42 (m, 1H), 7.39-7.30 (m, 3H), 2.47 (s, 3H).

4-Acetyl-6-bromopyridin-3-yl 4-methylbenzenesulfonate (110)

A 1-L 3-necked round bottom flask equipped with a nitrogen inlet, rubber septum, and an internal temperature probe was charged with a solution of 109 (10.9 g, 33.2 mmol) in tetrahydrofuran (130 mL). The resulting solution was cooled to −78° C. under a nitrogen atmosphere and lithium di-isopropyl amide solution (1 M in tetrahydrofuran/hexanes, 50 mL, 1.5 eq.) was slowly added via a cannula at such a rate that the internal temperature did not exceed −74° C. After the resulting slurry was stirred at −78° C. for 2 h, N-methoxy-N-methyl-acetamide (6.0 g, 58.1 mmol) was added dropwise maintaining the internal temperature below −75° C. The mixture was stirred at −78° C. for 1.5 h and then poured into an ice-cold saturated aq NaHCO$_3$ solution (120 mL). The mixture was diluted with water (50 mL) and extracted with ethyl acetate (3×). The combined organic layers were dried (Na$_2$SO$_4$) and concentrated to leave crude product as a red-brown oil (12.6 g). The oil was dissolved in 50 mL of dichloromethane and the solution was mixed with 70 g of silica gel. The solvent was allowed to evaporate and the residue was dry loaded on top of a 500 mL fritted funnel containing 65 g of flash silica gel wetted with 300 mL of dichloromethane. Washing the column with dichloromethane (~500 mL) followed by concentration gave 110 (5.36 g, 44%) as a colorless oil. $^1$H NMR (400 MHz, chloroform-d) δ 7.97 (s, 1H), 7.73-7.67 (m, 2H), 7.65 (s, 1H), 7.41-7.33 (m, 2H), 2.58 (s, 3H), 2.49 (s, 3H).

1-(2-Bromo-5-hydroxypyridin-4-yl)ethan-1-one (111a)

A solution of compound 110 (1.03 g, 2.78 mmol) in tetrahydrofuran (6 mL) at 0° C. was treated with LiOH monohydrate (233 mg, 5.56 mmol) in water (3 mL). The resulting mixture was stirred at 0° C. for 30 min, and then at room temperature for 4 h. The solution was concentrated to an aqueous residue that was diluted with water (6 mL), acidified (pH 3) with formic acid, and extracted with ethyl acetate (3×). The combined organic layers were dried (Na$_2$SO$_4$) and concentrated to give 111a (0.55 g, 92%) as an orange solid. $^1$H NMR (400 MHz, chloroform-d) δ 11.36 (s, 1H), 8.30 (d, J=0.6 Hz, 1H), 7.69 (d, J=0.6 Hz, 1H), 2.67 (s, 3H).

6-Bromo-4-oxo-4H-pyrano[2,3-c]pyridine-3-carbaldehyde (112)

To a solution of compound 111a (1.0 g, 4.63 mmol) in N,N-dimethylformamide (12 mL) was added tert-butoxybis(dimethylamino)methane (3.63 g, 20.83 mmol) and the mixture was heated at 45° C. for 16 h. The mixture was concentrated and the residue was dissolved in dichloromethane and directly purified by flash silica gel column chromatography (elution with 1% methanol in dichloromethane). Fractions with yellow color (~250 mL) were collected and evaporated to give crude (E)-1-(2-bromo-5-hydroxypyridin-4-yl)-3-(dimethylamino)prop-2-en-1-one (111b) (0.75 g, 60%) as a light orange solid. This solid was added to Vilsmeier reagent, which was prepared by adding trifluoromethanesulfonic anhydride (1.17 g, 4.15 mmol) dropwise to ice-cold anhydrous N,N-dimethylformamide (7.04 mL) followed by stirring at 0° C. for 5 min. The resulting mixture was stirred at room temperature for 3 h, poured into water (25 mL) and extracted with dichloromethane (3×). The combined organic phases were dried (Na$_2$SO$_4$) and concentrated to give 112 (620 mg, 88%) as a solid. $^1$H NMR (400 MHz, chloroform-d) δ 10.33 (s, 1H), 8.85 (d, J=0.7 Hz, 1H), 8.60 (s, 1H), 8.27 (d, J=0.7 Hz, 1H). MS m/z 253.94, 255.94 (M+H)$^+$.

6-Bromo-4-oxo-4H-pyrano[2,3-c]pyridine-3-carbonitrile (113)

A mixture of compound 112 (200 mg, 0.79 mmol) and hydroxylamine hydrochloride (65.6 mg, 0.95 mmol) in 4 mL ethanol was stirred at 60° C. for 1 h. The mixture was cooled at 0° C. for 30 min and the precipitated solid was collected, washed with ethanol and dried to give (E)-6-bromo-4-oxo-4H-pyrano[2,3-c]pyridine-3-carbaldehyde oxime (130 mg, 61%) as an off-white solid. $^1$H NMR (400 MHz, DMSO-d$_6$) δ 11.59 (s, 1H), 9.05 (s, 1H), 8.81 (s, 1H), 8.09 (s, 1H), 8.04 (s, 1H). MS m/z 268.9556, 270.9537 (M+H)$^+$. A suspension of the oxime (125 mg, 0.47 mmol) in acetic anhydride (8 mL) was stirred at 110° C. for 17 h. The mixture was concentrated to give crude nitrile 113 (115 mg, 99%) as an orange solid. $^1$H NMR (400 MHz, chloroform-d) δ 8.87 (d, J=0.7 Hz, 1H), 8.50 (s, 1H), 8.23 (d, J=0.7 Hz, 1H). MS m/z 250.94, 252.94 (M+H)$^+$.

Ethyl 2-amino-7-bromo-5-oxo-5H-pyrano[2,3-b:6,5-c']dipyridine-3-carboxylate (114)

A mixture of nitrile 113 (117 mg, 0.47 mmol), piperidine (40.5 mg, 0.48 mmol), ethyl cyanoacetate (68.5 mg, 0.61 mmol) and ethanol (2 mL) was heated at reflux for 2 h. After standing at room temperature for 2 h, the precipitated solid was collected, washed with ethanol and diethyl ether, and dried to afford 114 (130 mg, 77%) as a light orange solid. $^1$H NMR (400 MHz, chloroform-d) δ 9.11 (s, 1H), 8.77 (s, 1H), 8.54 (s, 1H), 8.22 (s, 1H), 6.02 (s, 1H), 4.42 (q, J=7.2 Hz, 2H), 1.44 (t, J=7.1 Hz, 3H). MS m/z 363.99, 365.99 (M+H)$^+$.

Ethyl 2-amino-5-oxo-7-(prop-1-en-2-yl)-5H-pyrano[2,3-b:6,5-c']dipyridine-3-carboxylate (115a)

A solution of tripotassium phosphate (402 mg, 1.90 mmol) in water (0.8 mL) was added to a suspension of compound 114 (115 mg, 0.32 mmol), 4,4,5,5-tetramethyl-2-(prop-1-en-2-yl)-1,3,2-dioxaborolane (127 mg, 0.76 mmol), triphenylphosphine (41.4 mg, 0.16 mmol), and Pd(OAc)$_2$ (9.22 mg, 0.04 mmol) in p-dioxane (8 mL) under nitrogen, and the mixture was heated at 100-105° C. for 2 h. The cooled mixture was diluted with water and extracted with dichloromethane (3×). The combined organic phases were dried (Na$_2$SO$_4$), concentrated to a solid that was triturated with small amounts of ethanol and then diethyl ether, and dried to give 115a (93 mg, 91%) as an off-white solid. $^1$H NMR (500 MHz, chloroform-d) δ 9.14 (s, 1H), 8.96 (d, J=0.7 Hz, 1H), 8.47 (s, 1H), 8.15 (d, J=0.7 Hz, 1H), 6.05 (dd, J=1.6, 0.8 Hz, 1H), 5.97 (s, 1H), 5.38 (t, J=1.6 Hz, 1H), 4.42 (q, J=7.1 Hz, 2H), 2.29 (dd, J=1.5, 0.8 Hz, 3H), 1.45 (t, J=7.1 Hz, 3H). MS m/z 326.11 (M+H)$^+$.

Ethyl 2-amino-7-(cyclohex-1-en-1-yl)-5-oxo-5H-pyrano[2,3-b:6,5-c']dipyridine-3-carboxylate (115c)

Similar reaction of tripotassium phosphate (350 mg, 1.65 mmol) in water (0.65 mL), compound 114 (100 mg, 0.28 mmol), 2-(cyclohex-1-en-1-yl)-4,4,5,5-tetramethyl-1,3,2-dioxaborolane (137 mg, 0.66 mmol), triphenylphosphine (36 mg, 0.14 mmol), Pd(OAc)$_2$ (8.0 mg, 0.04 mmol) and p-dioxane (6.5 mL) was carried out for 2.7 h. The same workup gave 115c (90 mg, 90%) as an off-white solid. $^1$H NMR (400 MHz, chloroform-d) δ 9.14 (s, 1H), 8.92 (d, J=0.7 Hz, 1H), 8.46 (s, 1H), 8.04 (s, 1H), 6.88 (d, J=4.2 Hz, 1H), 5.94 (s, 1H), 4.42 (q, J=7.1 Hz, 2H), 2.60-2.53 (m, 2H), 2.31 (d, J=6.3 Hz, 2H), 1.88-1.78 (m, 2H), 1.75-1.66 (m, 2H), 1.45 (t, J=7.1 Hz, 3H). MS m/z 366.14 (M+H)$^+$.

2-Amino-5-oxo-7-(prop-1-en-2-yl)-5H-pyrano[2,3-b:6,5-c']dipyridine-3-carboxylic acid (115b)

To a suspension of compound 115a (25 mg, 0.08 mmol) in ethanol (8 mL) and water (1.0 mL) was added 1N aq NaOH (1 mL). The mixture was stirred at 50° C. for 3 h and filtered. The filtrate was concentrated, diluted with water (20 mL) and acidified with 1N aq HCl to pH 3-4. The precipitated solids were stirred at room temperature for 7 h, stored at room temperature for 24 h, collected, washed with water, and dried to give 115b (20 mg, 88%) as a light orange solid. $^1$H NMR (500 MHz, DMSO-d$_6$) δ 9.01 (s, 1H), 8.78 (s, 1H), 8.46 (s, 1H), 8.39 (s, 1H), 8.01 (s, 1H), 6.04 (s, 1H), 5.37 (t, J=1.7 Hz, 1H), 2.22 (s, 3H). MS m/z 298.08 (M+H)$^+$.

2-Amino-7-(cyclohex-1-en-1-yl)-5-oxo-5H-pyrano[2,3-b:6,5-c']dipyridine-3-carboxylic acid (176)

Similar reaction of compound 115c (25 mg, 0.07 mmol) and 1N aq NaOH (1 mL) in EtOH (8 mL) and water (1 mL) followed by workup gave 176 (19 mg, 82%) as a solid. $^1$H NMR (400 MHz, DMSO-d$_6$) δ 13.59 (s, 1H), 8.96 (s, 1H), 8.77 (s, 1H), 8.47 (s, 1H), 8.38 (s, 1H), 7.85 (s, 1H), 6.85 (s, 1H), 3.33 (s, 2H), 2.25 (s, 2H), 1.75 (d, J=5.8 Hz, 2H), 1.64 (d, J=6.0 Hz, 2H). MS m/z 338.11 (M+H)+.

Ethyl 2-amino-7-isopropyl-5-oxo-5H-pyrano[2,3-b:6,5-c']dipyridine-3-carboxylate (116a)

A flask with a solution of compound 115a (85 mg, 0.26 mmol) in dichloromethane (55 mL) and ethanol (110 mL) was purged with nitrogen and 10% palladium on carbon (120 mg) was added. The mixture was then purged with nitrogen and hydrogen, and hydrogenated at 50 PSI using a Parr shaker at room temperature for 19 h. The mixture was filtered over celite and concentrated to a solid (120 mg) that was diluted with dichloromethane (25 mL). Precipitated impurities were filtered off and the filtrate was concentrated to a solid that was washed with a small amount of ethanol and dried to leave 116a (49 mg, 57%) as a white solid. $^1$H NMR (500 MHz, chloroform-d) δ 9.13 (s, 1H), 8.94 (d, J=0.8 Hz, 1H), 8.46 (s, 1H), 7.90 (s, 1H), 5.96 (s, 1H), 4.41 (t, J=7.1 Hz, 2H), 3.22 (p, J=6.9 Hz, 1H), 1.45 (t, J=7.1 Hz, 3H), 1.37 (d, J=6.9 Hz, 6H). MS m/z 328.13 (M+H)+.

Ethyl 2-amino-7-cyclohexyl-5-oxo-5H-pyrano[2,3-b:6,5-c']dipyridine-3-carboxylate (116b)

Similar reaction of compound 115c (75 mg, 0.21 mmol) in dichloromethane (25 mL) and ethanol (50 mL) over 10% palladium on carbon (110 mg) at 45 PSI for 18 h gave 108 mg of solid that was triturated in ethanol and dried to leave 116b (34 mg, 45%) as a white solid. $^1$H NMR (400 MHz, chloroform-d) δ 9.13 (s, 1H), 8.92 (d, J=0.8 Hz, 1H), 8.46 (s, 1H), 7.88 (s, 1H), 5.95 (s, 1H), 4.42 (q, J=7.1 Hz, 2H), 2.89-2.79 (m, 1H), 2.01 (d, J=12.8 Hz, 2H), 1.89 (d, J=12.9 Hz, 2H), 1.78 (d, J=12.3 Hz, 1H), 1.60 (d, J=3.4 Hz, 3H), 1.45 (t, J=7.1 Hz, 4H), 1.35-1.27 (m, 1H). MS m/z 368.16 (M+H)+.

2-Amino-7-isopropyl-5-oxo-5H-pyrano[2,3-b:6,5-c']dipyridine-3-carboxylic acid (117)

To a suspension of compound 116a (49 mg, 0.15 mmol) in ethanol (12 mL) and water (1.5 mL) was added 1N aq NaOH (1.5 mL). The mixture was stirred for 1.5 h at 50° C. and filtered. The filtrate was concentrated, diluted with water (20 mL) and acidified with 1N aq HCl to pH 3-4. The precipitated solids were stirred at room temperature for 16 h, stored at room temperature for 24 h, collected, washed with water, and dried to give 117 (32 mg, 71%) as a solid. $^1$H NMR (400 MHz, DMSO-d$_6$) δ 13.57 (s, 1H), 8.97 (s, 1H), 8.78 (s, 1H), 8.47 (s, 1H), 8.33 (s, 1H), 7.78 (s, 1H), 3.20 (p, J=6.8 Hz, 1H), 1.29 (d, J=6.9 Hz, 6H). MS m/z 300.10 (M+H)+.

2-Amino-7-cyclohexyl-5-oxo-5H-pyrano[2,3-b:6,5-c']dipyridine-3-carboxylic acid (180)

Similar reaction of compound 116b (34 mg, 0.09 mmol) and 1N aq NaOH (1.5 mL) in ethanol (12 mL) and water (1.5 mL) followed by workup gave 180 (28 mg, 89%) as a solid. $^1$H NMR (400 MHz, DMSO-d$_6$) δ 13.57 (s, 1H), 8.95 (s, 1H), 8.77 (s, 1H), 8.46 (s, 1H), 8.33 (s, 1H), 7.74 (s, 1H), 2.83 (t, J=11.9 Hz, 1H), 1.90 (d, J=12.5 Hz, 2H), 1.81 (d, J=12.3 Hz, 2H), 1.72 (d, J=13.0 Hz, 1H), 1.59-1.48 (m, 2H), 1.40 (q, J=12.8 Hz, 2H), 1.30-1.23 (m, 1H). MS m/z 340.13 (M+H)+.

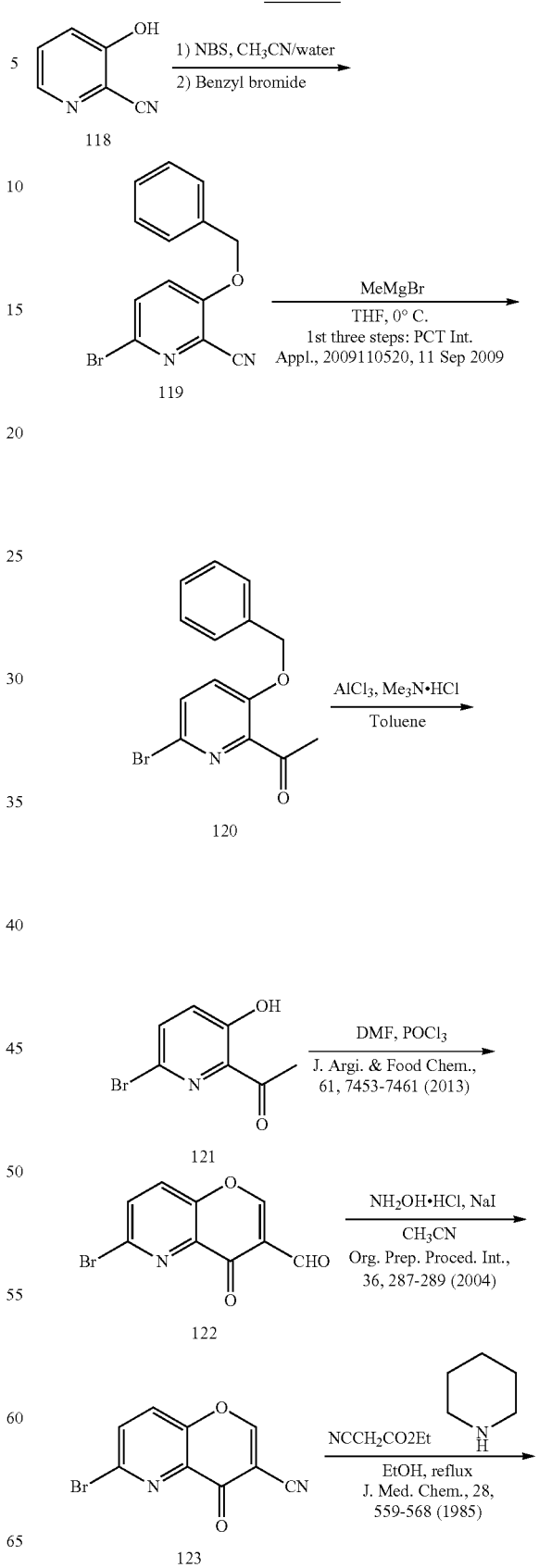

Scheme 25

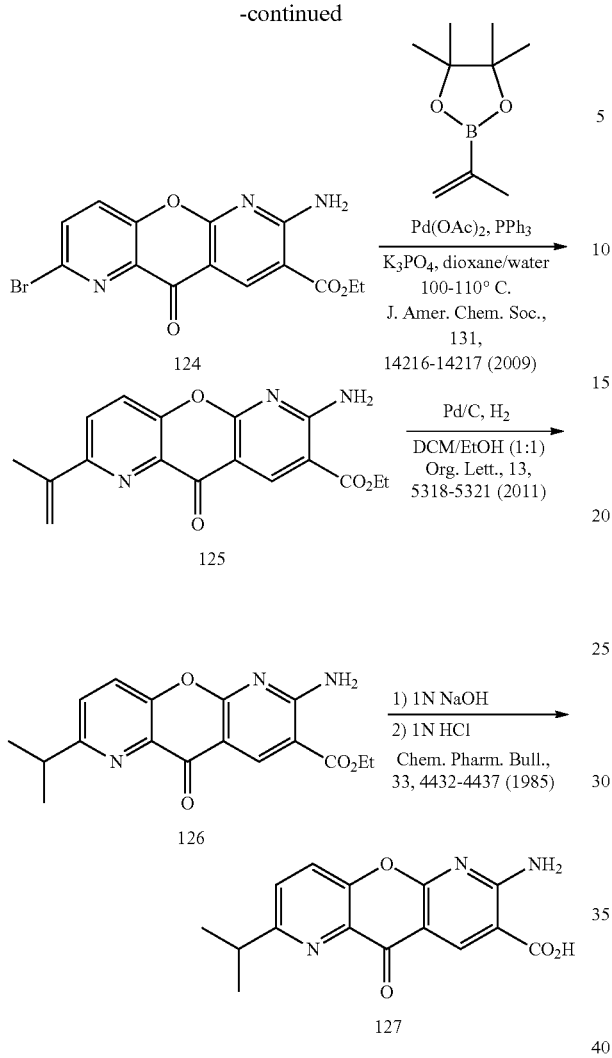
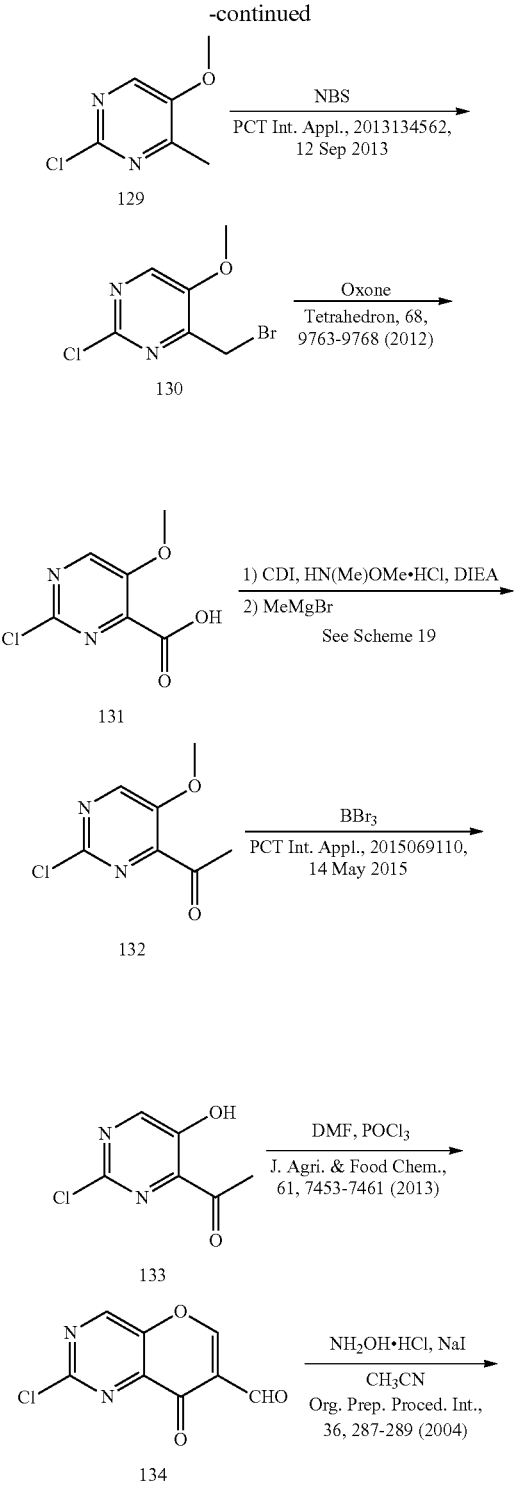

Ethyl 7-amino-2-bromo-10-oxo-10H-pyrano[2,3-b:5,6-b']dipyridine-8-carboxylate (124) is obtained starting from compound 118 and proceeding through the steps shown in Scheme 25.

Ethyl 7-amino-10-oxo-2-(prop-1-en-2-yl)-10H-pyrano[2,3-b:5,6-b']dipyridine-8-carboxylate (125) is obtained starting from compound 124 as shown in Scheme 25.

Ethyl 7-amino-2-isopropyl-10-oxo-10H-pyrano[2,3-b:5,6-b']dipyridine-8-carboxylate (126) is obtained starting from compound 125 as shown in Scheme 25.

7-Amino-2-isopropyl-10-oxo-10H-pyrano[2,3-b:5,6-b']dipyridine-8-carboxylic acid (127) is obtained starting from compound 126 as shown in Scheme 25.

Scheme 26

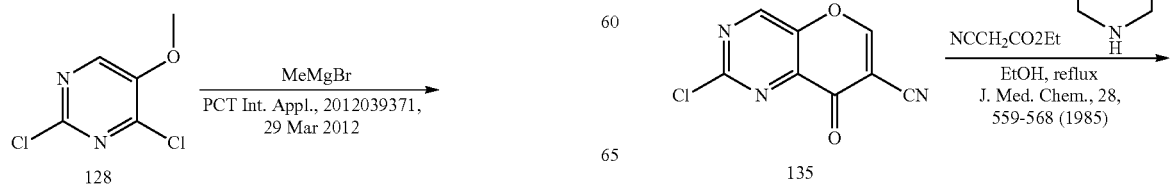

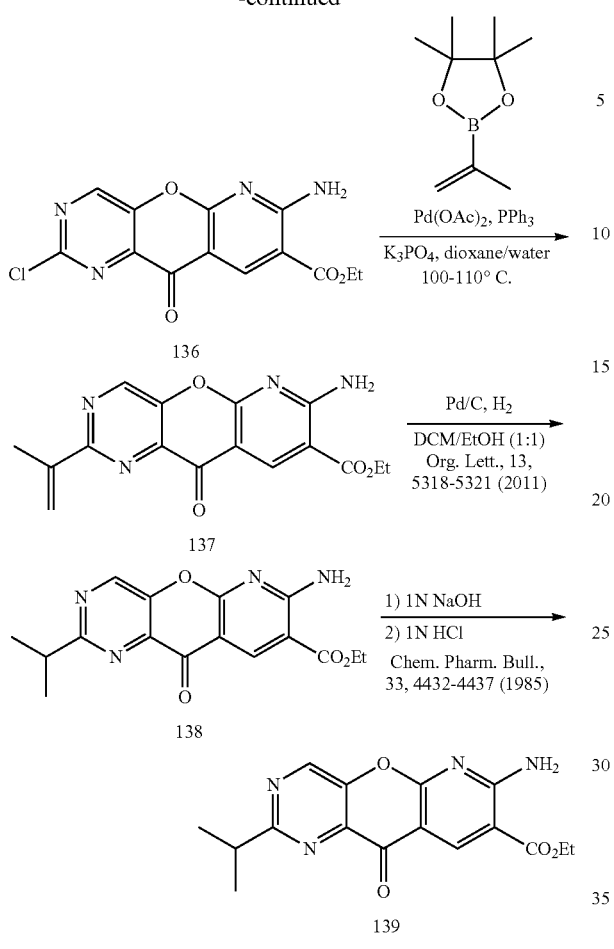

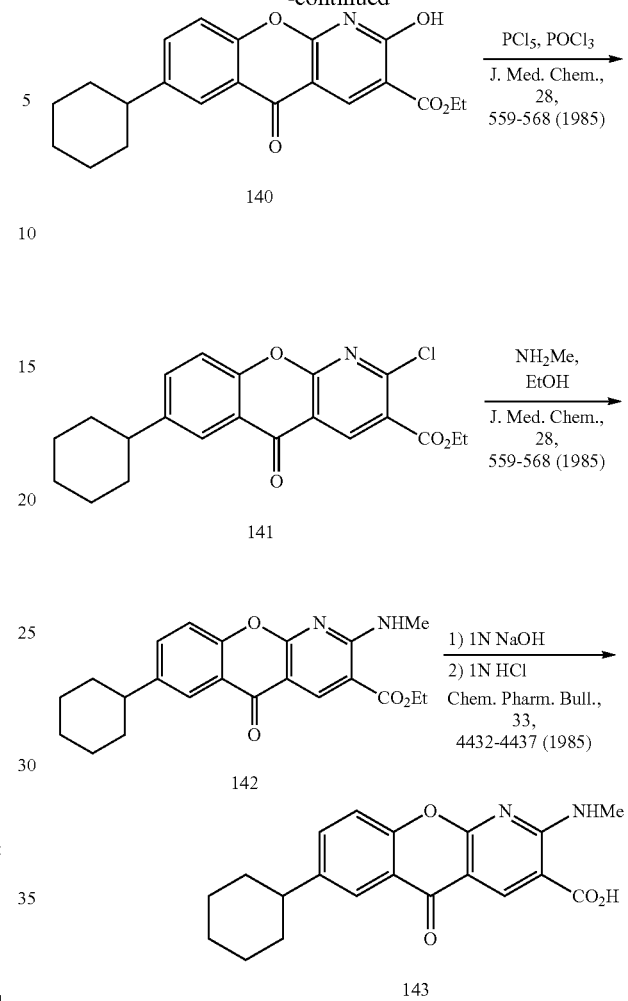

Ethyl 7-amino-2-chloro-10-oxo-10H-pyrido[3',2':5,6]pyrano[3,2-d]pyrimidine-8-carboxylate (136) is obtained starting from compound 128 and proceeding through the steps shown in Scheme 26.

Ethyl 7-amino-10-oxo-2-(prop-1-en-2-yl)-10H-pyrido[3',2':5,6]pyrano[3,2-d]pyrimidine-8-carboxylate (137) is obtained starting from compound 136 as shown in Scheme 26.

Ethyl 7-amino-2-isopropyl-10-oxo-10H-pyrido[3',2':5,6]pyrano[3,2-d]pyrimidine-8-carboxylate (138) is obtained starting from compound 137 as shown in Scheme 26.

7-Amino-2-isopropyl-10-oxo-10H-pyrido[3',2':5,6]pyrano[3,2-d]pyrimidine-8-carboxylic acid (139) is obtained starting from compound 138 as shown in Scheme 26.

Ethyl 7-cyclohexyl-2-hydroxy-5-oxo-5H-chromeno[2,3-b]pyridine-3-carboxylate (140) is obtained starting from compound 14 as shown in Scheme 27.

Ethyl 2-chloro-7-cyclohexyl-5-oxo-5H-chromeno[2,3-b]pyridine-3-carboxylate (141) was obtained starting from compound 140 as shown in Scheme 27.

Ethyl 7-cyclohexyl-2-(methylamino)-5-oxo-5H-chromeno[2,3-b]pyridine-3-carboxylate (142) is obtained starting from compound 141 as shown in Scheme 27.

7-Cyclohexyl-2-(methylamino)-5-oxo-5H-chromeno[2,3-b]pyridine-3-carboxylic acid (143) is obtained starting from compound 142 as shown in Scheme 27.

Scheme 27

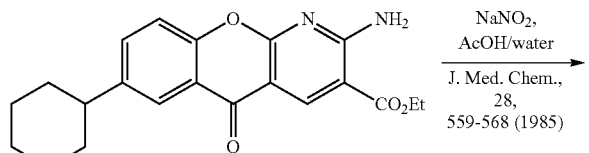

Scheme 28

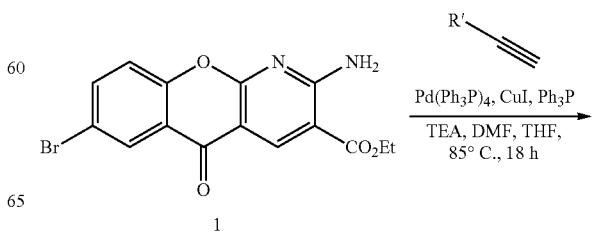

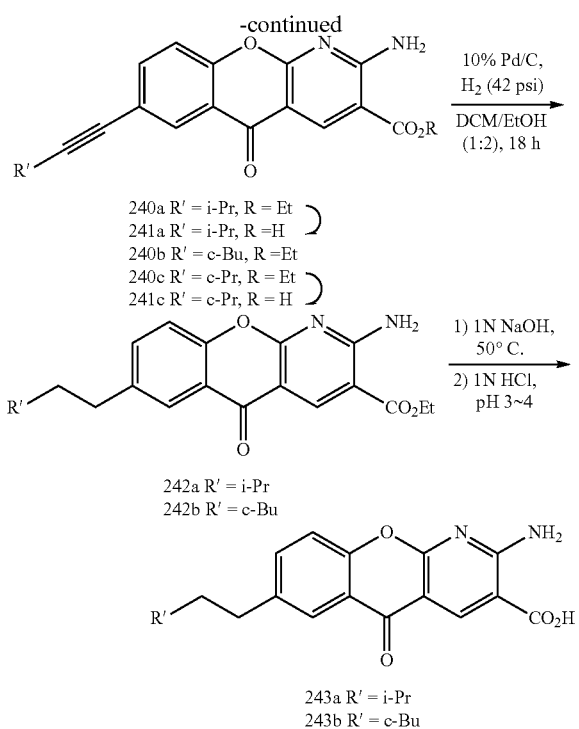

240a R' = i-Pr, R = Et
241a R' = i-Pr, R = H
240b R' = c-Bu, R = Et
240c R' = c-Pr, R = Et
241c R' = c-Pr, R = H

242a R' = i-Pr
242b R' = c-Bu

243a R' = i-Pr
243b R' = c-Bu

Ethyl 2-amino-7-(3-methylbut-1-yn-1-yl)-5-oxo-5H-chromeno[2,3-b]pyridine-3-carboxylate (240a)

A suspension of compound 1 (300 mg, 0.83 mmol), 3-methylbut-1-yne (338 mg, 4.96 mmol), triphenylphosphine (21.7 mg, 0.08 mmol), N,N-dimethylformamide (8 mL), tetrahydrofuran (8 mL), and triethylamine (7.5 mL) in a 100 mL sealed tube was degassed with nitrogen. Then Pd(PPh$_3$)$_4$ (47.7 mg, 0.04 mmol) and CuI (15.7 mg, 0.08 mmol) were added under an atmosphere of nitrogen and the suspension was heated at 85° C. for 18 h. The mixture was diluted with water and extracted with dichloromethane (2×). The organic phases were dried (Na$_2$SO$_4$) and concentrated to leave a solid that was triturated in ethanol and then diethyl ether, and dried to give 240a (246 mg, 85%) as a solid. $^1$H NMR (400 MHz, chloroform-d) δ 9.14 (s, 1H), 8.38 (s, 1H), 8.28 (d, J=2.1 Hz, 1H), 7.69 (dd, J=8.6, 2.1 Hz, 1H), 7.41 (d, J=8.6 Hz, 1H), 5.92 (s, 1H), 4.40 (q, J=7.1 Hz, 2H), 2.80 (p, J=6.9 Hz, 1H), 1.43 (dd, J=7.6, 6.7 Hz, 3H), 1.29 (dd, J=7.0, 1.0 Hz, 6H). MS m/z 351.13 (M+1)$^+$.

Ethyl 2-amino-7-(cyclobutylethynyl)-5-oxo-5H-chromeno[2,3-b]pyridine-3-carboxylate (240b)

Similar reaction of a mixture of compound 1 (200 mg, 0.55 mmol), triphenylphosphine (14.4 mg, 0.06 mmol), N,N-dimethylformamide (4 mL), tetrahydrofuran (4 mL), triethylamine (4 mL), ethynylcyclopropane (220 mg, 2.75 mmol; prepared by the method of Tetrahedron, 62(12), 2769-2778, 2006), Pd(PPh$_3$)$_4$ (31.7 mg, 0.03 mmol) and CuI (10.5 mg, 0.06 mmol) followed by the same workup gave 240b (173 mg, 87%) as a solid. The compound was used directly in the next step.

Ethyl 2-amino-7-(cyclopropylethynyl)-5-oxo-5H-chromeno[2,3-b]pyridine-3-carboxylate (240c)

Similar reaction of a mixture of compound 1 (500 mg, 1.38 mmol), ethynylcyclopropane (364 mg, 5.51 mmol), triphenylphosphine (36.1 mg, 0.14 mmol), N,N-dimethylformamide (10 mL), tetrahydrofuran (10 mL), triethylamine (10 mL) Pd(PPh$_3$)$_4$ (80 mg, 0.07 mmol) and CuI (26.2 mg, 0.14 mmol) followed by the same workup gave 240c (452 mg, 94%) as solid. $^1$H NMR (400 MHz, chloroform-d) δ 9.14 (s, 1H), 8.39 (s, 1H), 8.26 (s, 1H), 7.67 (dd, J=8.5, 2.1 Hz, 1H), 7.40 (d, J=8.6 Hz, 1H), 5.91 (s, 1H), 4.40 (q, J=7.1 Hz, 2H), 1.52-1.46 (m, 1H), 1.43 (t, J=7.2 Hz, 3H), 0.90 (d, J=8.1 Hz, 2H), 0.88-0.80 (m, 2H). MS m/z 349.12 (M+1)$^+$.

2-Amino-7-(3-methylbut-1-yn-1-yl)-5-oxo-5H-chromeno[2,3-b]pyridine-3-carboxylic acid (241a)

To a suspension of 240a (55 mg, 0.16 mmol) in ethanol (12 mL) and water (1.5 mL) was added 1N aq NaOH (1.5 mL). The mixture was stirred for 1.5 h at 50° C. and filtered. The filtrate was concentrated, diluted with water (20 mL) and acidified with 1N aq HCl to pH 3-4. The precipitated solids were stirred at room temperature for 2 h, stored at room temperature for 1 h, collected, washed with water, and dried to give 241a (40 mg, 79%) as a solid. $^1$H NMR (400 MHz, DMSO-d$_6$) δ 13.51 (s, 1H), 8.77 (s, 1H), 8.37 (s, 1H), 8.28 (s, 1H), 7.97 (d, J=2.1 Hz, 1H), 7.76 (dd, J=8.5, 2.2 Hz, 1H), 7.57 (d, J=8.6 Hz, 1H), 2.83 (p, J=6.8 Hz, 1H), 1.24 (d, J=6.9 Hz, 6H). MS m/z 323.10 (M+H)$^+$.

2-Amino-7-(cyclopropylethynyl)-5-oxo-5H-chromeno[2,3-b]pyridine-3-carboxylic acid (241c)

Similar reaction of compound 240c (35 mg, 0.10 mmol) and 1N aq NaOH (1.5 mL) in ethanol (12 mL) and water (1.5 mL) followed by workup (with stirring of precipitate at room temperature for 16 h and storage at room temperature for 2 h) gave 241c (26 mg, 81%) as a solid. $^1$H NMR (400 MHz, DMSO-d$_6$) δ 13.51 (s, 1H), 8.76 (s, 1H), 8.36 (s, 1H), 8.27 (s, 1H), 7.96 (s, 1H), 7.76 (d, J=8.6 Hz, 1H), 7.56 (d, J=8.6 Hz, 1H), 1.57 (s, 1H), 0.91 (dd, J=7.7, 3.1 Hz, 2H), 0.78 (d, J=5.3 Hz, 2H). MS m/z 321.09 (M+H)$^+$.

Ethyl 2-amino-7-isopentyl-5-oxo-5H-chromeno[2,3-b]pyridine-3-carboxylate (242a)

A flask with a solution of compound 240a (100 mg, 0.29 mmol) in dichloromethane (30 mL) and ethanol (60 mL) was purged with nitrogen and 10% palladium on carbon (90 mg) was added. The mixture was then purged with nitrogen and hydrogen, and hydrogenated at 42 PSI using a Parr shaker at room temperature for 18 h. The mixture was filtered over celite and concentrated to leave a solid that was triturated in ethanol and dried to give 242a (76 mg, 75%) as a white solid. $^1$H NMR (400 MHz, chloroform-d) δ 9.15 (s, 1H), 8.36 (s, 1H), 8.06 (d, J=2.2 Hz, 1H), 7.58-7.48 (m, 1H), 7.41 (d, J=8.5 Hz, 1H), 5.94 (s, 1H), 4.40 (q, J=7.1 Hz, 2H), 2.73 (t, J=7.9 Hz, 2H), 1.58 (tt, J=14.8, 6.6 Hz, 3H), 1.44 (t, J=7.1 Hz, 3H), 0.96 (d, J=6.2 Hz, 6H). MS m/z 355.17 (M+H)$^+$.

Ethyl 2-amino-7-(2-cyclobutylethyl)-5-oxo-5H-chromeno[2,3-b]pyridine-3-carboxylate (242b)

Similar reaction of compound 240b (173 mg, 0.48 mmol) in dichloromethane (35 mL) and ethanol (70 mL) over 10% palladium on carbon (150 mg) at 42 PSI for 18 h followed by the same workup gave 105 mg of impure product. Purification by silica gel preparative plate chromatography (elution with 0.3% methanol in dichloromethane) gave 242b (71 mg, 40%) as a white solid. $^1$H NMR (400 MHz, chloroform-d) δ 9.15 (s, 1H), 8.36 (s, 1H), 8.04 (d, J=2.2 Hz, 1H), 7.51 (dd, J=8.5, 2.3 Hz, 1H), 7.41 (d, J=8.5 Hz, 1H), 5.88 (s, 1H), 4.41 (q, J=7.1 Hz, 2H), 2.63 (dd, J=8.9, 6.7 Hz, 2H), 2.29 (p, J=7.8 Hz, 1H), 2.10-1.98 (m, 2H), 1.91-1.72 (m, 4H), 1.68-1.58 (m, 3H), 1.44 (t, J=7.1 Hz, 3H). MS m/z 367.17 (M+H)+.

2-Amino-7-isopentyl-5-oxo-5H-chromeno[2,3-b]pyridine-3-carboxylic acid (243a)

To a suspension of compound 242a (71 mg, 0.20 mmol) in ethanol (12 mL) and water (1.5 mL) was added 1N aq NaOH (1.5 mL). The mixture was stirred for 1.5 h at 50° C. and filtered. The filtrate was concentrated, diluted with water (20 mL), and acidified with 1N aq HCl to pH 3-4. The precipitated solids were stirred at room temperature for 2 h, stored at room temperature for 1 h, collected, washed with water, and dried to give 243a (46 mg, 70%) as a solid. $^1$H NMR (500 MHz, DMSO-$d_6$) δ 13.44 (s, 1H), 8.79 (s, 1H), 8.25 (s, 2H), 7.88 (s, 1H), 7.66 (d, J=8.5 Hz, 1H), 7.51 (d, J=8.5 Hz, 1H), 2.71 (t, J=7.8 Hz, 2H), 1.52 (dq, J=22.5, 6.8 Hz, 3H), 0.92 (d, J=6.2 Hz, 6H). MS m/z 327.13 (M+H)+.

2-Amino-7-(2-cyclobutylethyl)-5-oxo-5H-chromeno[2,3-b]pyridine-3-carboxylic acid (243b)

Similar reaction of compound 242b (78 mg, 0.19 mmol) and 1N aq NaOH (2 mL) in ethanol (16 mL) and water (2 mL) followed by workup gave 243b (50 mg, 76%) as a solid. $^1$H NMR (500 MHz, DMSO-$d_6$) δ 13.46 (s, 1H), 8.78 (s, 1H), 8.25 (s, 2H), 7.84 (s, 1H), 7.63 (d, J=8.5 Hz, 1H), 7.49 (d, J=8.6 Hz, 1H), 2.59 (t, J=7.8 Hz, 2H), 2.23 (p, J=7.8 Hz, 1H), 2.03-1.92 (m, 2H), 1.79 (p, J=9.0, 8.5 Hz, 2H), 1.69 (q, J=7.4 Hz, 2H), 1.62-1.47 (m, 2H). MS m/z 339.13 (M+H)+.

Scheme 29

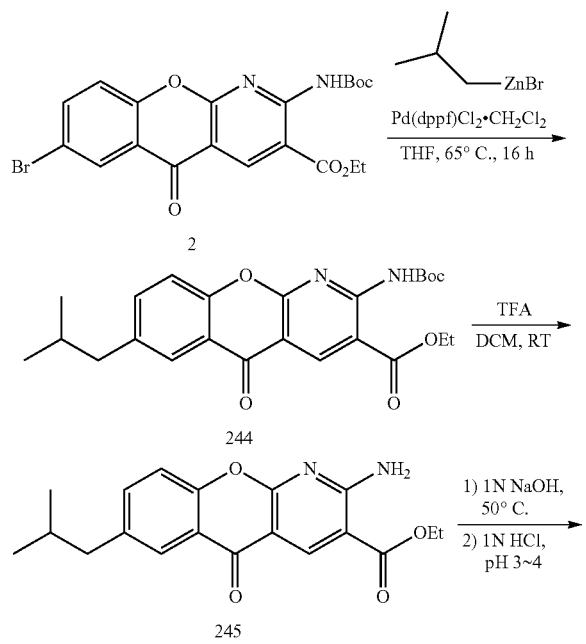

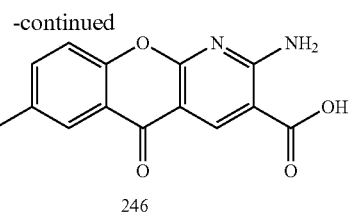

246

Ethyl 2-((tert-butoxycarbonyl)amino)-7-isobutyl-5-oxo-5H-chromeno[2,3-b]pyridine-3-carboxylate (244)

A mixture of isobutylzinc(II) bromide solution (7.5 ml, 0.5 M in tetrahydrofuran, 3.75 mmol), compound 2 (300 mg, 0.65 mmol) and PdCl$_2$(dppf).CH$_2$Cl$_2$ (53 mg, 0.07 mmol) was degassed with nitrogen and the reaction vial capped. The mixture was heated at 67° C. for 16 h, cooled, diluted with water, and extracted with dichloromethane (2×). The combined organic phases were washed with saturated aq NaHCO$_3$ and brine, dried (Na$_2$SO$_4$), and concentrated to leave a solid that was purified by silica gel preparative plate chromatography (elution with 0.2% methanol in dichloromethane) to afford 244 (72 mg, 25%). $^1$H NMR (400 MHz, chloroform-d) δ 10.89 (s, 1H), 9.29 (d, J=0.8 Hz, 1H), 8.04 (dd, J=1.8, 0.9 Hz, 1H), 7.54 (t, J=1.3 Hz, 2H), 4.46 (q, J=7.1 Hz, 2H), 2.61 (d, J=7.2 Hz, 2H), 1.94 (dt, J=13.6, 6.8 Hz, 1H), 1.58 (s, 9H), 1.47 (t, J=7.2 Hz, 3H), 0.94 (d, J=6.6 Hz, 6H). MS m/z 441.20 (M+H)+.

Ethyl 2-amino-7-isobutyl-5-oxo-5H-chromeno[2,3-b]pyridine-3-carboxylate (245)

A solution of compound 244 (71 mg, 0.16 mmol, trifluoroacetic acid (0.25 mL) and dichloromethane (10 mL) was stirred at RT for 15 min. The solution was washed with 5% aq Na$_2$CO$_3$, dried (Na$_2$SO$_4$), and concentrated to give 245 (53 mg, 97%) as a solid. $^1$H NMR (400 MHz, chloroform-d) δ 9.15 (s, 1H), 8.36 (s, 1H), 8.03 (d, J=2.1 Hz, 1H), 7.54-7.49 (m, 1H), 7.42 (d, J=8.5 Hz, 1H), 5.93 (s, 1H), 4.41 (q, J=7.1 Hz, 2H), 2.60 (d, J=7.2 Hz, 2H), 1.93 (dt, J=13.5, 6.8 Hz, 1H), 1.44 (t, J=7.1 Hz, 3H), 0.93 (d, J=6.6 Hz, 6H). MS m/z 341.15 (M+H)+.

2-Amino-7-isobutyl-5-oxo-5H-chromeno[2,3-b]pyridine-3-carboxylic acid (246)

To a suspension of compound 245 (53 mg, 0.16 mmol) in ethanol (12 mL) and water (1.5 mL) was added 1N aq NaOH (1.5 mL). The mixture was stirred at 50° C. for 1 h and filtered. The filtrate was concentrated, diluted with water (20 mL), and acidified with 1N aq HCl to pH 3-4. The precipitated solids were stirred at room temperature for 2 h, stored at room temperature for 1 h, collected, washed with water, and dried to give 246 (40 mg, 82%) as a solid. $^1$H NMR (400 MHz, DMSO-$d_6$) δ 13.46 (s, 1H), 8.80 (s, 1H), 8.27 (s, 2H), 7.85 (s, 1H), 7.64 (d, J=9.2 Hz, 1H), 7.53 (d, J=8.5 Hz, 1H), 2.59 (d, J=7.1 Hz, 2H), 1.88 (p, J=6.6 Hz, 1H), 0.88 (d, J=6.6 Hz, 6H). MS m/z 313.12 (M+H)+.

Scheme 30
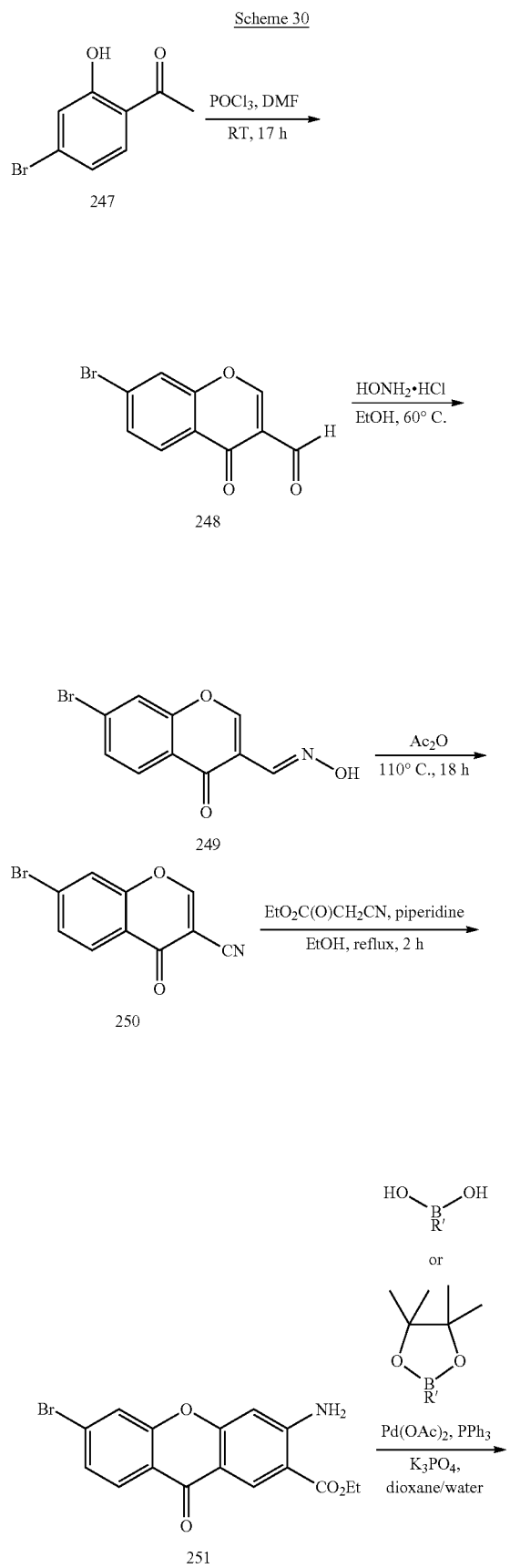
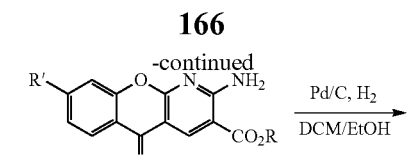
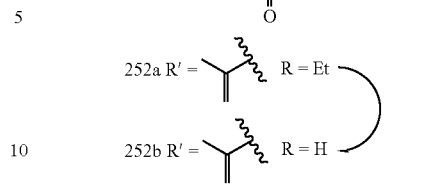
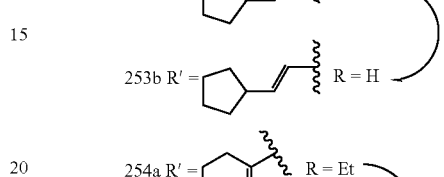
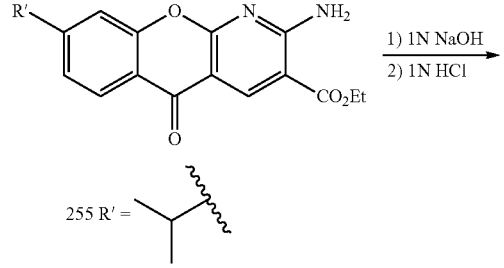
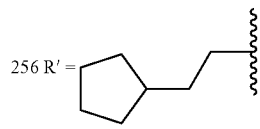
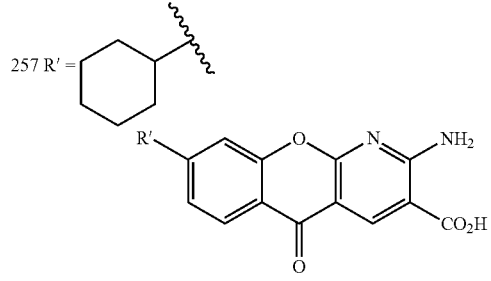
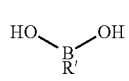
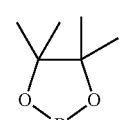
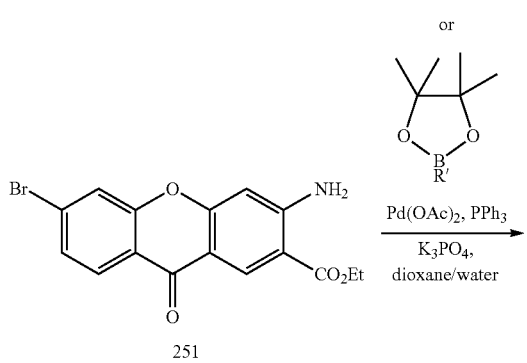

7-Bromo-4-oxo-4H-chromene-3-carbaldehyde (248)

POCl$_3$ (12 mL, 129 mmol) was added slowly over 30 min to a well stirred and cooled (0-5° C.) solution of 1-(4-bromo-2-hydroxyphenyl)ethan-1-one (247; 5.0 g, 23.25 mmol) in N,N-dimethylformamide (40 mL). After stirring at room temperature for 17 h, the suspension was poured into crushed ice and maintained at 0° C. for 1 h. The formed solid was collected, washed with water, and dried to give 248 (5.2 g, 88%) as a light orange solid. $^1$H NMR (500 MHz, chloroform-d) δ 10.36 (d, J=1.2 Hz, 1H), 8.51 (d, J=1.2 Hz, 1H), 8.16 (dd, J=8.5, 1.2 Hz, 1H), 7.74 (t, J=1.4 Hz, 1H), 7.63 (dt, J=8.5, 1.5 Hz, 1H). MS m/z 252.95, 254.95 (M+1)$^+$.

(E)-7-Bromo-4-oxo-4H-chromene-3-carbaldehyde oxime (249)

A suspension of compound 248 (200 mg, 0.79 mmol), hydroxylamine hydrochloride (65.9 mg, 0.95 mmol) and ethanol (4 mL) was stirred at 60° C. for 1 h. The mixture was maintained at 0° C. for 30 min and the solids were collected, washed with ethanol, and dried to leave 249 (170 mg, 80%) as an off-white solid. $^1$H NMR (400 MHz, DMSO-d$_6$) δ 11.46 (s, 1H), 8.66 (d, J=0.8 Hz, 1H), 8.05 (d, J=1.9 Hz, 1H), 8.05 (d, J=0.8 Hz, 1H), 8.00 (d, J=8.5 Hz, 1H), 7.70 (dd, J=8.5, 1.8 Hz, 1H). MS m/z 267.96, 269.96 (M+H)$^+$.

7-Bromo-4-oxo-4H-chromene-3-carbonitrile (250)

A suspension of compound 249 (165 mg, 0.62 mmol) in acetic anhydride (3 mL) was stirred at 110° C. for 18 h. The mixture was concentrated to leave 250 (150 mg, 97%) as an off-white solid. $^1$H NMR (400 MHz, chloroform-d) δ 8.39 (s, 1H), 8.12 (d, J=8.5 Hz, 1H), 7.75 (d, J=1.8 Hz, 1H), 7.66 (dd, J=8.5, 1.7 Hz, 1H). MS m/z 249.95, 251.95 (M+H)$^+$.

Ethyl 2-amino-8-bromo-5-oxo-5H-chromeno[2,3-b]pyridine-3-carboxylate (251)

A mixture of compound 250 (140 mg, 0.56 mmol), ethyl cyanoacetate (82 mg, 0.73 mmol), piperidine (48.6 mg, 0.57 mmol) and ethanol (4 mL) was heated at reflux for 2 h. After standing overnight at room temperature, the precipitated solids were collected, washed with ethanol, and dried to afford 251 (190 mg, 93%) as a white solid. $^1$H NMR (500 MHz, chloroform-d) δ 9.13 (s, 1H), 8.41 (s, 1H), 8.13 (d, J=8.4 Hz, 1H), 7.68 (d, J=1.7 Hz, 1H), 7.53 (dd, J=8.4, 1.8 Hz, 1H), 5.90 (s, 1H), 4.41 (q, J=7.1 Hz, 2H), 1.44 (t, J=7.1 Hz, 3H). MS m/z 362.10, 364.10 (M+H)$^+$.

Ethyl 2-amino-5-oxo-8-(prop-1-en-2-yl)-5H-chromeno[2,3-b]pyridine-3-carboxylate (252a)

A solution of tripotassium phosphate (666 mg, 3.14 mmol) in water (1.5 mL) was added to a suspension of compound 251 (190 mg, 0.52 mmol), 4,4,5,5-tetramethyl-2-(prop-1-en-2-yl)-1,3,2-dioxaborolane (211 mg, 1.26 mmol), triphenylphosphine (68.6 mg, 0.26 mmol), Pd(OAc)$_2$ (15.3 mg, 0.07 mmol) in p-dioxane (15 mL) under nitrogen, and the reaction was heated at 100-105° C. for 2 h. The cooled mixture was diluted with water and extracted with dichloromethane (2×). The combined organic phases were dried (Na$_2$SO$_4$) and concentrated to a solid that was triturated with small amounts of ethanol and diethyl ether and dried to give 252a (155 mg, 91%) as a white solid. $^1$H NMR (500 MHz, chloroform-d) δ 9.15 (s, 1H), 8.36 (s, 1H), 8.21 (d, J=8.2 Hz, 1H), 7.54 (d, J=1.6 Hz, 1H), 7.53-7.51 (m, 1H), 5.86 (s, 1H), 5.62-5.55 (m, 1H), 5.31 (t, J=1.5 Hz, 1H), 4.41 (q, J=7.1 Hz, 2H), 2.26-2.16 (m, 3H), 1.44 (t, J=7.1 Hz, 3H). MS m/z 325.1183 (M+H)$^+$.

Ethyl (E)-2-amino-8-(2-cyclopentylvinyl)-5-oxo-5H-chromeno[2,3-b]pyridine-3-carboxylate (253a)

Similar reaction of tripotassium phosphate (701 mg, 3.3 mmol) in water (1.35 mL), compound 251 (200 mg, 0.55 mmol)), (E)-(2-cyclopentylvinyl)boronic acid (96 mg, 0.69 mmol), triphenylphosphine (72.2 mg, 0.28 mmol), Pd(OAc)$_2$ (12.4 mg, 0.06 mmol) and p-dioxane (13.5 mL) was carried out for 1.5 h. The same workup gave 253a (189 mg, 91%) as a white solid. $^1$H NMR (400 MHz, chloroform-d) δ 9.13 (s, 1H), 8.35 (s, 1H), 8.17 (d, J=8.2 Hz, 1H), 7.45-7.39 (m, 1H), 7.36 (d, J=1.5 Hz, 1H), 6.49-6.42 (m, 2H), 5.86 (s, 1H), 4.40 (q, J=7.1 Hz, 2H), 2.73-2.59 (m, 1H), 1.95-1.84 (m, 2H), 1.80-1.59 (m, 6H), 1.43 (t, J=7.1 Hz, 3H). MS m/z 379.17 (M+H)$^+$.

Ethyl 2-amino-8-(cyclohex-1-en-1-yl)-5-oxo-5H-chromeno[2,3-b]pyridine-3-carboxylate (254a)

Similar reaction of tripotassium phosphate (701 mg, 3.3 mmol) in water (1.35 mL), compound 251 (200 mg, 0.55 mmol), 2-(cyclohex-1-en-1-yl)-4,4,5,5-tetramethyl-1,3,2-dioxaborolane (143 mg, 0.69 mmol), triphenylphosphine (72.2 mg, 0.28 mmol), Pd(OAc)$_2$ (12.4 mg, 0.06 mmol) and p-dioxane (13.5 mL) was carried out for 1.5 h. The same workup gave 254a (190 mg, 95%) as a white solid. $^1$H NMR (400 MHz, chloroform-d) δ 9.14 (s, 1H), 8.35 (s, 1H), 8.17 (d, J=8.9 Hz, 1H), 7.47-7.44 (m, 1H), 7.44 (s, 1H), 6.48-6.33 (m, 1H), 5.85 (s, 1H), 4.40 (q, J=7.1 Hz, 2H), 2.52-2.40 (m, 2H), 2.28 (q, J=2.8 Hz, 2H), 1.88-1.79 (m, 2H), 1.76-1.64 (m, 2H), 1.44 (t, J=7.1 Hz, 3H). MS m/z 365.15 (M+H)$^+$.

2-Amino-5-oxo-8-(prop-1-en-2-yl)-5H-chromeno[2,3-b]pyridine-3-carboxylic acid (252b)

To a suspension of 252a (50 mg, 0.15 mmol) in ethanol (8 mL) and water (1.0 mL) was added 1 N aq NaOH (1.0 mL). The mixture was stirred for 3 h at 50° C. and concentrated to a solid that was diluted with water (20 mL). The suspension was acidified with 1N aq HCl to pH 3-4. The precipitated solids were stirred at room temperature overnight, stored at room temperature for 2 h, collected, washed with water, and dried to give 252b (43 mg, 94%) as a solid. $^1$H NMR (400 MHz, DMSO-d$_6$) δ 13.48 (s, 1H), 8.78 (s, 1H), 8.32 (s, 1H), 8.25 (s, 1H), 8.04 (d, J=8.2 Hz, 1H), 7.65 (d, J=1.6 Hz, 1H), 7.63 (dd, J=8.4, 1.6 Hz, 1H), 5.72 (s, 1H), 5.35 (s, 1H), 2.19 (s, 3H). MS m/z 297.09 (M+H)$^+$.

(E)-2-Amino-8-(2-cyclopentylvinyl)-5-oxo-5H-chromeno[2,3-b]pyridine-3-carboxylic acid (253b)

Similar reaction of compound 253a (55 mg, 0.15 mmol) and 1N aq NaOH (1.0 mL) in ethanol (8 mL) and water (1.0 mL) followed by workup gave 253b (45 mg, 88%) as a solid. $^1$H NMR (400 MHz, DMSO-d$_6$) δ 13.46 (s, 1H), 8.77 (s, 1H), 8.30 (s, 1H), 8.23 (s, 1H), 7.99 (d, J=8.2 Hz, 1H), 7.56 (d, J=1.5 Hz, 1H), 7.53 (d, J=8.3 Hz, 1H), 6.64 (dd, J=15.9, 7.5 Hz, 1H), 6.55 (d, J=15.9 Hz, 1H), 2.65 (q, J=7.6 Hz, 1H), 1.84 (d, J=10.7 Hz, 2H), 1.74-1.55 (m, 4H), 1.43 (q, J=10.7, 9.1 Hz, 2H). MS m/z 351.13 (M+H)$^+$.

2-Amino-8-(cyclohex-1-en-1-yl)-5-oxo-5H-chromeno[2,3-b]pyridine-3-carboxylic acid (254b)

Similar reaction of compound 254a (55 mg, 0.15 mmol) and 1N aq NaOH (1.0 mL) in ethanol (8 mL) and water (1.0 mL) followed by workup gave 254b (42 mg, 83%) as a solid. $^1$H NMR (400 MHz, DMSO-$d_6$) δ 13.46 (s, 1H), 8.77 (s, 1H), 8.29 (s, 1H), 8.24 (s, 1H), 7.99 (d, J=8.2 Hz, 1H), 7.54 (d, J=1.7 Hz, 1H), 7.52 (s, 1H), 6.49 (s, 1H), 3.38-3.30 (m, 1H), 2.47-2.36 (m, 2H), 2.31-2.17 (m, 2H), 1.82-1.70 (m, 2H), 1.62 (t, J=5.9 Hz, 2H). MS m/z 337.1183 (M+H)$^+$.

Ethyl 2-amino-8-isopropyl-5-oxo-5H-chromeno[2,3-b]pyridine-3-carboxylate (255)

A flask with a solution of compound 252a (105 mg, 0.32 mmol) in dichloromethane (25 mL) and ethanol (50 mL) was purged with nitrogen and 10% palladium on carbon (80 mg) was added. The mixture was purged with nitrogen and hydrogen, and hydrogenated at 47 PSI using a Parr shaker at room temperature for 18 h. The mixture was filtered over celite and concentrated to a solid that was triturated with a small amount of ethanol and dried to leave 255 (81 mg, 77%) as a white solid. $^1$H NMR (400 MHz, chloroform-d) δ 9.15 (d, J=0.8 Hz, 1H), 8.35 (s, 1H), 8.19 (d, J=8.2 Hz, 1H), 7.33 (d, J=1.6 Hz, 1H), 7.31-7.27 (m, 1H), 5.93 (s, 1H), 4.40 (qd, J=7.1, 0.7 Hz, 2H), 3.06 (p, J=6.9 Hz, 1H), 1.44 (td, J=7.1, 0.8 Hz, 3H), 1.32 (dd, J=6.9, 0.8 Hz, 6H). MS m/z 327.13 (M+H)$^+$.

Ethyl 2-amino-8-(2-cyclopentylethyl)-5-oxo-5H-chromeno[2,3-b]pyridine-3-carboxylate (256)

Similar reaction of compound 253a (134 mg, 0.35 mmol) in dichloromethane (25 mL) and ethanol (50 mL) over 10% palladium on carbon (80 mg) gave 256 (96 mg, 71%) as a white solid. $^1$H NMR (400 MHz, chloroform-d) δ 9.14 (s, 1H), 8.35 (s, 1H), 8.16 (d, J=8.1 Hz, 1H), 7.29 (d, J=1.5 Hz, 1H), 7.23 (dd, J=8.1, 1.5 Hz, 1H), 5.94 (s, 1H), 4.40 (q, J=7.1 Hz, 2H), 2.81-2.71 (m, 2H), 1.79 (d, J=6.1 Hz, 3H), 1.73-1.58 (m, 4H), 1.53 (dq, J=8.7, 3.8 Hz, 2H), 1.14 (d, J=8.5 Hz, 2H). MS m/z 381.18 (M+H)$^+$.

Ethyl 2-amino-8-cyclohexyl-5-oxo-5H-chromeno[2,3-b]pyridine-3-carboxylate (257)

Similar reaction of compound 254a (135 mg, 0.37 mmol) in dichloromethane (25 mL) and ethanol (50 mL) over 10% palladium on carbon (80 mg) gave 257 (116 mg, 85%) as a white solid. $^1$H NMR (400 MHz, chloroform-d) δ 9.14 (s, 1H), 8.34 (s, 1H), 8.17 (d, J=8.1 Hz, 1H), 7.31 (d, J=1.6 Hz, 1H), 7.29-7.23 (m, 1H), 5.87 (s, 1H), 4.40 (q, J=7.1 Hz, 2H), 2.65 (t, J=10.6 Hz, 1H), 1.98-1.84 (m, 4H), 1.79 (d, J=12.9 Hz, 1H), 1.53-1.36 (m, 7H), 1.36-1.22 (m, 1H). MS m/z 367.17 (M+H)$^+$.

2-Amino-8-isopropyl-5-oxo-5H-chromeno[2,3-b]pyridine-3-carboxylic acid (258)

To a suspension of compound 255 (81 mg, 0.25 mmol) in ethanol (15 mL) and water (1.5 mL) was added 1N aq NaOH (1.5 mL). The mixture was stirred for 1 h at 50° C. and filtered. The filtrate was concentrated to a solid that was diluted with water (20 mL) and acidified with 1N aq HCl to pH 3-4. The precipitated solids were stirred at room temperature overnight, stored at room temperature for 2 h, collected, washed with water, and dried to give 258 (58 mg, 78%) as a white solid. $^1$H NMR (400 MHz, DMSO-$d_6$) δ 13.46 (s, 1H), 8.78 (s, 1H), 8.30 (s, 1H), 8.23 (s, 1H), 8.01 (d, J=8.1 Hz, 1H), 7.46 (d, J=1.6 Hz, 1H), 7.41-7.31 (m, 1H), 3.07 (p, J=6.9 Hz, 1H), 1.27 (d, J=6.9 Hz, 6H). MS m/z 299.10 (M+H)$^+$.

2-Amino-8-(2-cyclopentylethyl)-5-oxo-5H-chromeno[2,3-b]pyridine-3-carboxylic acid (259)

Similar reaction of compound 256 (96 mg, 0.25 mmol) and 1N aq NaOH (3.0 mL) in ethanol (24 mL) and water (3.0 mL) gave 259 (84 mg, 94%) as a solid. $^1$H NMR (400 MHz, DMSO-$d_6$) δ 13.46 (s, 1H), 8.78 (s, 1H), 8.29 (s, 1H), 8.23 (s, 1H), 7.99 (d, J=8.0 Hz, 1H), 7.42 (s, 1H), 7.31 (d, J=8.1 Hz, 1H), 2.74 (t, J=7.8 Hz, 2H), 1.75 (m, 4H), 1.65-1.51 (m, 3H), 1.47 (d, J=5.7 Hz, 2H), 1.13 (m, 2H). MS m/z 353.15 (M+H)$^+$.

2-Amino-8-cyclohexyl-5-oxo-5H-chromeno[2,3-b]pyridine-3-carboxylic acid (260)

Similar reaction of compound 257 (135 mg, 0.37 mmol) and 1N aq NaOH (3.0 mL) in ethanol (24 mL) and water (3.0 mL) gave 260 (102 mg, 82%) as a solid. $^1$H NMR (400 MHz, DMSO-$d_6$) δ 13.44 (s, 1H), 8.78 (s, 1H), 8.28 (s, 1H), 8.25 (s, 1H), 8.00 (d, J=8.1 Hz, 1H), 7.43 (d, J=1.5 Hz, 1H), 7.35 (dd, J=8.2, 1.6 Hz, 1H), 2.69 (t, J=11.4 Hz, 1H), 1.82 (m, 4H), 1.72 (m, 1H), 1.39 (m, 5H). MS m/z 339.13 (M+H)$^+$.

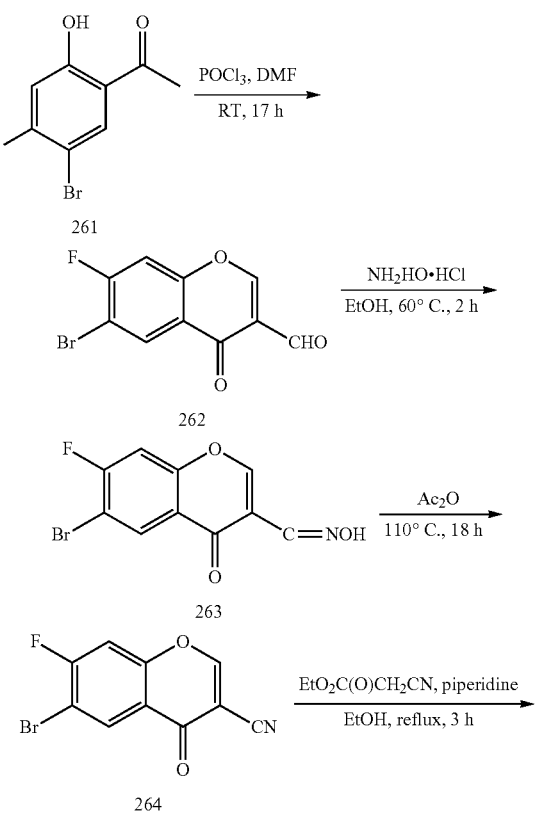

Scheme 31

171
-continued

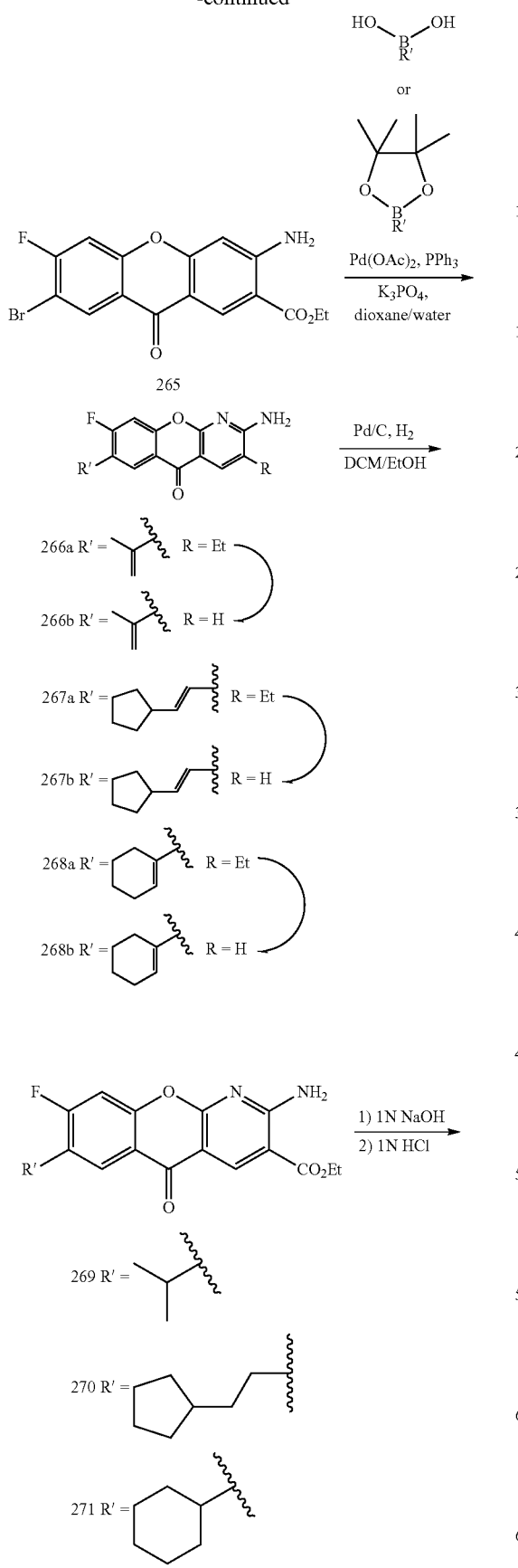

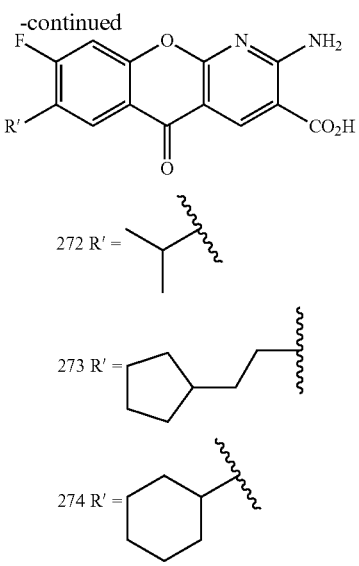

6-Bromo-7-fluoro-4-oxo-4H-chromene-3-carbaldehyde (262)

POCl$_3$ (3.64 g, 23.8 mmol) was added slowly over 10 min to a well stirred and cooled (0-5° C.) solution of 1-(5-bromo-4-fluoro-2-hydroxyphenyl)ethan-1-one (261; 1.0 g, 4.29 mmol) in N,N-dimethylformamide (7.0 mL). After stirring at room temperature for 17 h, the suspension was poured into crushed ice and maintained at 0° C. for 1 h. The precipitated solids were collected, washed with water, and dried to give 262 (0.85 g, 73%) as a light orange solid. $^1$H NMR (400 MHz, chloroform-d) δ 10.35 (s, 1H), 8.53 (d, J=7.1 Hz, 2H), 7.33 (d, J=7.9 Hz, 1H). MS m/z 270.94, 272.94 (M+1)$^+$.

6-Bromo-7-fluoro-4-oxo-4H-chromene-3-carbaldehyde oxime (263)

A suspension of compound 262 (850 mg, 3.14 mmol), hydroxylamine hydrochloride (262 mg, 3.76 mmol) and ethanol (16 mL) was stirred at 60° C. for 2 h. The mixture was stored at 0° C. for 30 min and the precipitated solids were collected, washed with ethanol, and dried to leave 263 (593 mg, 66%) as an off-white solid. $^1$H NMR (400 MHz, DMSO-d$_6$) δ 11.50 (s, 1H), 8.72 (d, J=0.8 Hz, 1H), 8.32 (d, J=7.7 Hz, 1H), 8.04 (d, J=0.8 Hz, 1H), 7.95 (d, J=9.1 Hz, 1H). MS m/z 285.95, 287.95 (M+H)$^+$.

6-Bromo-7-fluoro-4-oxo-4H-chromene-3-carbonitrile (264)

A suspension of compound 263 (590 mg, 2.06 mmol) in acetic anhydride (20 mL) was stirred at 110° C. for 18 h. The mixture was concentrated to leave 264 (0.52 g, 94%) as an off-white solid. $^1$H NMR (500 MHz, chloroform-d) δ 8.50 (d, J=7.4 Hz, 1H), 8.40 (s, 1H), 7.34 (d, J=7.8 Hz, 1H). MS m/z 267.94, 269.94 (M+H)$^+$.

Ethyl 2-amino-7-bromo-8-fluoro-5-oxo-5H-chromeno[2,3-b]pyridine-3-carboxylate (265)

A mixture of compound 264 (0.52 g, 1.94 mmol), ethyl cyanoacetate (0.285 g, 2.52 mmol), piperidine (0.168 g, 1.98 mmol) and ethanol (15 mL) was heated at reflux for 3 h. After standing overnight at room temperature, the precipitated solids were collected, washed with ethanol, and dried to afford 265 (666 mg, 90%) as an off-white solid. $^1$H NMR (400 MHz, chloroform-d) δ 9.13 (s, 1H), 8.49 (d, J=7.6 Hz, 1H), 8.44 (s, 1H), 7.27 (d, J=7.6 Hz, 1H), 5.90 (s, 1H), 4.41 (q, J=7.1 Hz, 2H), 1.44 (t, J=7.1 Hz, 3H). MS m/z 380.99, 382.99 (M+H)$^+$.

Ethyl 2-amino-8-fluoro-5-oxo-7-(prop-1-en-2-yl)-5H-chromeno[2,3-b]pyridine-3-carboxylate (266a)

A solution of tripotassium phosphate (668 mg, 3.15 mmol) in water (1.5 mL) was added to a suspension of compound 265 (200 mg, 0.53 mmol), 4,4,5,5-tetramethyl-2-(prop-1-en-2-yl)-1,3,2-dioxaborolane (212 mg, 1.26 mmol), triphenylphosphine (68.8 mg, 0.26 mmol), Pd(OAc)$_2$ (15.3 mg, 0.07 mmol) in p-dioxane (15 mL) under nitrogen, and the mixture was heated at 100-105° C. for 2 h. The cooled mixture was diluted with water and extracted with dichloromethane (3×). The combined organic phases were dried (Na$_2$SO$_4$), concentrated to a solid that was triturated with a small amount of ethanol, and dried to give 266a (170 mg, 95%) as a white solid. $^1$H NMR (400 MHz, chloroform-d) δ 9.14 (s, 1H), 8.39 (s, 1H), 8.22 (d, J=8.5 Hz, 1H), 7.18 (d, J=10.9 Hz, 1H), 5.86 (s, 1H), 5.39-5.30 (m, 2H), 4.41 (q, J=7.1 Hz, 2H), 2.20 (q, J=1.2 Hz, 3H), 1.44 (t, J=7.1 Hz, 3H). MS m/z 343.11 (M+H)$^+$.

Ethyl (E)-2-amino-7-(2-cyclopentylvinyl)-8-fluoro-5-oxo-5H-chromeno[2,3-b]pyridine-3-carboxylate (267a)

Similar reaction of tripotassium phosphate (668 mg, 3.15 mmol) in water (1.3 mL), compound 265 (200 mg, 0.53 mmol), (E)-(2-cyclopentylvinyl)boronic acid (92 mg, 0.66 mmol), triphenylphosphine (68.8 mg, 0.26 mmol), Pd(OAc)$_2$ (11.8 mg, 0.05 mmol) and p-dioxane (13 mL) was carried out for 1.5 h. The same workup gave 267a (189 mg, 91%) as a white solid. $^1$H NMR (500 MHz, chloroform-d) δ 9.14 (s, 1H), 8.38 (s, 1H), 8.34 (d, J=8.4 Hz, 1H), 7.14 (d, J=10.4 Hz, 1H), 6.53 (d, J=16.0 Hz, 1H), 6.45 (dd, J=15.9, 7.5 Hz, 1H), 5.84 (s, 1H), 4.41 (q, J=7.1 Hz, 2H), 2.66 (h, J=8.0 Hz, 1H), 1.90 (dd, J=11.6, 4.5 Hz, 2H), 1.74 (tt, J=9.0, 5.0 Hz, 2H), 1.68-1.59 (m, 2H), 1.44 (t, J=7.1 Hz, 5H). MS m/z 397.16 (M+H)$^+$.

Ethyl 2-amino-7-(cyclohex-1-en-1-yl)-8-fluoro-5-oxo-5H-chromeno[2,3-b]pyridine-3-carboxylate (268a)

Similar reaction of tripotassium phosphate (668 mg, 3.15 mmol) in water (1.3 mL), compound 265 (200 mg, 0.53 mmol), 2-(cyclohex-1-en-1-yl)-4,4,5,5-tetramethyl-1,3,2-dioxaborolane (136 mg, 0.66 mmol), triphenylphosphine (68.8 mg, 0.26 mmol), Pd(OAc)$_2$ (11.8 mg, 0.05 mmol) and p-dioxane (13 mL) was carried out for 1.5 h. The same workup gave 268a (180 mg, 90%) as a white solid. $^1$H NMR (400 MHz, chloroform-d) δ 9.14 (s, 1H), 8.38 (s, 1H), 8.14 (d, J=8.4 Hz, 1H), 7.15 (d, J=10.8 Hz, 1H), 6.05 (s, 1H), 5.84 (s, 1H), 4.41 (q, J=7.2 Hz, 2H), 2.40 (s, 2H), 2.24 (dd, J=6.5, 3.1 Hz, 2H), 1.82-1.76 (m, 2H), 1.70 (p, J=5.8 Hz, 2H), 1.44 (t, J=7.1 Hz, 3H). MS m/z 383.14 (M+H)$^+$.

2-Amino-8-fluoro-5-oxo-7-(prop-1-en-2-yl)-5H-chromeno[2,3-b]pyridine-3-carboxylic acid (266b)

To a suspension of compound 266a (67 mg, 0.20 mmol) in ethanol (12 mL) and water (1.5 mL) was added 1N aq NaOH (1.5 mL). The mixture was stirred for 3.5 h at 50° C. and concentrated to a solid that was diluted with water (25 mL) and acidified with 1N aq HCl to pH 3-4. The precipitated solids were stirred at room temperature for 18 h, stored at room temperature for 24 h, collected, washed with water, and dried to give 266b (53 mg, 86%) as a solid. $^1$H NMR (400 MHz, DMSO-d$_6$) δ 8.75 (s, 1H), 8.33 (s, 2H), 8.01 (d, J=8.5 Hz, 1H), 7.57 (d, J=11.6 Hz, 1H), 5.36 (d, J=12.1 Hz, 2H), 2.15 (s, 3H). MS m/z 315.08 (M+H)$^+$.

(E)-2-Amino-7-(2-cyclopentylvinyl)-8-fluoro-5-oxo-5H-chromeno[2,3-b]pyridine-3-carboxylic acid (267b)

Similar reaction of 267a (94 mg, 0.24 mmol) and 1N aq NaOH (3 mL) in ethanol (24 mL) and water (3 mL) gave 267b (74 mg, 85%) as a solid. $^1$H NMR (400 MHz, DMSO-d$_6$) δ 13.51 (s, 1H), 8.78 (s, 1H), 8.33 (s, 2H), 8.20 (d, J=8.5 Hz, 1H), 7.57 (d, J=11.1 Hz, 1H), 6.59-6.44 (m, 2H), 2.72-2.61 (m, 1H), 1.83 (s, 2H), 1.74-1.64 (m, 2H), 1.65-1.52 (m, 2H), 1.49-1.35 (m, 2H). MS m/z 369.12 (M+H)$^+$.

2-Amino-7-(cyclohex-1-en-1-yl)-8-fluoro-5-oxo-5H-chromeno[2,3-b]pyridine-3-carboxylic acid (268b)

Similar reaction of compound 268a (72 mg, 0.19 mmol) and 1N aq NaOH (3 mL) in ethanol (24 mL) and water (3 mL) gave 268b (48 mg, 72%) as a solid. $^1$H NMR (400 MHz, DMSO-d$_6$) δ 13.48 (s, 1H), 8.74 (s, 1H), 8.31 (s, 1H), 8.25 (s, 1H), 7.90 (d, J=8.5 Hz, 1H), 7.50 (d, J=11.4 Hz, 1H), 6.02 (s, 1H), 2.34 (s, 2H), 2.26-2.10 (m, 2H), 1.81-1.69 (m, 2H), 1.67-1.50 (m, 2H). MS m/z 355.11 (M+H)$^+$.

Ethyl 2-amino-8-fluoro-7-isopropyl-5-oxo-5H-chromeno[2,3-b]pyridine-3-carboxylate (269)

A flask with a solution of compound 266a (100 mg, 0.29 mmol) in dichloromethane (15 mL) was purged with nitrogen, and 10% palladium on carbon (100 mg) was added. The mixture was purged with nitrogen and hydrogen, and then hydrogenated at room temperature for 17 h. The mixture was filtered over celite and the filtrate was concentrated to a solid that was washed with a small amount of ethanol to leave 269 (61 mg, 60%) as a white solid. $^1$H NMR (400 MHz, chloroform-d) δ 9.14 (s, 1H), 8.37 (s, 1H), 8.16 (d, J=8.3 Hz, 1H), 7.14 (d, J=10.4 Hz, 1H), 5.86 (s, 1H), 4.41 (q, J=7.1 Hz, 2H), 3.30 (p, J=6.8 Hz, 1H), 1.44 (t, J=7.1 Hz, 3H), 1.33 (d, J=6.9 Hz, 6H). MS m/z 345.13 (M+H)$^+$.

Ethyl 2-amino-7-(2-cyclopentylethyl)-8-fluoro-5-oxo-5H-chromeno[2,3-b]pyridine-3-carboxylate (270)

Similar reaction of compound 267a (100 mg, 0.25 mmol) in dichloromethane (25 mL) and ethanol (25 mL) over 10% palladium on carbon (85 mg) for 19 h gave 270 (75 mg, 75%) as a white solid. $^1$H NMR (400 MHz, chloroform-d) δ 9.14 (s, 1H), 8.37 (s, 1H), 8.11 (d, J=8.3 Hz, 1H), 7.14 (d, J=9.9 Hz, 1H), 5.85 (s, 1H), 4.41 (q, J=7.1 Hz, 2H), 2.79-2.70 (m, 2H), 1.82 (s, 3H), 1.73-1.60 (m, 2H), 1.55 (d, J=17.9 Hz, 4H), 1.44 (t, J=7.1 Hz, 3H), 1.16 (s, 2H). MS m/z 399.17 (M+H)$^+$.

Ethyl 2-amino-7-cyclohexyl-8-fluoro-5-oxo-5H-chromeno[2,3-b]pyridine-3-carboxylate (271)

Similar reaction of compound 268a (100 mg, 0.26 mmol) in dichloromethane (25 mL) and ethanol (25 mL) over 10% palladium on carbon (85 mg) for 19 h gave 271 (67 mg, 67%) as a white solid. $^1$H NMR (400 MHz, chloroform-d) δ 9.14 (s, 1H), 8.37 (s, 1H), 8.15 (d, J=8.2 Hz, 1H), 7.14 (d, J=10.3 Hz, 1H), 5.84 (s, 1H), 4.41 (q, J=7.1 Hz, 2H), 2.91 (t, J=11.8 Hz, 1H), 1.90 (d, J=10.4 Hz, 4H), 1.79 (d, J=13.2 Hz, 1H), 1.57 (s, 4H), 1.44 (t, J=7.1 Hz, 3H), 1.37-1.20 (m, 1H). MS m/z 385.16 (M+H)$^+$.

2-Amino-8-fluoro-7-isopropyl-5-oxo-5H-chromeno[2,3-b]pyridine-3-carboxylic acid (272)

To a suspension of 269 (61 mg, 0.18 mmol) in ethanol (12 mL) and water (1.5 mL) was added 1N aq NaOH (1.5 mL). The mixture was stirred for 2 h at 50° C. and filtered. The filtrate was concentrated, diluted with water (30 mL) and acidified with 1N aq HCl to pH 3-4. The precipitated solids were stirred at room temperature for 18 h, stored at room temperature for 2 h, collected, washed with water, and dried to give 272 (43 mg, 77%) as a white solid. $^1$H NMR (400 MHz, DMSO-d$_6$) δ 13.50 (s, 1H), 8.77 (s, 1H), 8.31 (s, 1H), 8.25 (s, 1H), 8.00 (d, J=8.4 Hz, 1H), 7.51 (d, J=10.8 Hz, 1H), 3.30-3.10 (m, 1H), 1.27 (d, J=6.8 Hz, 6H). MS m/z 317.10 (M+H)$^+$.

2-Amino-7-(2-cyclopentylethyl)-8-fluoro-5-oxo-5H-chromeno[2,3-b]pyridine-3-carboxylic acid (273)

Similar reaction of compound 270 (71 mg, 0.18 mmol) and 1N aq NaOH (3 mL) in ethanol (24 mL) and water (3 mL) gave 273 (45 mg, 68%) as a solid. $^1$H NMR (400 MHz, DMSO-d$_6$) δ 13.48 (s, 1H), 8.77 (s, 1H), 8.31 (s, 1H), 8.24 (s, 1H), 7.98 (d, J=8.5 Hz, 1H), 7.51 (d, J=10.5 Hz, 1H), 2.71 (t, J=7.9 Hz, 2H), 1.76 (m, 3H), 1.65-1.50 (m, 4H), 1.47 (m, 2H), 1.13 (m, 2H). MS m/z 371.14 (M+H)$^+$.

2-Amino-7-cyclohexyl-8-fluoro-5-oxo-5H-chromeno[2,3-b]pyridine-3-carboxylic acid (274)

Similar reaction of compound 271 (62 mg, 0.16 mmol) and 1N aq NaOH (3 mL) in ethanol (24 mL) and water (3 mL) gave 274 (52 mg, 90%) as a solid. $^1$H NMR (400 MHz, DMSO-d$_6$) δ 13.49 (s, 1H), 8.77 (s, 1H), 8.31 (s, 1H), 8.25 (s, 1H), 7.97 (d, J=8.2 Hz, 1H), 7.52 (d, J=10.8 Hz, 1H), 2.85 (t, J=11.6 Hz, 1H), 1.82 (d, J=11.2 Hz, 4H), 1.72 (d, J=12.4 Hz, 1H), 1.40 (ddq, J=50.1, 24.5, 12.2 Hz, 5H). MS m/z 357.12 (M+H)$^+$.

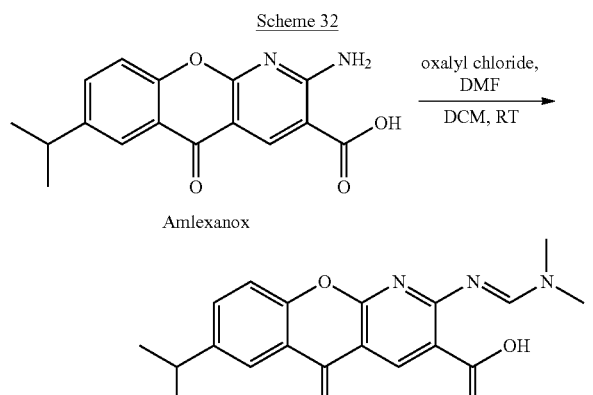

(E)-2-(((Dimethylamino)methylene)amino)-7-isopropyl-5-oxo-5H-chromeno[2,3-b]pyridine-3-carboxylic acid (275)

To a stirred mixture of amlexanox (100 mg, 0.34 mmol) and N,N-dimethylformamide (24.5 mg, 0.34 mmol) in anhydrous dichloromethane (10 mL) was added oxalyl chloride (128 mg, 1.0 mmol). The resulting suspension mixture was stirred at room temperature for 16 h. The mixture was concentrated to afford 275 (105 mg, 89%) as a white solid. $^1$H NMR (400 MHz, DMSO-d$_6$) δ 9.37 (s, 1H), 8.98 (d, J=1.0 Hz, 1H), 7.96 (d, J=2.2 Hz, 1H), 7.82 (dd, J=8.7, 2.3 Hz, 1H), 7.60 (d, J=8.6 Hz, 1H), 3.56 (s, 3H), 3.32 (s, 3H), 3.08 (p, J=6.9 Hz, 1H), 1.26 (d, J=6.9 Hz, 6H). MS m/z 354.0 (M+1)$^+$.

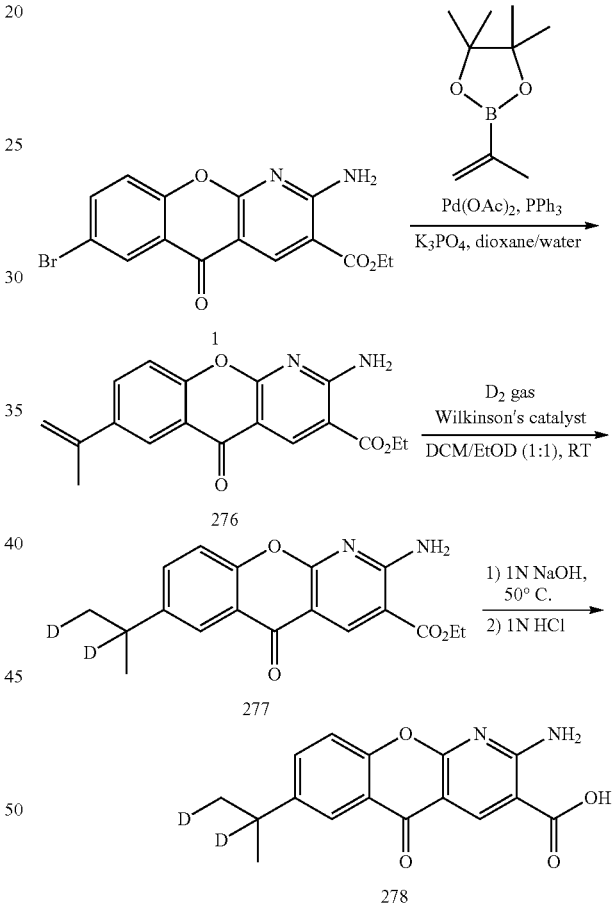

Ethyl 2-amino-5-oxo-7-(prop-1-en-2-yl)-5H-chromeno[2,3-b]pyridine-3-carboxylate (276)

A solution of tripotassium phosphate (2.63 g, 43.30 mmol) in water (6 mL) was added to a suspension of compound 1 (750 mg, 2.07 mmol), 4,4,5,5-tetramethyl-2-(prop-1-en-2-yl)-1,3,2-dioxaborolane (833 mg, 4.96 mmol), triphenylphosphine (271 mg, 1.03 mmol), and Pd(OAc)$_2$ (60.3 mg, 0.27 mmol) in p-dioxane (60 mL) under nitrogen, and the mixture was heated at 100-105° C. for 2 h. The cooled mixture was diluted with water and extracted with dichloromethane (2×). The combined organic phases were dried (Na$_2$SO$_4$), concentrated to a solid that was triturated with small amounts of ethanol and then diethyl ether, and dried to give 276 (610 mg, 91%) as a white solid. $^1$H NMR (400 MHz, chloroform-d) δ δ 9.16 (s, 1H), 8.38 (s, 1H), 8.31 (d, J=2.3 Hz, 1H), 7.86 (dd, J=8.8, 2.4 Hz, 1H), 7.47 (d, J=8.7 Hz, 1H), 5.86 (s, 1H), 5.49 (d, J=1.3 Hz, 1H), 5.23-5.18 (m, 1H), 4.41 (q, J=7.1 Hz, 2H), 2.24 (dd, J=1.5, 0.8 Hz, 3H), 1.45 (t, J=7.1 Hz, 3H). MS m/z 325.12 (M+H)$^+$.

Ethyl 2-amino-5-oxo-7-(propan-2-yl-1,2-d$_2$)-5H-chromeno[2,3-b]pyridine-3-carboxylate (277)

Wilkinson's catalyst (339 mg, 0.37 mmol) was dissolved in anhydrous dichloromethane (10 mL) and ethanol-d$_1$ (10 mL) under nitrogen in a 250-mL 3-neck flask attached with a balloon. The flask containing a clear red-brown solution was evacuated by a water aspirator and then filled with deuterium gas. The evacuation/fill procedure was repeated three times, and the mixture was then stirred under a balloon pressure for 20 min at room temperature. Then a solution of compound 276 (360 mg, 1.11 mmol) in warm 1:1 v/v dichloromethane:ethanol-d$_1$ (150 mL) was added by syringe. The resulting mixture was stirred at room temperature for 4.5 h, and concentrated to a solid that was washed with a small amount of benzene and further purified by flash silica gel chromatography (elution with 0.5-1.0% methanol in dichloromethane) to give 277 (315 mg, 86%) as a while solid. $^1$H NMR (400 MHz, chloroform-d) δ 9.16 (s, 1H), 8.34 (s, 1H, exchanges D$_2$O), 8.11 (d, J=2.3 Hz, 1H), 7.59 (dd, J=8.6, 2.3 Hz, 1H), 7.44 (d, J=8.6 Hz, 1H), 5.84 (s, 1H, exchanges D$_2$O), 4.41 (q, J=7.1 Hz, 2H), 1.44 (t, J=7.1 Hz, 3H), 1.30 (d, J=6.5 Hz, 5H). MS m/z 329.15 (M+H)$^+$.

2-Amino-5-oxo-7-(propan-2-yl-1,2-d$_2$)-5H-chromeno[2,3-b]pyridine-3-carboxylic acid (278)

To a suspension of compound 277 (460 mg, 1.4 mmol) in ethanol (80 mL) and water (10 mL) was added 1N aq NaOH (10 mL). The mixture was stirred at 50° C. for 90 min at which point TLC (5% methanol in dichloromethane) showed consumption of 277. The mixture was filtered and the filtrate was concentrated to a residue that was dissolved in water (50 mL) and acidified with 1N aq HCl to pH~3. The formed suspension was stirred at room temperature for 20 h and then stored at room temperature for 24 h. The precipitate was collected, washed with water, and dried in vacuo at 60° C. for 4 h to give 278 (385 mg, 92%) as an off-white solid. $^1$H NMR (500 MHz, DMSO-d$_6$) δ 13.45 (s, 1H), 8.80 (s, 1H), 8.25 (br s, 2H), 7.92 (d, J=2.3 Hz, 1H), 7.73 (dd, J=8.6, 2.4 Hz, 1H), 7.53 (d, J=8.6 Hz, 1H), 1.24 (d, J=8.6 Hz, 5H). MS m/z 301.12 (M+H)$^+$.

Scheme 34

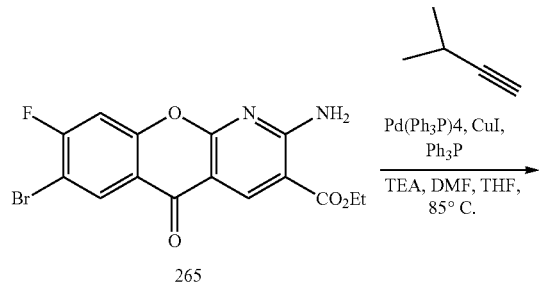

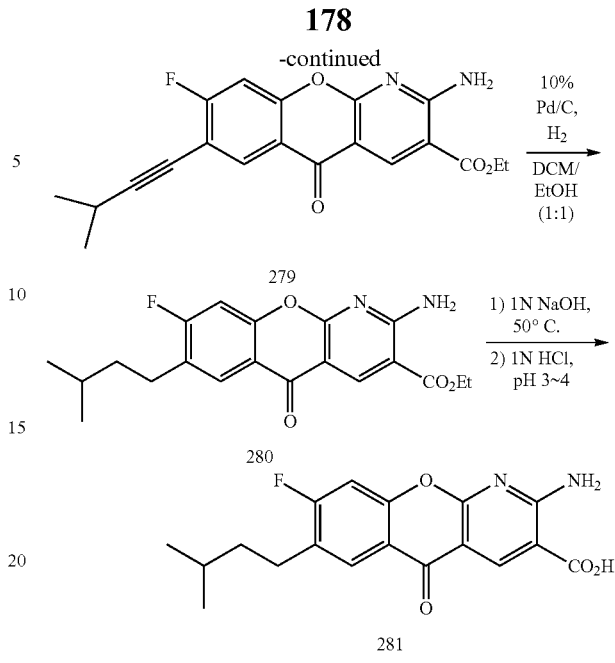

Ethyl 2-amino-8-fluoro-7-(3-methylbut-1-yn-1-yl)-5-oxo-5H-chromeno[2,3-b]pyridine-3-carboxylate (279)

A suspension of compound 265 (40 mg, 0.11 mmol), 3-methylbut-1-yne (43 mg, 0.63 mmol), and triphenylphosphine (2.8 mg, 10.5 umol), N,N-dimethylformamide (2 mL), tetrahydrofuran (2 mL), and triethylamine (2 mL) in a sealed tube was degassed with nitrogen. Then Pd(PPh$_3$)$_4$ (6.1 mg, 5.3 μmol) and CuI (2.0 mg, 10.5 μmol) were added under an atmosphere of nitrogen and the suspension was heated at 85° C. for 18 h. The mixture was diluted with water and extracted with dichloromethane (2×). The organic phases were dried (Na$_2$SO$_4$) and concentrated to leave a solid that was triturated in ethanol and dried to give 279 (26 mg, 67%) as a solid. $^1$H NMR (500 MHz, chloroform-d) δ 9.12 (s, 1H), 8.40 (s, 1H), 8.32 (d, J=7.8 Hz, 1H), 7.17 (d, J=9.2 Hz, 1H), 5.89 (s, 1H), 4.40 (q, J=7.1 Hz, 2H), 2.83 (q, J=6.9 Hz, 1H), 1.43 (t, J=7.2 Hz, 3H), 1.35-1.26 (m, 6H). MS m/z 369.12 (M+1).

Ethyl 2-amino-8-fluoro-7-isopentyl-5-oxo-5H-chromeno[2,3-b]pyridine-3-carboxylate (280)

A solution of compound 279 (26 mg, 0.07 mmol) in dichloromethane (10 mL) and ethanol (10 mL) was purged with nitrogen and 10% palladium on carbon (14 mg) was added. The flask was then purged with nitrogen and hydrogen and hydrogenated under balloon pressure for 19 h. The mixture was filtered over celite concentrated to a solid that was triturated in ethanol and dried to give 280 (18 mg, 68%) as a white solid. $^1$H NMR (400 MHz, chloroform-d) δ 9.13 (d, J=2.0 Hz, 1H), 8.37 (s, 1H), 8.18-8.04 (m, 1H), 7.14 (dd, J=9.9, 2.0 Hz, 1H), 5.86 (s, 1H), 4.47-4.33 (m, 2H), 2.77-2.68 (m, 2H), 1.68-1.57 (m, 3H), 1.44 (td, J=7.1, 2.0 Hz, 3H), 0.97 (dd, J=6.5, 2.0 Hz, 6H). MS m/z 373.16 (M+H)$^+$.

2-Amino-8-fluoro-7-isopentyl-5-oxo-5H-chromeno[2,3-b]pyridine-3-carboxylic acid (281)

To a suspension of compound 280 (18 mg, 0.05 mmol) in ethanol (8 mL) and water (1.0 mL) was added 1N aq NaOH (1.0 mL). The mixture was stirred for 1.5 h at 50° C. and filtered. The filtrate was concentrated, diluted with water (10 mL) and acidified with 1N aq HCl to pH 3-4. The precipitated solids were stirred at room temperature for 24 h, stored at room temperature for 4 h, collected, washed with water, and dried to give 281 (12 mg, 72%) as a solid. $^1$H NMR (500 MHz, DMSO-d$_6$) δ 13.47 (s, 1H), 8.77 (s, 1H), 8.27 (d, J=22.6 Hz, 2H), 7.98 (d, J=8.3 Hz, 1H), 7.51 (d, J=10.3 Hz, 1H), 2.71 (d, J=8.5 Hz, 2H), 1.64-1.54 (m, 1H), 1.48 (d, J=7.7 Hz, 2H), 0.93 (d, J=6.5 Hz, 6H). MS m/z 345.12 (M+H)$^+$.

Example 5

Additional Exemplary Compounds

The following are exemplary compounds within the scope herein, organized according to the synthesis schemes useful for their synthesis.

Scheme 22:
2-Amino-7-cyclobutyl-3-(hydroxymethyl)-5H-chromeno[2,3-b]pyridin-5-one
2-Amino-7-cyclopentyl-3-(hydroxymethyl)-5H-chromeno[2,3-b]pyridin-5-one
2-Amino-7-cyclohexyl-3-(hydroxymethyl)-5H-chromeno[2,3-b]pyridin-5-one Schemes 16, 20, 21, 22, 23, 27:
7-Isopropyl-2-(methylamino)-5-oxo-5H-pyrano[2,3-b:6,5-b']dipyridine-3-carboxylic acid
2-Amino-7-(cyclopent-1-en-1-yl)-5-oxo-5H-pyrano[2,3-b:6,5-b']dipyridine-3-carboxylic acid
2-Amino-7-cyclopentyl-5-oxo-5H-pyrano[2,3-b:6,5-b']dipyridine-3-carboxylic acid
7-Cyclopentyl-2-(methylamino)-5-oxo-5H-pyrano[2,3-b:6,5-b']dipyridine-3-carboxylic acid
2-Amino-7-(cyclohex-1-en-1-yl)-5-oxo-5H-pyrano[2,3-b:6,5-b']dipyridine-3-carboxylic acid
2-Amino-7-cyclohexyl-5-oxo-5H-pyrano[2,3-b:6,5-b']dipyridine-3-carboxylic acid
7-Cyclohexyl-2-(methylamino)-5-oxo-5H-pyrano[2,3-b:6,5-b']dipyridine-3-carboxylic acid
(E)-2-Amino-7-(2-cyclohexylvinyl)-5-oxo-5H-pyrano[2,3-b:6,5-b']dipyridine-3-carboxylic acid
2-Amino-7-(2-cyclohexyl ethyl)-5-oxo-5H-pyrano[2,3-b:6,5-b']dipyridine-3-carboxylic acid
2-Amino-7-(2-cyclopentylethyl)-5-oxo-5H-pyrano[2,3-b:6,5-b']dipyridine-3-carboxylic acid
2-Amino-7-(2-morpholinoethyl)-5-oxo-5H-pyrano[2,3-b:6,5-b']dipyridine-3-carboxylic acid
2-Amino-7-cyclobutyl-5-oxo-5H-pyrano[2,3-b:6,5-b']dipyridine-3-carboxylic acid
7-Cyclobutyl-2-(methylamino)-5-oxo-5H-pyrano[2,3-b:6,5-b']dipyridine-3-carboxylic acid
2-Amino-7-(oxetan-3-yl)-5-oxo-5H-pyrano[2,3-b:6,5-b']dipyridine-3-carboxylic acid
2-Amino-7-(azetidin-3-yl)-5-oxo-5H-pyrano[2,3-b:6,5-b']dipyridine-3-carboxylic acid
2-Amino-7-isopropyl-3-(1H-tetrazol-5-yl)-5H-pyrano[2,3-b:6,5-b']dipyridin-5-one
2-Amino-7-cyclopentyl-3-(1H-tetrazol-5-yl)-5H-pyrano[2,3-b:6,5-b']dipyridin-5-one
2-Amino-7-cyclohexyl-3-(1H-tetrazol-5-yl)-5H-pyrano[2,3-b:6,5-b']dipyridin-5-one
2-Amino-3-(hydroxymethyl)-7-isopropyl-5H-pyrano[2,3-b:6,5-b']dipyridin-5-one
2-Amino-7-cyclobutyl-3-(hydroxymethyl)-5H-pyrano[2,3-b:6,5-b']dipyridin-5-one
2-Amino-7-cyclopentyl-3-(hydroxymethyl)-5H-pyrano[2,3-b:6,5-b']dipyridin-5-one
2-Amino-7-cyclohexyl-3-(hydroxymethyl)-5H-pyrano[2,3-b:6,5-b']dipyridin-5-one Schemes 16, 20, 21, 22, 24, 27:
7-Isopropyl-2-(methylamino)-5-oxo-5H-pyrano[2,3-b:6,5-c']dipyridine-3-carboxylic acid
2-Amino-7-(cyclopent-1-en-1-yl)-5-oxo-5H-pyrano[2,3-b:6,5-c']dipyridine-3-carboxylic acid
2-Amino-7-cyclopentyl-5-oxo-5H-pyrano[2,3-b:6,5-c']dipyridine-3-carboxylic acid
7-Cyclopentyl-2-(methylamino)-5-oxo-5H-pyrano[2,3-b:6,5-c']dipyridine-3-carboxylic acid
2-Amino-7-(cyclohex-1-en-1-yl)-5-oxo-5H-pyrano[2,3-b:6,5-c']dipyridine-3-carboxylic acid
2-Amino-7-cyclohexyl-5-oxo-5H-pyrano[2,3-b:6,5-c']dipyridine-3-carboxylic acid
7-Cyclohexyl-2-(methylamino)-5-oxo-5H-pyrano[2,3-b:6,5-c']dipyridine-3-carboxylic acid
(E)-2-Amino-7-(2-cyclohexylvinyl)-5-oxo-5H-pyrano[2,3-b:6,5-c']dipyridine-3-carboxylic acid
2-Amino-7-(2-cyclohexyl ethyl)-5-oxo-5H-pyrano[2,3-b:6,5-c']dipyridine-3-carboxylic acid
2-Amino-7-(2-cyclopentylethyl)-5-oxo-5H-pyrano[2,3-b:6,5-c']dipyridine-3-carboxylic acid
2-Amino-7-(2-morpholinoethyl)-5-oxo-5H-pyrano[2,3-b:6,5-c']dipyridine-3-carboxylic acid
2-Amino-7-cyclobutyl-5-oxo-5H-pyrano[2,3-b:6,5-c']dipyridine-3-carboxylic acid
7-Cyclobutyl-2-(methylamino)-5-oxo-5H-pyrano[2,3-b:6,5-c']dipyridine-3-carboxylic acid
2-Amino-7-(oxetan-3-yl)-5-oxo-5H-pyrano[2,3-b:6,5-c']dipyridine-3-carboxylic acid
2-Amino-7-(azetidin-3-yl)-5-oxo-5H-pyrano[2,3-b:6,5-c']dipyridine-3-carboxylic acid
2-Amino-7-isopropyl-3-(1H-tetrazol-5-yl)-5H-pyrano[2,3-b:6,5-c']dipyridin-5-one
2-Amino-7-cyclopentyl-3-(1H-tetrazol-5-yl)-5H-pyrano[2,3-b:6,5-c']dipyridin-5-one
2-Amino-7-cyclohexyl-3-(1H-tetrazol-5-yl)-5H-pyrano[2,3-b:6,5-c']dipyridin-5-one
2-Amino-3-(hydroxymethyl)-7-isopropyl-5H-pyrano[2,3-b:6,5-c']dipyridin-5-one
2-Amino-7-cyclobutyl-3-(hydroxymethyl)-5H-pyrano[2,3-b:6,5-c']dipyridin-5-one
2-Amino-7-cyclopentyl-3-(hydroxymethyl)-5H-pyrano[2,3-b:6,5-c']dipyridin-5-one
2-Amino-7-cyclohexyl-3-(hydroxymethyl)-5H-pyrano[2,3-b:6,5-c']dipyridin-5-one Schemes 16, 20, 21, 22, 25, 27:
2-Isopropyl-7-(methylamino)-10-oxo-10H-pyrano[2,3-b:5,6-b']dipyridine-8-carboxylic acid
7-Amino-2-(cyclopent-1-en-1-yl)-10-oxo-10H-pyrano[2,3-b:5,6-b']dipyridine-8-carboxylic acid
7-Amino-2-cyclopentyl-10-oxo-10H-pyrano[2,3-b:5,6-b']dipyridine-8-carboxylic acid
2-Cyclopentyl-7-(methylamino)-10-oxo-10H-pyrano[2,3-b:5,6-b']dipyridine-8-carboxylic acid
7-Amino-2-(cyclohex-1-en-1-yl)-10-oxo-10H-pyrano[2,3-b:5,6-b']dipyridine-8-carboxylic acid
7-Amino-2-cyclohexyl-10-oxo-10H-pyrano[2,3-b:5,6-b']dipyridine-8-carboxylic acid
2-Cyclohexyl-7-(methylamino)-10-oxo-0H-pyrano[2,3-b:5,6-b']dipyridine-8-carboxylic acid
(E)-7-Amino-2-(2-cyclohexylvinyl)-10-oxo-10H-pyrano[2,3-b:5,6-b']dipyridine-8-carboxylic acid 7-Amino-2-(2-cyclohexylethyl)-10-oxo-10H-pyrano[2,3-b:5,6-b']dipyridine-8-carboxylic acid
7-Amino-2-(2-cyclopentylethyl)-10-oxo-10H-pyrano[2,3-b:5,6-b']dipyridine-8-carboxylic acid
7-Amino-2-(2-morpholinoethyl)-10-oxo-10H-pyrano[2,3-b:5,6-b']dipyridine-8-carboxylic acid
7-Amino-2-cyclobutyl-10-oxo-10H-pyrano[2,3-b:5,6-b']dipyridine-8-carboxylic acid
2-Cyclobutyl-7-(methylamino)-10-oxo-10H-pyrano[2,3-b:5,6-b']dipyridine-8-carboxylic acid
7-Amino-2-(oxetan-3-yl)-10-oxo-10H-pyrano[2,3-b:5,6-b']dipyridine-8-carboxylic acid
7-Amino-2-(azetidin-3-yl)-10-oxo-10H-pyrano[2,3-b:5,6-b']dipyridine-8-carboxylic acid
7-Amino-2-isopropyl-8-(1H-tetrazol-5-yl)-10H-pyrano[2,3-b:5,6-b']dipyridin-10-one
7-Amino-2-cyclopentyl-8-(1H-tetrazol-5-yl)-10H-pyrano[2,3-b:5,6-b']dipyridin-10-one
7-Amino-2-cyclohexyl-8-(1H-tetrazol-5-yl)-10H-pyrano[2,3-b:5,6-b']dipyridin-10-one
7-Amino-8-(hydroxymethyl)-2-isopropyl-10H-pyrano[2,3-b:5,6-b']dipyridin-10-one
7-Amino-2-cyclobutyl-8-(hydroxymethyl)-10H-pyrano[2,3-b:5,6-b']dipyridin-10-one
7-Amino-2-cyclopentyl-8-(hydroxymethyl)-10H-pyrano[2,3-b:5,6-b']dipyridin-10-one
7-Amino-2-cyclohexyl-8-(hydroxymethyl)-10H-pyrano[2,3-b:5,6-b']dipyridin-10-one
Schemes 16, 20, 21, 22, 26, 27:
2-Isopropyl-7-(methylamino)-10-oxo-10H-pyrido[3',2':5,6]pyrano[3,2-d]pyrimidine-8-carboxylic acid
7-Amino-2-(cyclopent-1-en-1-yl)-10-oxo-10H-pyrido[3',2':5,6]pyrano[3,2-d]pyrimidine-8-carboxylic acid
7-Amino-2-cyclopentyl-10-oxo-10H-pyrido[3',2':5,6]pyrano[3,2-d]pyrimidine-8-carboxylic acid
2-Cyclopentyl-7-(methylamino)-10-oxo-10H-pyrido[3',2':5,6]pyrano[3,2-d]pyrimidine-8-carboxylic acid
7-Amino-2-(cyclohex-1-en-1-yl)-10-oxo-10H-pyrido[3',2':5,6]pyrano[3,2-d]pyrimidine-8-carboxylic acid
7-Amino-2-cyclohexyl-10-oxo-10H-pyrido[3',2':5,6]pyrano[3,2-d]pyrimidine-8-carboxylic acid
2-Cyclohexyl-7-(methylamino)-10-oxo-10H-pyrido[3',2':5,6]pyrano[3,2-d]pyrimidine-8-carboxylic acid
(E)-7-Amino-2-(2-cyclohexylvinyl)-10-oxo-10H-pyrido[3',2':5,6]pyrano[3,2-d]pyrimidine-8-carboxylic acid
7-Amino-2-(2-cyclohexylethyl)-10-oxo-10H-pyrido[3',2':5,6]pyrano[3,2-d]pyrimidine-8-carboxylic acid
7-Amino-2-(2-cyclopentylethyl)-10-oxo-10H-pyrido[3',2':5,6]pyrano[3,2-d]pyrimidine-8-carboxylic acid
7-Amino-2-(2-morpholinoethyl)-10-oxo-10H-pyrido[3',2':5,6]pyrano[3,2-d]pyrimidine-8-carboxylic acid
7-Amino-2-cyclobutyl-10-oxo-10H-pyrido[3',2':5,6]pyrano[3,2-d]pyrimidine-8-carboxylic acid
2-Cyclobutyl-7-(methylamino)-10-oxo-10H-pyrido[3',2':5,6]pyrano[3,2-d]pyrimidine-8-carboxylic acid
7-Amino-2-(oxetan-3-yl)-10-oxo-10H-pyrido[3',2':5,6]pyrano[3,2-d]pyrimidine-8-carboxylic acid
7-Amino-2-(azetidin-3-yl)-10-oxo-10H-pyrido[3',2':5,6]pyrano[3,2-d]pyrimidine-8-carboxylic acid
7-Amino-2-isopropyl-8-(1H-tetrazol-5-yl)-10H-pyrido[3',2':5,6]pyrano[3,2-d]pyrimidin-10-one
7-Amino-2-cyclopentyl-8-(1H-tetrazol-5-yl)-10H-pyrido[3',2':5,6]pyrano[3,2-d]pyrimidin-10-one
7-Amino-2-cyclohexyl-8-(1H-tetrazol-5-yl)-10H-pyrido[3',2':5,6]pyrano[3,2-d]pyrimidin-10-one
7-Amino-8-(hydroxymethyl)-2-isopropyl-10H-pyrido[3',2':5,6]pyrano[3,2-d]pyrimidin-10-one
7-Amino-2-cyclobutyl-8-(hydroxymethyl)-10H-pyrido[3',2':5,6]pyrano[3,2-d]pyrimidin-10-one
7-Amino-2-cyclopentyl-8-(hydroxymethyl)-10H-pyrido[3',2':5,6]pyrano[3,2-d]pyrimidin-10-one
7-Amino-2-cyclohexyl-8-(hydroxymethyl)-10H-pyrido[3',2':5,6]pyrano[3,2-d]pyrimidin-10-one Scheme 27:
7-Isopropyl-2-(methylamino)-5-oxo-5H-chromeno[2,3-b]pyridine-3-carboxylic acid
7-Cyclobutyl-2-(methylamino)-5-oxo-5H-chromeno[2,3-b]pyridine-3-carboxylic acid
7-Cyclopentyl-2-(methylamino)-5-oxo-5H-chromeno[2,3-b]pyridine-3-carboxylic acid
2-((2-Hydroxyethyl)amino)-7-isopropyl-5-oxo-5H-chromeno[2,3-b]pyridine-3-carboxylic acid
7-Isopropyl-2-((2-morpholinoethyl)amino)-5-oxo-5H-chromeno[2,3-b]pyridine-3-carboxylic acid
7-Isopropyl-2-(4-methylpiperazin-1-yl)-5-oxo-5H-chromeno[2,3-b]pyridine-3-carboxylic acid Scheme 32:
(E)-2-(((Dimethylamino)methylene)amino)-7-isobutyl-5-oxo-5H-chromeno[2,3-b]pyridine-3-carboxylic acid
(E)-2-(((Dimethylamino)methylene)amino)-7-isopentyl-5-oxo-5H-chromeno[2,3-b]pyridine-3-carboxylic acid
(E)-7-Cyclobutyl-2-(((dimethylamino)methylene)amino)-5-oxo-5H-chromeno[2,3-b]pyridine-3-carboxylic acid
(E)-7-Cyclopentyl-2-(((dimethylamino)methylene)amino)-5-oxo-5H-chromeno[2,3-b]pyridine-3-carboxylic acid
(E)-7-Cyclohexyl-2-(((dimethylamino)methylene)amino)-5-oxo-5H-chromeno[2,3-b]pyridine-3-carboxylic acid
7-((E)-2-Cyclopropylvinyl)-2-(((E)-(dimethylamino)methylene)amino)-5-oxo-5H-chromeno[2,3-b]pyridine-3-carboxylic acid
(E)-7-(2-Cyclopropylethyl)-2-(((dimethylamino)methylene)amino)-5-oxo-5H-chromeno[2,3-b]pyridine-3-carboxylic acid
(E)-7-(2-Cyclopentylethyl)-2-(((dimethylamino)methylene)amino)-5-oxo-5H-chromeno[2,3-b]pyridine-3-carboxylic acid
(E)-2-(((Dimethylamino)methylene)amino)-8-fluoro-7-isopropyl-5-oxo-5H-chromeno[2,3-b]pyridine-3-carboxylic acid
(E)-2-(((Dimethylamino)methylene)amino)-8-isopropyl-5-oxo-5H-chromeno[2,3-b]pyridine-3-carboxylic acid
(E)-2-(((dimethylamino)methylene)amino)-6-isopropyl-5-oxo-5H-chromeno[2,3-b]pyridine-3-carboxylic acid Example 6

Exemplary Compounds

TABLE 3 provides a list of exemplary synthesized compounds.

| 282 | (structure) |
| 283 | (structure) |

TABLE 3-continued
provides a list of exemplary synthesized compounds.
284 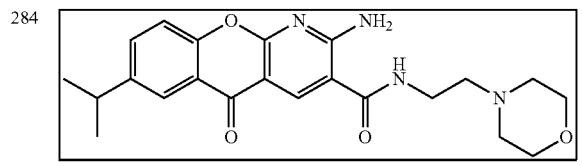
285 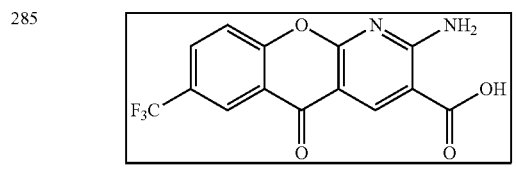
286 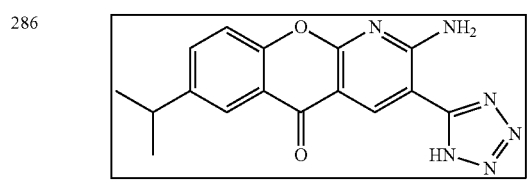
287 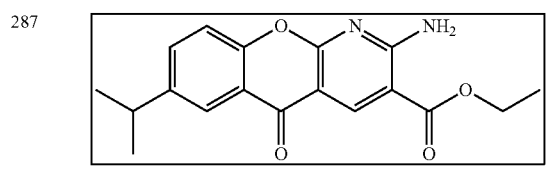
288 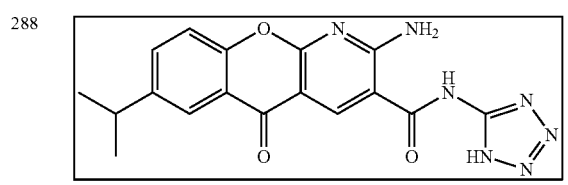
289 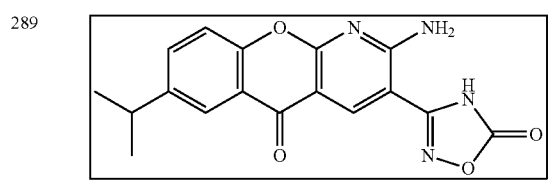
290 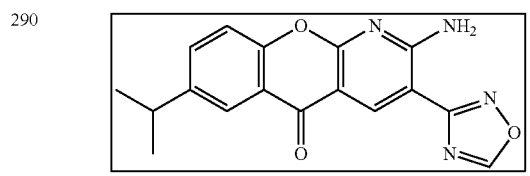
291 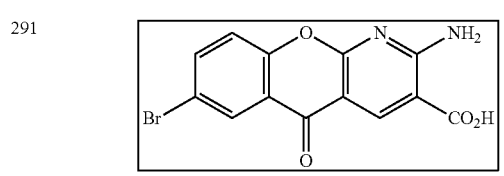
TABLE 3-continued
provides a list of exemplary synthesized compounds.
292 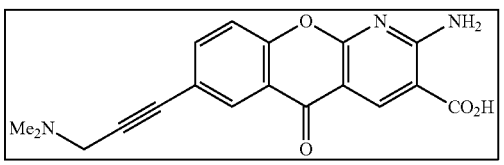 [SMILES: CN(C)CC#Cc1ccc2oc3nc(N)c(C(=O)O)cc3c(=O)c2c1]
293 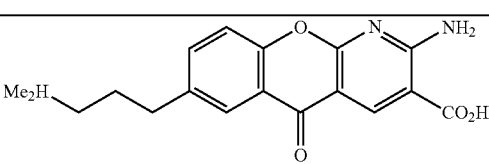
294 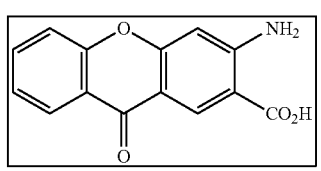 [SMILES: Nc1cc2oc3ccccc3c(=O)c2cc1C(=O)O]
295 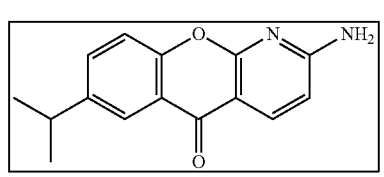 [SMILES: CC(C)c1ccc2oc3nc(N)ccc3c(=O)c2c1]
296 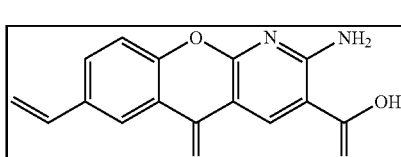
297 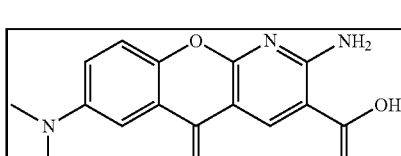
298 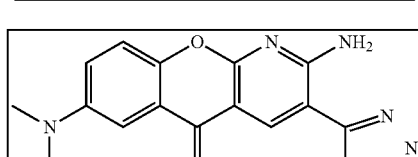
299 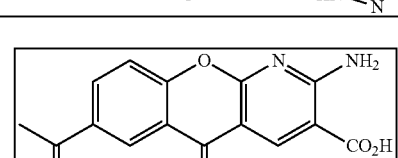
Example 7
Kinase Assays
Kinase assays are commonly used for determining the ability of a small molecule to inhibit enzyme activity. By measuring the degree of phosphorylation of a substrate at varying concentrations of inhibitor, the concentration of inhibitor resulting in 50% enzymatic activity (IC50) can be obtained. The IC50 is defined as the inflection point of the sigmoidal graph obtained when plotting substrate phosphorylation vs. inhibitor concentration. Experiments were conducted during development of embodiments herein using radiolabeled ATP to detect substrate phosphorylation in the presence of amlexanox analogs to determine the potency (IC50) of said analogs.

TBK1 (residues 1-657) and IKKε (residues 1-655) were purified from insect cells to ≥90% purity by coomassie staining. Reactions containing 50 nM TBK1 or IKKε, 7 μM myelin basic protein (MBP), and inhibitor in reaction buffer (50 mM HEPES pH 7.5, 10 mM NaCl, 10 mM MgCl2, 1 mM DTT) were initiated with 5 μM ATP spiked with [γ-32P]-ATP and allowed to proceed for 30 minutes at room temperature. Reactions were quenched with SDS gel loading dye, run on 4-15% SDS-PAGE gels, and imaged on phosphorimaging screens. Band intensities corresponding to phosphorylated MBP were quantified with ImageQuant and the data analyzed in Prism 6. Dose-response assay band intensities were normalized and fit to a sigmoidal dose-response equation with the Hill slope fixed at −1 and the top constrained to 100.

Assays were first performed with 2 μM, the reported IC50 of amlexanox, of each inhibitor. Inhibitors were compared to amlexanox by dividing the MBP band intensity for individual inhibitors by the intensity for amlexanox (FIGS. 1 and 2; Table 4). Ratios less than 1 correspond to inhibitors with greater potency than amlexanox at 2 μM.

TABLE 4

Quantified results from single-point kinase assays.

| Compound Number | TBK1 Ratio | IKKε Ratio |
|---|---|---|
| Amlexanox | 1.0 | 1.0 |
| 5 | 1.8 | 2.1 |
| 8 | 0.8 | 1.0 |
| 11 | 1.6 | 2.4 |
| 13 | 1.0 | 1.3 |
| 15 | 2.2 | 2.7 |
| 19 | 1.8 | 1.9 |
| 24 | 0.5 | 0.9 |
| 26 | 1.2 | 0.6 |
| 28 | 1.1 | 0.5 |
| 30 | 1.5 | 1.8 |
| 34 | 2.7 | 2.3 |
| 36 | 0.3 | 0.6 |
| 38 | 0.3 | 0.5 |
| 40 | 0.2 | 0.3 |
| 42 | 0.4 | 0.6 |
| 45 | 1.9 | 2.3 |
| 47 | 1.2 | 1.6 |
| 51 | 1.7 | 2.2 |
| 52 | 2.7 | 2.7 |
| 53 | 0.6 | 0.6 |
| 55a | 2.2 | 1.8 |
| 55b | 1.9 | 2.1 |
| 55c | 1.0 | 1.2 |
| 55d | 3.1 | 2.7 |
| 56d | 2.2 | 2.2 |
| 57a | 2.4 | 3.0 |
| 57b | 0.8 | 1.0 |
| 57c | 2.5 | 2.9 |
| 59 | 1.1 | 0.9 |
| 61 | 1.8 | 2.2 |
| 62 | 3.7 | 3.4 |
| 65 | 1.5 | 1.8 |
| 67 | 2.2 | 2.2 |
| 69 | 0.9 | 0.5 |
| 71 | 1.1 | 1.3 |
| 74 | 0.9 | 1.3 |
| 76 | 1.0 | 1.1 |
| 78 | 0.9 | 0.9 |
| 80 | 0.9 | 1.3 |
| 81 | 0.4 | 0.8 |
| 97 | 2.7 | 2.7 |
| 115b | 2.3 | 1.6 |
| 117 | 1.3 | 1.3 |
| 176 | 1.7 | 1.8 |
| 180 | 1.1 | 1.9 |
| 241a | 2.1 | 1.6 |
| 241c | 2.5 | 1.6 |
| 243a | 1.3 | 1.8 |
| 243b | 1.8 | 1.3 |
| 246 | 1.3 | 1.8 |
| 252b | 1.7 | 1.7 |
| 253b | 3.1 | 2.2 |
| 254b | 2.2 | 2.4 |
| 258 | 1.0 | 1.5 |
| 259 | 3.0 | 2.2 |
| 260 | 1.9 | 1.6 |
| 275 | 0.2 | 0.8 |
| 283 | 2.9 | 2.5 |
| 284 | 3.2 | 2.5 |
| 285 | 2.0 | 2.6 |
| 286 | 0.6 | 0.5 |
| 287 | 3.6 | 4.1 |
| 288 | 1.3 | 0.7 |
| 289 | 2.2 | 1.7 |
| 290 | 3.9 | 4.3 |
| 291 | 2.5 | 2.3 |
| 293 | 2.0 | 2.5 |
| 294 | 1.0 | 1.5 |
| 295 | 2.2 | 2.2 |
| 295 | n.d. | 1.6 |
| 296 | 1.0 | 1.4 |
| 297 | 0.8 | 0.9 |
| 298 | 1.7 | 0.7 |
| 299 | 1.8 | 2.1 |
| BX795 | 0.2 | 0.3 |
| MRT67307 | 0.1 | 0.2 |

Figure 2:
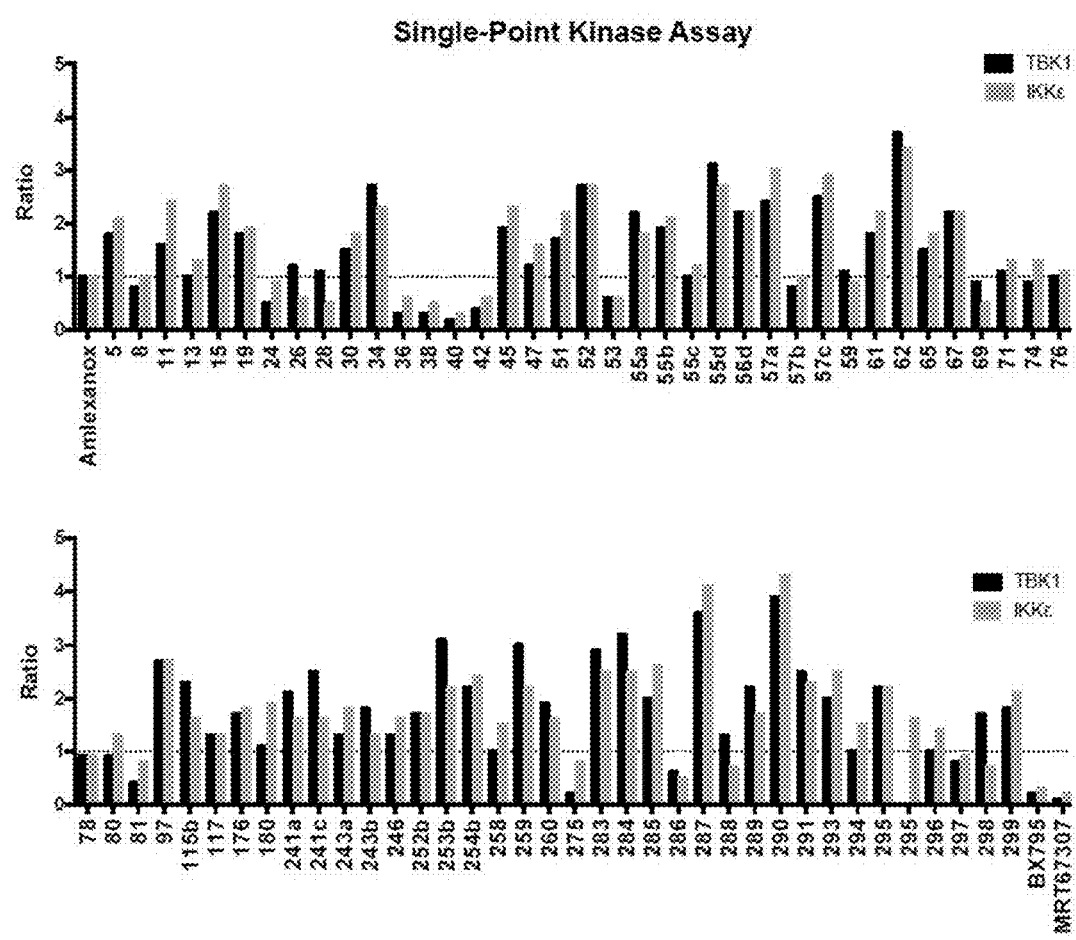
FIG. 2. Results from single-point kinase assays displayed in relation to amlexanox. The inhibition ratio was calculated by dividing the band intensity for analogs by the band intensity of amlexanox. The dotted line corresponds to 1. Values less than 1 represent less phosphorylation when compared to amlexanox and indicate greater inhibition and potency at 2 μM.

The ratio of band intensity for each analog was compared to the band intensity for amlexanox using the equation Ratio = inhibitor band intensity/amlexanox band intensity FIG. 1. Ratios less than 1 correspond to inhibitors with greater potency than amlexanox at 2 μM.

Figure 3:
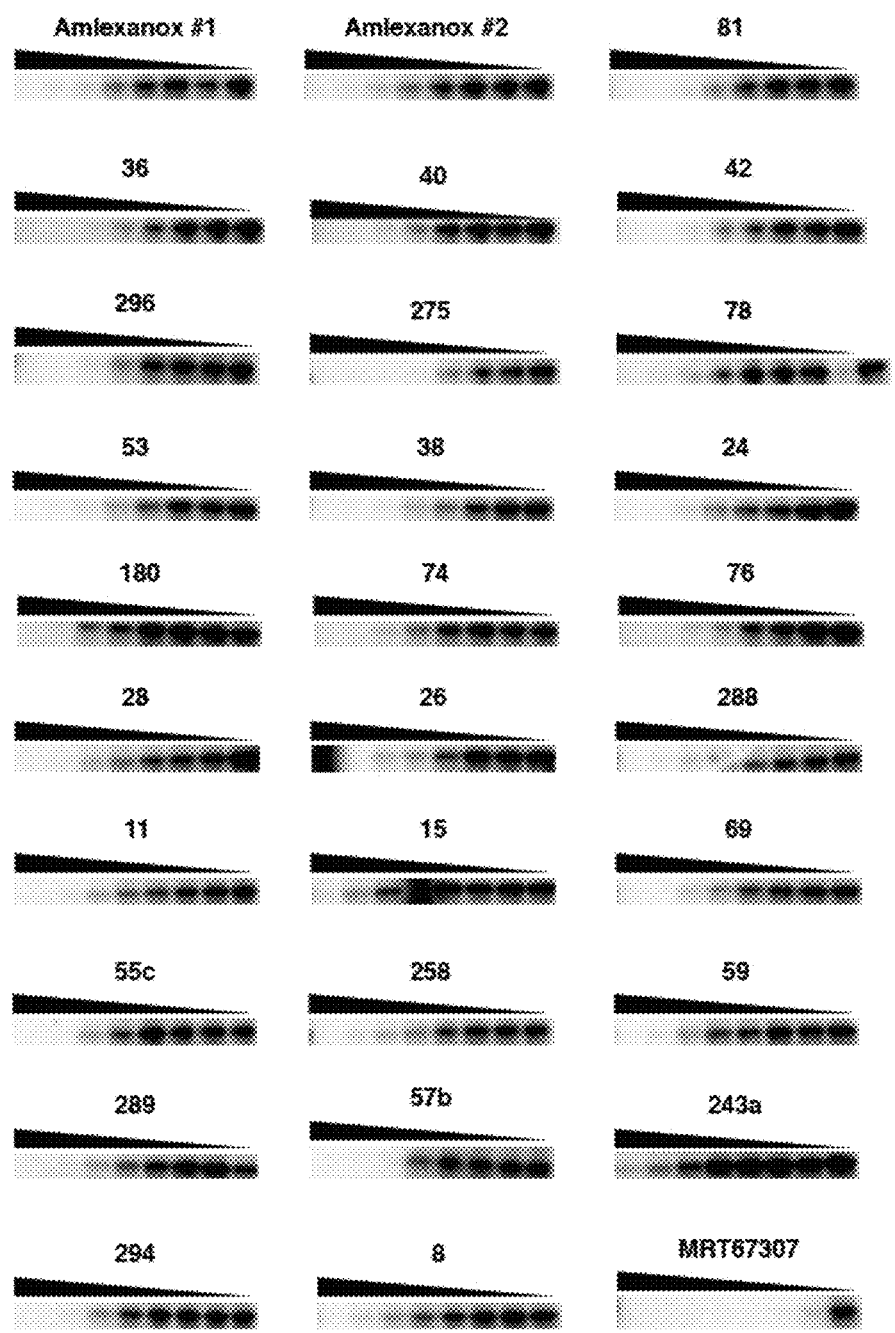
FIG. 3. Representative gels from TBK1 dose-response assays. Band intensities were quantified and used to calculate IC50 values for each analog. Inhibitor concentrations ranged from 400 μM to 0 μM from left to right.
Figure 4:
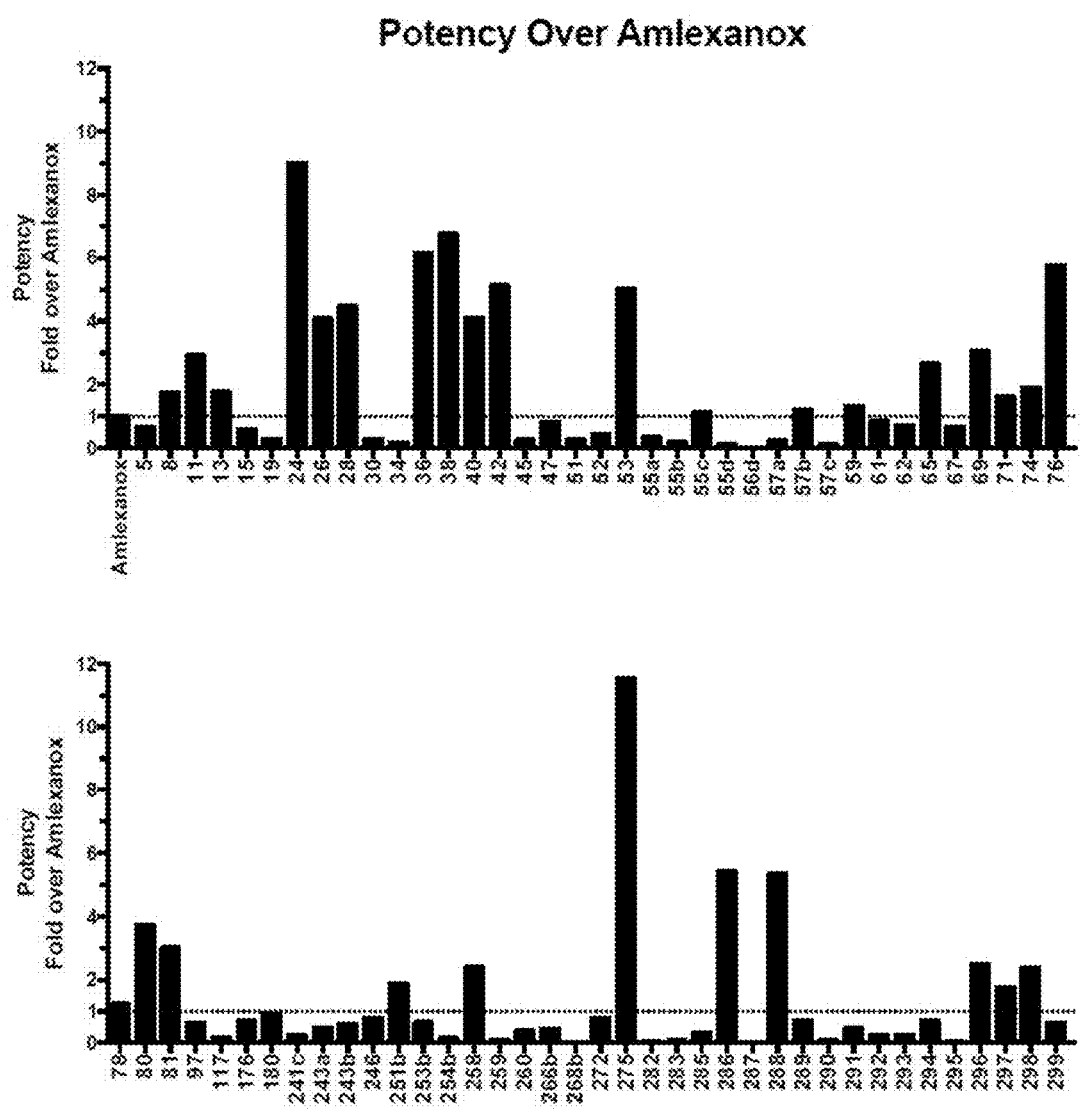
FIG. 4. TBK1 Dose-response kinase assay results compared to amlexanox. The dotted line=1. Bars greater than 1 represent improved potency when compared to amlexanox, while inhibitors less than 1 have decreased potency.
Figure 5:
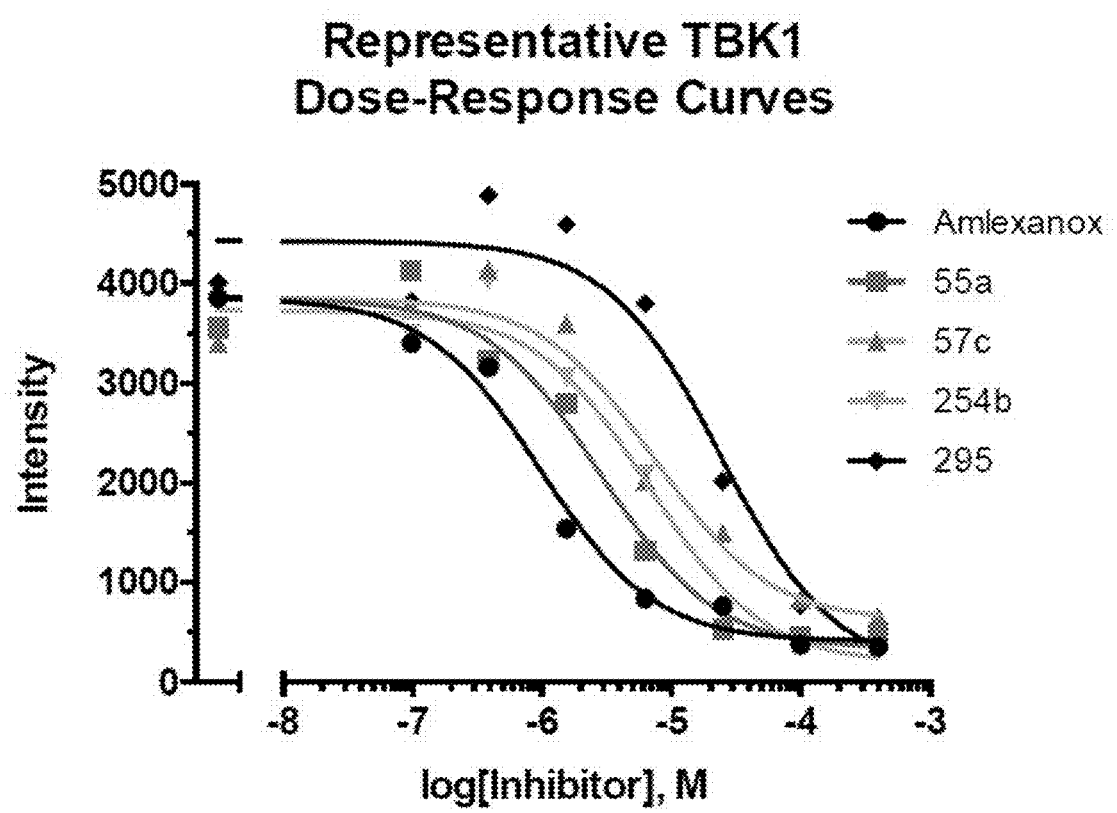
FIG. 5. A representative set of TBK1 dose-response curves. The hill slope was fixed at −1 as only one inhibitor binding site is known.

Inhibitors with a ratio ≤1 and select inhibitors with ratios between 1 and 1.25 were further assessed in dose-response experiments with eight concentrations of inhibitor ranging from 400 μM or 40 μM to 0 μM (Table 5; FIG. 3-5). Potent commercial inhibitors BX795 and MRT67307 are included as positive controls.

TABLE 5

Quantified IC50 values from TBK1 dose-response assays.

| Compound Number | TBK1 IC$_{50}$ (μM) | Fold Over Amlexanox |
|---|---|---|
| Amlexanox | 0.98 | 1.00 |
| 5 | 1.51 | 0.65 |
| 8 | 0.56 | 1.75 |
| 11 | 0.34 | 2.92 |
| 13 | 0.56 | 1.76 |
| 15 | 1.67 | 0.59 |
| 19 | 3.65 | 0.27 |
| 24 | 0.11 | 9.02 |
| 26 | 0.24 | 4.09 |
| 28 | 0.22 | 4.47 |
| 30 | 3.46 | 0.28 |
| 34 | 6.10 | 0.16 |
| 36 | 0.16 | 6.16 |
| 38 | 0.15 | 6.75 |
| 40 | 0.24 | 4.11 |
| 42 | 0.19 | 5.13 |

TABLE 5-continued

Quantified IC50 values from TBK1 dose-response assays.

| Compound Number | TBK1 IC$_{50}$ (μM) | Fold Over Amlexanox |
|---|---|---|
| 45 | 3.76 | 0.26 |
| 47 | 1.20 | 0.82 |
| 51 | 3.83 | 0.26 |
| 52 | 2.30 | 0.43 |
| 53 | 0.19 | 5.04 |
| 55a | 2.84 | 0.35 |
| 55b | 4.85 | 0.20 |
| 55c | 0.88 | 1.12 |
| 55d | 8.82 | 0.11 |
| 56d | 41.50 | 0.02 |
| 57a | 4.24 | 0.23 |
| 57b | 0.80 | 1.22 |
| 57c | 7.52 | 0.13 |
| 59 | 0.74 | 1.33 |
| 61 | 1.17 | 0.84 |
| 62 | 1.41 | 0.70 |
| 65 | 0.37 | 2.65 |
| 67 | 1.45 | 0.68 |
| 69 | 0.32 | 3.07 |
| 71 | 0.60 | 1.63 |
| 74 | 0.51 | 1.91 |
| 76 | 0.17 | 5.78 |
| 78 | 0.79 | 1.23 |
| 80 | 0.26 | 3.73 |
| 81 | 0.33 | 3.01 |
| 97 | 1.56 | 0.63 |
| 117 | 6.59 | 0.15 |
| 176 | 1.40 | 0.70 |
| 180 | 1.07 | 0.92 |
| 241c | 3.98 | 0.25 |
| 243a | 2.01 | 0.49 |
| 243b | 1.67 | 0.59 |
| 246 | 1.23 | 0.80 |
| 251b | 0.52 | 1.88 |
| 253b | 1.49 | 0.66 |
| 254b | 6.73 | 0.15 |
| 258 | 0.41 | 2.40 |
| 259 | 11.40 | 0.09 |
| 260 | 2.58 | 0.38 |
| 266b | 2.16 | 0.45 |
| 268b | 450.00 | 0.00 |
| 272 | 1.24 | 0.79 |
| 275 | 0.08 | 11.55 |
| 282 | 19.50 | 0.05 |
| 283 | 10.40 | 0.09 |
| 285 | 3.01 | 0.33 |
| 286 | 0.18 | 5.42 |
| 287 | 123.00 | 0.01 |
| 288 | 0.18 | 5.35 |
| 289 | 1.40 | 0.70 |
| 290 | 14.40 | 0.07 |
| 291 | 2.05 | 0.48 |
| 292 | 4.24 | 0.23 |
| 293 | 3.76 | 0.26 |
| 294 | 1.39 | 0.71 |
| 295 | 24.40 | 0.04 |
| 296 | 0.39 | 2.50 |
| 297 | 0.55 | 1.77 |
| 298 | 0.41 | 2.38 |
| 299 | 1.53 | 0.64 |

Data were fit to a sigmoidal dose-response function with the hill slope constrained to −1 in Prism.

The data demonstrate that analogs displaying increased potency compared to amlexanox tend to display greater aqueous solubility. In contrast to in vivo efficacy results, 15 displays decreased potency compared to amlexanox which may be explained by its poor solubility. However, the hydrophobic nature of the analog may allow for improved cellular permeability and increased cellular response.

Introduction of an additional nitrogen at the 8 position (e.g., Compound 180 vs. Compound 15) does not significantly improve potency. Introduction of hydrophobic rings with a carbon linker at the 7 position (e.g., Compound 55c) do not improve potency, likely due to their decreased solubility profile, but display increased efficacy in vivo.

Analogs containing a modification to the carboxylic acid (e.g., Compound 286) are at least as potent as amlexanox as long as the modification is an acid isostere/mimic. Modification to the acid moiety that are not acid mimics are detrimental and result in inhibitors with very poor potency or compounds that do not inhibit at all.

Example 8

IL-6 Secretion

Adipocytes are a primary target of amlexanox action (Reilly et al. *Nat Med* 19, 313-321, 2013; incorporated by reference in its entirety). In adipocytes, amlexanox promotes cAMP signaling through inhibition of phosphodiesterase 3B, a downstream target of IKKε/TBK1 (Mowers et al. *Elife*. 2013; incorporated by reference in its entirety). One consequence of cAMP signaling in adipocytes is robust Il-6 secretion, which was determined to be a key factor in reversing the diabetic phenotype in the obese animals (Reilly et al. *Nat Commun* 6, 6047, (2015); incorporated by reference in its entirety). Therefore, serum Il-6 levels are a useful indicator of the effectiveness of IKKε/TBK1 inhibitors in vivo. Furthermore, in cell culture, Il-6 secretion from differentiated adipocytes is also a good measure of efficacy of IKKε/TBK1 inhibitors.

Figure 6:
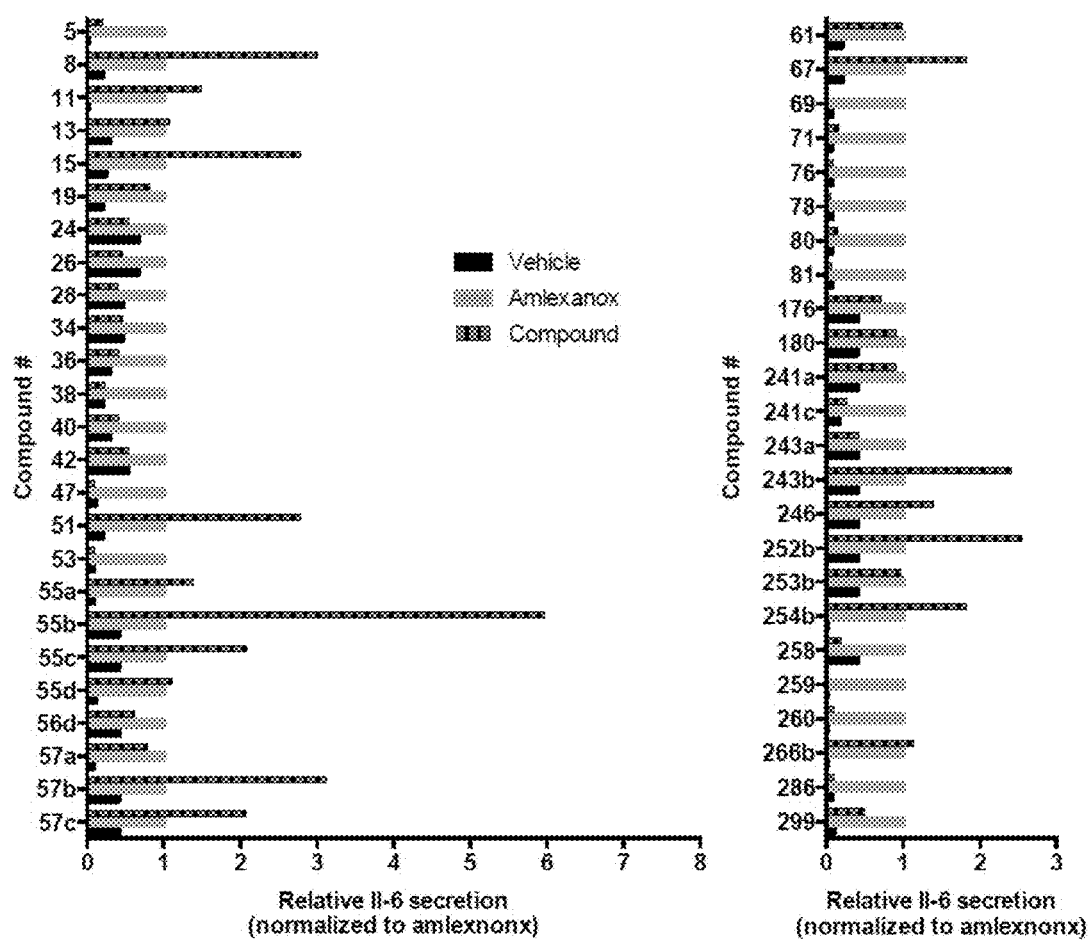
FIG. 6. Normalized Il-6 secretion from 3T3-L1 adipocytes treated with 100 μM compound. Il-6 secretion values for the vehicle control and test compound are normalized to the Il-6 secretion measured for amlexanox in that experiment.
Figure 7:
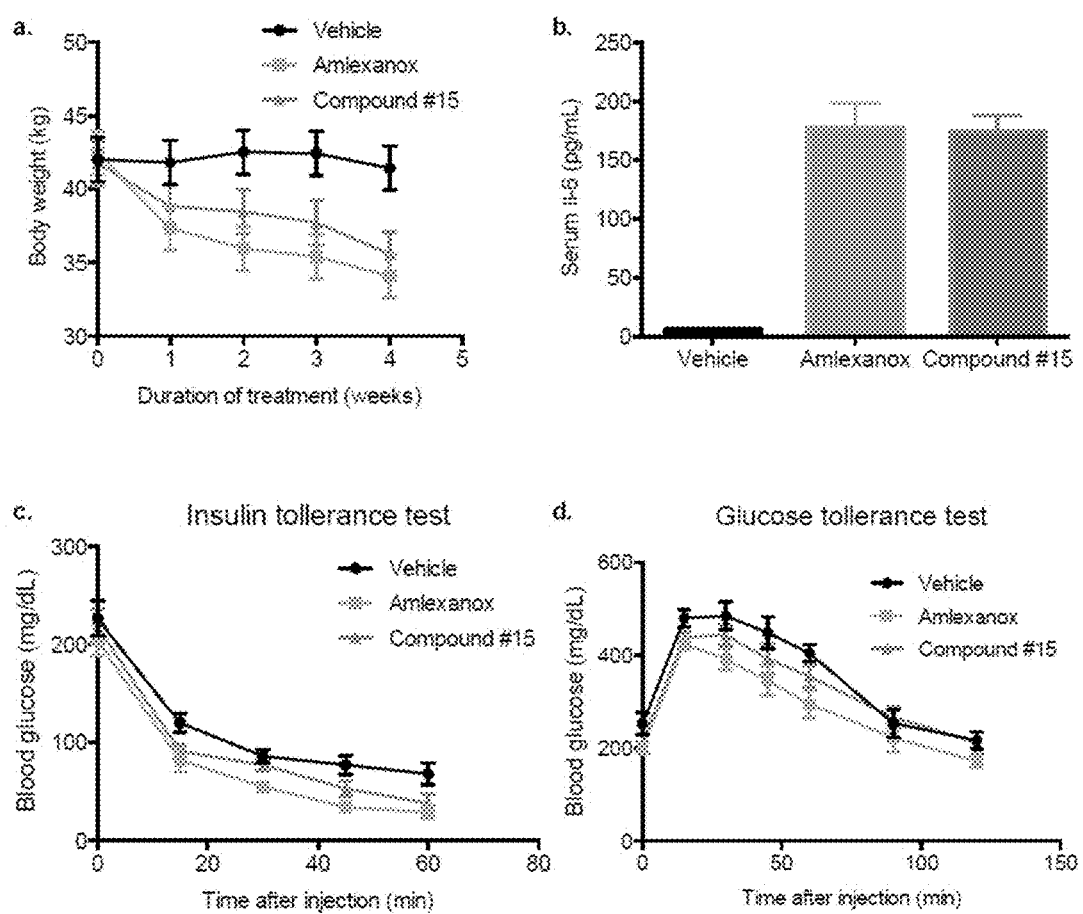
FIG. 7. In vivo efficacy of compound 15. Amlexanox, compound 15 and vehicle control were used in a 4-week trial. Animals were treated by daily oral gavage with 25 mg/kg, (n=7 per treatment group). Panel a) Serum Il-6 response after 6 hours of treatment. Panel b) body weight over the 4-week treatment period. Panel c) Glucose tolerance test after 3 weeks of treatment. Panel d) insulin tolerance test after 4 weeks of treatment.

Experiments were conducted conducted during development of embodiments herein to measure the Il-6 secretion from 3T3-L1 adipocytes treated with 100 μM compound, compared to vehicle control, normalized to the effect of amlexanox (FIG. 6). Additionally, in vivo efficacy of compounds were measured in mice, including the effect on body eight, serum IL-6, insulin tolerance, and glucose tolerance. FIG. 7 depicts exemplary data for Compound 15.

The invention claimed is:

1. A composition comprising a compound of Formula (I):

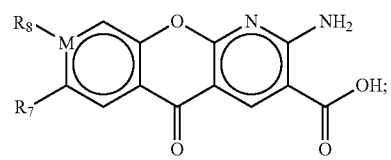

wherein, when M is N, R$_7$ is selected from the group consisting of H, Br, Cl, F, I, D (deuterium), methyl, ethyl, propyl, isopropyl, butyl, CH$_2$F, CH$_2$CH$_2$Cl, CHBrCH$_3$, CF$_2$H, CH$_2$CCl$_2$H, CBr$_3$, CF$_3$, CCl$_3$, CH$_2$CBr$_3$, CH$_2$CF$_3$, CH$_2$CCl$_3$, 1-(trifluoromethyl)cyclopropyl, 1-(trichloromethyl)cyclohexyl, an alkene, an alkyne, NH$_2$, NH-methyl, NH-ethyl, NH—CH$_2$-Ph, (CH$_2$)$_{1-6}$—NH$_2$(CH$_2$)$_{1-6}$—NH—(CH$_2$)$_{1-5}$CH$_3$, (CH$_2$)$_{1-6}$—N(CH$_3$)$_2$, alkene-N(CH$_3$)$_2$, alkyne-N(CH$_3$)$_2$, N(CH$_3$)$_2$, O-alkyl, NH—(CH$_2$)$_{2-6}$—OH, OH, (CH$_2$)$_{1-6}$OH, CH$_2$CHOHCH$_2$OH, cycloalkyl, (CH$_2$)$_{1-6}$-cycloalkyl, alkene-cycloalkyl, cycloalkene, alkyl-cycloalkenyl, alkene-cycloalkenyl, (CH$_2$)$_{0-6}$-(non-aromatic heterocycle), and (CH$_2$)$_{0-6}$-(heteroaryl);

wherein, when M is C, R$_7$ is selected from the group consisting of H, Br, F, I, D (deuterium), CH$_2$F, CH$_2$CH$_2$Cl, CHBrCH$_3$, CF$_2$H, CH$_2$CCl$_2$H, CBr$_3$, CF$_3$, CCl$_3$, CH$_2$CBr$_3$, CH$_2$CF$_3$, CH$_2$CCl$_3$, 1-(trifluoromethyl)cyclopropyl, 1-(trichloromethyl)cyclohexyl, an alkenyl, an alkynyl, NH$_2$, NH-methyl, NH-ethyl, NH—CH$_2$-Ph, (CH$_2$)$_{1-6}$—NH$_2$(CH$_2$)$_{1-6}$—NH—(CH$_2$)$_{1-5}$CH$_3$, (CH$_2$)$_{1-6}$—N(CH$_3$)$_2$, alkenyl-N(CH$_3$)$_2$, alkynyl-N(CH$_3$)$_2$, NH—(CH$_2$)$_{2-6}$—OH, OH, (CH$_2$)$_{1-6}$OH, CH$_2$CHOHCH$_2$OH, cycloalkyl, (CH$_2$)$_{1-6}$-cycloalkyl, alkenyl-cycloalkyl, cycloalkenyl, alkyl-cycloalkenyl, alkenyl-cycloalkenyl, (CH$_2$)$_{0-6}$-(non-aromatic heterocycle), and (CH$_2$)$_{0-6}$-(heteroaryl);
wherein, when M is C, R$_7$ is not (CH$_2$)$_2$-cyclohexyl;
wherein, when M is C, and R$_7$ is H or D, R$_8$ is selected from the group consisting of Br, Cl, F, I, D (deuterium), methyl, ethyl, propyl, isopropyl, butyl, CH$_2$F, CH$_2$CH$_2$Cl, CHBrCH$_3$, CF$_2$H, CH$_2$CCl$_2$H, CBr$_3$, CF$_3$, CCl$_3$, CH$_2$CBr$_3$, CH$_2$CF$_3$, CH$_2$CCl$_3$, 1-(trifluoromethyl)cyclopropyl, 1-(trichloromethyl)cyclohexyl, an alkene, an alkyne, NH$_2$, NH-methyl, NH-ethyl, NH—CH$_2$-Ph, (CH$_2$)$_{1-6}$—NH$_2$, (CH$_2$)$_{1-6}$—NH—(CH$_2$)$_{1-5}$CH$_3$, (CH$_2$)$_{1-6}$—N(CH$_3$)$_2$, alkenyl-N(CH$_3$)$_2$, alkynyl-N(CH$_3$)$_2$, N(CH$_3$)$_2$, O-alkyl, NH—(CH$_2$)$_{2-6}$—OH, (CH$_2$)$_{1-6}$OH, CH$_2$CHOHCH$_2$OH, cycloalkyl, (CH$_2$)$_{1-6}$-cycloalkyl, alkenyl-cycloalkyl, cycloalkenyl, alkyl-cycloalkenyl, alkenyl-cycloalkenyl, (CH$_2$)$_{0-6}$-(non-aromatic heterocycle), and (CH$_2$)$_{0-6}$-(heteroaryl),
wherein, when M is C, and R$_7$ is not H or D, R$_8$ is H, F, or D; and
wherein R$_8$ is absent if M is N.

2. The composition of claim 1, wherein the compound is selected from the group consisting of:

(Compound 5)

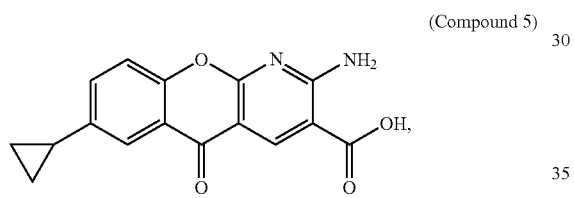

(Compound 24)

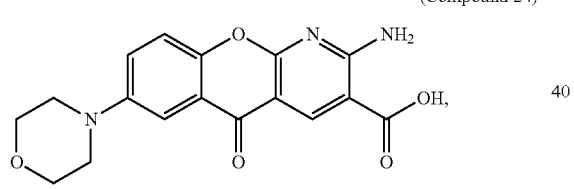

(Compound 11)

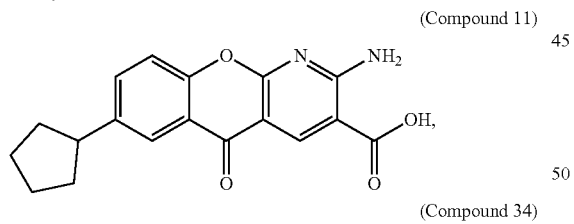

(Compound 34)

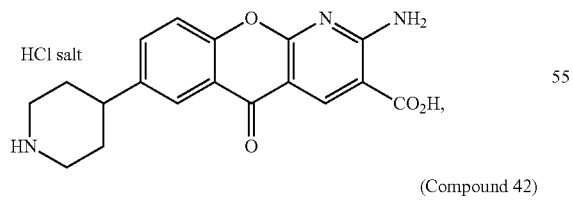

(Compound 42)

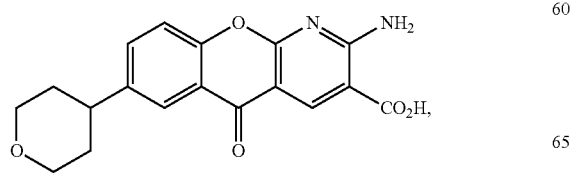

(Compound 15)

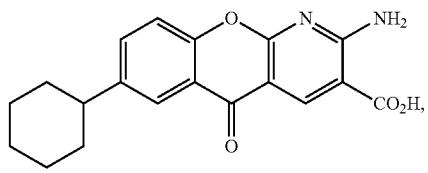

(Compound 40)

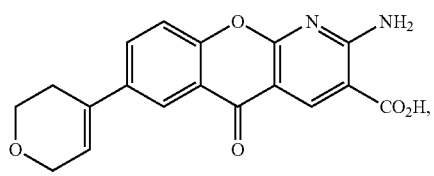

(Compound 13)

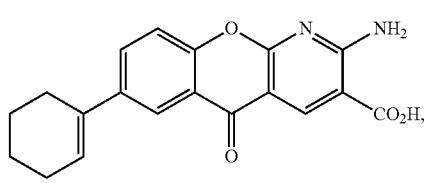

(Compound 30)

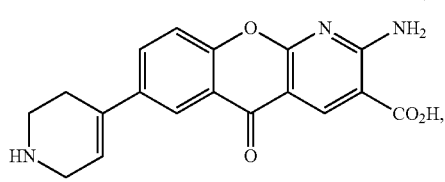

(Compound 67)

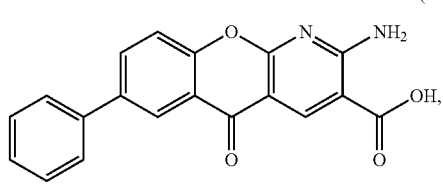

(Compound 8)

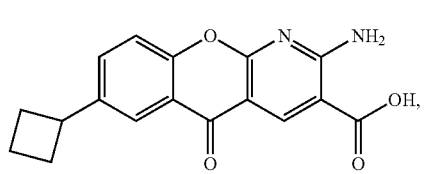

(Compound 19)

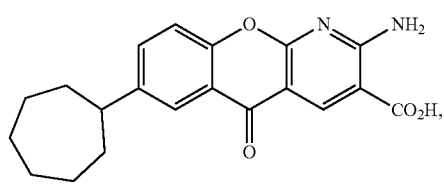

(Compound 74)

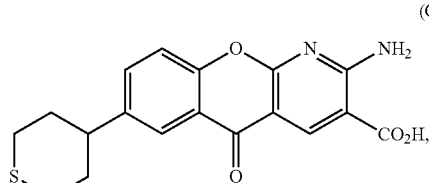

-continued (Compound 55a)

(Compound 55b)

(Compound 55c)

(Compound 57a)

(Compound 57b)

(Compound 57c)

(Compound 89)

(Compound 96a)

-continued (Compound 96c)

(Compound 175)

(Compound 176)

(Compound 177)

(Compound 178)

(Compound 179)

(Compound 180)

(Compound 181)

-continued (Compound 185)
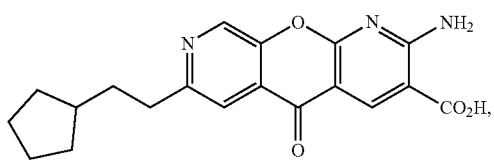

(Compound 186)
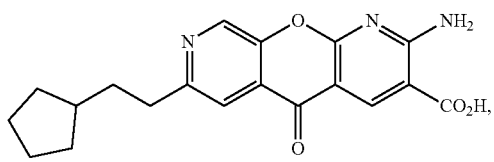

(Compound 187)
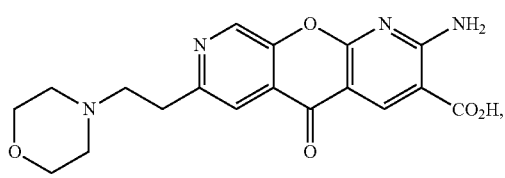

(Compound 188)
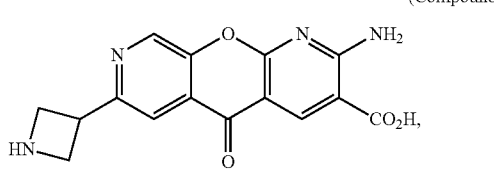

(Compound 285)
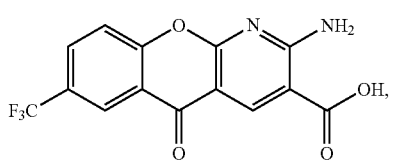

-continued (Compound 292)
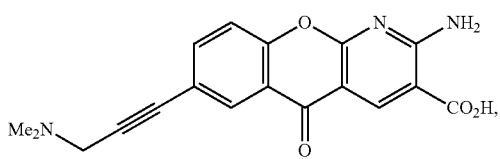

(Compound 293)
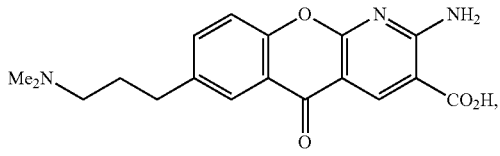

(Compound 296)
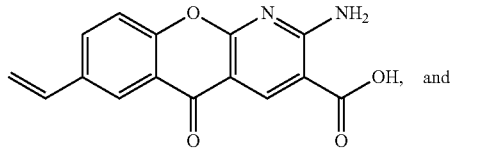

(Compound 299)
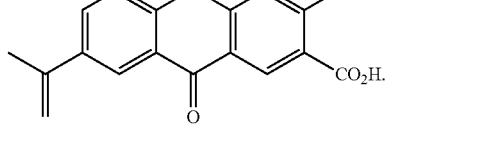

3. A method of treating obesity, insulin resistance, diabetes, and/or steatosis comprising administering a composition of claim 1 to a subject.

4. A method of treating obesity, insulin resistance, diabetes, and/or steatosis comprising administering a composition of claim 2 to a subject.

* * * * *